US010680188B2

(12) United States Patent
Ji et al.

(10) Patent No.: US 10,680,188 B2
(45) Date of Patent: Jun. 9, 2020

(54) ORGANIC ELECTROLUMINESCENT MATERIALS AND DEVICES

(71) Applicant: Universal Display Corporation, Ewing, NJ (US)

(72) Inventors: Zhiqiang Ji, Ewing, NJ (US); Lichang Zeng, Ewing, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 197 days.

(21) Appl. No.: 15/719,662

(22) Filed: Sep. 29, 2017

(65) Prior Publication Data

US 2018/0138427 A1 May 17, 2018

Related U.S. Application Data

(60) Provisional application No. 62/420,839, filed on Nov. 11, 2016.

(51) Int. Cl.

| | |
|---|---|
| ***H01L 51/00*** | (2006.01) |
| ***C07D 495/04*** | (2006.01) |
| ***C07F 15/00*** | (2006.01) |
| ***C09K 11/02*** | (2006.01) |
| ***C09K 11/06*** | (2006.01) |
| *H01L 51/50* | (2006.01) |

(52) U.S. Cl.

CPC ........ *H01L 51/0085* (2013.01); *C07D 495/04* (2013.01); *C07F 15/0033* (2013.01); *C09K 11/02* (2013.01); *C09K 11/06* (2013.01); *H01L 51/0071* (2013.01); *C09K 2211/1037* (2013.01); *C09K 2211/185* (2013.01); *H01L 51/5012* (2013.01); *H01L 51/5016* (2013.01)

(58) Field of Classification Search

None

See application file for complete search history.

(56) References Cited

U.S. PATENT DOCUMENTS

| | | | |
|---|---|---|---|
| 4,769,292 | A | 9/1988 | Tang |
| 5,061,569 | A | 10/1991 | Vanslyke |
| 5,247,190 | A | 9/1993 | Friend |
| 5,703,436 | A | 12/1997 | Forrest |
| 5,707,745 | A | 1/1998 | Forrest |
| 5,834,893 | A | 11/1998 | Bulovic |
| 5,844,363 | A | 12/1998 | Gu |
| 6,013,982 | A | 1/2000 | Thompson |
| 6,087,196 | A | 7/2000 | Sturm |

(Continued)

FOREIGN PATENT DOCUMENTS

| | | |
|---|---|---|
| EP | 0650955 | 5/1995 |
| EP | 1238981 | 9/2002 |

(Continued)

OTHER PUBLICATIONS

Wong, Wai-Yeung, "Multifunctional Iridium Complexes Based on Carbazole Modules as Highly Efficient Electrophosphors," Angew. Chem. Int. Ed., 45:7800-7803 (2006).

(Continued)

*Primary Examiner* — Robert S Loewe

(74) *Attorney, Agent, or Firm* — Riverside Law LLP

(57) ABSTRACT

The present invention includes novel six member aromatic or heteroaromatic rings fused to aza-DBX as ligands for making dopants for OLED applications.

20 Claims, 2 Drawing Sheets

(56) References Cited

U.S. PATENT DOCUMENTS

| | | | | |
|---|---|---|---|---|
| 6,091,195 | A | 7/2000 | Forrest | |
| 6,097,147 | A | 8/2000 | Baldo | |
| 6,294,398 | B1 | 9/2001 | Kim | |
| 6,303,238 | B1 | 10/2001 | Thompson | |
| 6,337,102 | B1 | 1/2002 | Forrest | |
| 6,468,819 | B1 | 10/2002 | Kim | |
| 6,528,187 | B1 | 3/2003 | Okada | |
| 6,687,266 | B1 | 2/2004 | Ma | |
| 6,835,469 | B2 | 12/2004 | Kwong | |
| 6,921,915 | B2 | 7/2005 | Takiguchi | |
| 7,087,321 | B2 | 8/2006 | Kwong | |
| 7,090,928 | B2 | 8/2006 | Thompson | |
| 7,154,114 | B2 | 12/2006 | Brooks | |
| 7,250,226 | B2 | 7/2007 | Tokito | |
| 7,279,704 | B2 | 10/2007 | Walters | |
| 7,332,232 | B2 | 2/2008 | Ma | |
| 7,338,722 | B2 | 3/2008 | Thompson | |
| 7,393,599 | B2 | 7/2008 | Thompson | |
| 7,396,598 | B2 | 7/2008 | Takeuchi | |
| 7,431,968 | B1 | 10/2008 | Shtein | |
| 7,445,855 | B2 | 11/2008 | MacKenzie | |
| 7,534,505 | B2 | 5/2009 | Lin | |
| 7,968,146 | B2 | 6/2011 | Wagner | |
| 8,409,729 | B2 | 4/2013 | Zeng | |
| 2002/0034656 | A1 | 3/2002 | Thompson | |
| 2002/0134984 | A1 | 9/2002 | Igarashi | |
| 2002/0158242 | A1 | 10/2002 | Son | |
| 2003/0138657 | A1 | 7/2003 | Li | |
| 2003/0152802 | A1 | 8/2003 | Tsuboyama | |
| 2003/0162053 | A1 | 8/2003 | Marks | |
| 2003/0175553 | A1 | 9/2003 | Thompson | |
| 2003/0230980 | A1 | 12/2003 | Forrest | |
| 2004/0036077 | A1 | 2/2004 | Ise | |
| 2004/0137267 | A1 | 7/2004 | Igarashi | |
| 2004/0137268 | A1 | 7/2004 | Igarashi | |
| 2004/0174116 | A1 | 9/2004 | Lu | |
| 2005/0025993 | A1 | 2/2005 | Thompson | |
| 2005/0112407 | A1 | 5/2005 | Ogasawara | |
| 2005/0238919 | A1 | 10/2005 | Ogasawara | |
| 2005/0244673 | A1 | 11/2005 | Satoh | |
| 2005/0260441 | A1 | 11/2005 | Thompson | |
| 2005/0260449 | A1 | 11/2005 | Walters | |
| 2006/0008670 | A1 | 1/2006 | Lin | |
| 2006/0202194 | A1 | 9/2006 | Jeong | |
| 2006/0240279 | A1 | 10/2006 | Adamovich | |
| 2006/0251923 | A1 | 11/2006 | Lin | |
| 2006/0263635 | A1 | 11/2006 | Ise | |
| 2006/0280965 | A1 | 12/2006 | Kwong | |
| 2007/0190359 | A1 | 8/2007 | Knowles | |
| 2007/0278938 | A1 | 12/2007 | Yabunouchi | |
| 2008/0015355 | A1 | 1/2008 | Schafer | |
| 2008/0018221 | A1 | 1/2008 | Egen | |
| 2008/0106190 | A1 | 5/2008 | Yabunouchi | |
| 2008/0124572 | A1 | 5/2008 | Mizuki | |
| 2008/0220265 | A1 | 9/2008 | Xia | |
| 2008/0297033 | A1 | 12/2008 | Knowles | |
| 2009/0008605 | A1 | 1/2009 | Kawamura | |
| 2009/0009065 | A1 | 1/2009 | Nishimura | |
| 2009/0017330 | A1 | 1/2009 | Iwakuma | |
| 2009/0030202 | A1 | 1/2009 | Iwakuma | |
| 2009/0039776 | A1 | 2/2009 | Yamada | |
| 2009/0045730 | A1 | 2/2009 | Nishimura | |
| 2009/0045731 | A1 | 2/2009 | Nishimura | |
| 2009/0101870 | A1 | 4/2009 | Prakash | |
| 2009/0108737 | A1 | 4/2009 | Kwong | |
| 2009/0115316 | A1 | 5/2009 | Zheng | |
| 2009/0165846 | A1 | 7/2009 | Johannes | |
| 2009/0167162 | A1 | 7/2009 | Lin | |
| 2009/0179554 | A1 | 7/2009 | Kuma | |
| 2010/0219407 | A1* | 9/2010 | Kamatani | C07C 17/14 257/40 |
| 2012/0061654 | A1* | 3/2012 | Rayabarapu | C07F 15/0033 257/40 |
| 2013/0026452 | A1 | 1/2013 | Kottas | |
| 2013/0119354 | A1 | 5/2013 | Ma | |
| 2013/0140549 | A1* | 6/2013 | Xia | C07D 401/14 257/40 |
| 2014/0054564 | A1 | 2/2014 | Kim | |
| 2014/0124760 | A1* | 5/2014 | Das | H01L 51/0085 257/40 |
| 2015/0171348 | A1* | 6/2015 | Stoessel | C07F 15/0033 252/301.16 |
| 2015/0236276 | A1* | 8/2015 | Boudreault | H01L 51/0085 257/40 |
| 2015/0318487 | A1 | 11/2015 | Ito | |
| 2016/0093818 | A1 | 3/2016 | Inoue | |
| 2016/0233442 | A1 | 8/2016 | Yen | |

FOREIGN PATENT DOCUMENTS

| | | | |
|---|---|---|---|
| EP | 1725079 | | 11/2006 |
| EP | 2034538 | | 3/2009 |
| EP | 2551932 | | 1/2013 |
| EP | 2977378 | | 1/2016 |
| JP | 200511610 | | 1/2005 |
| JP | 2007123392 | | 5/2007 |
| JP | 2007254297 | | 10/2007 |
| JP | 2008074939 | A | 4/2008 |
| JP | 2010135467 | | 6/2010 |
| JP | 5707818 | | 4/2012 |
| WO | 0139234 | | 5/2001 |
| WO | 0202714 | | 1/2002 |
| WO | 0215645 | | 2/2002 |
| WO | 03040257 | | 5/2003 |
| WO | 03060956 | | 7/2003 |
| WO | 2004093207 | | 10/2004 |
| WO | 2004107822 | | 12/2004 |
| WO | 2004111066 | | 12/2004 |
| WO | 2005014551 | | 2/2005 |
| WO | 2005019373 | | 3/2005 |
| WO | 2005030900 | | 4/2005 |
| WO | 2005089025 | | 9/2005 |
| WO | 2005123873 | | 12/2005 |
| WO | 2006009024 | | 1/2006 |
| WO | 2006056418 | | 6/2006 |
| WO | 2006072002 | | 7/2006 |
| WO | 2006082742 | | 8/2006 |
| WO | 2006098120 | | 9/2006 |
| WO | 2006100298 | | 9/2006 |
| WO | 2006103874 | | 10/2006 |
| WO | 2006114966 | | 11/2006 |
| WO | 2006132173 | | 12/2006 |
| WO | 2007002683 | | 1/2007 |
| WO | 2007004380 | | 1/2007 |
| WO | 2007063754 | | 6/2007 |
| WO | 2007063796 | | 6/2007 |
| WO | 2008044723 | | 4/2008 |
| WO | 2008056746 | | 5/2008 |
| WO | 2008057394 | | 5/2008 |
| WO | 2008101842 | | 8/2008 |
| WO | 2008132085 | | 11/2008 |
| WO | 2009000673 | | 12/2008 |
| WO | 2009003898 | | 1/2009 |
| WO | 2009008311 | | 1/2009 |
| WO | 2009018009 | | 2/2009 |
| WO | 2009021126 | A2 | 2/2009 |
| WO | 2009050290 | | 4/2009 |
| WO | 2009062578 | | 5/2009 |
| WO | 2009063833 | | 5/2009 |
| WO | 2009066778 | | 5/2009 |
| WO | 2009066779 | | 5/2009 |
| WO | 2009086028 | | 7/2009 |
| WO | 2009100991 | | 8/2009 |
| WO | 2010011390 | | 1/2010 |
| WO | 2010111175 | | 9/2010 |
| WO | 2010126234 | | 11/2010 |
| WO | 2015104045 | | 7/2015 |

OTHER PUBLICATIONS

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

(56) References Cited

OTHER PUBLICATIONS

Mi, Bao-Xiu et al., "Thermally Stable Hole-Transporting Material for Organic Light-Emitting Diode: an Isoindole Derivative," Chem. Mater., 15(16):3148-3151 (2003).
Okumoto, Kenji et al., "Green Fluorescent Organic Light-Emitting Device with External Quantum Efficiency of Nearly 10%," Appl. Phys. Lett., 89:063504-1-063504-3 (2006).
Paulose, Betty Marie Jennifer S, et al., "First Examples of Alkenyl Pyridines as Organic Ligands for Phosphorescent Iridium Complexes," Adv. Mater., 16(22):2003-2007 (2004).
Tang, C.W. And VanSlyke, S.A., "Organic Electroluminescent Diodes," Appl. Phys. Lett., 51(12):913-915 (1987).
T. Ostergard et al., "Langmuir-Blodgett Light-Emitting Diodes of Poly(3-Hexylthiophene): Electro-Optical Characteristics Related to Structure," Synthetic Metals, 87:171-177 (1997).
Tung, Yung-Liang et al., "Organic Light-Emitting Diodes Based on Charge-Neutral Ru II PHosphorescent Emitters," Adv. Mater., 17(8):1059-1064 (2005).
Van Slyke, S. A. et al., "Organic Electroluminescent Devices with Improved Stability," Appl. Phys. Lett, 69(15 ):2160-2162 (1996).
Wong, Keith Man-Chung et al., "A Novel Class of Phosphorescent Gold(III) Alkynyl-Based Organic Light-Emitting Devices with Tunable Colour," Chem. Commun., 2906-2908 (2005).
Adachi, Chihaya et al., "Organic Electroluminescent Device Having a Hole Conductor as an Emitting Layer," Appl. Phys. Lett., 55(15):1489-1491 (1989).
Baldo et al., "Highly Efficient Phosphorescent Emission from Organic Electroluminescent Devices," Nature, vol. 395,151-154, (1998).
Gao, Zhiqiang et al., "Bright-Blue Electroluminescence From a Silyl-Substituted ter-(phenylene-vinylene) derivative," Appl. Phys. Lett., 74(6):865- 867 (1999).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Wang, Y. et al., "Highly Efficient Electroluminescent Materials Based on Fluorinated Organometallic Iridium Compounds," Appl. Phys. Lett., 79(4):449-451 (2001).
Kwong, Raymond C. et al., "High Operational Stability of Electrophosphorescent Devices," Appl. Phys. Lett., 81(1):162-164 (2002).
Holmes, R.J. et al., "Blue Organic Electrophosphorescence Using Exothermic Host-Guest Energy Transfer," Appl. Phys. Lett., 82(15):2422-2424 (2003).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1153505-3 (2005).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
Adachi, Chihaya et al., "High-Efficiency Red Electrophosphorescence Devices," Appl. Phys. Lett., 78(11):1622-1624 (2001).
Hamada, Yuji et al., "High Luminance in Organic Electroluminescent Devices with Bis(10-hydroxybenzo[h]quinolinato)beryllium as an Emitter," Chem. Lett., 905-906 (1993).
Nishida, Jun-ichi et al., "Preparation, Characterization, and Electroluminescence Characteristics of a-Diimine-type Platinum(II) Complexes with Perfluorinated Phenyl Groups as Ligands," Chem. Lett., 34(4):592-593 (2005).
Baldo et al., "Very high-efficiency green organic light-emitting devices based on electrophosphorescence," Appl. Phys. Lett., vol. 75, No. 3, 4-6 (1999).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Niu, Yu-Hua et al., "Highly Efficient Electrophosphorescent Devices with Saturated Red Emission from a Neutral Osmium Complex," Chem. Mater., 17(13):3532-3536 (2005).
Lo, Shih-Chun et al., "Blue Phosphorescence from Iridium(III) Complexes at Room Temperature," Chem. Mater., 18(21):5119-5129 (2006).
Takizawa, Shin-ya et al., "Phosphorescent Iridium Complexes Based on 2-Phenylimidazo[1,2-a]pyridine Ligands: Tuning of Emission Color toward the Blue Region and Application to Polymer Light-Emitting Devices," Inorg. Chem., 46(10):4308-4319 (2007).
Lamansky, Sergey et al., "Synthesis and Characterization of Phosphorescent Cyclometalated Iridium Complexes," Inorg. Chem., 40(7):1704-1711 (2001).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Noda, Tetsuya and Shirota,Yasuhiko, "5,6-Bis(dinnesitylboryl)-2,2'-bithiophene and 5,5"-Bis(dimesitylbory1)-2,2':5',2"-terthiophene as a Novel Family of Electron-Transporting Amorphous Molecular Materials," J. Am. Chem. Soc., 120 (37):9714-9715 (1998).
Sakamoto, Youichi et al., "Synthesis, Characterization, and Electron-Transport Property of Perfluorinated Phenylene Dendrimers," J. Am. Chem. Soc., 122(8):1832-1833 (2000).
Adachi, Chihaya et al., "Nearly 100% Internal Phosphorescence Efficiency in an Organic Light Emitting Device," J. Appl. Phys., 90(10):5048-5051 (2001).
Shirota, Yasuhiko et al., "Starburst Molecules Based on π-Electron Systems as Materials for Organic Electroluminescent Devices," Journal of Luminescence, 72-74:985-991 (1997).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kido, Junji et al.,"1,2,4-Triazole Derivative as an Electron Transport Layer in Organic Electroluminescent Devices," Jpn. J. Appl. Phys., 32:L917-L920 (1993).
Guo, Tzung-Fang et al., "Highly Efficient Electrophosphorescent Polymer Light-Emitting Devices," Organic Electronics, 1:15-20 (2000).
Palilis, Leonidas C., "High Efficiency Molecular Organic Light-Emitting Diodes Based on Silole Derivatives and Their Exciplexes," Organic Electronics, 4:113-121 (2003).
Ikeda, Hisao et al., "P-185: Low-Drive-Voltage OLEDs with a Buffer Layer Having Molybdenum Oxide," SID Symposium Digest, 37:923-926 (2006).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Salbeck, J. et al., "Low Molecular Organic Glasses for Blue Electroluminescence," Synthetic Metals, 91:209-215 (1997).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Hung, L.S. et al., "Anode Modification in Organic Light-Emitting Diodes by Low-Frequency Plasma Polymerization of CHF3,"Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Seo et al., 2014, "High efficiency yellowish green phosphorescent emitter derived from phenylbenzothienopyridine ligand," Organic Electronics 15:2068-2072.

* cited by examiner

ORGANIC ELECTROLUMINESCENT MATERIALS AND DEVICES

CROSS-REFERENCE TO RELATED APPLICATIONS

This application claims priority to U.S. Provisional Patent Application Ser. No. 62/420,839, filed Nov. 11, 2016, the entire contents of which are incorporated herein by reference.

FIELD

The present invention relates to compounds for use as emitters, and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted $Ir(ppy)_3$, which has the following structure:

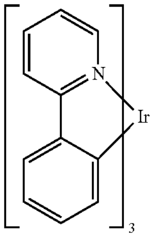

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

There is a need in the art for novel ligands that can be used to make dopants for improving the performance of organic electroluminescent devices. The present invention addresses this need in the art.

SUMMARY

According to an embodiment, a compound is provided that includes a ligand $L_A$ of the structure of Formula (I) shown below:

(I)

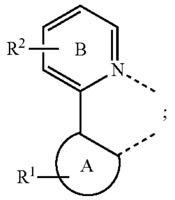

wherein ring A is a 5-membered or 6-membered carbocyclic or heterocyclic ring;

wherein $R^1$ represents from none to the maximum possible number of substitution;

wherein $R^2$ represents from two to the maximum possible number of substitution;

wherein at least two adjacent $R^2$s are joined to form ring C and have the following formula, wherein ring C is fused to ring B:

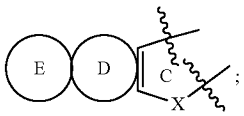

wherein the wave lines indicate bonds to ring B;

wherein ring D and ring E are each independently a 6-membered aromatic ring;

wherein ring D fuses to ring C, and ring E fuses to ring D;

wherein ring D and ring E can be further substituted by one or more substituents;

wherein X is selected from the group consisting of O, S, Se, and NR;

wherein $R^1$, $R^2$, and R are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein any two adjacent substituents are optionally joined to form into a ring;

wherein $L_A$ is coordinated to a metal M;

wherein $L_A$ is optionally linked with other ligands to comprise a tridentate, tetradentate, pentadentate, or hexadentate ligand; and wherein M is optionally coordinated to other ligands.

According to another embodiment, an organic light emitting diode/device (OLED) is also provided. The OLED can include an anode, a cathode, and an organic layer, disposed between the anode and the cathode. The organic layer can include a compound including a ligand $L_A$ of Formula (I). According to yet another embodiment, the organic light emitting device is incorporated into one or more devices selected from a consumer product, an electronic component module, and/or a lighting panel.

According to yet another embodiment, a formulation containing a compound including a ligand $L_A$ of Formula (I) is provided.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
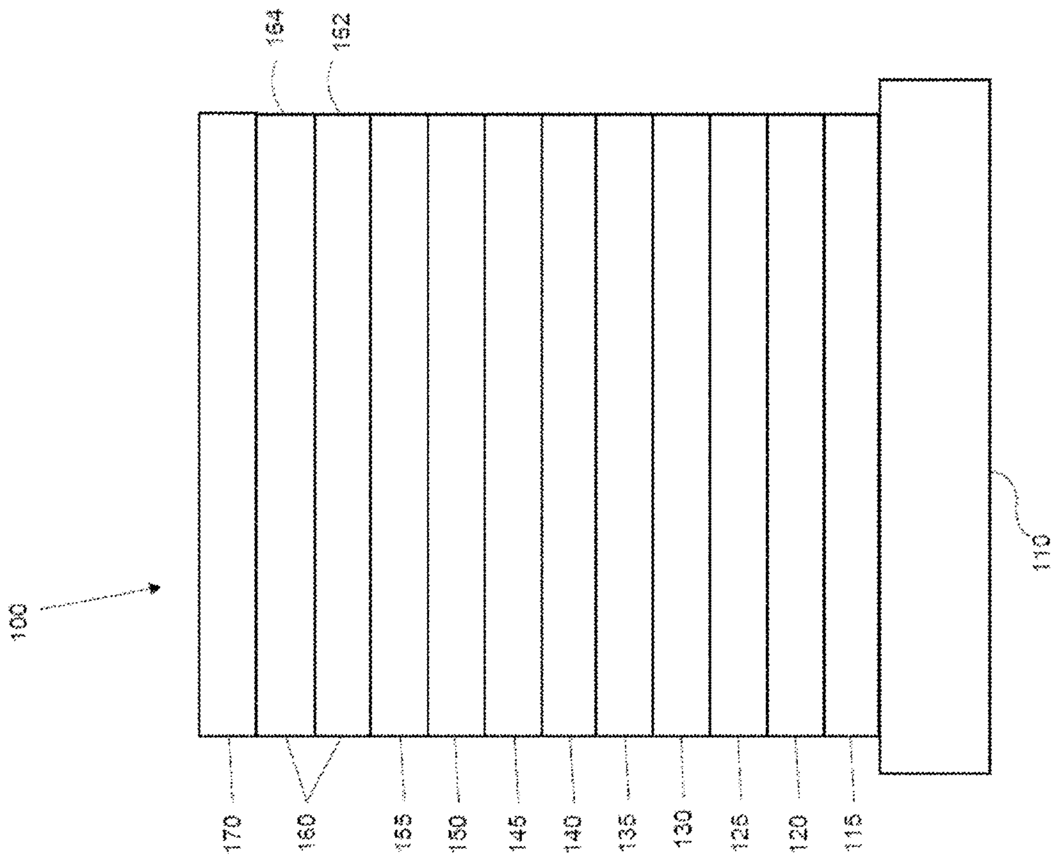
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
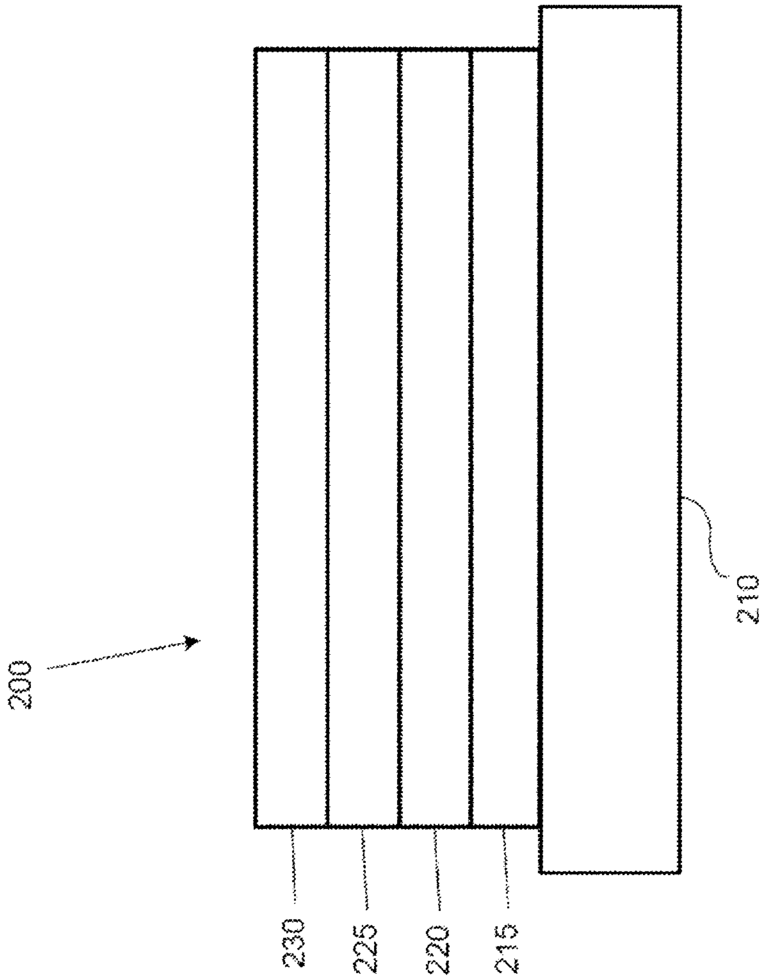
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, and a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" as used herein contemplates cyclic alkyl radicals. Preferred cycloalkyl groups are those containing 3 to 10 ring carbon atoms and includes cyclopropyl, cyclopentyl, cyclohexyl, adamantyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Hetero-aromatic cyclic radicals also means heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" as used herein contemplates single-ring hetero-aromatic groups that may include from one to five heteroatoms. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

Compounds of the Invention

In part, the present invention discloses novel pyridine ligands that are fused with a five-, six-, or six member aromatic or heteroaromatic rings. These ligands may be useful for making dopants that can improve the performance of organic electroluminescent devices.

In one aspect, the present invention includes a compound comprising a ligand $L_A$ of Formula (I):

(I)

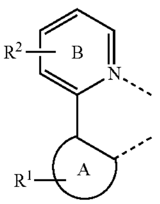

;

wherein ring A is a 5-membered or 6-membered carbocyclic or heterocyclic ring;

wherein $R^1$ represents from none to the maximum possible number of substitution;

wherein $R^2$ represents from two to the maximum possible number of substitution;

wherein at least two adjacent $R^2$s are joined to form ring C and have the following formula, wherein ring C is fused to ring B:

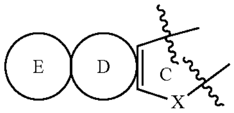

;

wherein the wave lines indicate bonds to ring B;

wherein ring D and ring E are each independently a 6-membered aromatic ring;

wherein ring D fuses to ring C, and ring E fuses to ring D;

wherein ring D and ring E can be further substituted by one or more substituents;

wherein X is selected from the group consisting of O, S, Se, and NR;

wherein $R^1$, $R^2$, and R are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein any two adjacent substituents are optionally joined to form into a ring;

wherein $L_A$ is coordinated to a metal M;

wherein $L_A$ is optionally linked with other ligands to comprise a tridentate, tetradentate, pentadentate, or hexadentate ligand; and wherein M is optionally coordinated to other ligands.

In one embodiment, M is selected from the group consisting of Ir, Rh, Re, Ru, Os, Pt, Au, and Cu. In one embodiment, M is Ir or Pt.

In one embodiment, X is O or S. In one embodiment, X is NR.

In one embodiment, ring D and ring E are benzene. In one embodiment, one of ring D and ring E is benzene, and the other one is pyridine. In one embodiment, ring A is benzene.

In one embodiment, ligand $L_A$ is selected from the group consisting of:

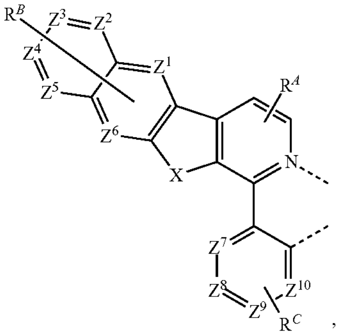

,

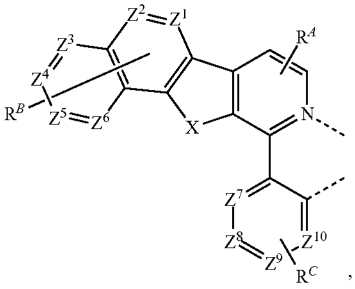

,

-continued
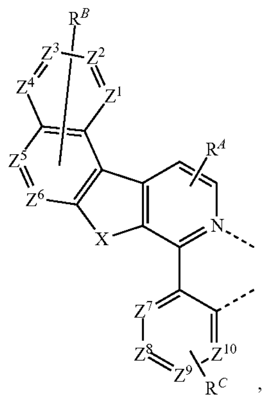
,
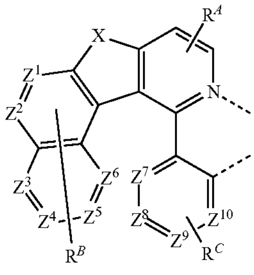
,
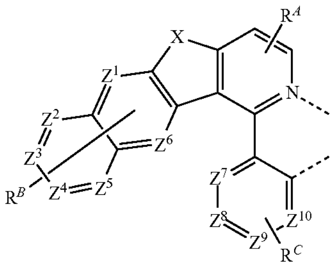
,
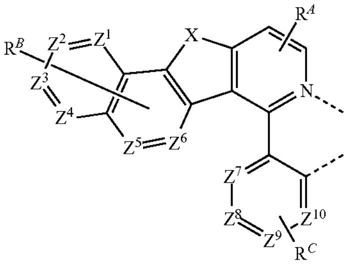
,
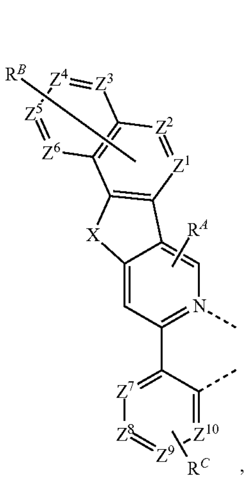
,
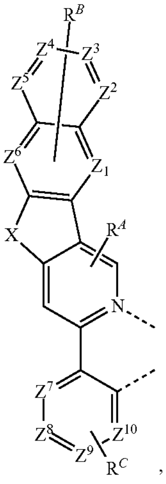
,
-continued
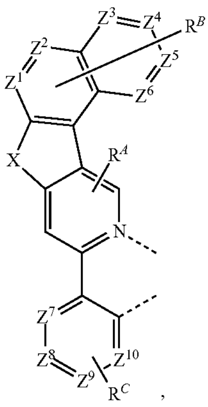
,
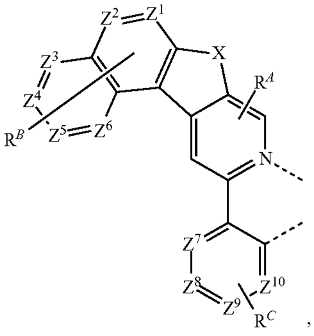
,
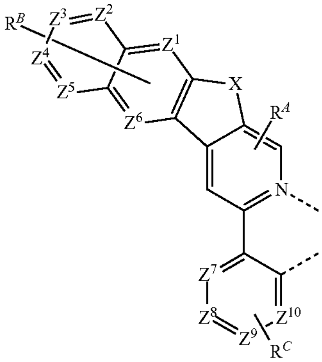
,
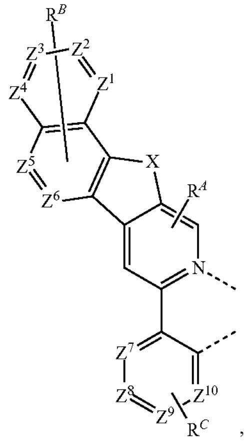
,
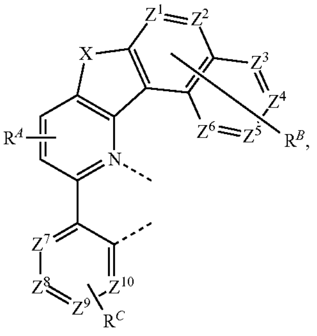

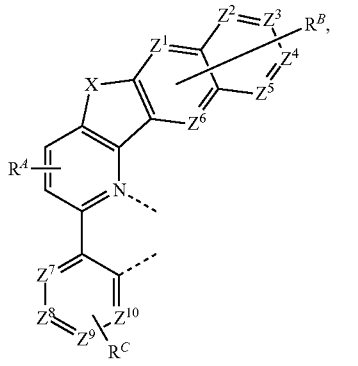
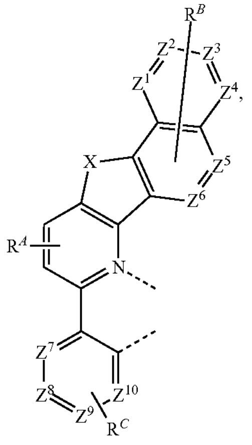
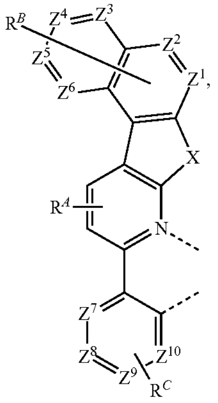
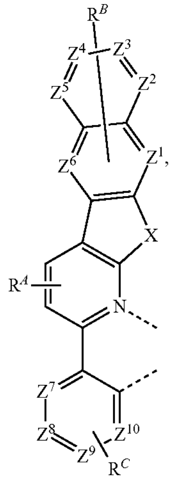
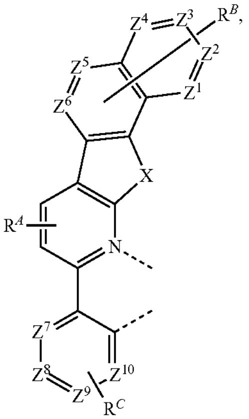
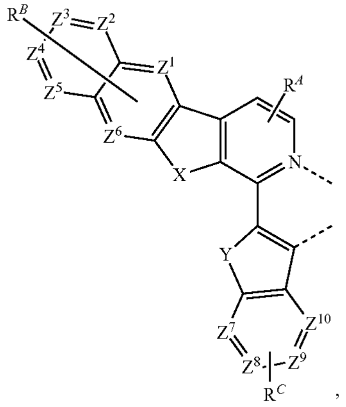
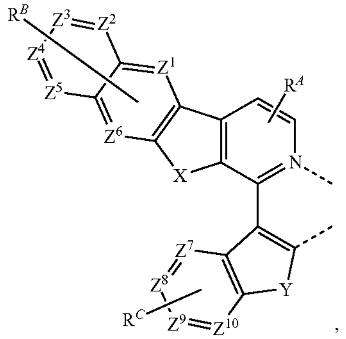
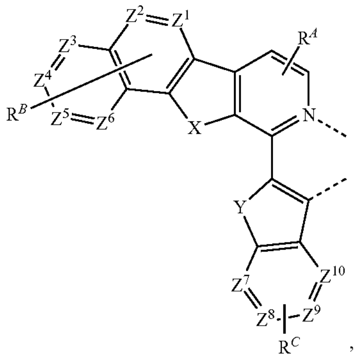
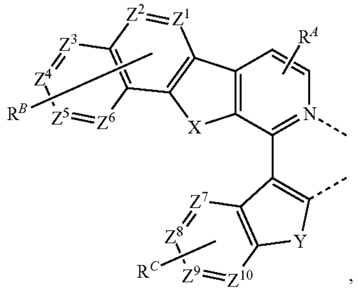

-continued
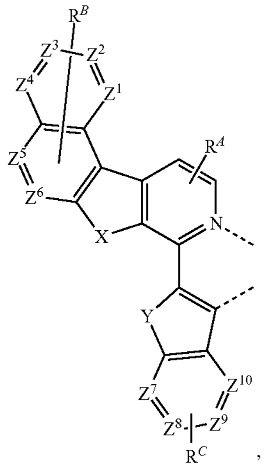
,
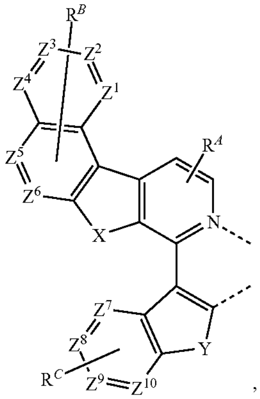
,
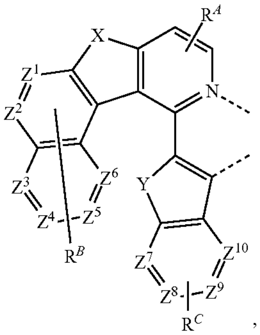
,
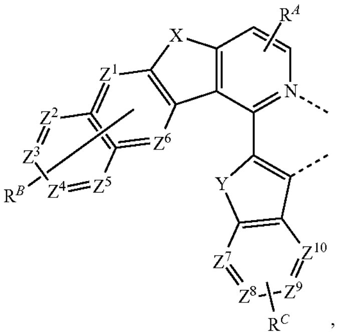
,
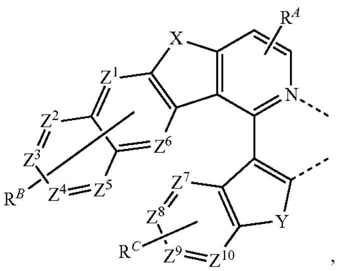
,
-continued
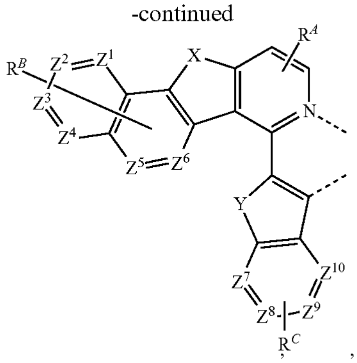
,
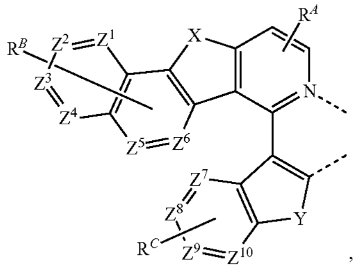
,
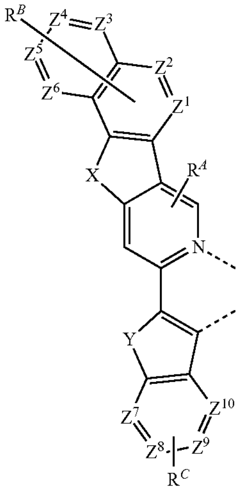
,
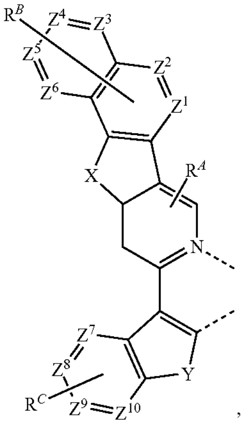
,
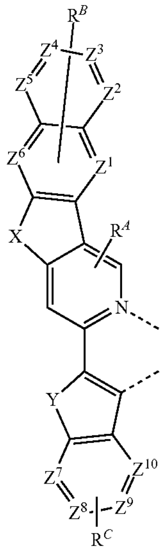
,
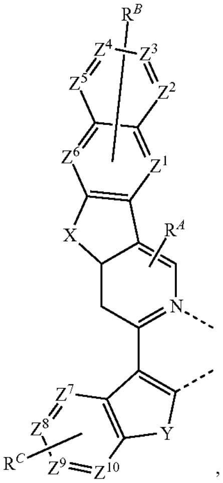
, -continued
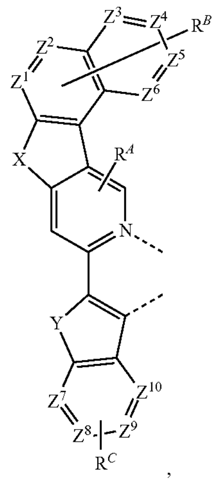
,
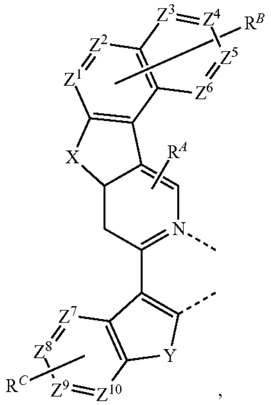
,
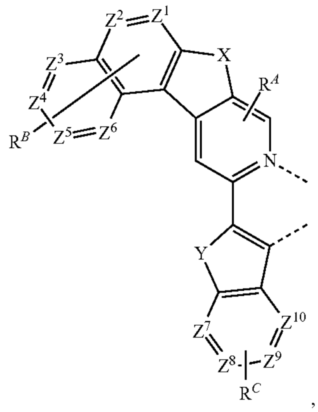
,
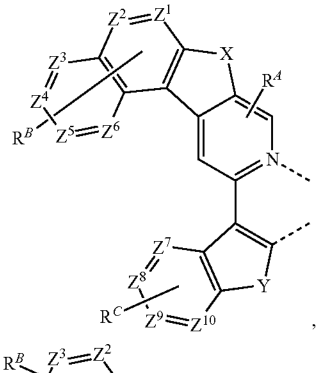
,
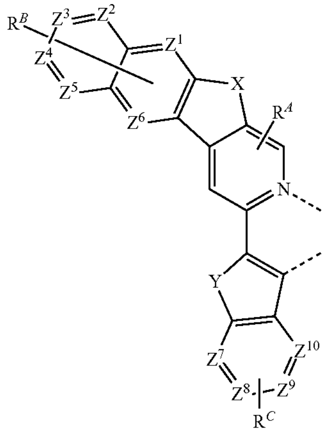
,
-continued
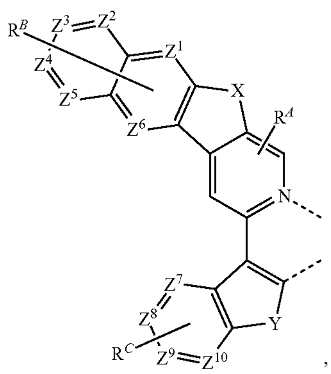
,
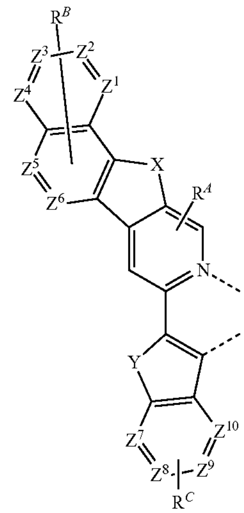
,
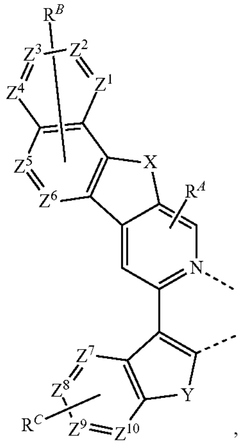
,
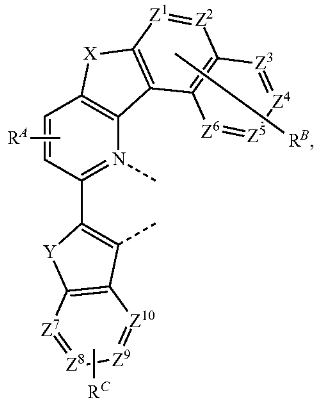
,
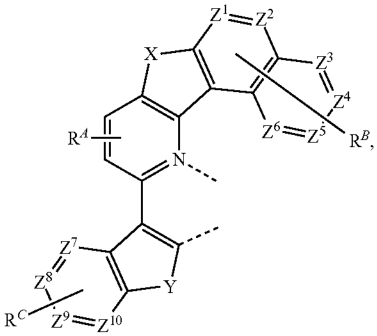
, -continued
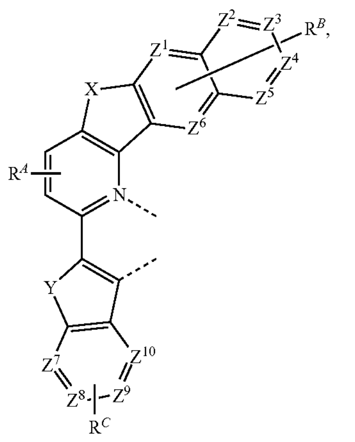
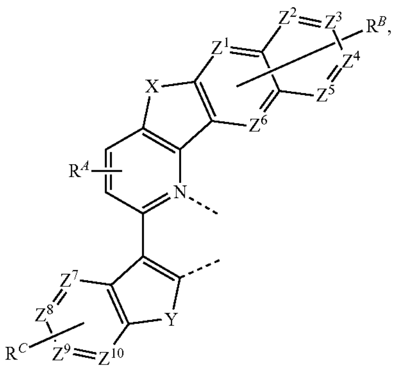
-continued
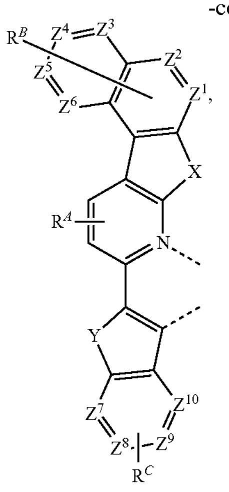
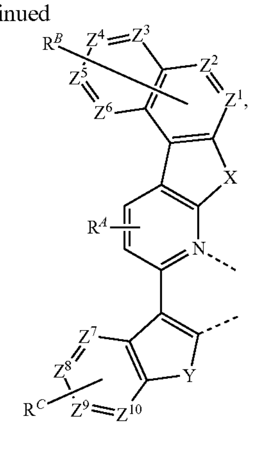
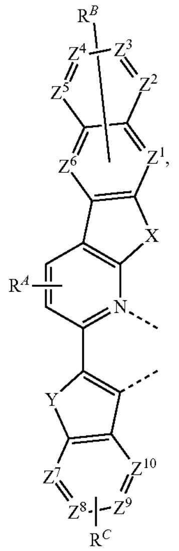
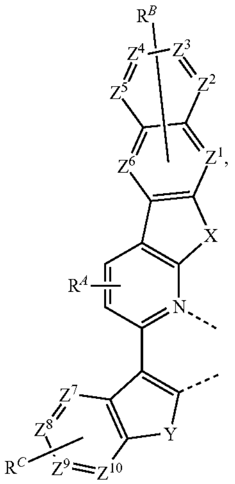
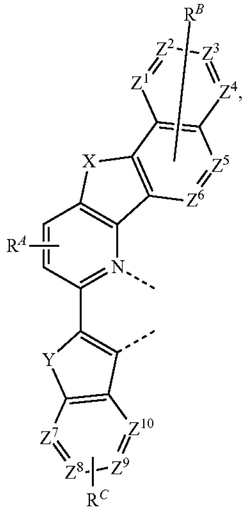
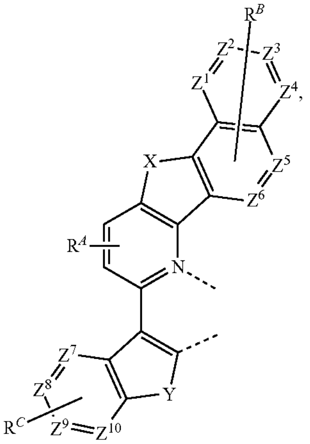
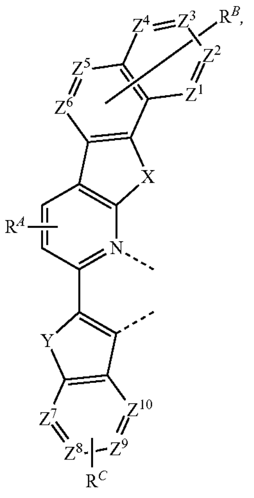
and -continued

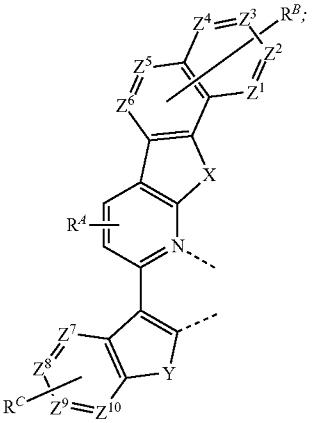

wherein Y is selected from the group consisting of O, S, Se, and $NR^D$;

wherein $R^A$, $R^B$, $R^C$, and $R^D$ each independently represents from none to the e maximum possible number of substitution;

wherein $R^A$, $R^B$, $R^C$, and $R^D$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein any two adjacent substituents are optionally joined to form into a ring; and wherein $Z^1$ to $Z^{10}$ is each independently selected from CH and N.

In one embodiment, the ligand $L_A$ is selected from the group consisting of:

$L_{A1}$

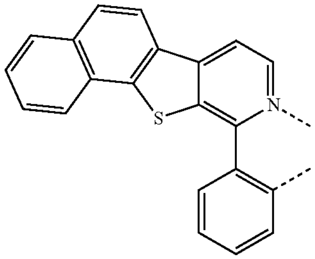

, $L_{A2}$

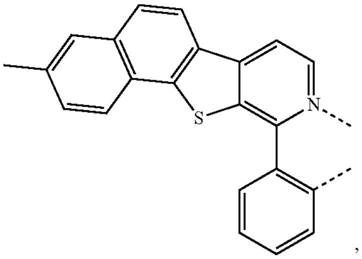

,

-continued $L_{A3}$

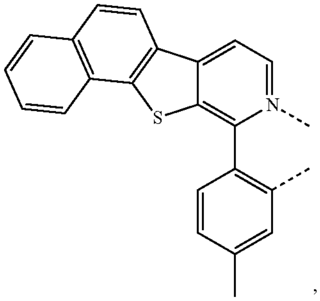

, $L_{A4}$

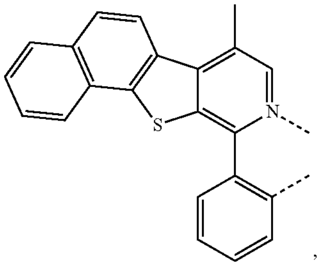

, $L_{A5}$

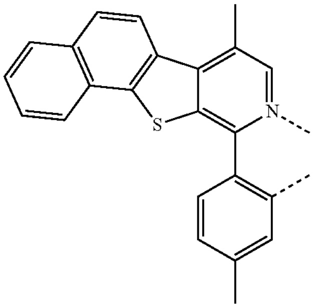

, $L_{A6}$

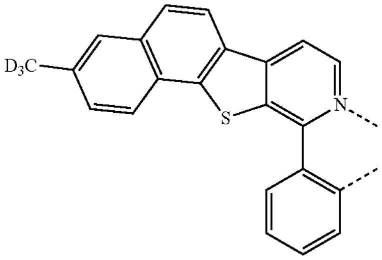

, $L_{A7}$

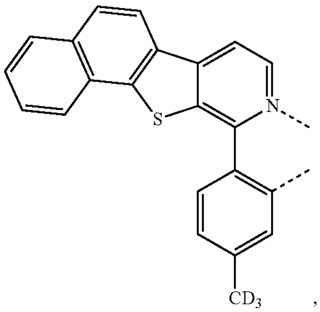

,

-continued
$L_{A8}$
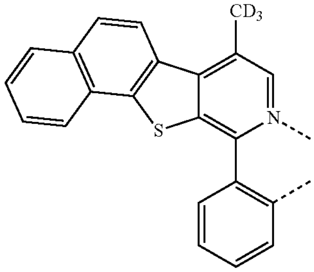
,
$L_{A9}$
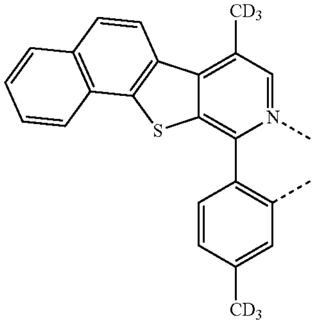
,
$L_{A10}$
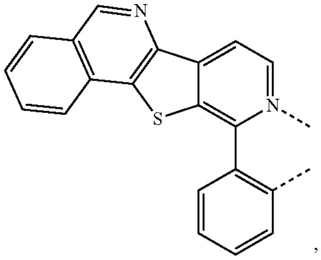
,
$L_{A11}$
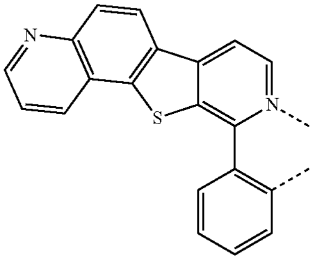
,
$L_{A12}$
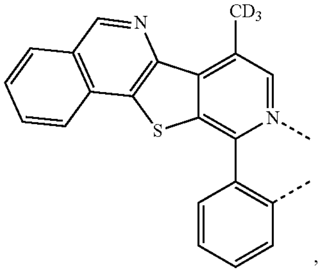
,
-continued
$L_{A13}$
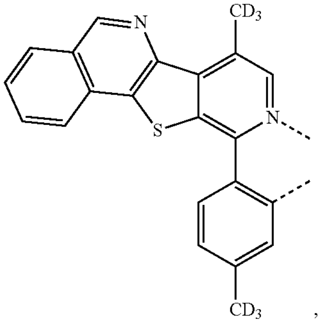
,
$L_{A14}$
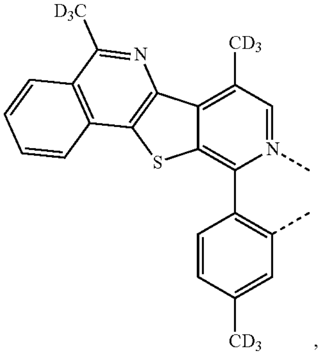
,
$L_{A15}$
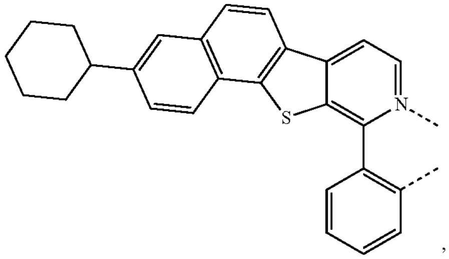
,
$L_{A16}$
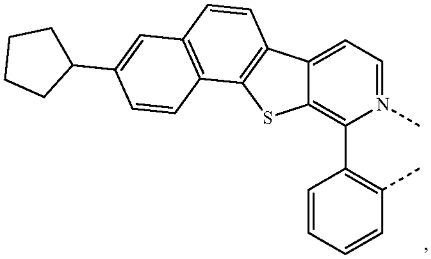
,
$L_{A17}$
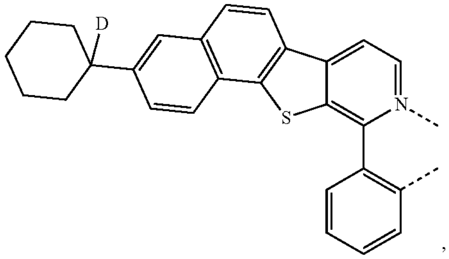
, -continued
$L_{A18}$
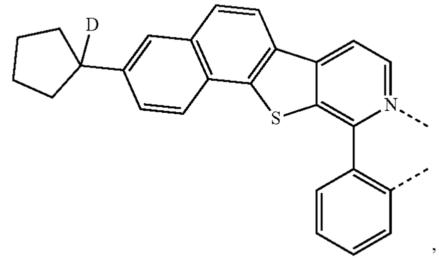
,
$L_{A19}$
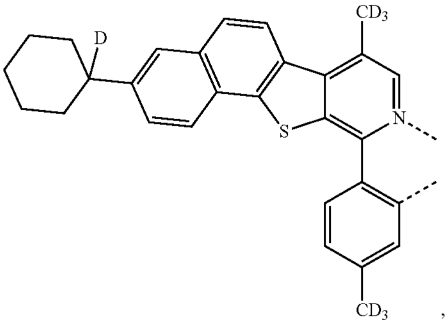
,
$L_{A20}$
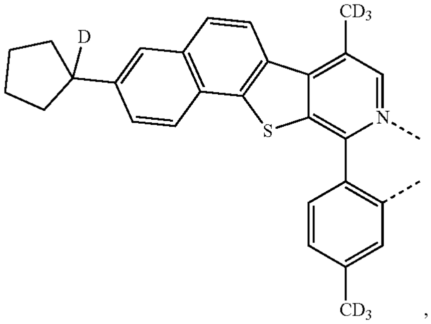
,
$L_{A21}$
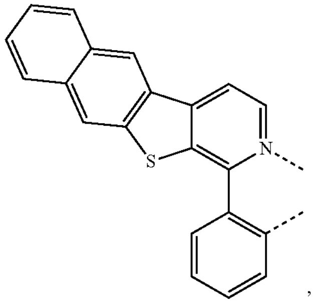
,
$L_{A22}$
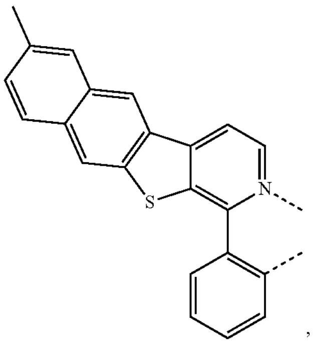
,
-continued
$L_{A23}$
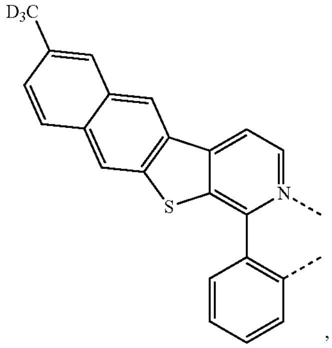
,
$L_{A24}$
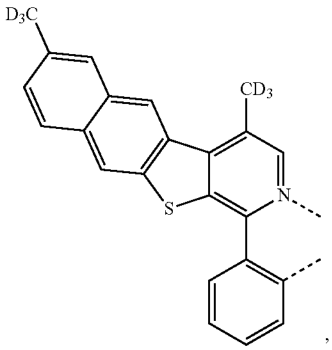
,
$L_{A25}$
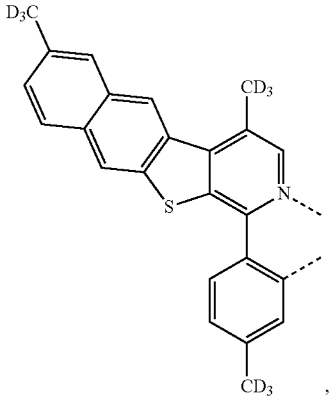
,
$L_{A26}$
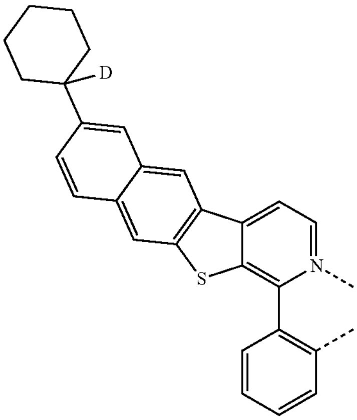
, -continued
$L_{A27}$
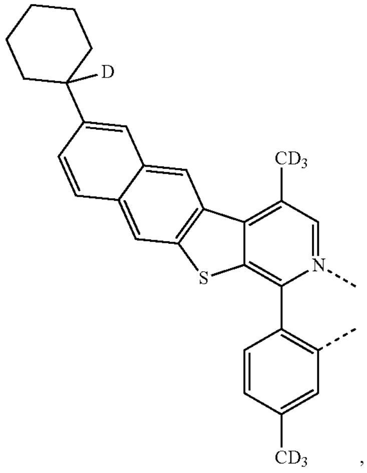
,
$L_{A28}$
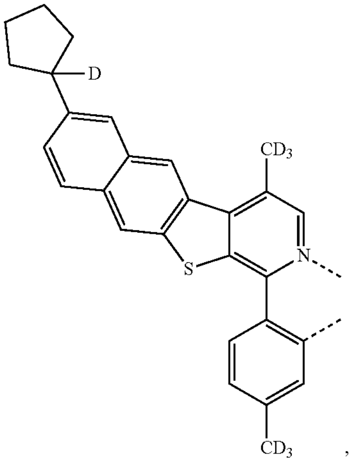
,
$L_{A29}$
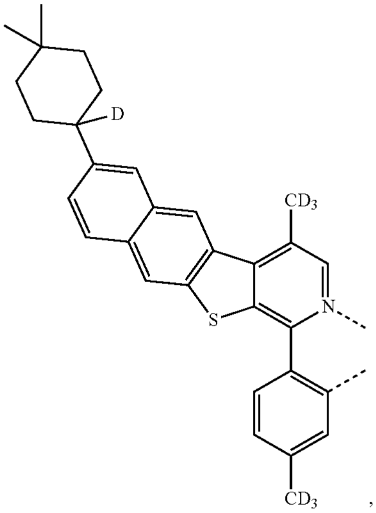
,
-continued
$L_{A30}$
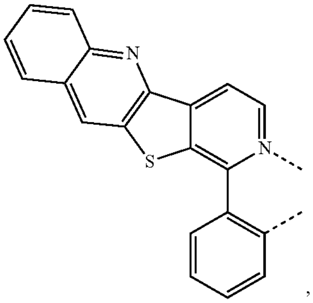
,
$L_{A31}$
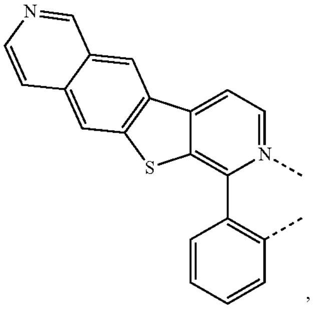
,
$L_{A32}$
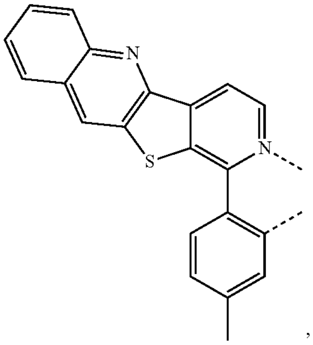
,
$L_{A33}$
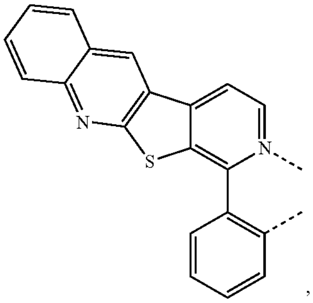
,
$L_{A34}$
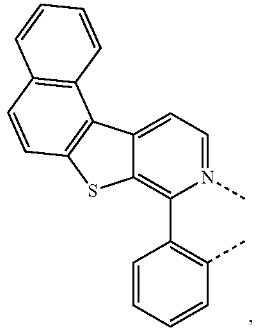
, -continued
$L_{A35}$
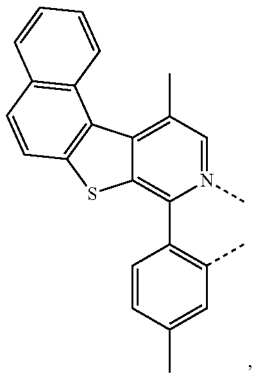
,
$L_{A36}$
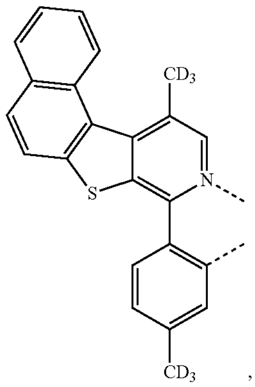
,
$L_{A37}$
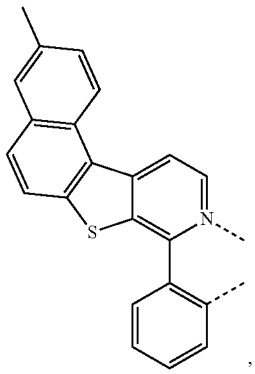
,
$L_{A38}$
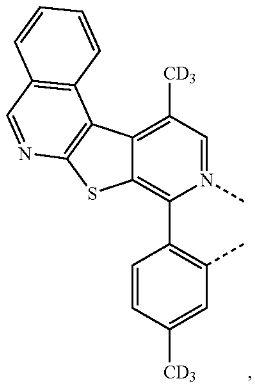
,
-continued
$L_{A39}$
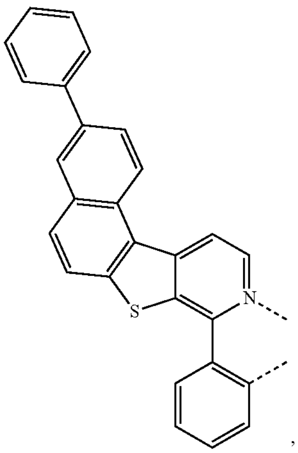
,
$L_{A40}$
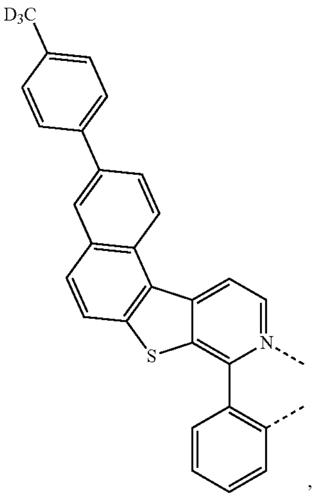
,
$L_{A41}$
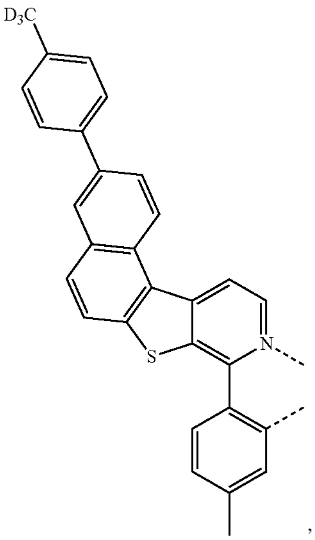
, -continued
$L_{A42}$
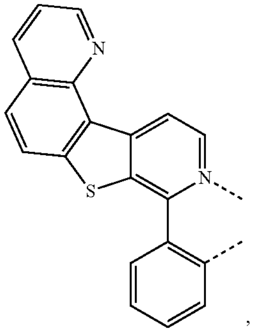
,
$L_{A43}$
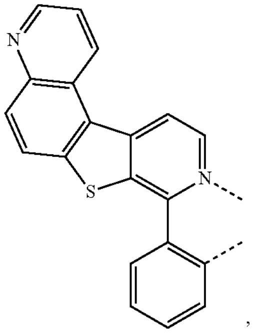
,
$L_{A44}$
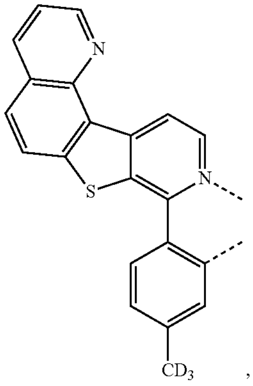
,
$L_{A45}$
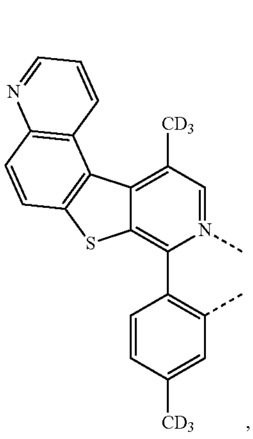
,
-continued
$L_{A46}$
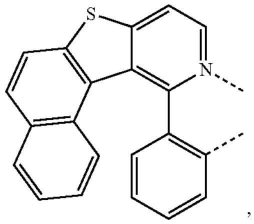
,
$L_{A47}$
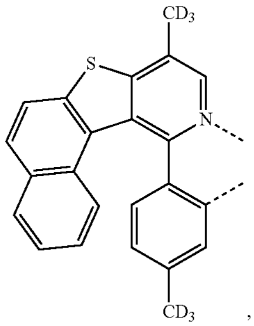
,
$L_{A48}$
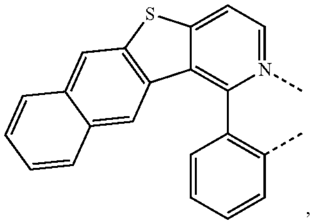
,
$L_{A49}$
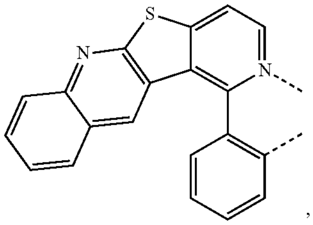
,
$L_{A50}$
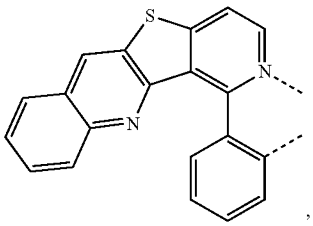
,
$L_{A51}$
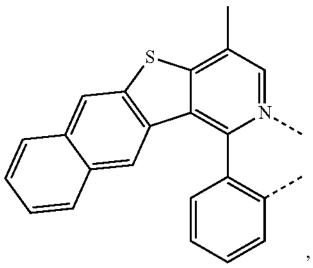
, -continued
$L_{A52}$
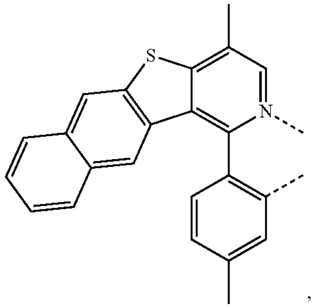
,
$L_{A53}$
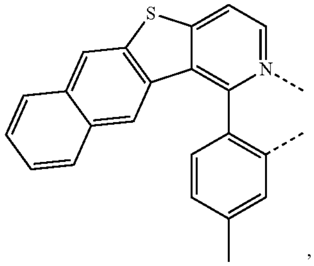
,
$L_{A54}$
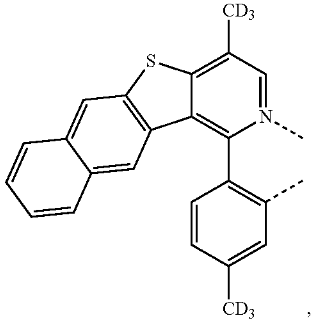
,
$L_{A55}$
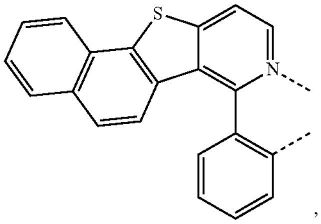
,
$L_{A56}$
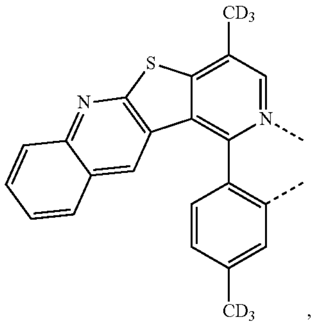
,
-continued
$L_{A57}$
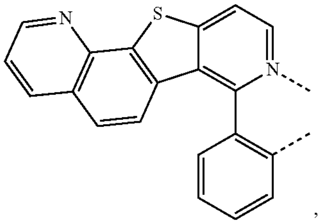
,
$L_{A58}$
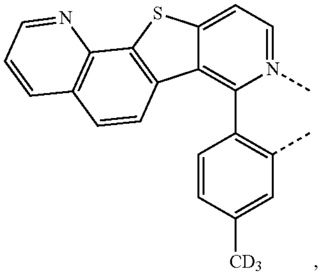
,
$L_{A59}$
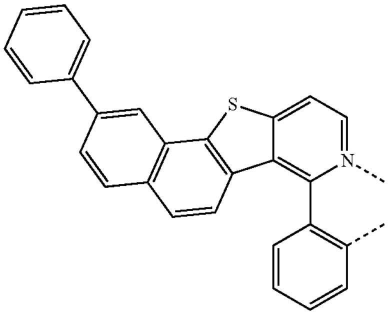
,
$L_{A60}$
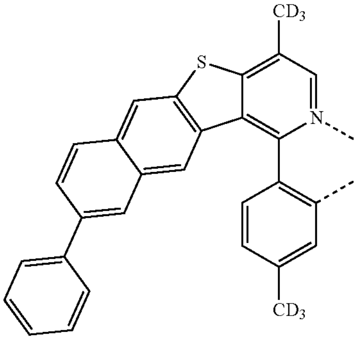
,
$L_{A61}$
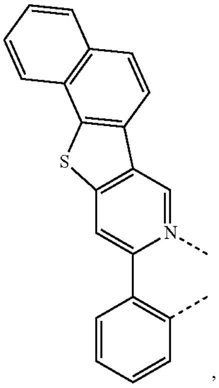
, -continued
$L_{A62}$
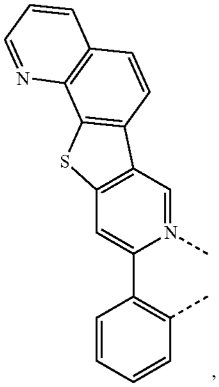
,
$L_{A63}$
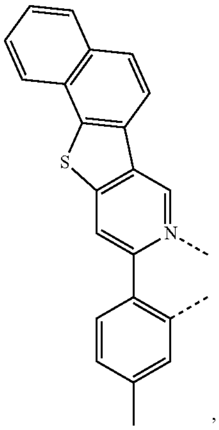
,
$L_{A64}$
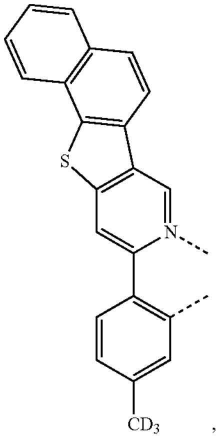
,
-continued
$L_{A65}$
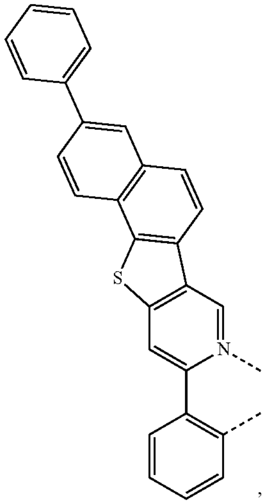
,
$L_{A66}$
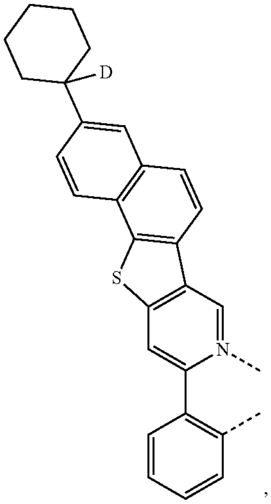
,
$L_{A67}$
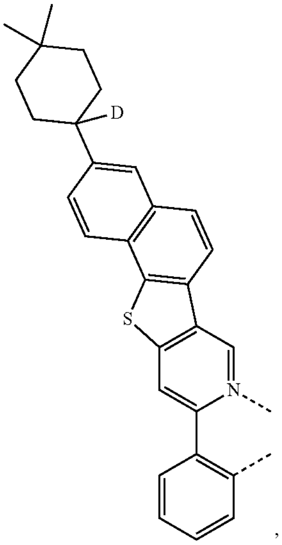
, -continued
L$_{A68}$
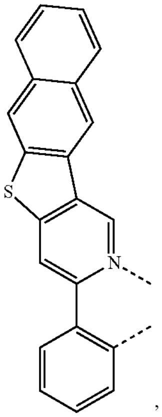
,
L$_{A69}$
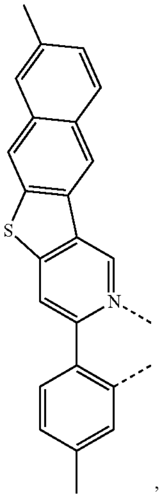
,
L$_{A70}$
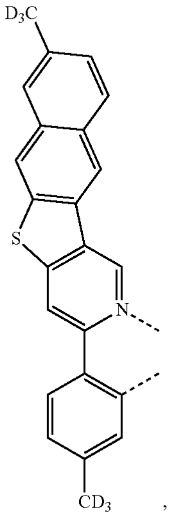
,
-continued
L$_{A71}$
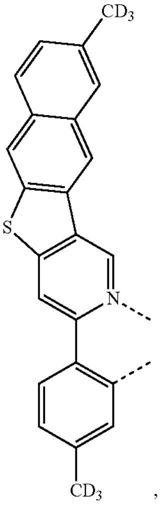
,
L$_{A72}$
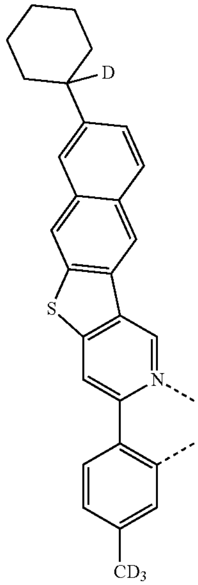
, -continued
$L_{A73}$
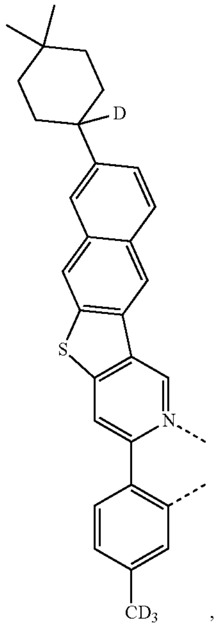
,
$L_{A74}$
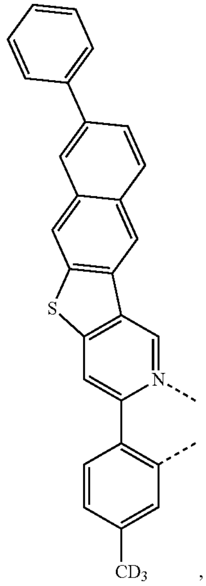
,
$L_{A75}$
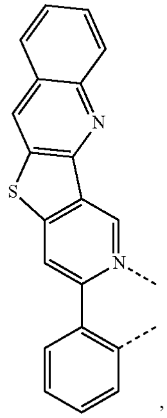
,
-continued
$L_{A76}$
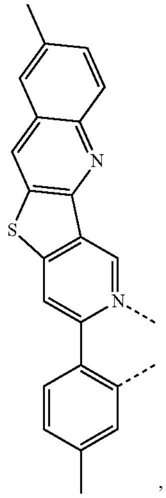
,
$L_{A77}$
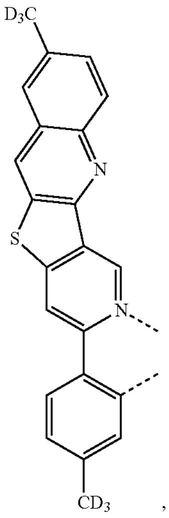
,
$L_{A78}$
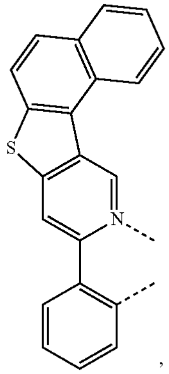
, -continued
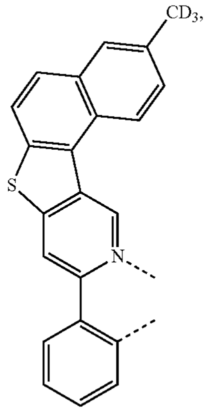
$L_{A79}$
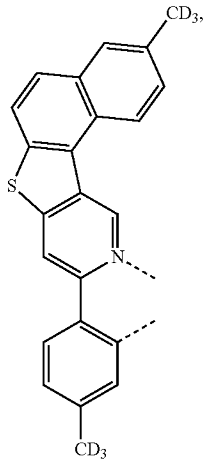
$L_{A80}$
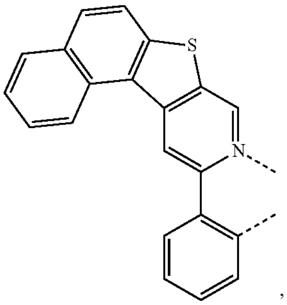
$L_{A81}$
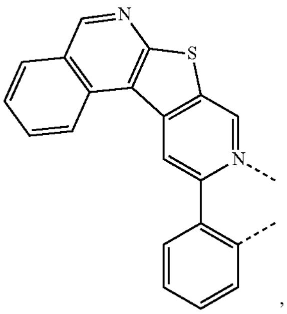
$L_{A82}$
-continued
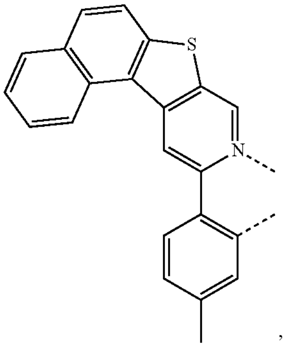
$L_{A83}$
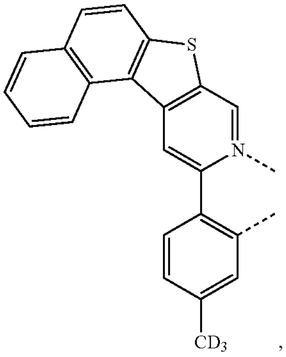
$L_{A84}$
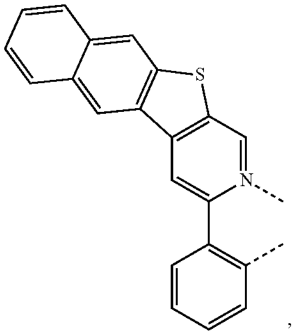
$L_{A85}$
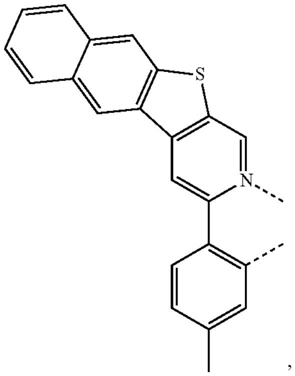
$L_{A86}$ -continued
$L_{A87}$
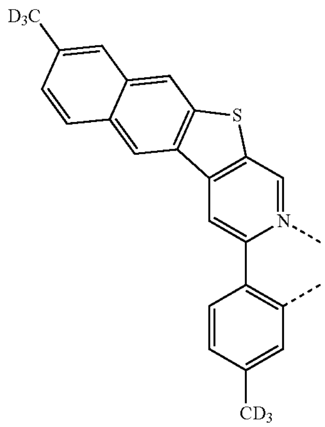
,
$L_{A88}$
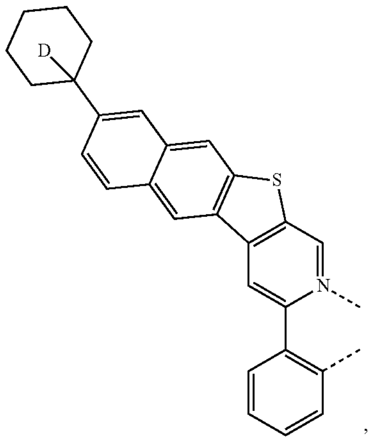
,
$L_{A89}$
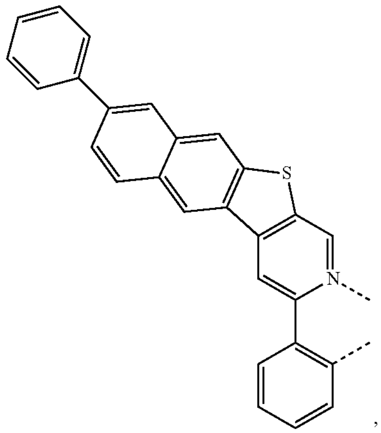
,
-continued
$L_{A90}$
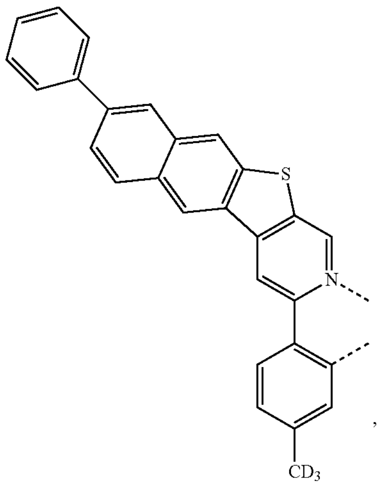
,
$L_{A91}$
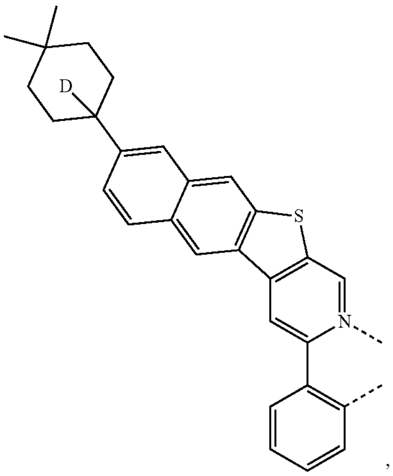
,
$L_{A92}$
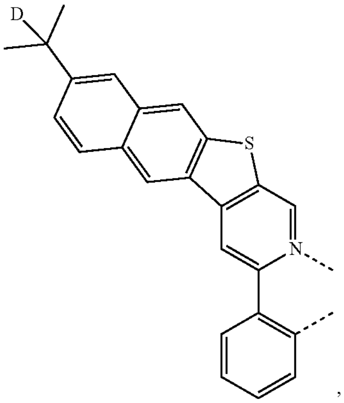
, -continued
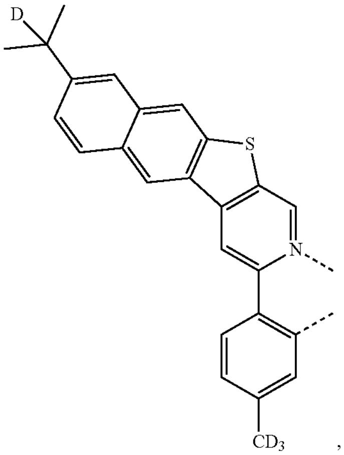
$L_{A93}$
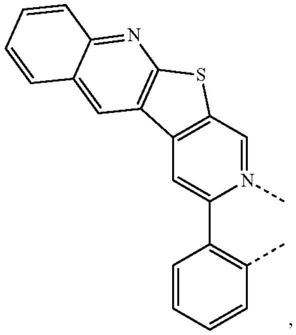
$L_{A94}$
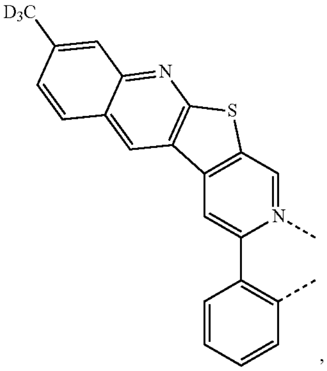
$L_{A95}$
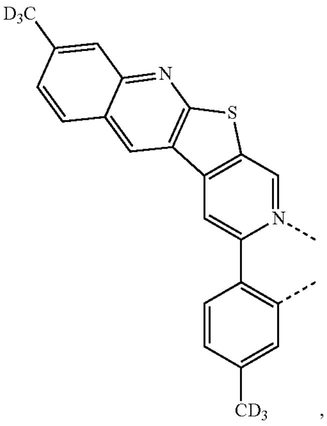
$L_{A96}$
-continued
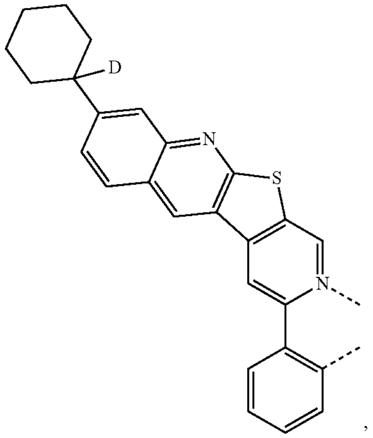
$L_{A97}$
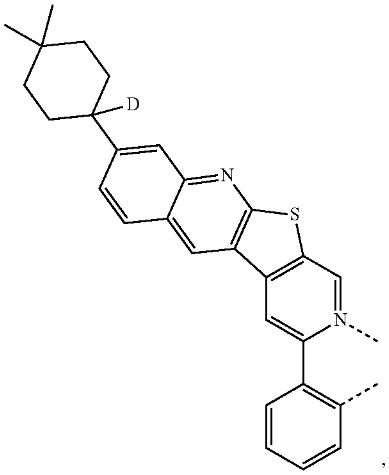
$L_{A98}$
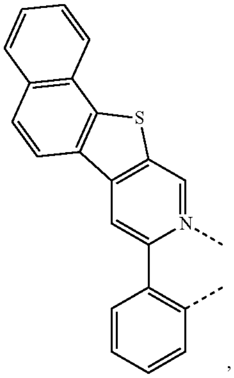
$L_{A99}$
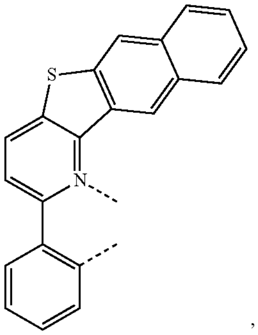
$L_{A100}$ -continued
$L_{A101}$
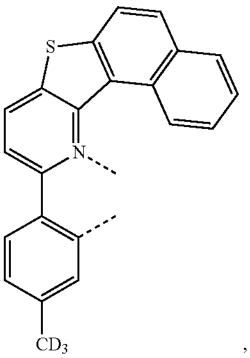
,
$L_{A102}$
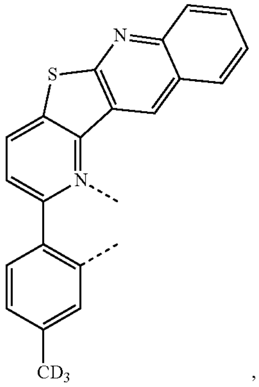
,
$L_{A103}$
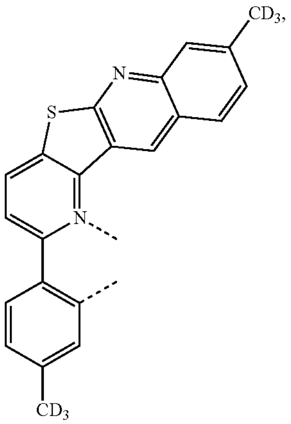
$L_{A104}$
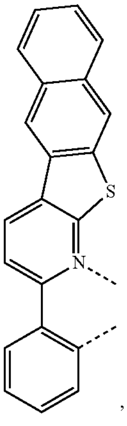
,
-continued
$L_{A105}$
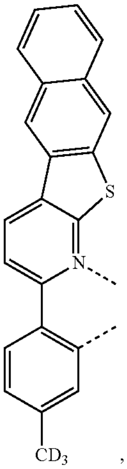
,
$L_{A106}$
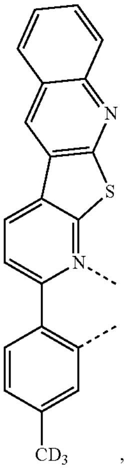
,
$L_{A107}$
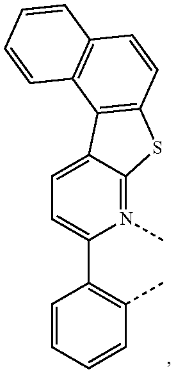
, -continued
$L_{A108}$
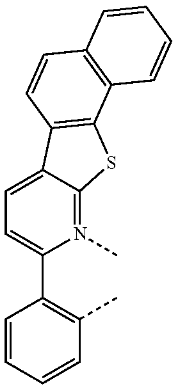
,
$L_{A109}$
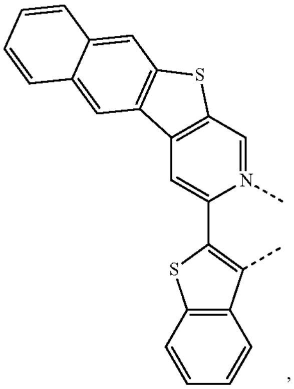
,
$L_{A110}$
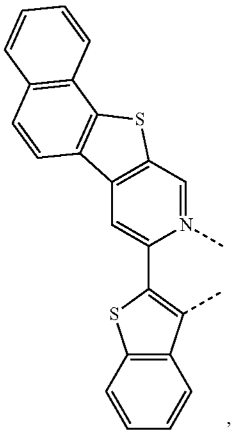
,
$L_{A111}$
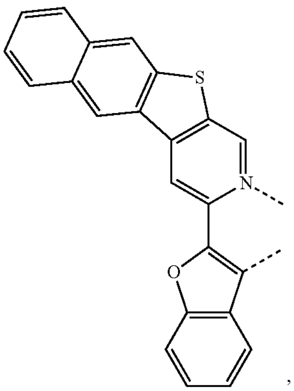
,
-continued
$L_{A112}$
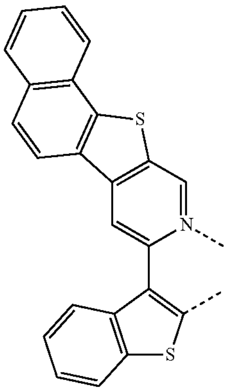
,
$L_{A113}$
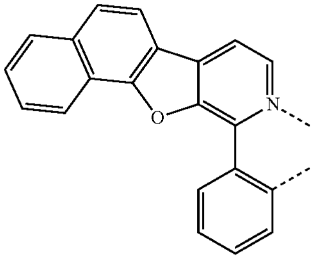
,
$L_{A114}$
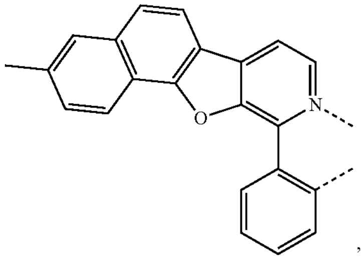
,
$L_{A115}$
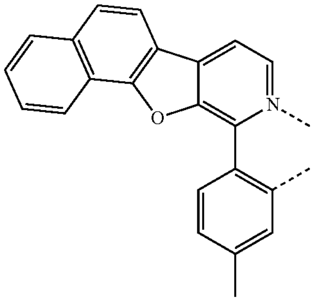
,
$L_{A116}$
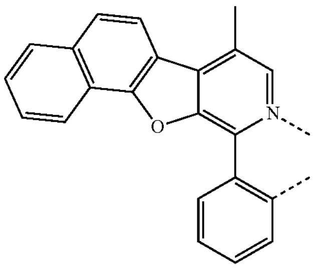
, -continued
$L_{A117}$
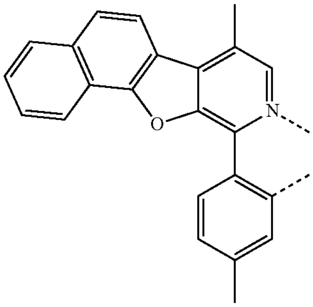
,
$L_{A118}$
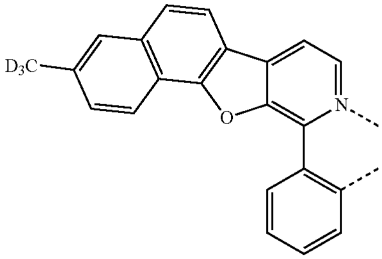
,
$L_{A119}$
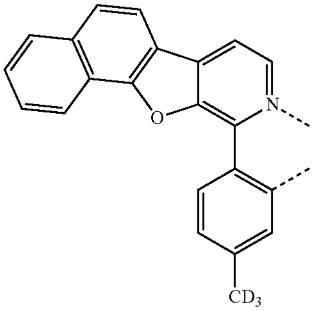
,
$L_{A120}$
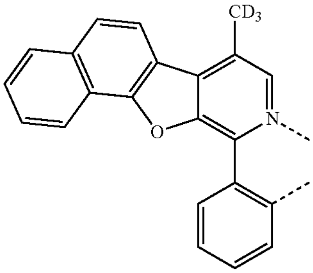
,
$L_{A121}$
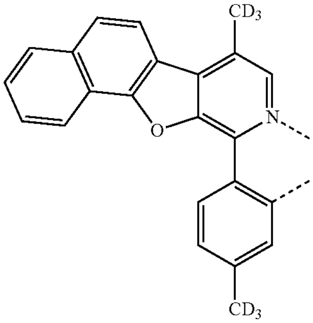
,
-continued
$L_{A122}$
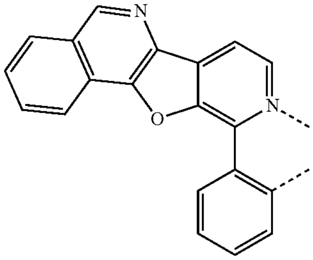
,
$L_{A123}$
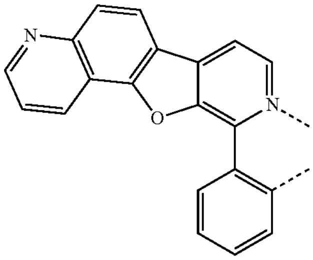
,
$L_{A124}$
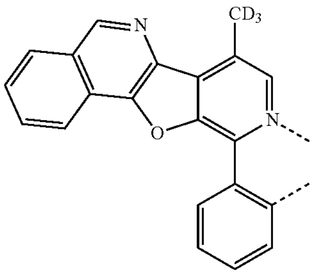
,
$L_{A125}$
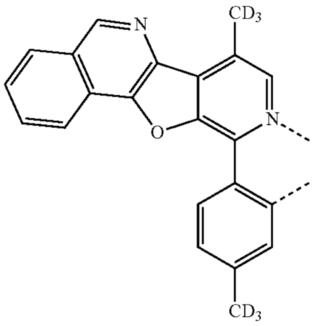
,
$L_{A126}$
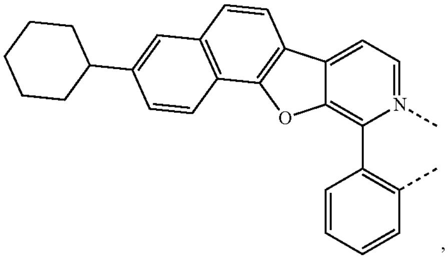
, -continued
$L_{A127}$
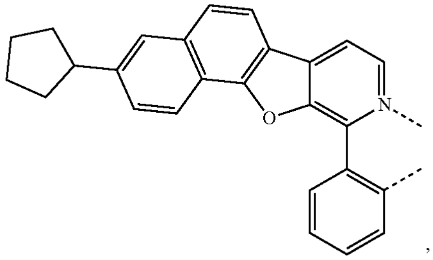
,
$L_{A128}$
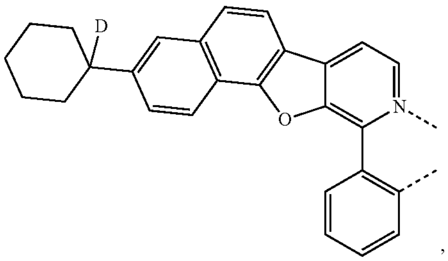
,
$L_{A129}$
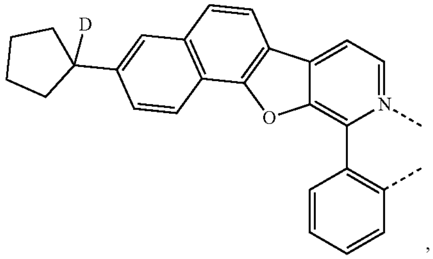
,
$L_{A130}$
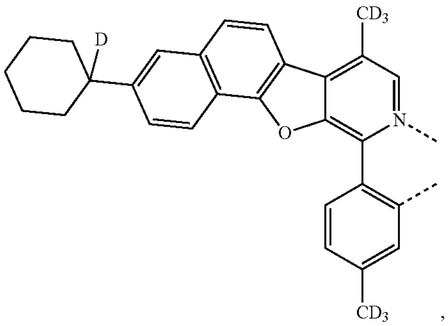
,
$L_{A131}$
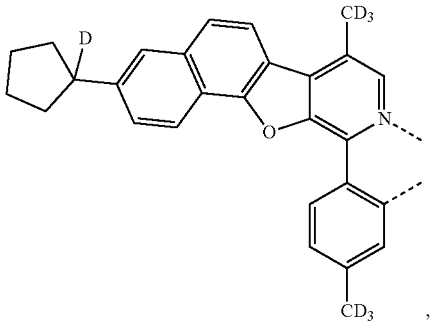
,
-continued
$L_{A132}$
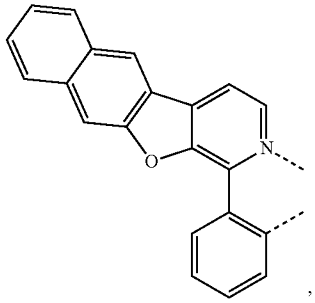
,
$L_{A133}$
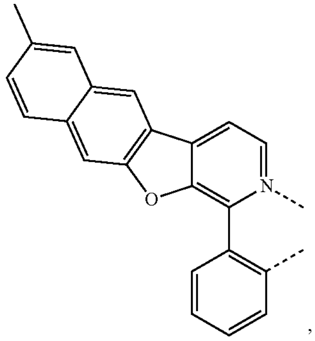
,
$L_{A134}$
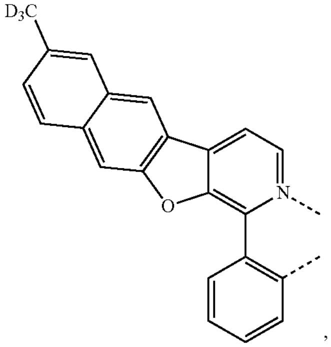
,
$L_{A135}$
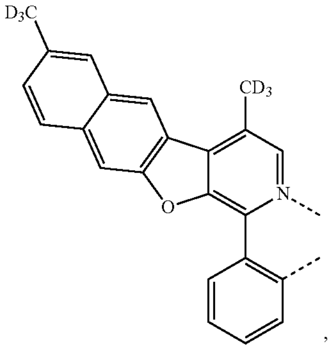
, -continued
$L_{A136}$
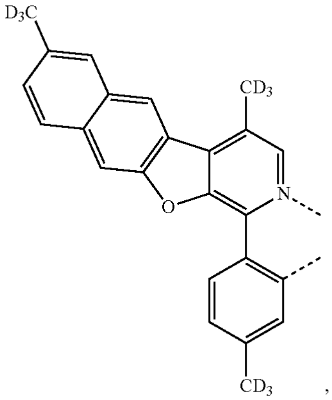
,
$L_{A137}$
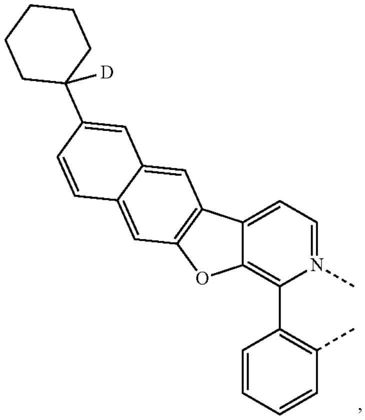
,
$L_{A138}$
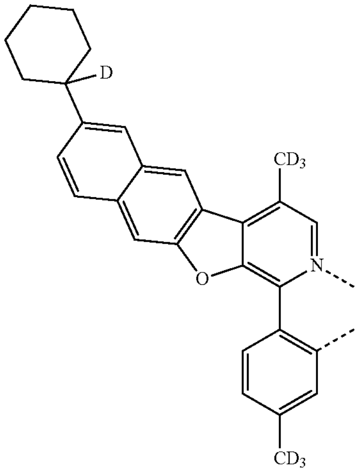
,
-continued
$L_{A139}$
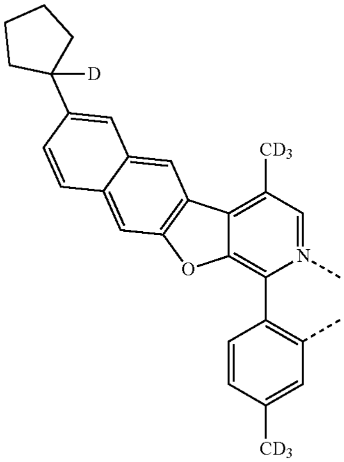
,
$L_{A140}$
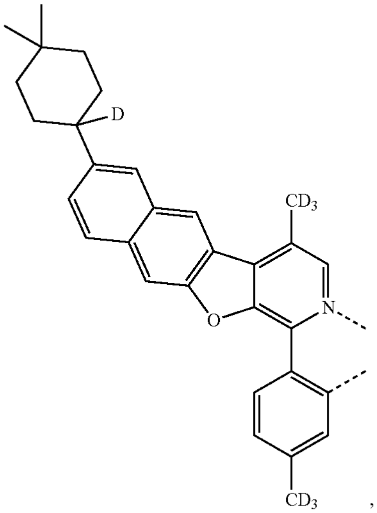
,
$L_{A141}$
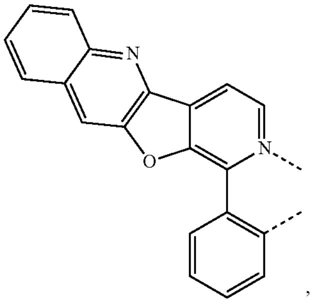
,
$L_{A142}$
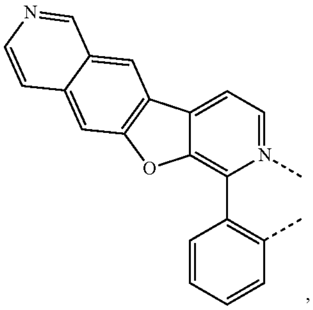
, $L_{A143}$
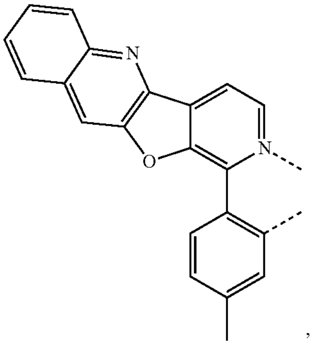
,
$L_{A144}$
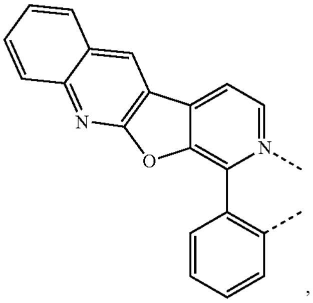
,
$L_{A145}$
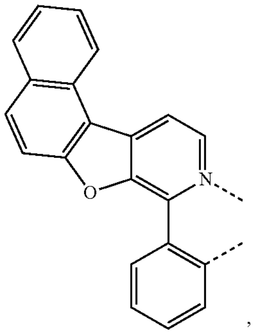
,
$L_{A146}$
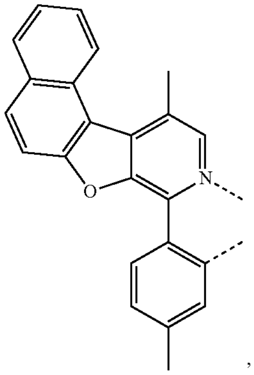
,
$L_{A147}$
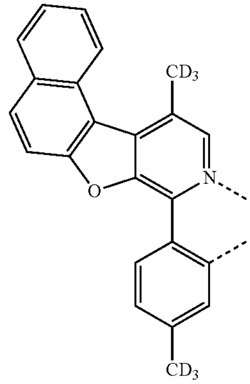
,
$L_{A148}$
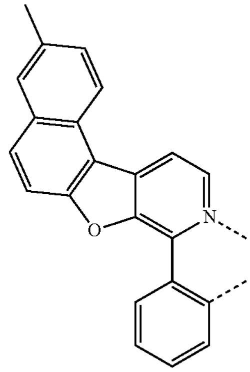
,
$L_{A149}$
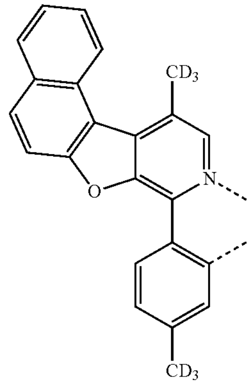
,
$L_{A150}$
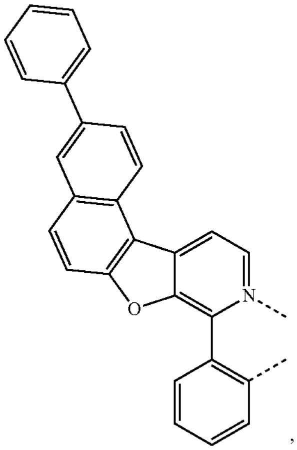
, -continued
$L_{A151}$
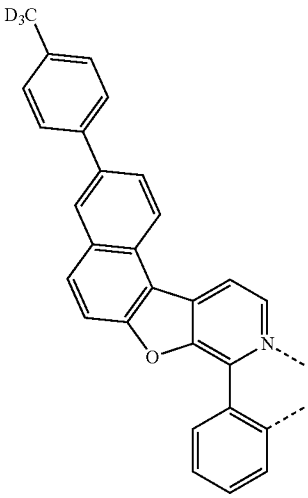
,
$L_{A152}$
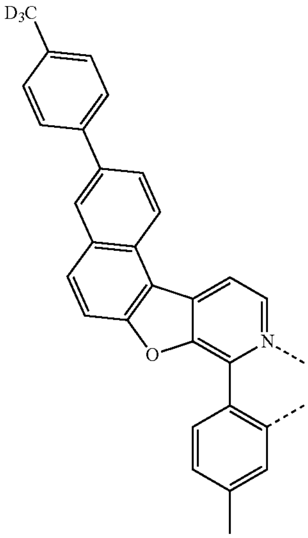
,
$L_{A153}$
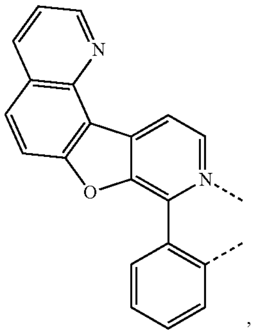
,
-continued
$L_{A154}$
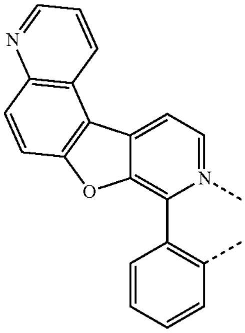
,
$L_{A155}$
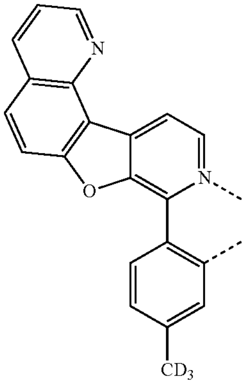
,
$L_{A156}$
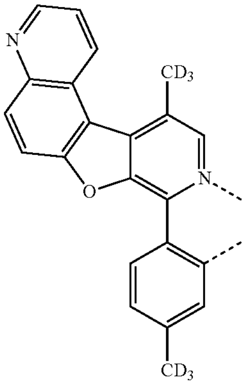
,
$L_{A157}$
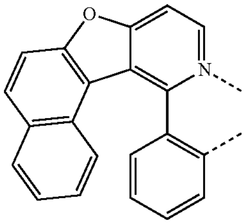
, -continued
L$_{A158}$
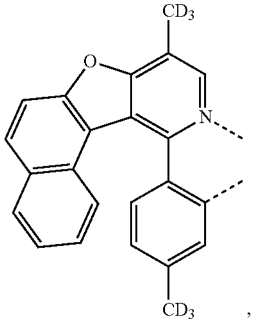
,
L$_{A159}$
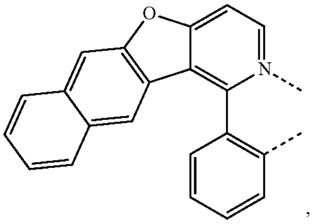
,
L$_{A160}$
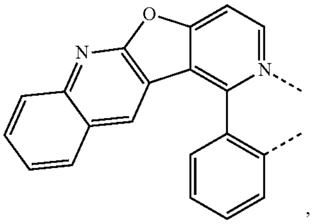
,
L$_{A161}$
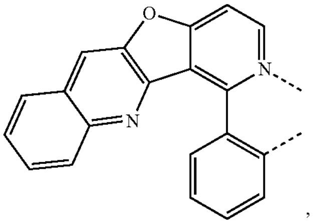
,
L$_{A162}$
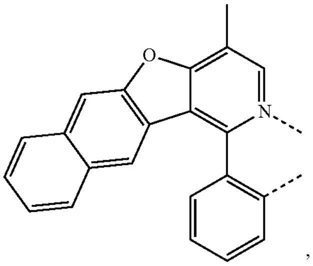
,
L$_{A163}$
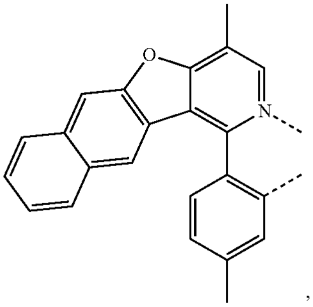
,
-continued
L$_{A164}$
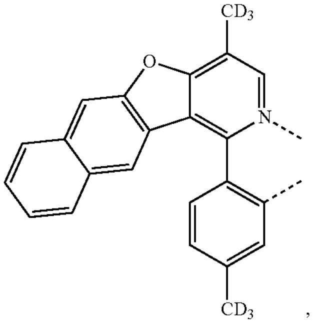
,
L$_{A165}$
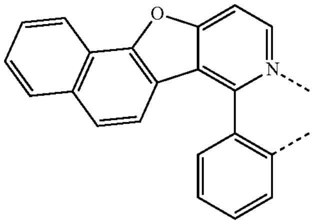
,
L$_{A166}$
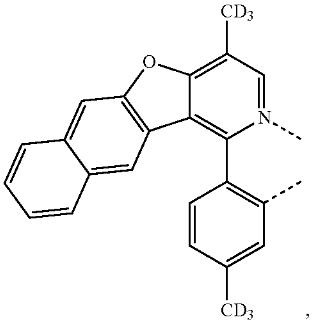
,
L$_{A167}$
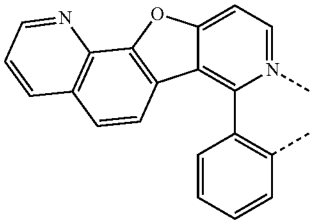
,
L$_{A168}$
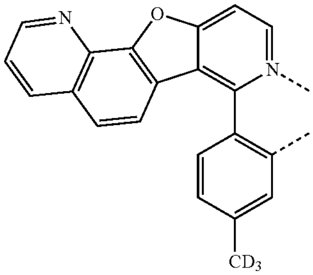
, -continued
$L_{A169}$
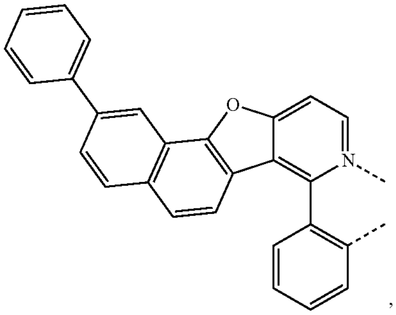
,
$L_{A170}$
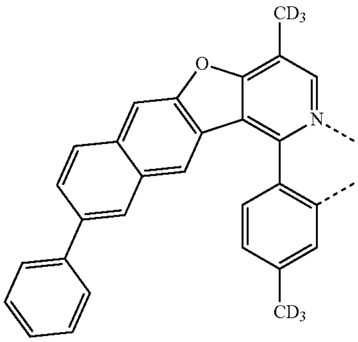
,
$L_{A171}$
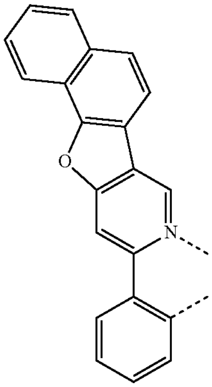
,
$L_{A172}$
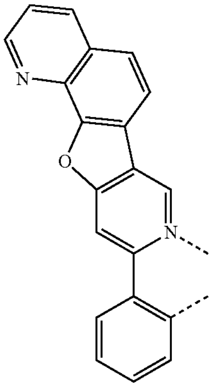
,
-continued
$L_{A173}$
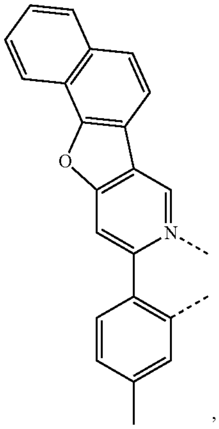
,
$L_{A174}$
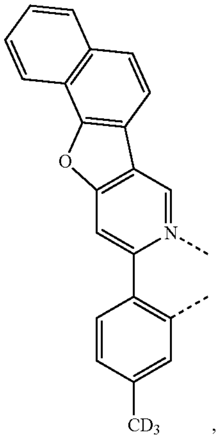
,
$L_{A175}$
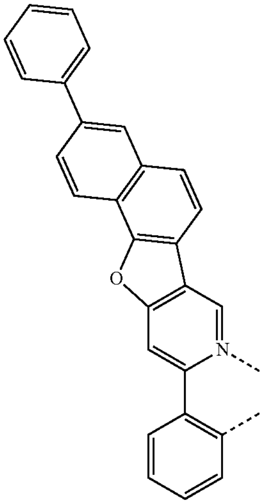
, -continued
L$_{A176}$
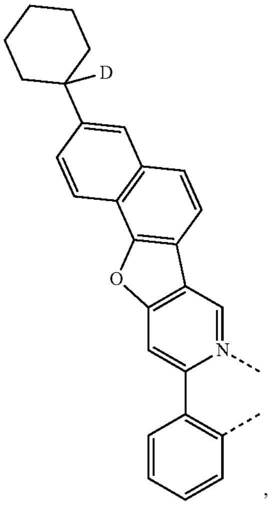
,
L$_{A177}$
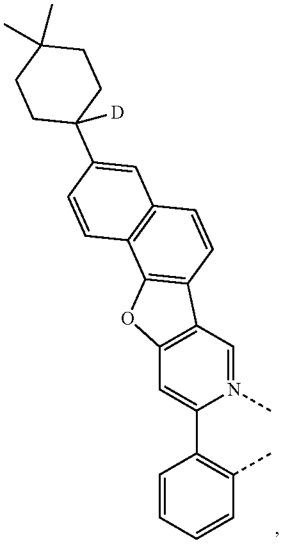
,
L$_{A178}$
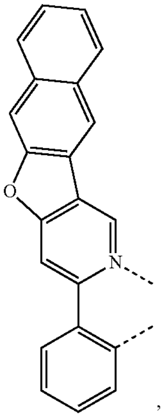
,
-continued
L$_{A179}$
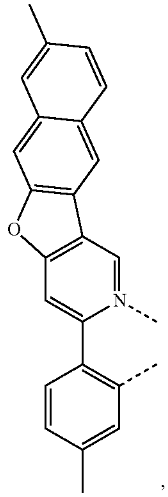
,
L$_{A180}$
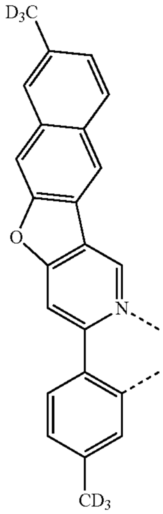
,
L$_{A181}$
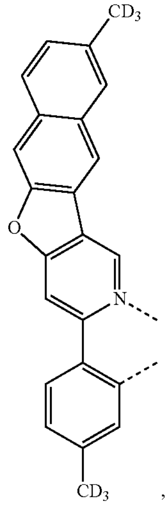
, $L_{A182}$
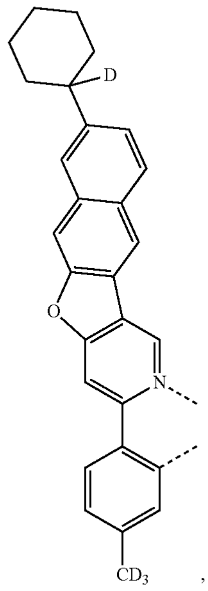
,
$L_{A183}$
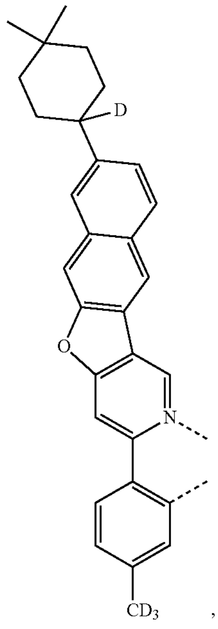
,
$L_{A184}$
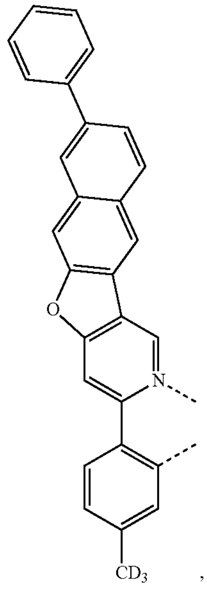
,
$L_{A185}$
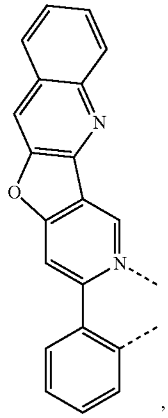
,
$L_{A186}$
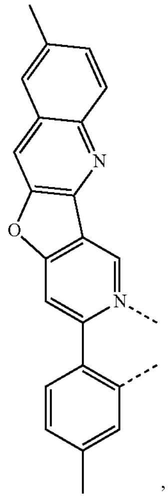
, -continued
$L_{A187}$
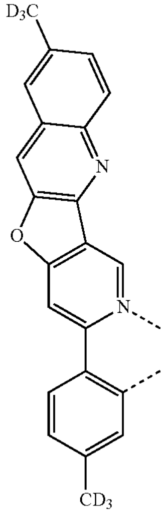
,
$L_{A188}$
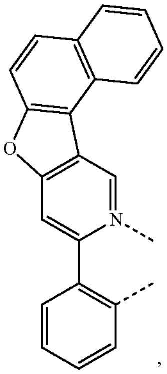
,
$L_{A189}$
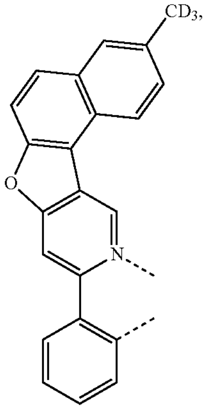
-continued
$L_{A190}$
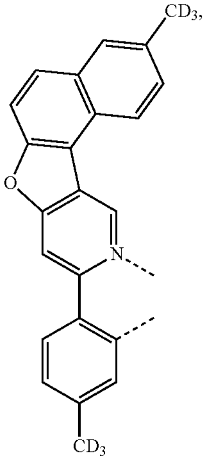
$L_{A191}$
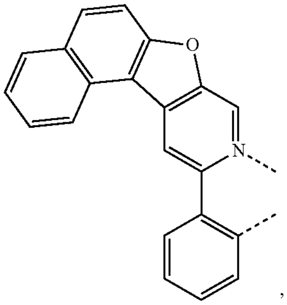
,
$L_{A192}$
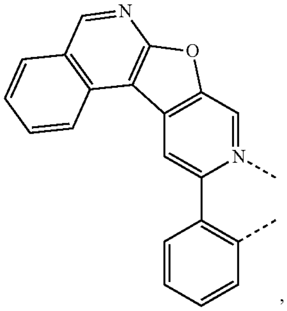
,
$L_{A193}$
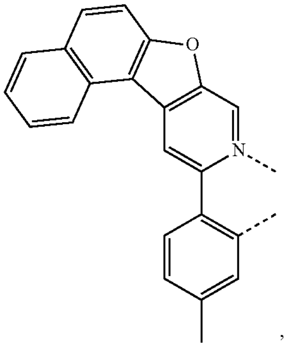
, -continued
$L_{A194}$
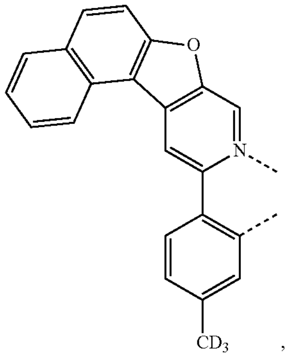
,
$L_{A195}$
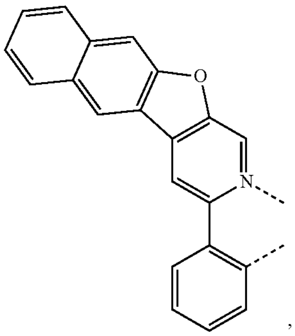
,
$L_{A196}$
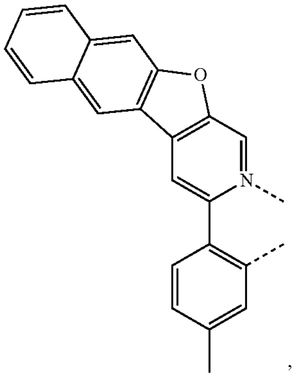
,
$L_{A197}$
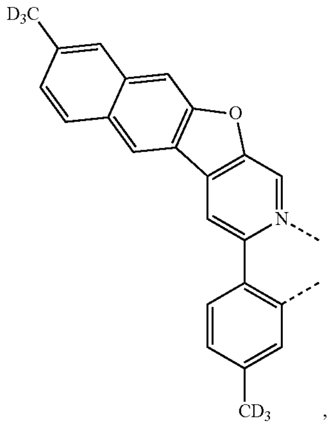
,
-continued
$L_{A198}$
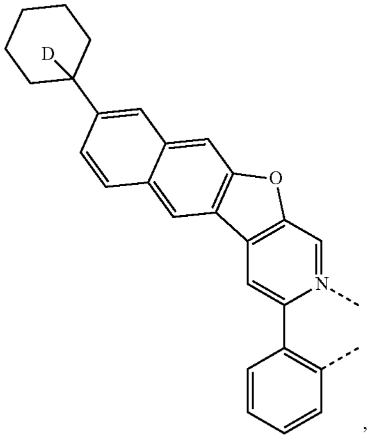
,
$L_{A199}$
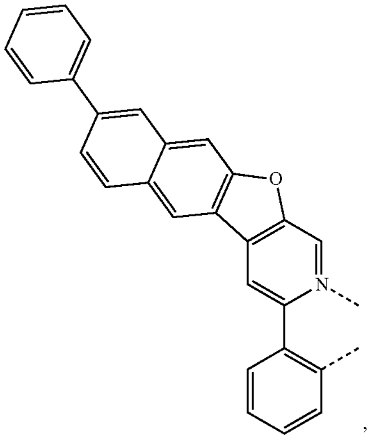
,
$L_{A200}$
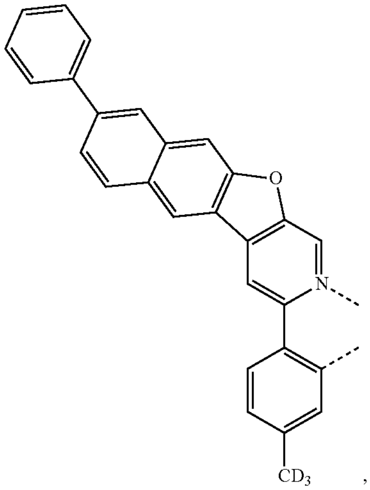
, -continued
L$_{A201}$
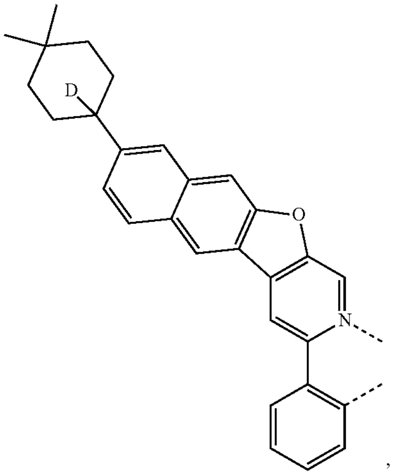
,
L$_{A202}$
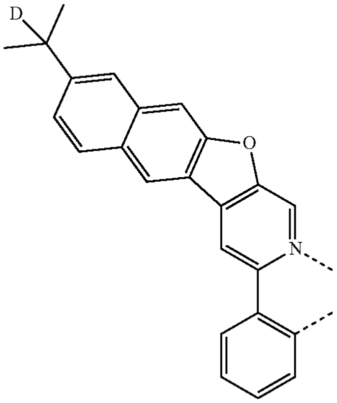
,
L$_{A203}$
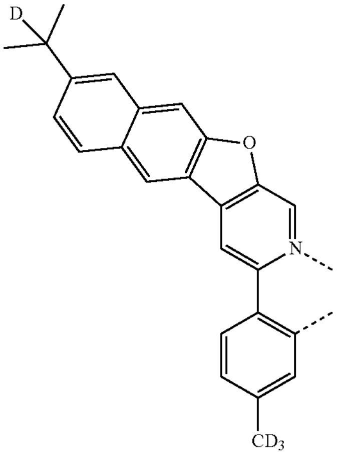
,
-continued
L$_{A204}$
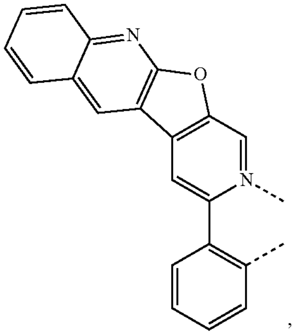
,
L$_{A205}$
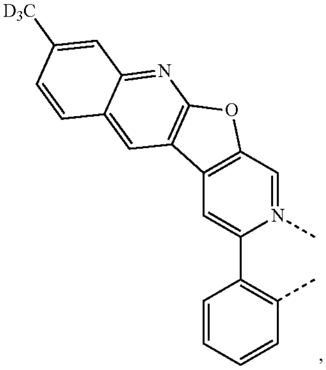
,
L$_{A206}$
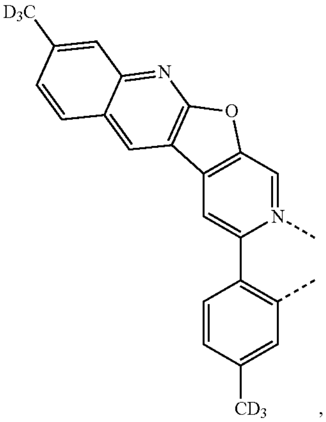
,
L$_{A207}$
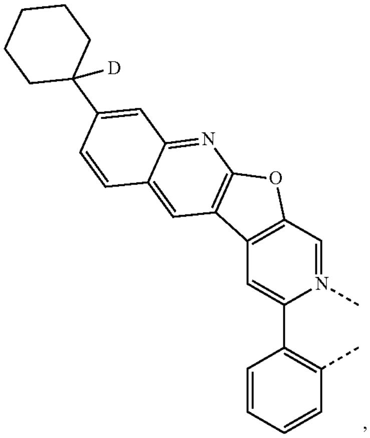
, -continued
L_{A208}
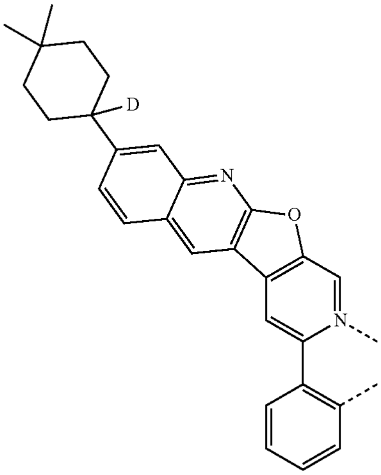
,
L_{A209}
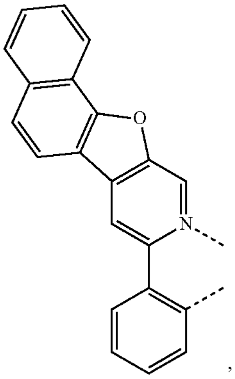
,
L_{A210}
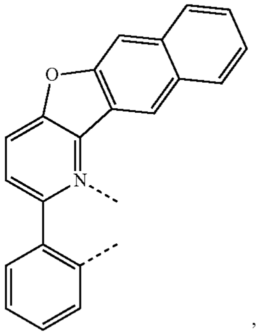
,
L_{A211}
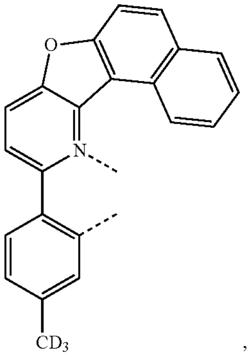
,
-continued
L_{A212}
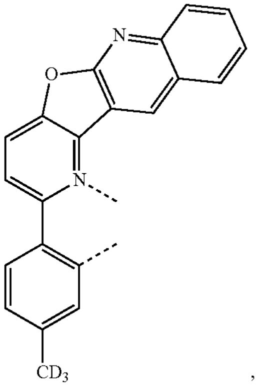
,
L_{A213}
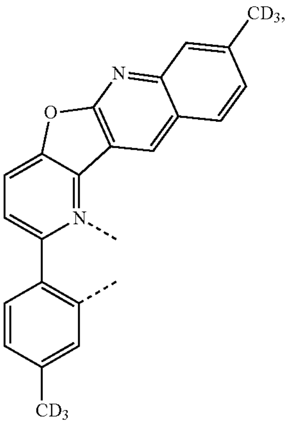
L_{A214}
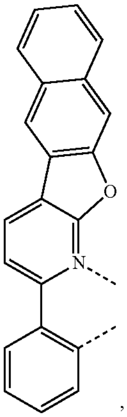
, -continued
$L_{A215}$
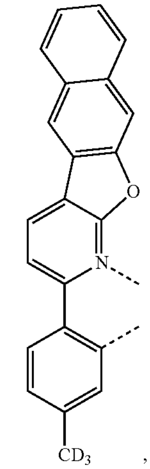
,
$L_{A216}$
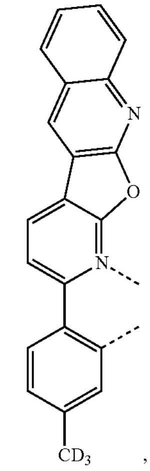
,
$L_{A217}$
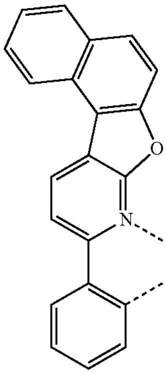
,
-continued
$L_{A218}$
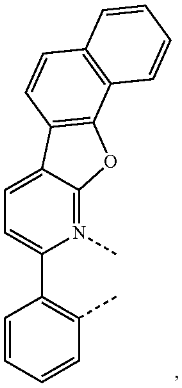
,
$L_{A219}$
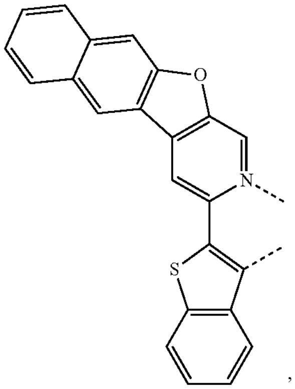
,
$L_{A220}$
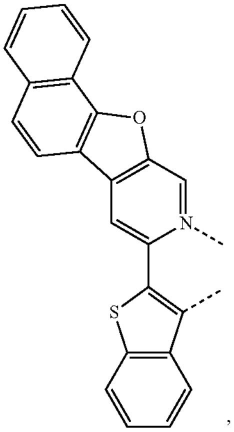
,
$L_{A221}$
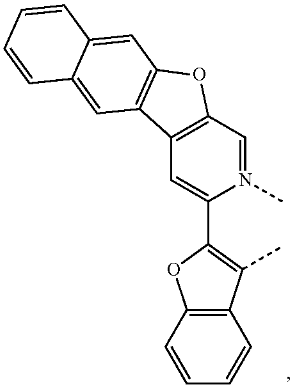
, -continued
L$_{A222}$
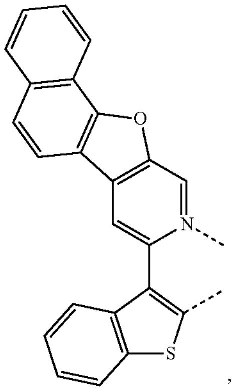
,
L$_{A223}$
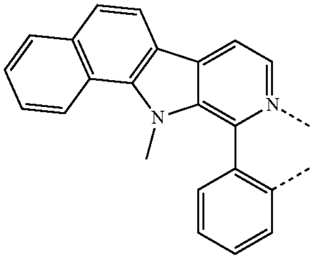
,
L$_{A224}$
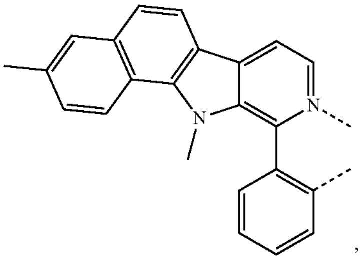
,
L$_{A225}$
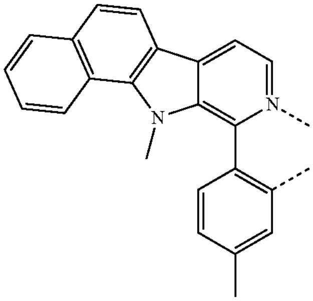
,
L$_{A226}$
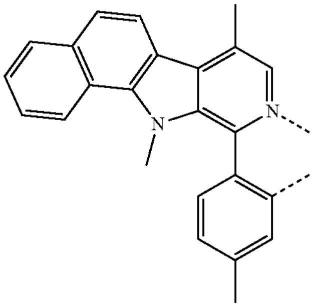
,
-continued
L$_{A227}$
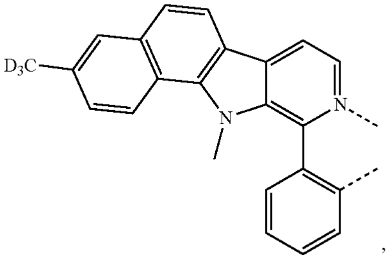
,
L$_{A228}$
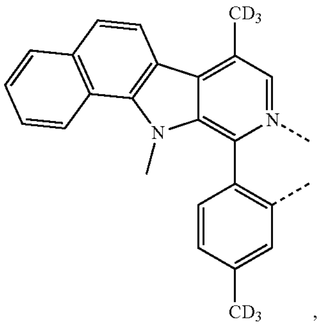
,
L$_{A229}$
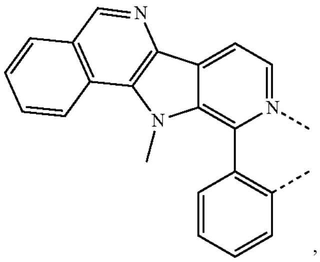
,
L$_{A230}$
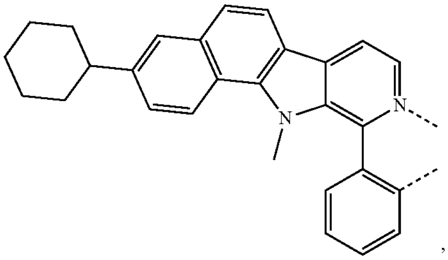
,
L$_{A231}$
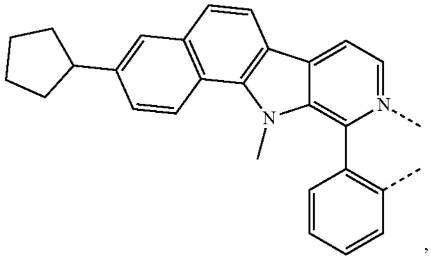
, L_{A232}
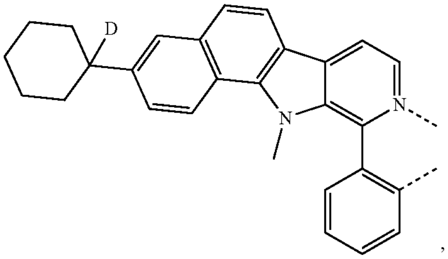
,
L_{A233}
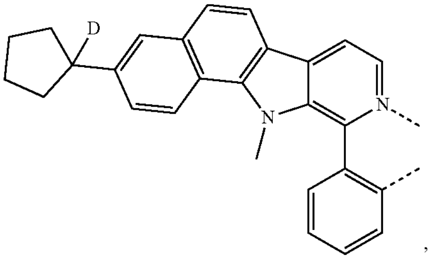
,
L_{A234}
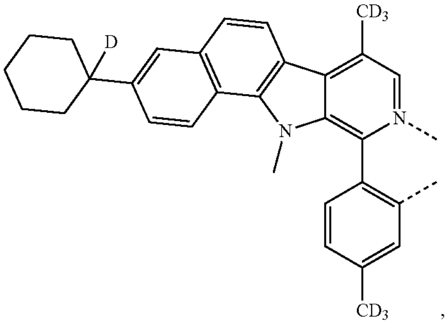
,
L_{A235}
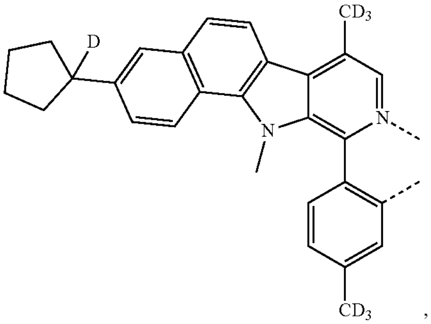
,
L_{A236}
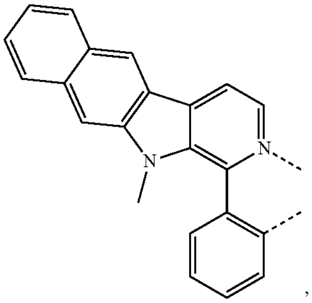
,
L_{A237}
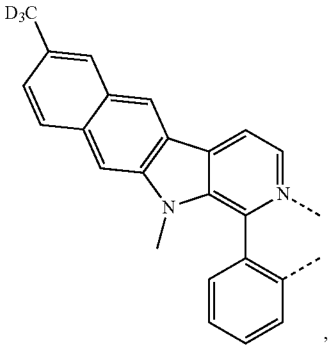
,
L_{A238}
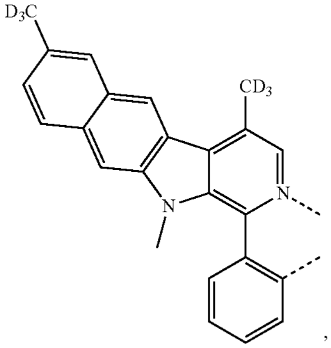
,
L_{A239}
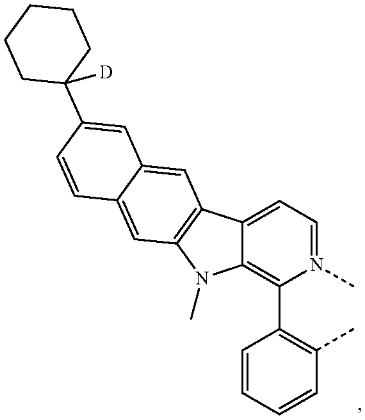
,
L_{A240}
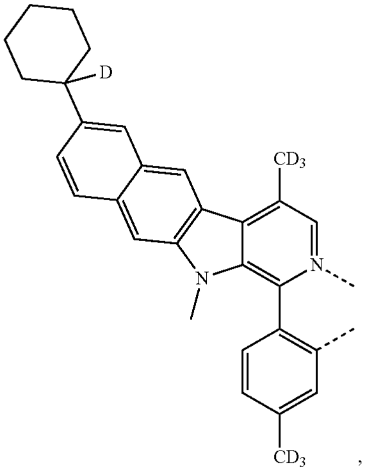
, -continued
$L_{A241}$
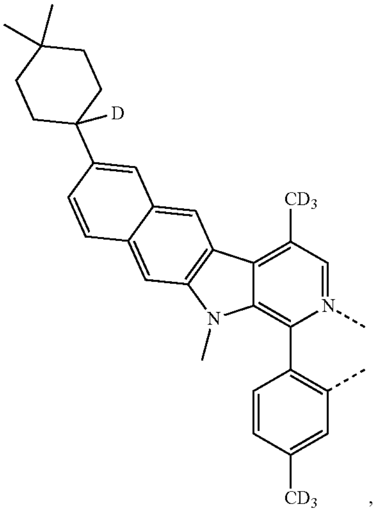
,
$L_{A242}$
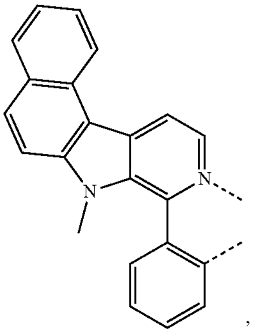
,
$L_{A243}$
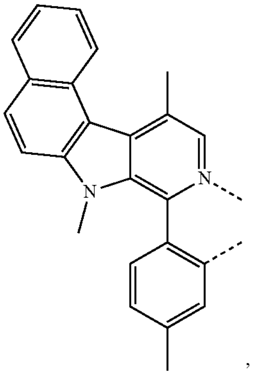
,
$L_{A244}$
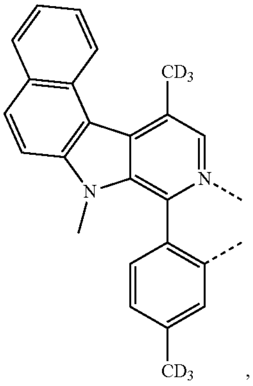
,
-continued
$L_{A245}$
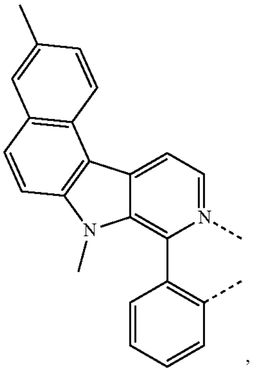
,
$L_{A246}$
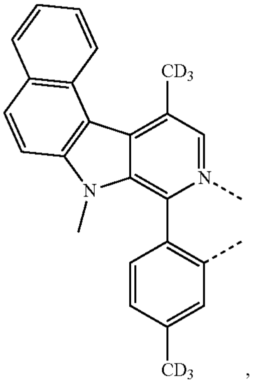
,
$L_{A247}$
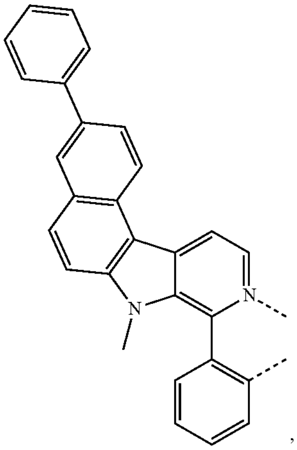
, -continued
$L_{A248}$
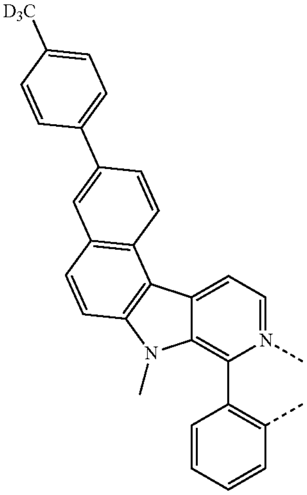
,
$L_{A249}$
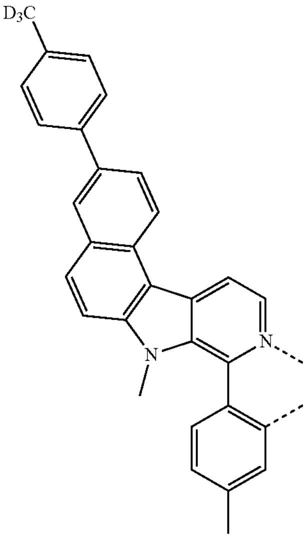
,
$L_{A250}$
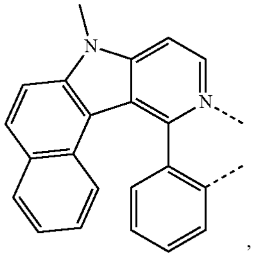
,
$L_{A251}$
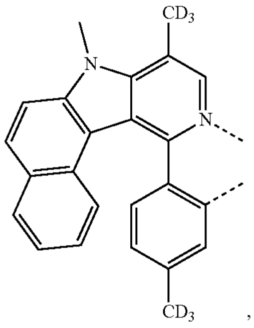
,
-continued
$L_{A252}$
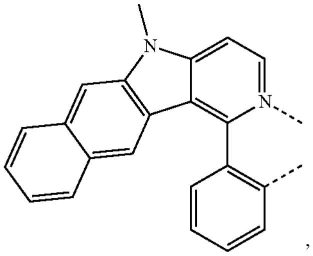
,
$L_{A253}$
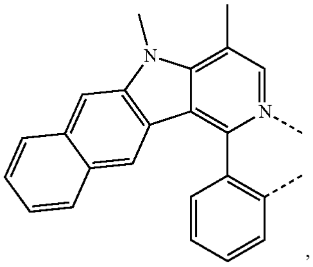
,
$L_{A254}$
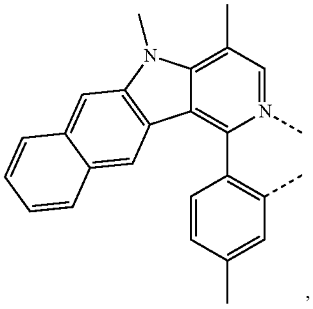
,
$L_{A255}$
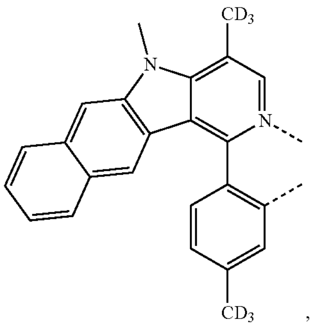
,
$L_{A256}$
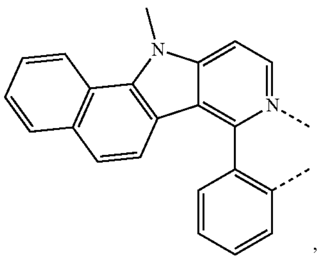
, -continued
$L_{A257}$
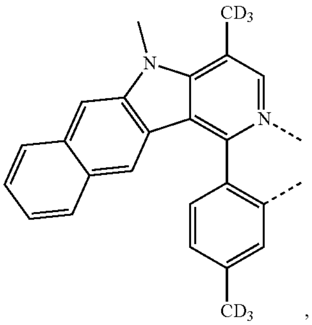
,
$L_{A258}$
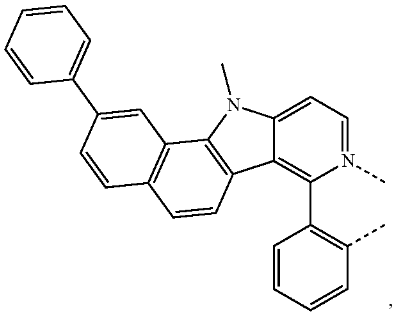
,
$L_{A259}$
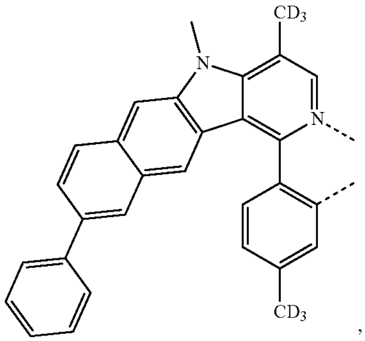
,
$L_{A260}$
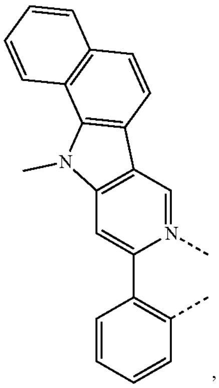
,
-continued
$L_{A261}$
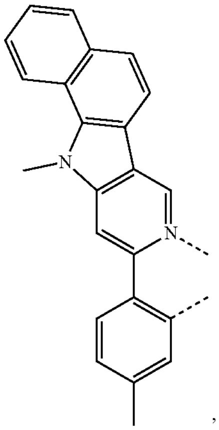
,
$L_{A262}$
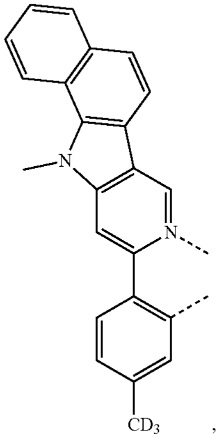
,
$L_{A263}$
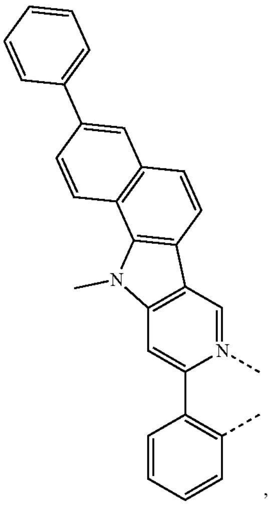
, -continued
L$_{A264}$
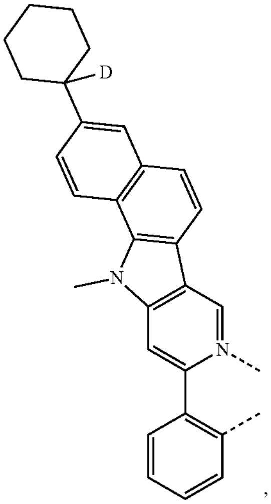
,
L$_{A265}$
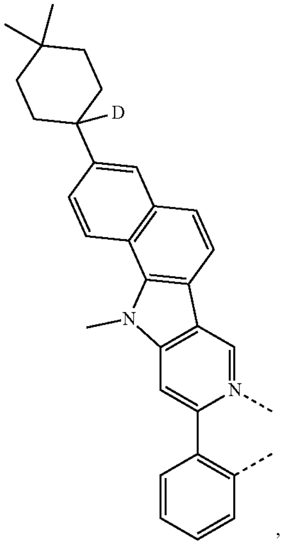
,
L$_{A266}$
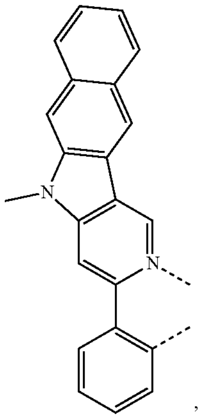
,
-continued
L$_{A267}$
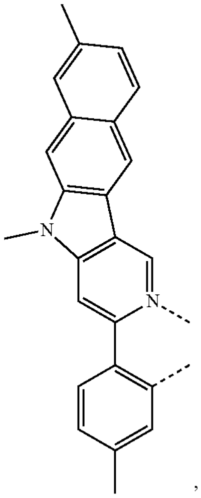
,
L$_{A268}$
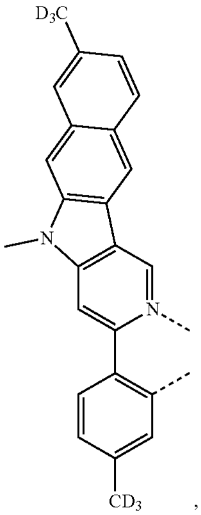
,
L$_{A269}$
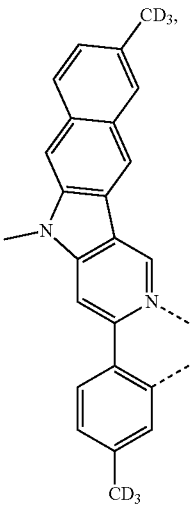

-continued
$L_{A270}$
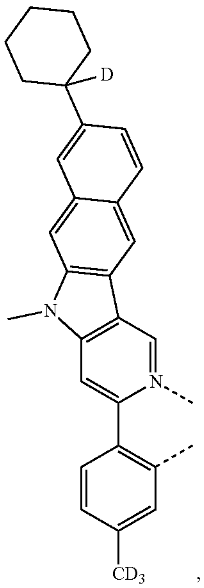
,
$L_{A271}$
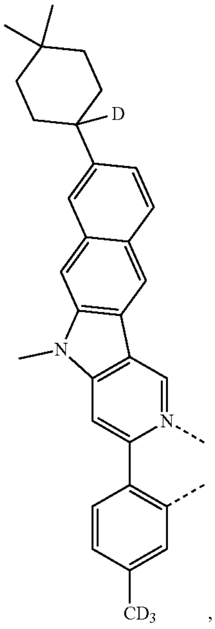
,
-continued
$L_{A272}$
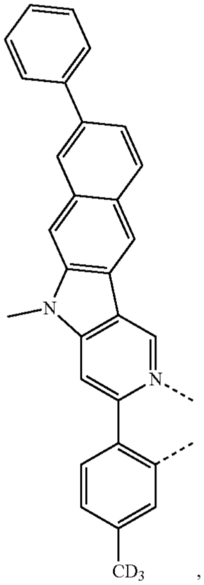
,
$L_{A273}$
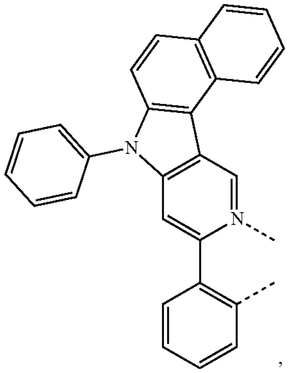
,
$L_{A274}$
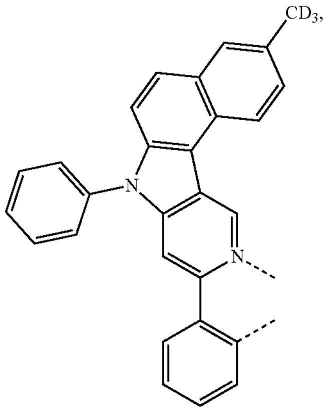

-continued
L_{A275}
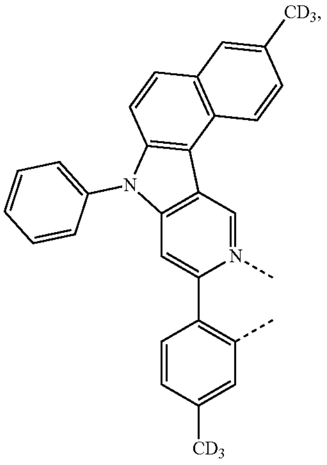
L_{A276}
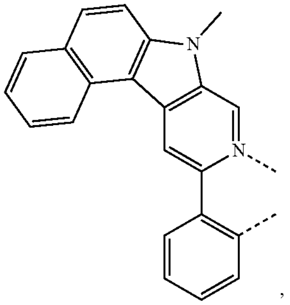
L_{A277}
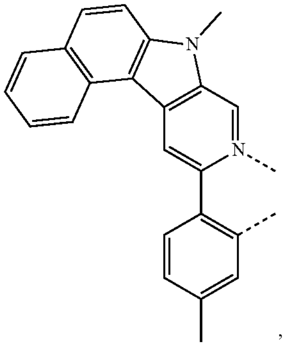
L_{A278}
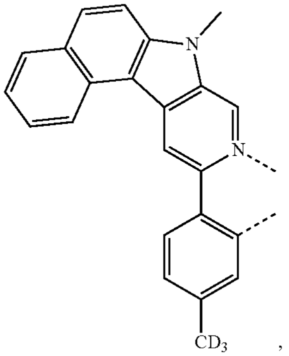
-continued
L_{A279}
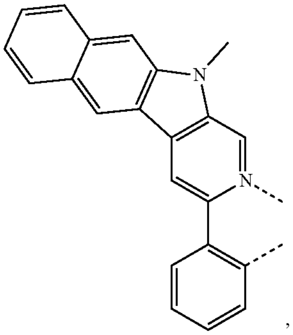
L_{A280}
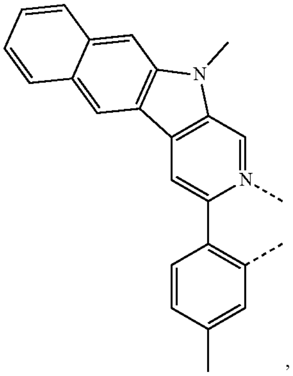
L_{A281}
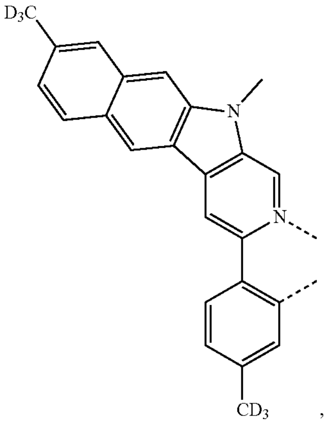
L_{A282}
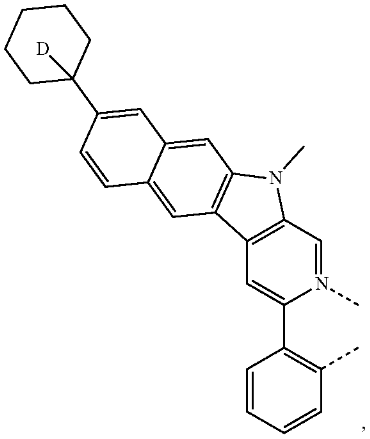

-continued
L$_{A283}$
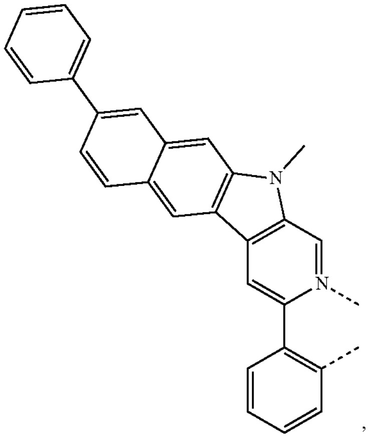
,
L$_{A284}$
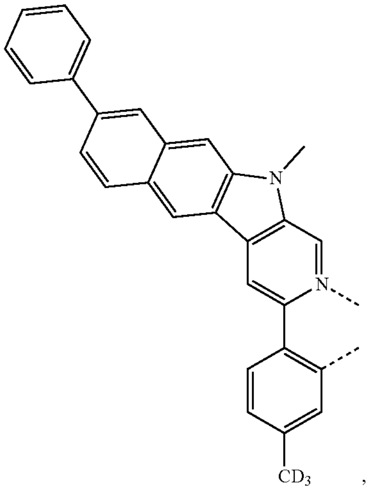
,
L$_{A285}$
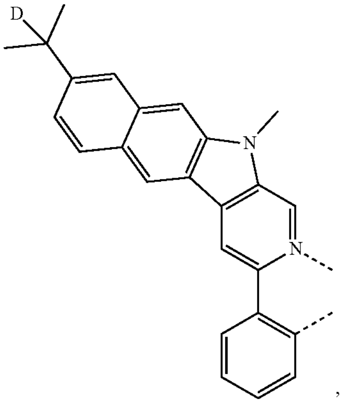
,
-continued
L$_{A286}$
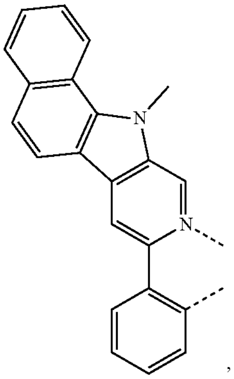
,
L$_{A287}$
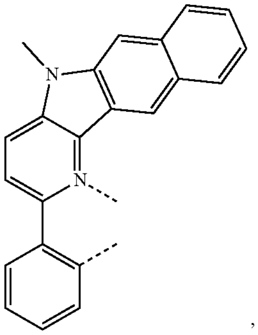
,
L$_{A289}$
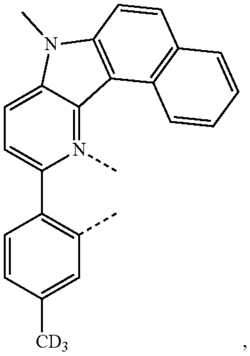
, -continued
$L_{A290}$
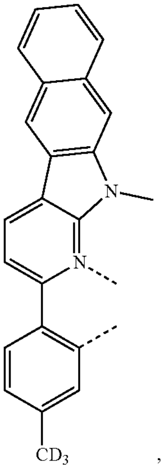
,
$L_{A291}$
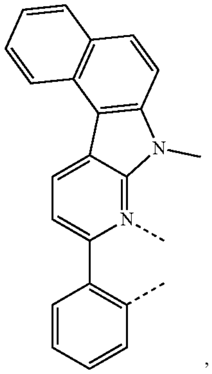
,
$L_{A292}$
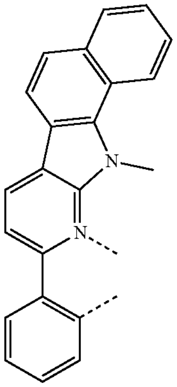
,
$L_{A293}$
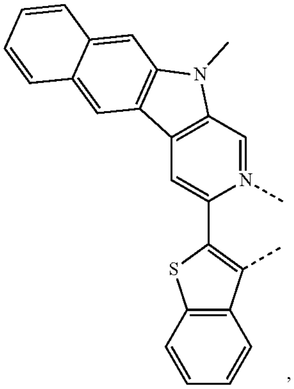
,
-continued
$L_{A294}$
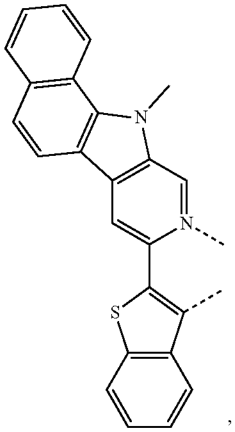
,
$L_{A295}$
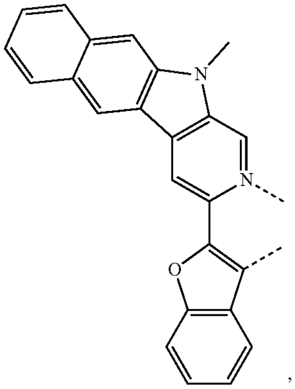
,
$L_{A296}$
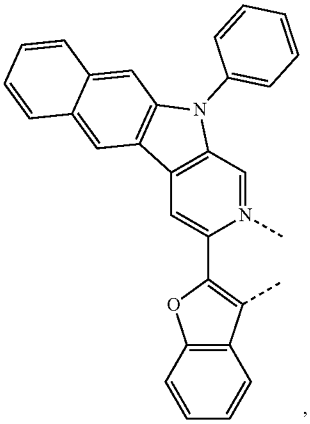
,
$L_{A297}$
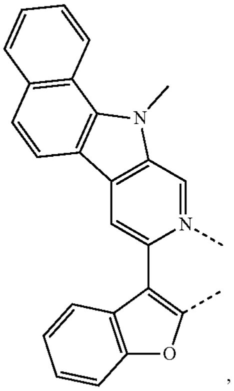
, -continued $L_{A298}$

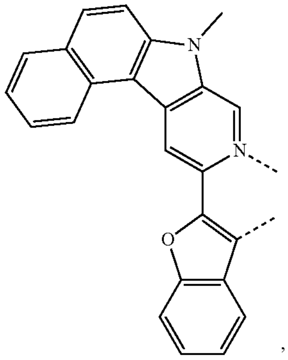

, $L_{A299}$

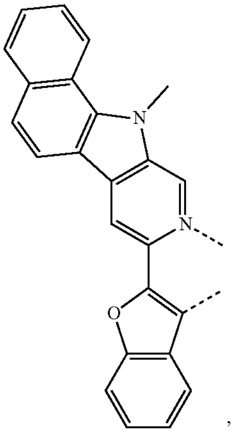

, and $L_{A300}$

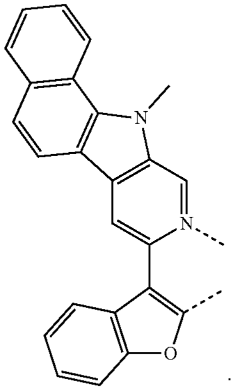

.

In one embodiment, the compound has formula $(L_A)_nIr(L_B)_{3-n}$;

wherein $L_B$ is a bidentate ligand; and n is 1, 2, or 3.

In one embodiment, $L_B$ is selected from the group consisting of:

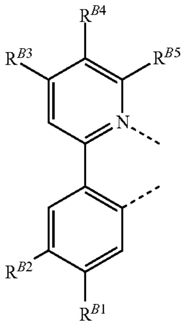

| $L_{Bj}$, j | $R^{B1}$ | $R^{B2}$ | $R^{B3}$ | $R^{B4}$ | $R^{B5}$ |
|---|---|---|---|---|---|
| 1. | H | H | H | H | H |
| 2. | $CH_3$ | H | H | H | H |
| 3. | H | $CH_3$ | H | H | H |
| 4. | H | H | $CH_3$ | H | H |
| 5. | H | H | H | $CH_3$ | H |
| 6. | $CH_3$ | H | $CH_3$ | H | H |
| 7. | $CH_3$ | H | H | $CH_3$ | H |
| 8. | H | $CH_3$ | $CH_3$ | H | H |
| 9. | H | $CH_3$ | H | $CH_3$ | H |
| 10. | H | H | $CH_3$ | $CH_3$ | H |
| 11. | $CH_3$ | $CH_3$ | $CH_3$ | H | H |
| 12. | $CH_3$ | $CH_3$ | H | $CH_3$ | H |
| 13. | $CH_3$ | H | $CH_3$ | $CH_3$ | H |
| 14. | H | $CH_3$ | $CH_3$ | $CH_3$ | H |
| 15. | $CH_3$ | $CH_3$ | $CH_3$ | $CH_3$ | H |
| 16. | 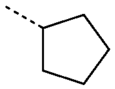 | H | H | H | H |
| 17. | 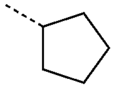 | $CH_3$ | H | H | H |
| 18. | 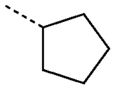 | H | $CH_3$ | H | H |

-continued
| $L_{Bj}$, j | $R^{B1}$ | $R^{B2}$ | $R^{B3}$ | $R^{B4}$ | $R^{B5}$ |
|---|---|---|---|---|---|
| 19. | 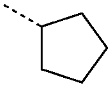 | H | H | $CH_3$ | H |
| 20. | 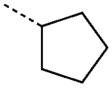 | $CH_3$ | $CH_3$ | H | H |
| 21. | 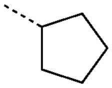 | $CH_3$ | H | $CH_3$ | H |
| 22. | 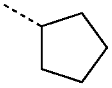 | H | $CH_3$ | $CH_3$ | H |
| 23. | 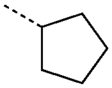 | $CH_3$ | $CH_3$ | $CH_3$ | H |
| 24. | H | 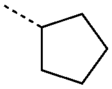 | H | H | H |
| 25. | $CH_3$ | 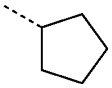 | H | H | H |
| 26. | H | 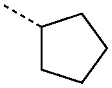 | $CH_3$ | H | H |
| 27. | H | 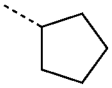 | H | $CH_3$ | H |
| 28. | $CH_3$ | 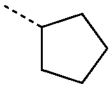 | $CH_3$ | H | H |
| 29. | $CH_3$ | 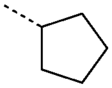 | H | $CH_3$ | H |
| 30. | H | 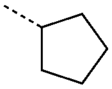 | $CH_3$ | $CH_3$ | H |
| 31. | $CH_3$ | 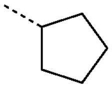 | $CH_3$ | $CH_3$ | H |
| 32. | H | H | 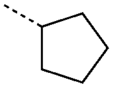 | H | H |
| 33. | $CH_3$ | H | 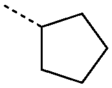 | H | H |

-continued
| $L_{Bj}$, j | $R^{B1}$ | $R^{B2}$ | $R^{B3}$ | $R^{B4}$ | $R^{B5}$ |
|---|---|---|---|---|---|
| 34. | H | $CH_3$ | 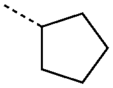 | H | H |
| 35. | H | H | 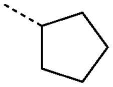 | $CH_3$ | H |
| 36. | $CH_3$ | $CH_3$ | 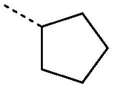 | H | H |
| 37. | $CH_3$ | H | 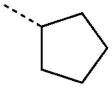 | $CH_3$ | H |
| 38. | H | $CH_3$ | 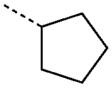 | $CH_3$ | H |
| 39. | $CH_3$ | $CH_3$ | 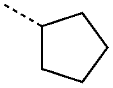 | $CH_3$ | H |
| 40. | 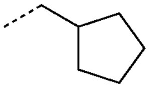 | H | H | H | H |
| 41. | 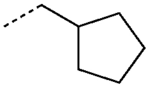 | $CH_3$ | H | H | H |
| 42. | 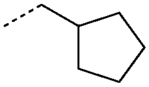 | H | $CH_3$ | H | H |
| 43. | 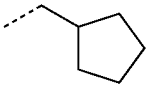 | H | H | $CH_3$ | H |
| 44. | 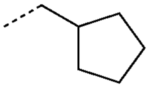 | $CH_3$ | $CH_3$ | H | H |
| 45. | 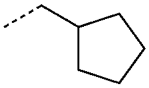 | $CH_3$ | H | $CH_3$ | H |
| 46. | 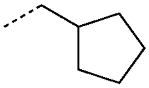 | H | $CH_3$ | $CH_3$ | H |
| 47. | 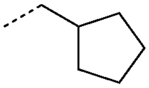 | $CH_3$ | $CH_3$ | $CH_3$ | H |
| 48. | H | 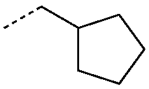 | H | H | H |

-continued
| $L_{Bj}$, j | $R^{B1}$ | $R^{B2}$ | $R^{B3}$ | $R^{B4}$ | $R^{B5}$ |
|---|---|---|---|---|---|
| 49. | $CH_3$ | 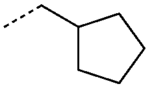 | H | H | H |
| 50. | H | 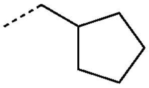 | $CH_3$ | H | H |
| 51. | H | 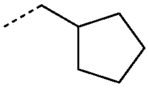 | H | $CH_3$ | H |
| 52. | $CH_3$ | 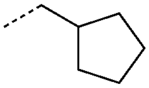 | $CH_3$ | H | H |
| 53. | $CH_3$ | 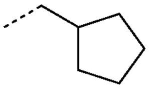 | H | $CH_3$ | H |
| 54. | H | 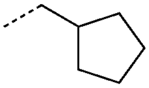 | $CH_3$ | $CH_3$ | H |
| 55. | $CH_3$ | 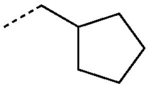 | $CH_3$ | $CH_3$ | H |
| 56. | H | H | 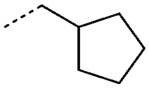 | H | H |
| 57. | $CH_3$ | H | 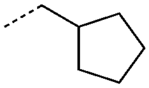 | H | H |
| 58. | H | $CH_3$ | 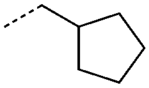 | H | H |
| 59. | H | H | 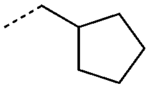 | $CH_3$ | H |
| 60. | $CH_3$ | $CH_3$ | 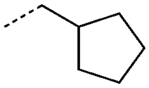 | H | H |
| 61. | $CH_3$ | H | 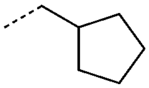 | $CH_3$ | H |
| 62. | H | $CH_3$ | 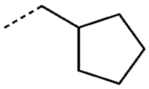 | $CH_3$ | H |
| 63. | $CH_3$ | $CH_3$ | 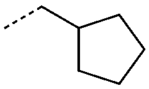 | $CH_3$ | H |
| 64. | 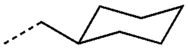 | H | H | H | H |

-continued
| $L_{Bj}$, j | $R^{B1}$ | $R^{B2}$ | $R^{B3}$ | $R^{B4}$ | $R^{B5}$ |
|---|---|---|---|---|---|
| 65. | 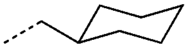 | $CH_3$ | H | H | H |
| 66. | 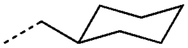 | H | $CH_3$ | H | H |
| 67. | 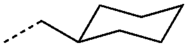 | H | H | $CH_3$ | H |
| 68. | 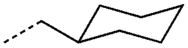 | $CH_3$ | $CH_3$ | H | H |
| 69. | 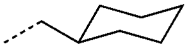 | $CH_3$ | H | $CH_3$ | H |
| 70. | 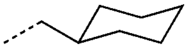 | H | $CH_3$ | $CH_3$ | H |
| 71. | 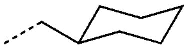 | $CH_3$ | $CH_3$ | $CH_3$ | H |
| 72. | H | 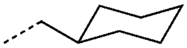 | H | H | H |
| 73. | $CH_3$ | 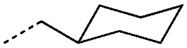 | H | H | H |
| 74. | H | 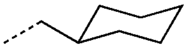 | $CH_3$ | H | H |
| 75. | H | 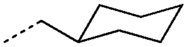 | H | $CH_3$ | H |
| 76. | $CH_3$ | 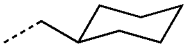 | $CH_3$ | H | H |
| 77. | $CH_3$ | 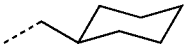 | H | $CH_3$ | H |
| 78. | H | 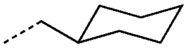 | $CH_3$ | $CH_3$ | H |
| 79. | $CH_3$ | 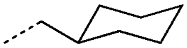 | $CH_3$ | $CH_3$ | H |
| 80. | H | H | 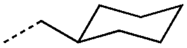 | H | H |
| 81. | $CH_3$ | H | 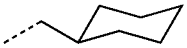 | H | H |
| 82. | H | $CH_3$ | 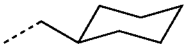 | H | H |
| 83. | H | H | 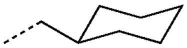 | $CH_3$ | H |
| 84. | $CH_3$ | $CH_3$ | 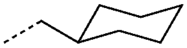 | H | H |
| 85. | $CH_3$ | H | 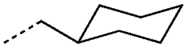 | $CH_3$ | H |
| 86. | H | $CH_3$ | 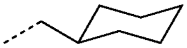 | $CH_3$ | H |
| 87. | $CH_3$ | $CH_3$ | 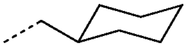 | $CH_3$ | H |
| 88. | 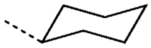 | H | H | H | H |

-continued
| $L_{Bj}$, j | $R^{B1}$ | $R^{B2}$ | $R^{B3}$ | $R^{B4}$ | $R^{B5}$ |
|---|---|---|---|---|---|
| 89. | 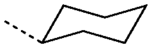 | $CH_3$ | H | H | H |
| 90. | 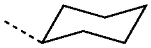 | H | $CH_3$ | H | H |
| 91. | 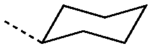 | H | H | $CH_3$ | H |
| 92. | 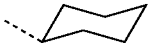 | $CH_3$ | $CH_3$ | H | H |
| 93. | 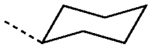 | $CH_3$ | H | $CH_3$ | H |
| 94. | 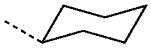 | H | $CH_3$ | $CH_3$ | H |
| 95. | 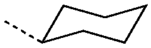 | $CH_3$ | $CH_3$ | $CH_3$ | H |
| 96. | H | 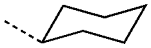 | H | H | H |
| 97. | $CH_3$ | 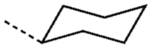 | H | H | H |
| 98. | H | 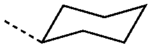 | $CH_3$ | H | H |
| 99. | H | 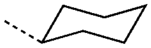 | H | $CH_3$ | H |
| 100. | $CH_3$ | 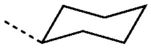 | $CH_3$ | H | H |
| 101. | $CH_3$ | 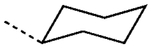 | H | $CH_3$ | H |
| 102. | H | 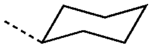 | $CH_3$ | $CH_3$ | H |
| 103. | $CH_3$ | 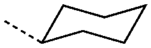 | $CH_3$ | $CH_3$ | H |
| 104. | H | H | 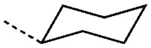 | H | H |
| 105. | $CH_3$ | H | 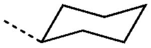 | H | H |
| 106. | H | $CH_3$ | 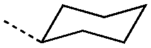 | H | H |
| 107. | H | H | 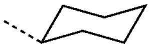 | $CH_3$ | H |
| 108. | $CH_3$ | $CH_3$ | 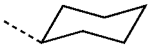 | H | H |
| 109. | $CH_3$ | H | 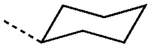 | $CH_3$ | H |
| 110. | H | $CH_3$ | 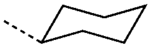 | $CH_3$ | H |
| 111. | $CH_3$ | $CH_3$ | 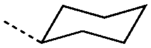 | $CH_3$ | H |
| 112. | 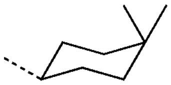 | H | H | H | H |

-continued
| $L_{Bj}$, j | $R^{B1}$ | $R^{B2}$ | $R^{B3}$ | $R^{B4}$ | $R^{B5}$ |
|---|---|---|---|---|---|
| 113. | 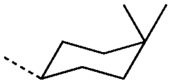 | $CH_3$ | H | H | H |
| 114. | 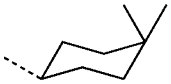 | H | $CH_3$ | H | H |
| 115. | 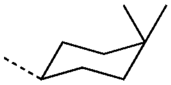 | H | H | $CH_3$ | H |
| 116. | 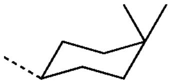 | $CH_3$ | $CH_3$ | H | H |
| 117. | 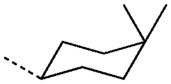 | $CH_3$ | H | $CH_3$ | H |
| 118. | 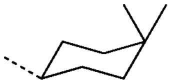 | H | $CH_3$ | $CH_3$ | H |
| 119. | 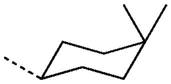 | $CH_3$ | $CH_3$ | $CH_3$ | H |
| 120. | H | 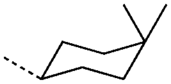 | H | H | H |
| 121. | $CH_3$ | 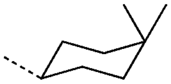 | H | H | H |
| 122. | H | 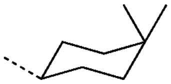 | $CH_3$ | H | H |
| 123. | H | 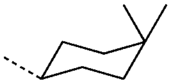 | H | $CH_3$ | H |
| 124. | $CH_3$ | 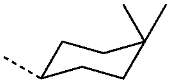 | $CH_3$ | H | H |
| 125. | $CH_3$ | 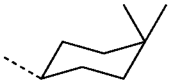 | H | $CH_3$ | H |
| 126. | H | 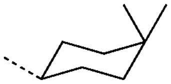 | $CH_3$ | $CH_3$ | H |
| 127. | $CH_3$ | 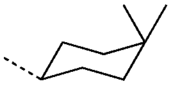 | $CH_3$ | $CH_3$ | H |
| 128. | H | H | 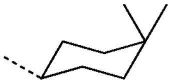 | H | H |

-continued
| $L_{Bj}$, j | $R^{B1}$ | $R^{B2}$ | $R^{B3}$ | $R^{B4}$ | $R^{B5}$ |
|---|---|---|---|---|---|
| 129. | $CH_3$ | H | 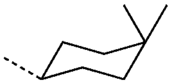 | H | H |
| 130. | H | $CH_3$ | 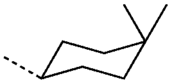 | H | H |
| 131. | H | H | 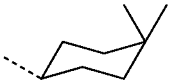 | $CH_3$ | H |
| 132. | $CH_3$ | $CH_3$ | 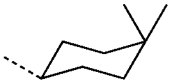 | H | H |
| 133. | $CH_3$ | H | 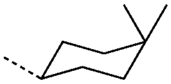 | $CH_3$ | H |
| 134. | H | $CH_3$ | 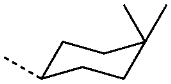 | $CH_3$ | H |
| 135. | $CH_3$ | $CH_3$ | 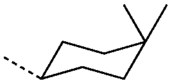 | $CH_3$ | H |
| 136. | 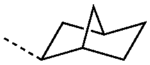 | H | H | H | H |
| 137. | 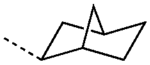 | $CH_3$ | H | H | H |
| 138. | 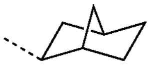 | H | $CH_3$ | H | H |
| 139. | 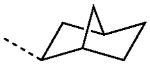 | H | H | $CH_3$ | H |
| 140. | 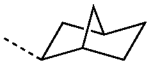 | $CH_3$ | $CH_3$ | H | H |
| 141. | 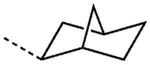 | $CH_3$ | H | $CH_3$ | H |
| 142. | 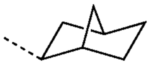 | H | $CH_3$ | $CH_3$ | H |
| 143. | 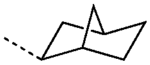 | $CH_3$ | $CH_3$ | $CH_3$ | H |
| 144. | H | 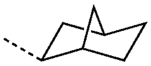 | H | H | H |
| 145. | $CH_3$ | 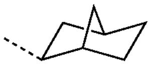 | H | H | H |
| 146. | H | 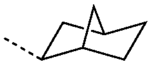 | $CH_3$ | H | H |

-continued
| $L_{Bj}$, j | $R^{B1}$ | $R^{B2}$ | $R^{B3}$ | $R^{B4}$ | $R^{B5}$ |
|---|---|---|---|---|---|
| 147. | H | 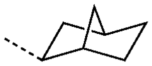 | H | $CH_3$ | H |
| 148. | $CH_3$ | 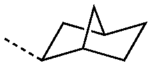 | $CH_3$ | H | H |
| 149. | $CH_3$ | 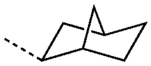 | H | $CH_3$ | H |
| 150. | H | 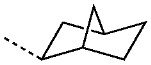 | $CH_3$ | $CH_3$ | H |
| 151. | $CH_3$ | 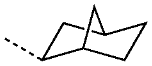 | $CH_3$ | $CH_3$ | H |
| 152. | H | H | 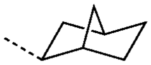 | H | H |
| 153. | $CH_3$ | H | 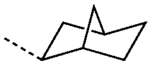 | H | H |
| 154. | H | $CH_3$ | 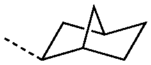 | H | H |
| 155. | H | H | 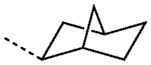 | $CH_3$ | H |
| 156. | $CH_3$ | $CH_3$ | 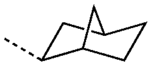 | H | H |
| 157. | $CH_3$ | H | 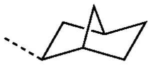 | $CH_3$ | H |
| 158. | H | $CH_3$ | 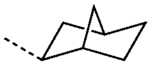 | $CH_3$ | H |
| 159. | $CH_3$ | $CH_3$ | 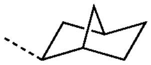 | $CH_3$ | H |
| 160. | 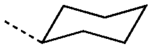 | H | 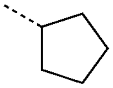 | H | H |
| 161. | 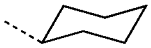 | H | 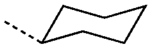 | H | H |
| 162. | 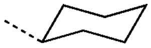 | H | 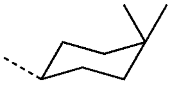 | H | |
| 163. | 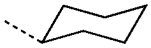 | H | 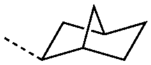 | H | H |
| 164. | 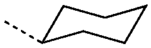 | H | 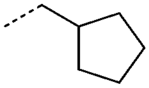 | H | H |
| 165. | 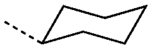 | H | 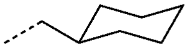 | H | H |

-continued
| $L_{Bj}$, j | $R^{B1}$ | $R^{B2}$ | $R^{B3}$ | $R^{B4}$ | $R^{B5}$ |
|---|---|---|---|---|---|
| 166. | 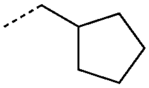 | H | 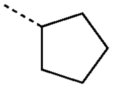 | H | H |
| 167. | 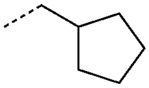 | H | 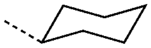 | H | H |
| 168. | 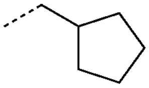 | H | 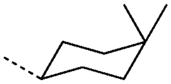 | H | H |
| 169. | 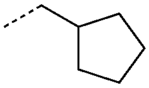 | H | 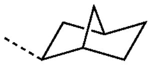 | H | H |
| 170. | 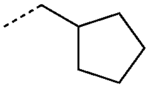 | H | 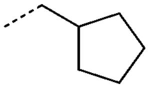 | H | H |
| 171. | 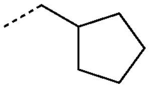 | H | 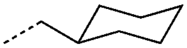 | H | H |
| 172. | 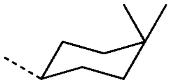 | H | 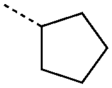 | H | H |
| 173. | 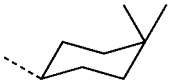 | H | 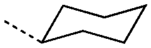 | H | H |
| 174. | 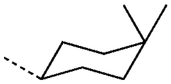 | H | 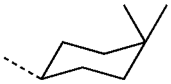 | H | H |
| 175. | 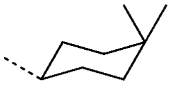 | H | 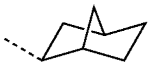 | H | H |
| 176. | 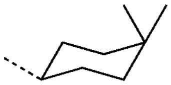 | H | 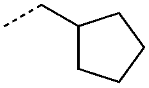 | H | H |
| 177. | 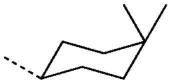 | H | 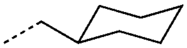 | H | H |
| 178. | $CD_3$ | H | H | H | H |
| 179. | H | $CD_3$ | H | H | H |
| 180. | H | H | $CD_3$ | H | H |
| 181. | H | H | H | $CD_3$ | H |
| 182. | $CD_3$ | H | $CD_3$ | H | H |
| 183. | $CD_3$ | H | H | $CD_3$ | H |
| 184. | H | $CD_3$ | $CD_3$ | H | H |
| 185. | H | $CD_3$ | H | $CD_3$ | H |
| 186. | H | H | $CD_3$ | $CD_3$ | H |
| 187. | $CD_3$ | $CD_3$ | $CD_3$ | H | H |
| 188. | $CD_3$ | $CD_3$ | H | $CD_3$ | H |
| 189. | $CD_3$ | H | $CD_3$ | $CD_3$ | H |
| 190. | H | $CD_3$ | $CD_3$ | $CD_3$ | H |
| 191. | $CD_3$ | $CD_3$ | $CD_3$ | $CD_3$ | H |
| 192. | H | H | H | H | $CD_3$ |
| 193. | $CH_3$ | H | H | H | $CD_3$ |
| 194. | H | $CH_3$ | H | H | $CD_3$ |

-continued

| $L_{Bj}$, j | $R^{B1}$ | $R^{B2}$ | $R^{B3}$ | $R^{B4}$ | $R^{B5}$ |
|---|---|---|---|---|---|
| 195. | H | H | $CH_3$ | H | $CD_3$ |
| 196. | H | H | H | $CH_3$ | $CD_3$ |
| 197. | $CH_3$ | H | $CH_3$ | H | $CD_3$ |
| 198. | $CH_3$ | H | H | $CH_3$ | $CD_3$ |
| 199. | H | $CH_3$ | $CH_3$ | H | $CD_3$ |
| 200. | H | $CH_3$ | H | $CH_3$ | $CD_3$ |
| 201. | H | H | $CH_3$ | $CH_3$ | $CD_3$ |
| 202. | $CH_3$ | $CH_3$ | $CH_3$ | H | $CD_3$ |
| 203. | $CH_3$ | $CH_3$ | H | $CH_3$ | $CD_3$ |
| 204. | $CH_3$ | H | $CH_3$ | $CH_3$ | $CD_3$ |
| 205. | H | $CH_3$ | $CH_3$ | $CH_3$ | $CD_3$ |
| 206. | $CH_3$ | $CH_3$ | $CH_3$ | $CH_3$ | $CD_3$ |
| 207. | 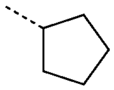 | H | H | H | $CD_3$ |
| 208. | 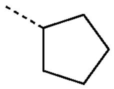 | $CH_3$ | H | H | $CD_3$ |
| 209. | 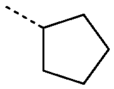 | H | $CH_3$ | H | $CD_3$ |
| 210. | 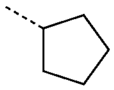 | H | H | $CH_3$ | $CD_3$ |
| 211. | 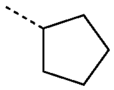 | $CH_3$ | $CH_3$ | H | $CD_3$ |
| 212. | 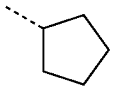 | $CH_3$ | H | $CH_3$ | $CD_3$ |
| 213. | 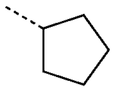 | H | $CH_3$ | $CH_3$ | $CD_3$ |
| 214. | 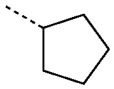 | $CH_3$ | $CH_3$ | $CH_3$ | $CD_3$ |
| 215. | H | 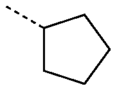 | H | H | $CD_3$ |
| 216. | $CH_3$ | 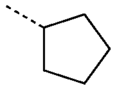 | H | H | $CD_3$ |
| 217. | H | 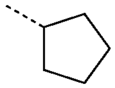 | $CH_3$ | H | $CD_3$ |
| 218. | H | 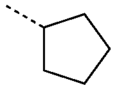 | H | $CH_3$ | $CD_3$ |
| 219. | $CH_3$ | 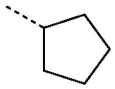 | $CH_3$ | H | $CD_3$ |

-continued
| $L_{Bj}$, j | $R^{B1}$ | $R^{B2}$ | $R^{B3}$ | $R^{B4}$ | $R^{B5}$ |
|---|---|---|---|---|---|
| 220. | $CH_3$ | 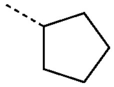 | H | $CH_3$ | $CD_3$ |
| 221. | H | 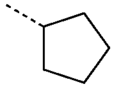 | $CH_3$ | $CH_3$ | $CD_3$ |
| 222. | $CH_3$ | 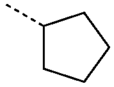 | $CH_3$ | $CH_3$ | $CD_3$ |
| 223. | H | H | 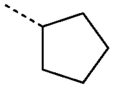 | H | $CD_3$ |
| 224. | $CH_3$ | H | 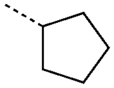 | H | $CD_3$ |
| 225. | H | $CH_3$ | 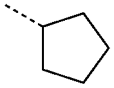 | H | $CD_3$ |
| 226. | H | H | 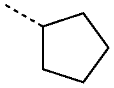 | $CH_3$ | $CD_3$ |
| 227. | $CH_3$ | $CH_3$ | 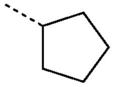 | H | $CD_3$ |
| 228. | $CH_3$ | H | 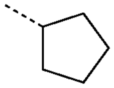 | $CH_3$ | $CD_3$ |
| 229. | H | $CH_3$ | 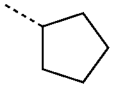 | $CH_3$ | $CD_3$ |
| 230. | $CH_3$ | $CH_3$ | 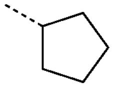 | $CH_3$ | $CD_3$ |
| 231. | 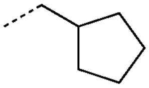 | H | H | H | $CD_3$ |
| 232. | 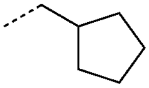 | $CH_3$ | H | H | $CD_3$ |
| 233. | 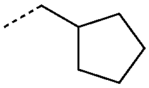 | H | $CH_3$ | H | $CD_3$ |
| 234. | 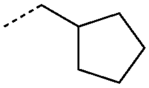 | H | H | $CH_3$ | $CD_3$ |

-continued
| $L_{Bj}$, j | $R^{B1}$ | $R^{B2}$ | $R^{B3}$ | $R^{B4}$ | $R^{B5}$ |
|---|---|---|---|---|---|
| 235. | 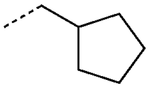 | $CH_3$ | $CH_3$ | H | $CD_3$ |
| 236. | 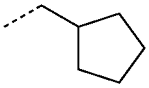 | $CH_3$ | H | $CH_3$ | $CD_3$ |
| 237. | 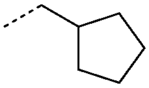 | H | $CH_3$ | $CH_3$ | $CD_3$ |
| 238. | 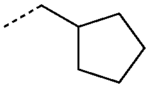 | $CH_3$ | $CH_3$ | $CH_3$ | $CD_3$ |
| 239. | H | 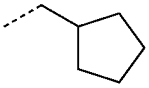 | H | H | $CD_3$ |
| 240. | $CH_3$ | 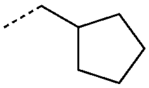 | H | H | $CD_3$ |
| 241. | H | 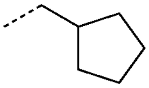 | $CH_3$ | H | $CD_3$ |
| 242. | H | 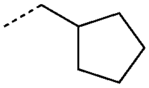 | H | $CH_3$ | $CD_3$ |
| 243. | $CH_3$ | 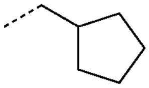 | $CH_3$ | H | $CD_3$ |
| 244. | $CH_3$ | 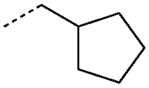 | H | $CH_3$ | $CD_3$ |
| 245. | H | 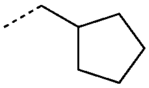 | $CH_3$ | $CH_3$ | $CD_3$ |
| 246. | $CH_3$ | 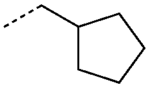 | $CH_3$ | $CH_3$ | $CD_3$ |
| 247. | H | H | 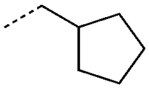 | H | $CD_3$ |
| 248. | $CH_3$ | H | 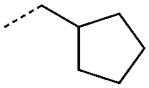 | H | $CD_3$ |
| 249. | H | $CH_3$ | 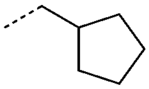 | H | $CD_3$ |

-continued
| $L_{Bj}$, j | $R^{B1}$ | $R^{B2}$ | $R^{B3}$ | $R^{B4}$ | $R^{B5}$ |
|---|---|---|---|---|---|
| 250. | H | H | 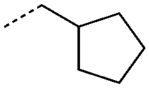 | $CH_3$ | $CD_3$ |
| 251. | $CH_3$ | $CH_3$ | 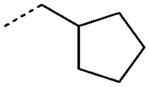 | H | $CD_3$ |
| 252. | $CH_3$ | H | 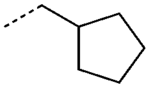 | $CH_3$ | $CD_3$ |
| 253. | H | $CH_3$ | 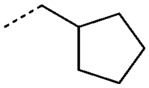 | $CH_3$ | $CD_3$ |
| 254. | $CH_3$ | $CH_3$ | 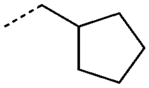 | $CH_3$ | $CD_3$ |
| 255. | 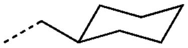 | H | H | H | $CD_3$ |
| 256. | 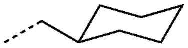 | $CH_3$ | H | H | $CD_3$ |
| 257. | 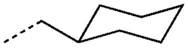 | H | $CH_3$ | H | $CD_3$ |
| 258. | 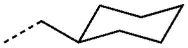 | H | H | $CH_3$ | $CD_3$ |
| 259. | 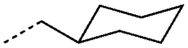 | $CH_3$ | $CH_3$ | H | $CD_3$ |
| 260. | 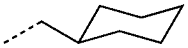 | $CH_3$ | H | $CH_3$ | $CD_3$ |
| 261. | 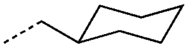 | H | $CH_3$ | $CH_3$ | $CD_3$ |
| 262. | 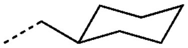 | $CH_3$ | $CH_3$ | $CH_3$ | $CD_3$ |
| 263. | H | 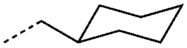 | H | H | $CD_3$ |
| 264. | $CH_3$ | 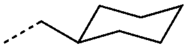 | H | H | $CD_3$ |
| 265. | H | 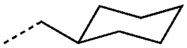 | $CH_3$ | H | $CD_3$ |
| 266. | H | 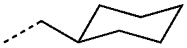 | H | $CH_3$ | $CD_3$ |
| 267. | $CH_3$ | 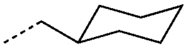 | $CH_3$ | H | $CD_3$ |
| 268. | $CH_3$ | 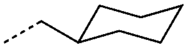 | H | $CH_3$ | $CD_3$ |
| 269. | H | 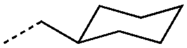 | $CH_3$ | $CH_3$ | $CD_3$ |
| 270. | $CH_3$ | 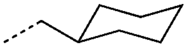 | $CH_3$ | $CH_3$ | $CD_3$ |

-continued

| $L_{Bj}$, j | $R^{B1}$ | $R^{B2}$ | $R^{B3}$ | $R^{B4}$ | $R^{B5}$ |
|---|---|---|---|---|---|
| 271. | H | H | 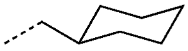 | H | $CD_3$ |
| 272. | $CH_3$ | H | 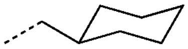 | H | $CD_3$ |
| 273. | H | $CH_3$ | 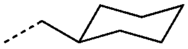 | H | $CD_3$ |
| 274. | H | H | 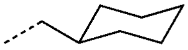 | $CH_3$ | $CD_3$ |
| 275. | $CD_3$ | $CD_3$ | $CD_3$ | $CD_3$ | $CD_3$ |

In one embodiment, the compound is selected from the group consisting of Compound 1 through Compound 75650 where each Compound x has the formula $Ir(L_{Ak})(L_{Ej})_2$;

wherein x=275j+k−275, k is an integer from 1 to 300, and j is an integer from 1 to 275.

In one embodiment, the compound has formula $(L_A)_mPt(L_C)_{2-m}$; wherein $L_C$ is a bidentate ligand; and m is 1, or 2.

In one embodiment, m is 1, and $L_A$ is connected to $L_C$ to form a tetradentate ligand.

According to another aspect of the present disclosure, an OLED is also provided. The OLED includes an anode, a cathode, and an organic layer disposed between the anode and the cathode. The organic layer may include a host and a phosphorescent dopant. The organic layer can include a compound comprising a ligand $L_A$ of Formula (I), and its variations as described herein.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

In one embodiment, the consumer product is selected from the group consisting of a flat panel display, a computer monitor, a medical monitors television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video walls comprising multiple displays tiled together, a theater or stadium screen, and a sign.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In one embodiment, the organic layer is an emissive layer and the compound is an emissive dopant or a non-emissive dopant.

In some embodiments of the emissive region, the emissive region further comprises a host, wherein the host comprises at least one selected from the group consisting of metal complex, triphenylene, carbazole, dibenzothiophene, dibenzofuran, dibenzoselenophene, aza-triphenylene, aza-carbazole, aza-dibenzothiophene, aza-dibenzofuran, and aza-dibenzoselenophene.

In some embodiment of the emissive region, the emissive region further comprises a host, wherein the host is selected from the group consisting of:

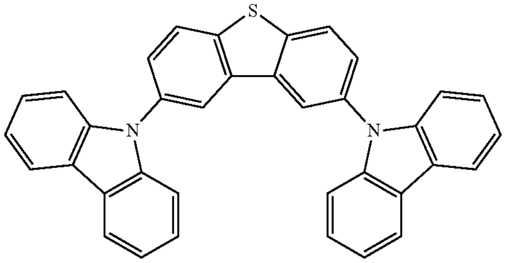

,

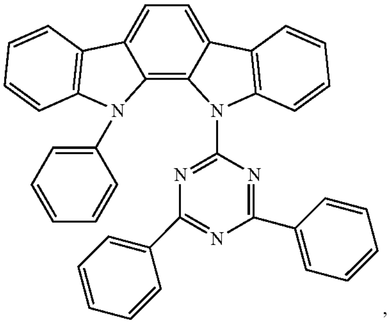

,

-continued
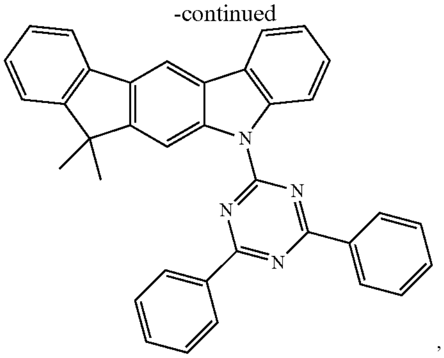
,
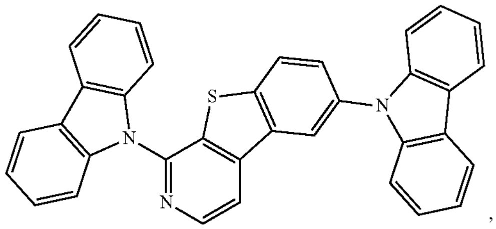
,
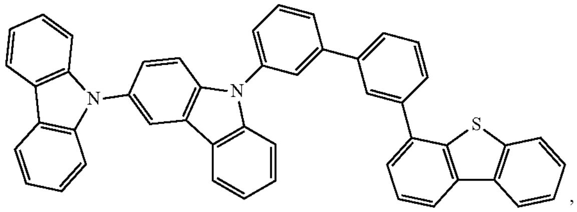
,
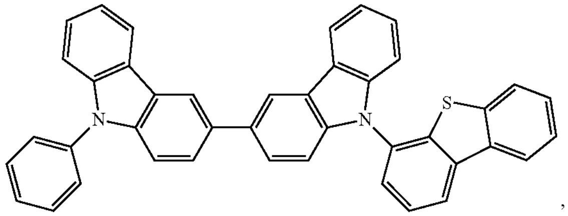
,
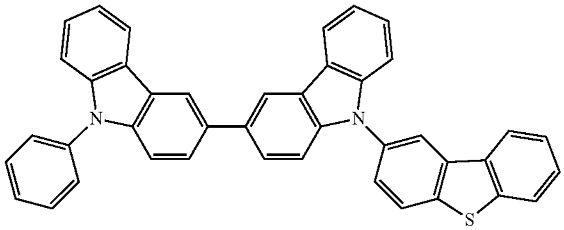
,
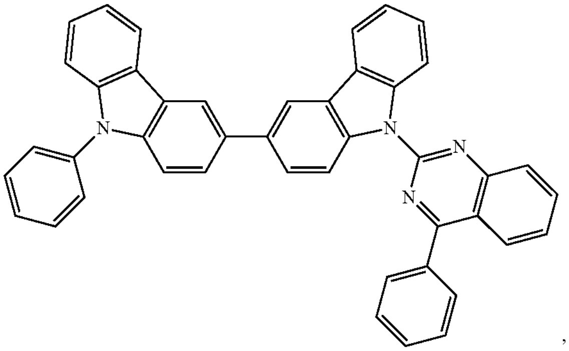
,
-continued
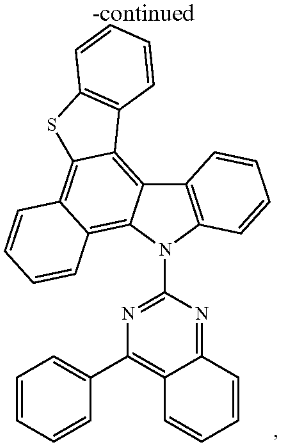
,
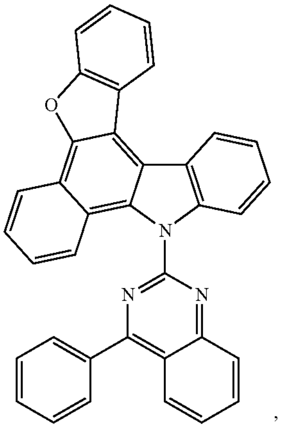
,
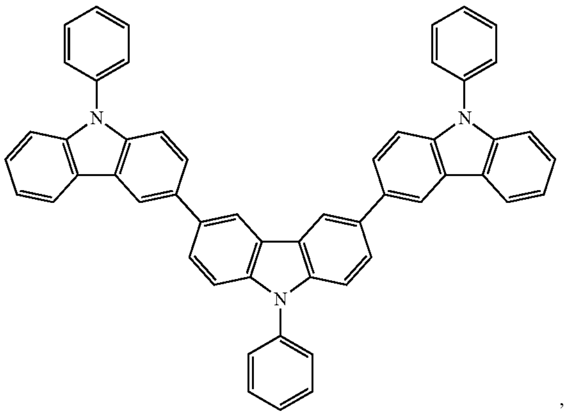
,
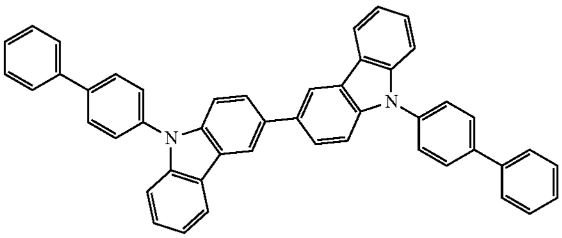
,
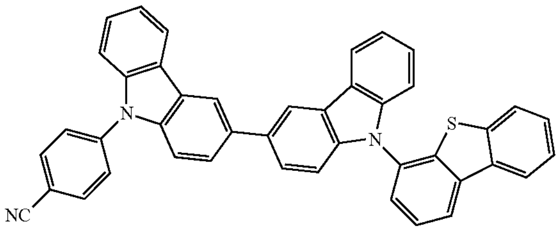
, -continued

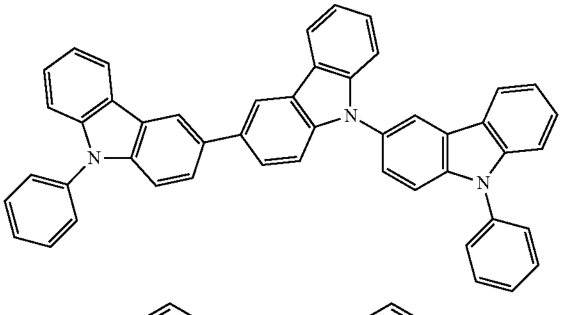

,

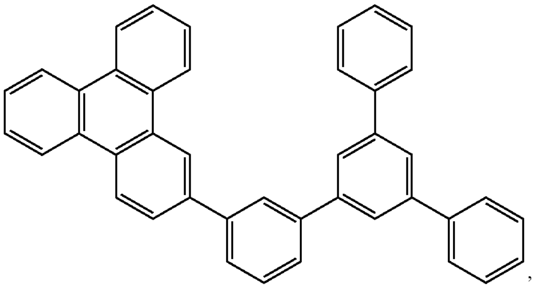

,

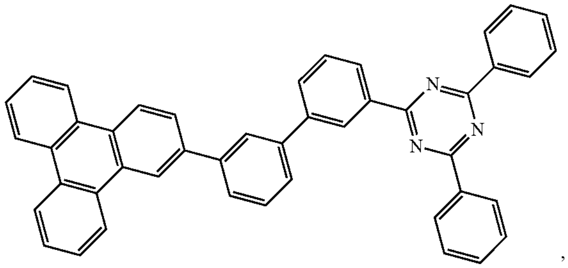

,

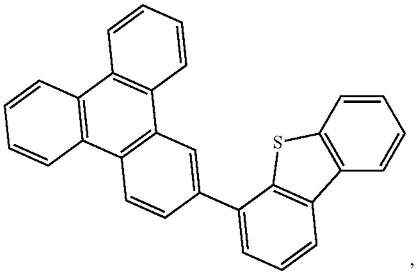

,

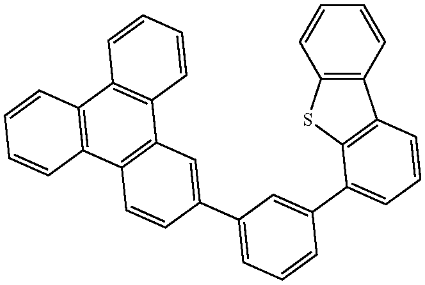

,

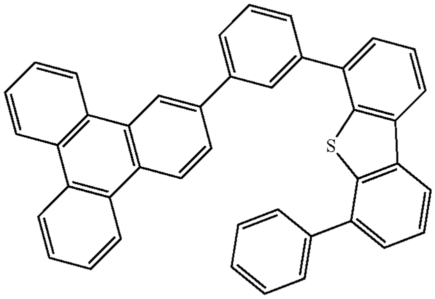

,

-continued

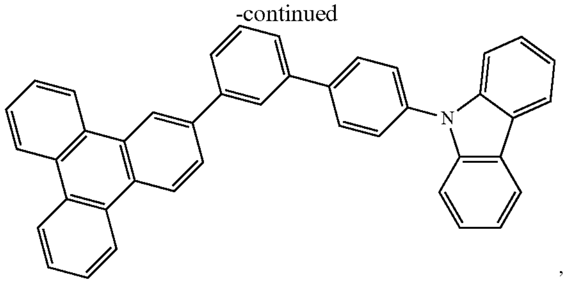

,

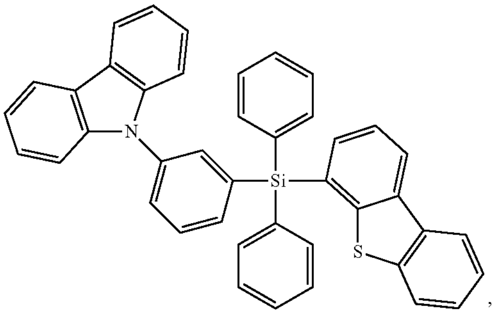

,

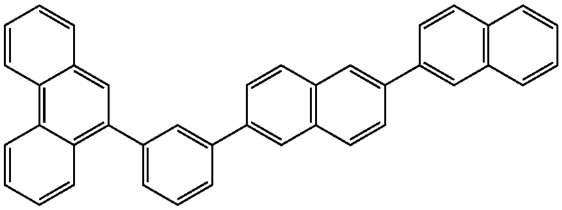

, and combinations thereof.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

According to another aspect, a formulation comprising the compound described herein is also disclosed.

The organic layer can also include a host. In some embodiments, two or more hosts are preferred. In some embodiments, the hosts used maybe a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}OC_nH_{2n+1}$, $OAr_1$, $N(C_nH_{2n+1})_2$, $N(Ar_1)(Ar_2)$, $CH{=}CH{-}C_nH_{2n+1}$, $C{\equiv}C_nH_{2n+1}$, $Ar_1$, $Ar_1$-$Ar_2$, and $C_nH_{2n}{-}Ar_1$, or the host has no substitutions. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof. The host can be an inorganic compound. For example, a Zn containing inorganic material e.g. ZnS.

The host can be a compound comprising at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene. The host can include a metal complex. In one embodiment, the host comprises a metal complex. The host can be, but is not limited to, a specific compound selected from the group consisting of:

-continued
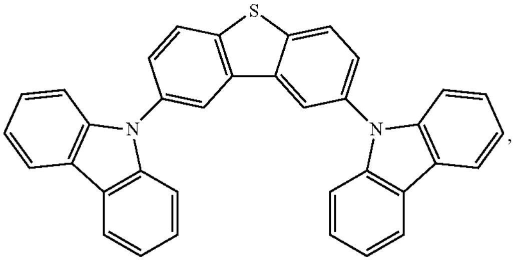,
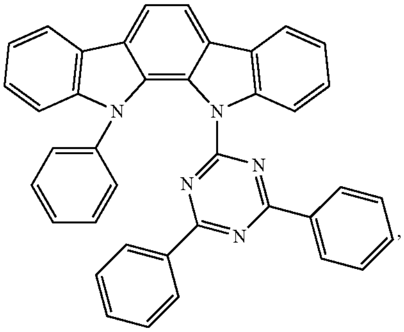,
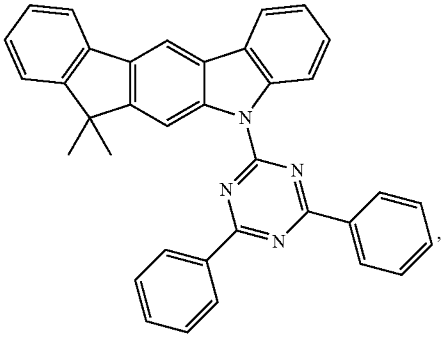,
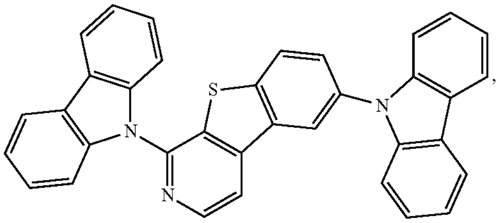,
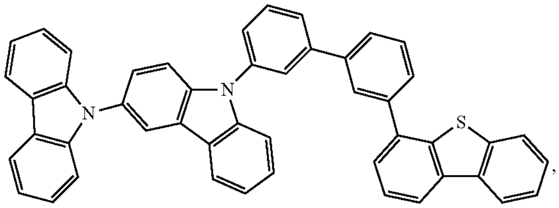,
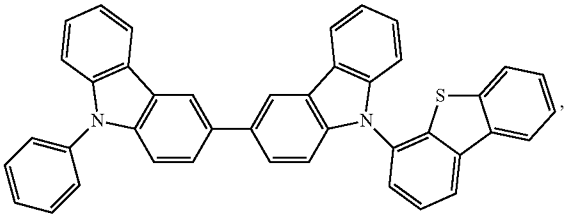,
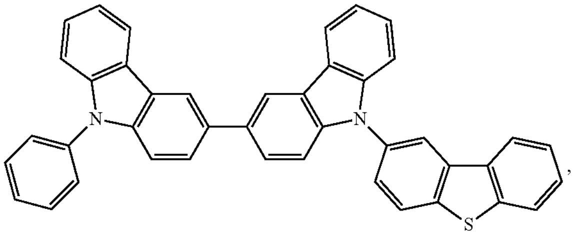,
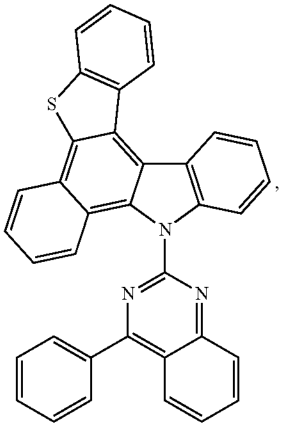,
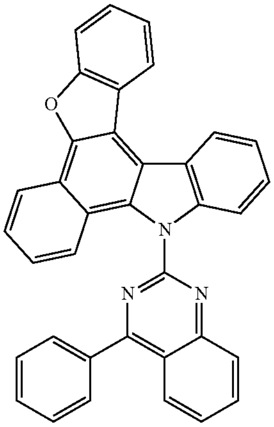,
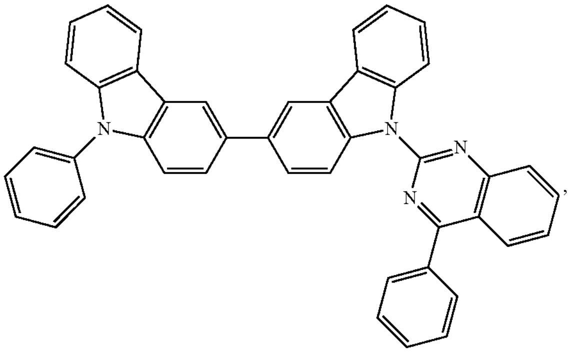,
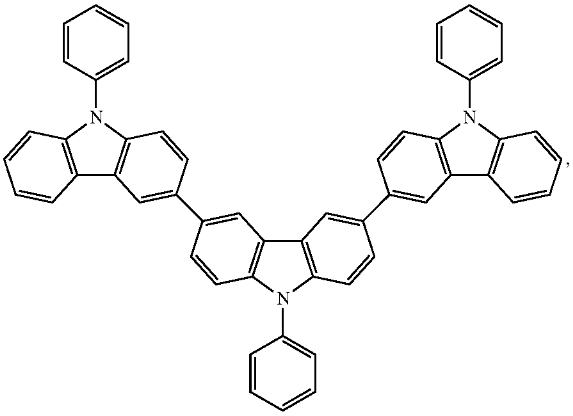,
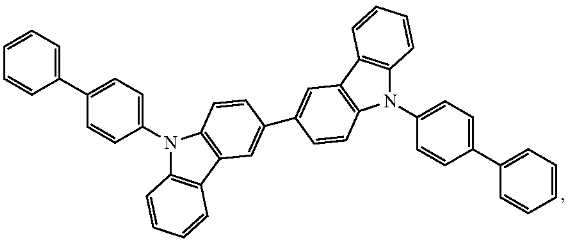, -continued

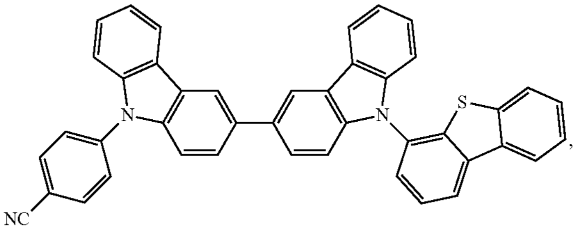

,

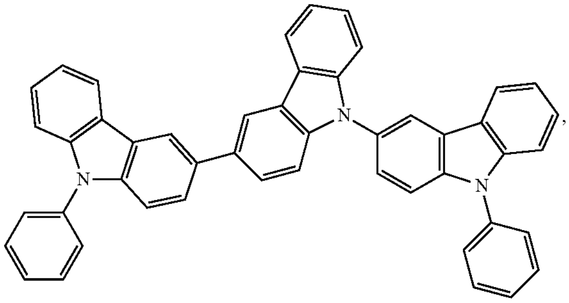

,

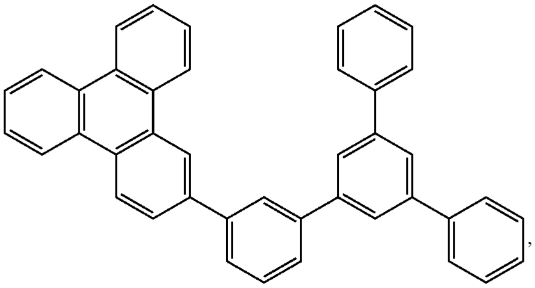

,

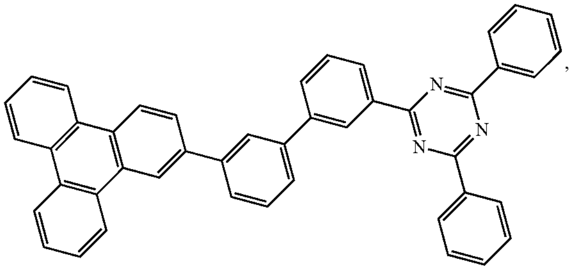

,

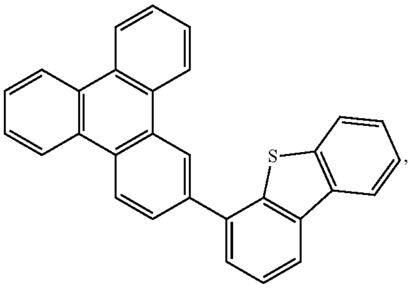

,

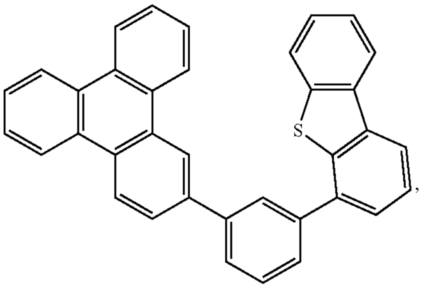

,

-continued

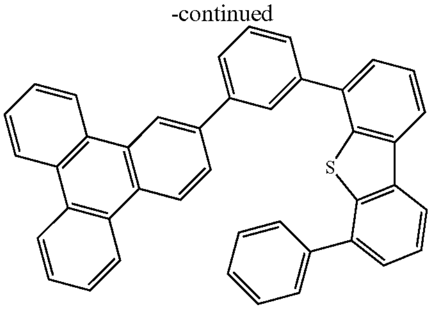

,

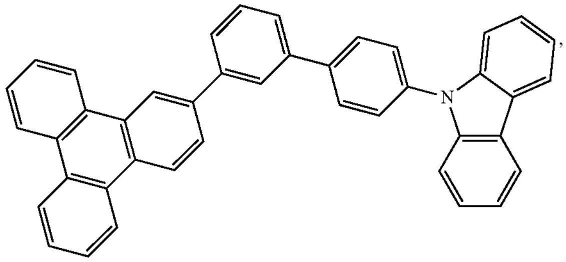

,

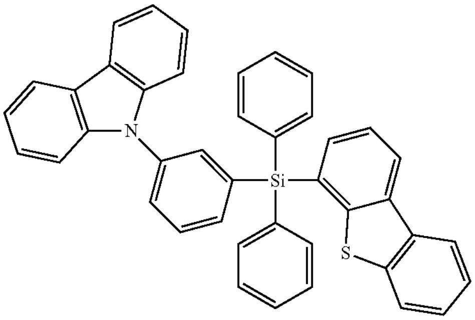

,

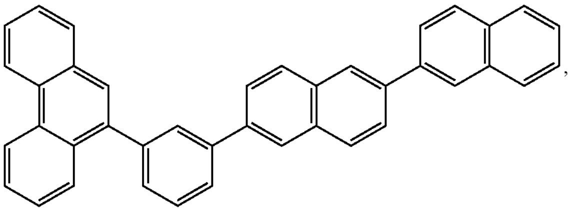

, and combinations thereof.

Additional information on possible hosts is provided below.

In yet another aspect of the present disclosure, a formulation that comprises the novel compound disclosed herein is described. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804 and US2012146012.

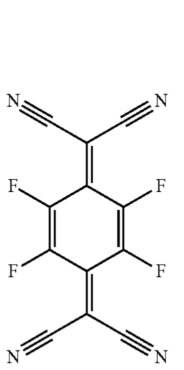

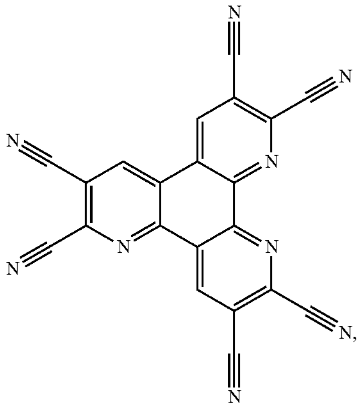

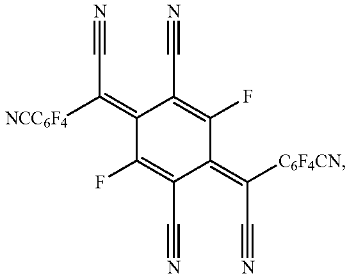

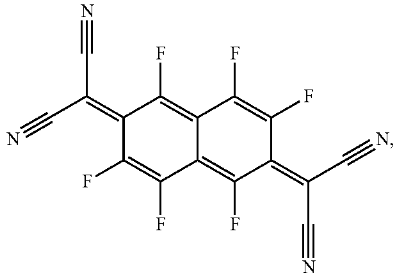

-continued

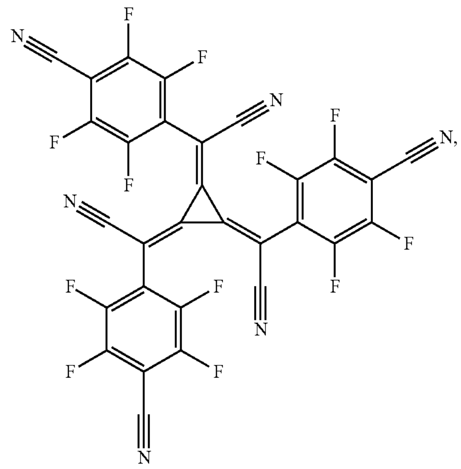

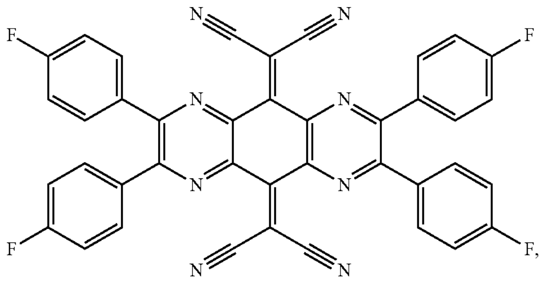

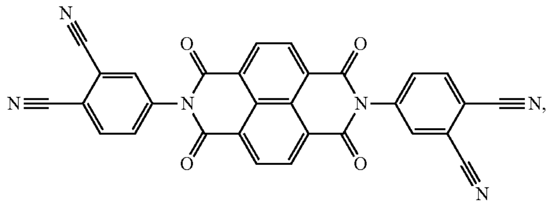

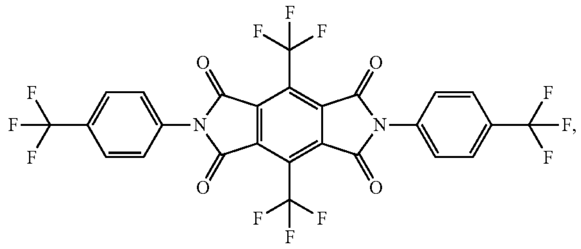

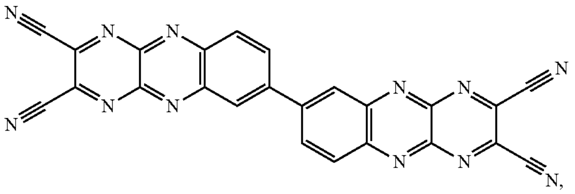

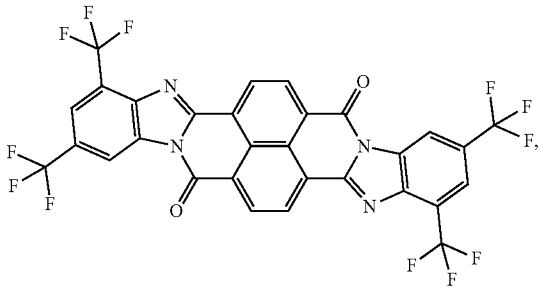

-continued

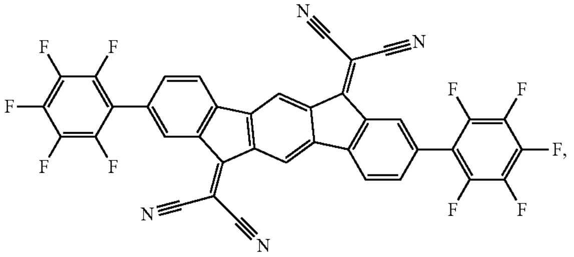

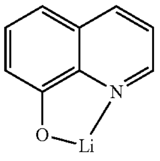

, and

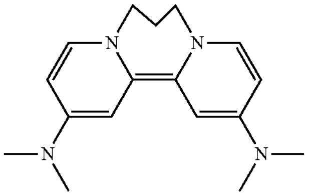

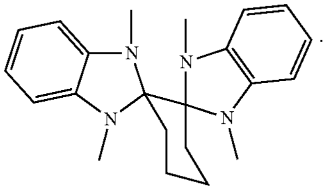

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

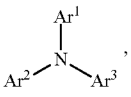

,

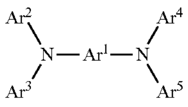

,

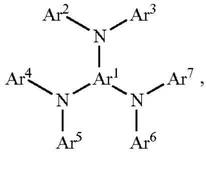

,

-continued

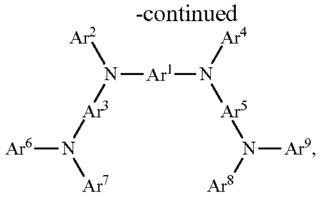

and

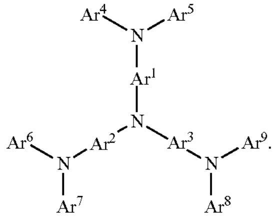

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocathazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

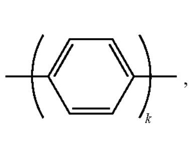

,

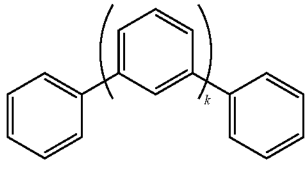

,

-continued

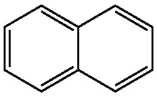, 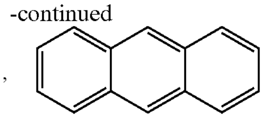,

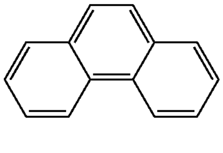, 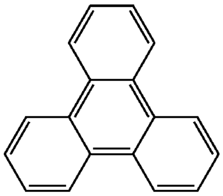,

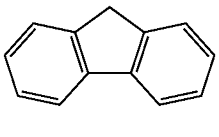, and 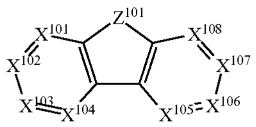, wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

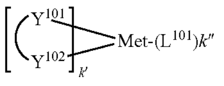

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^{+}$/Fc couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Pat. No. 06,517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

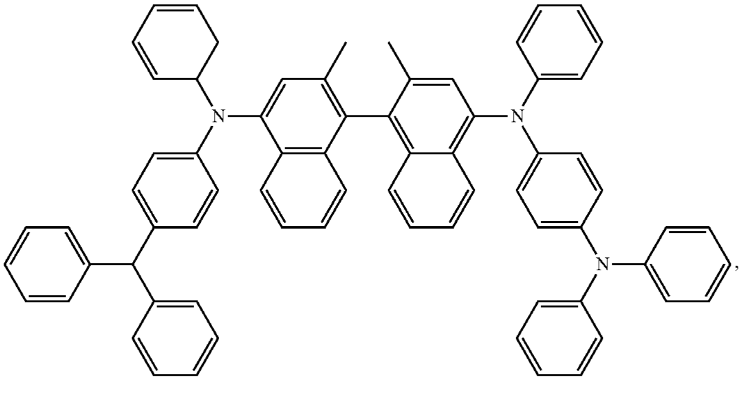,

-continued
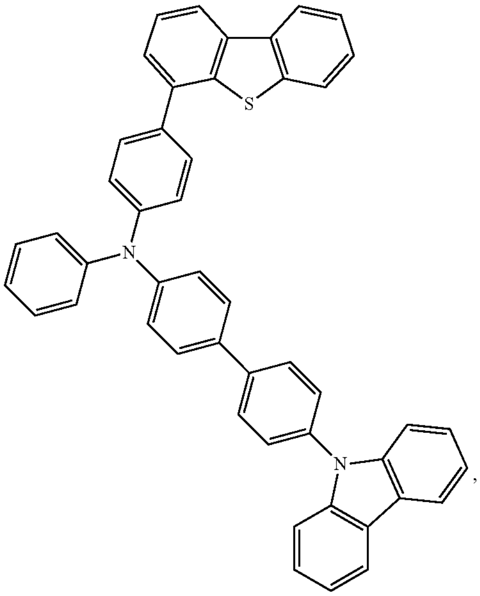
,
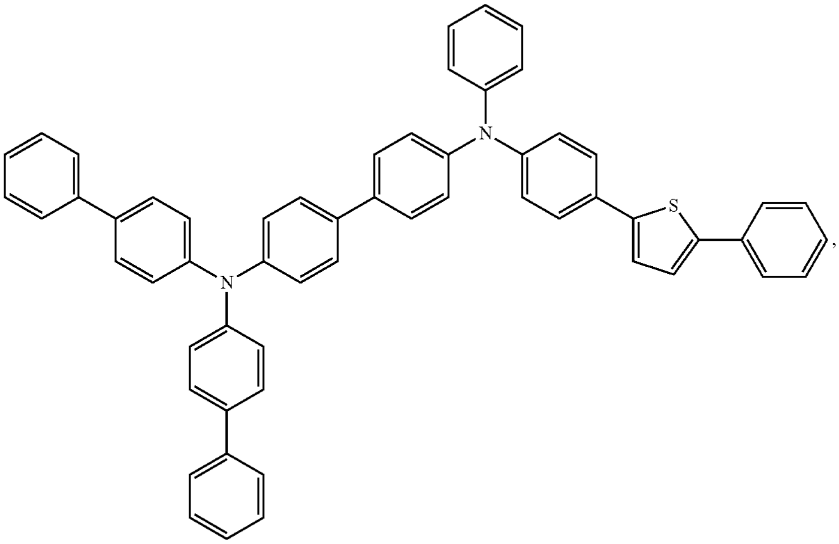
,
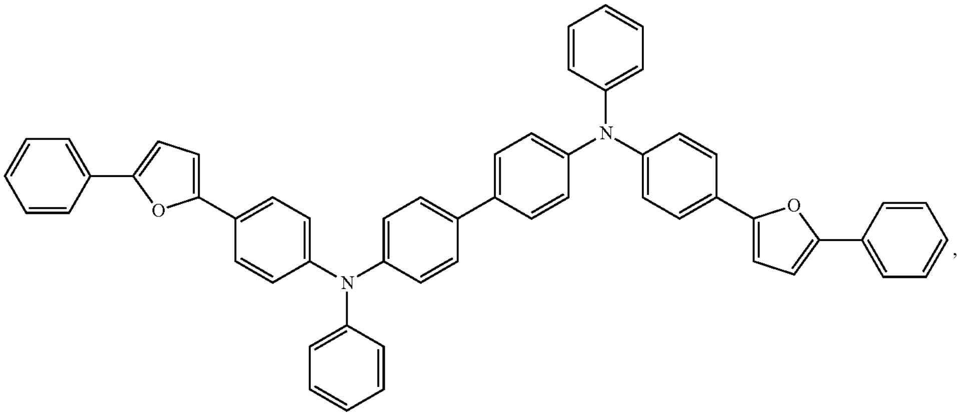
,

-continued
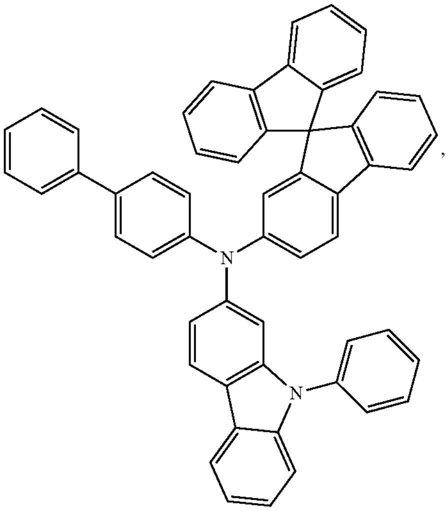
,
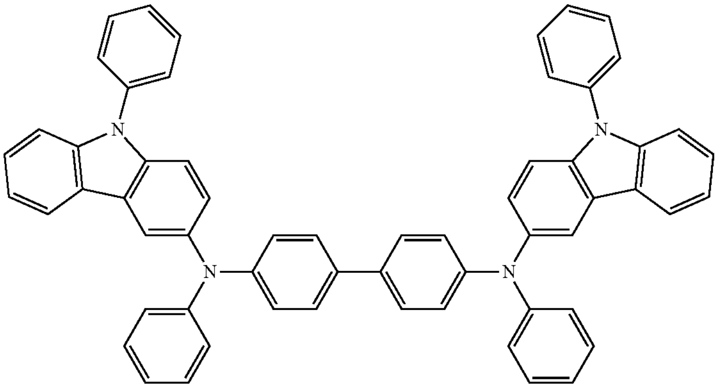
,
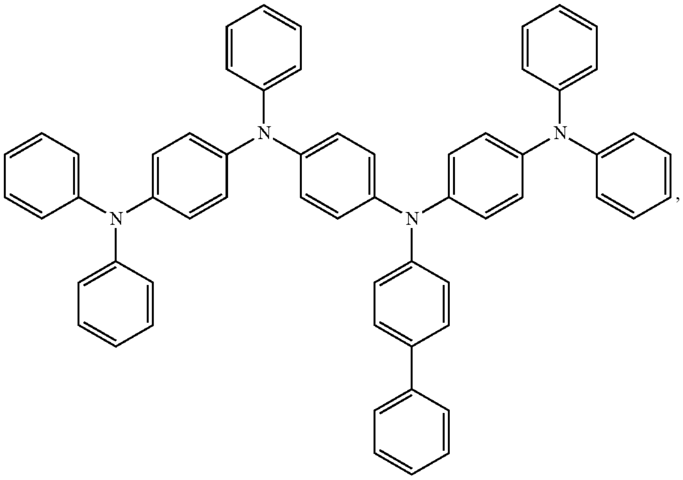
,
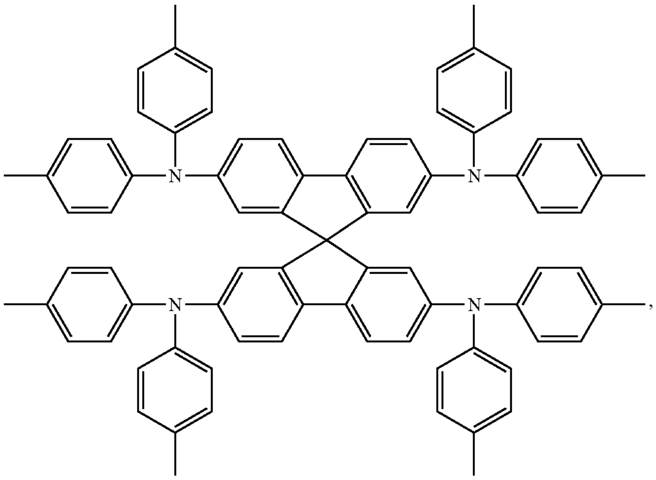
,

-continued
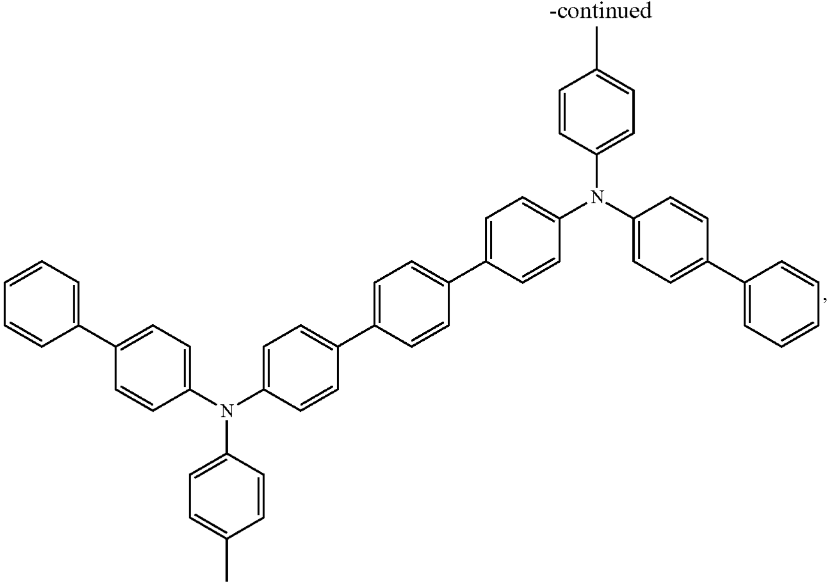
,
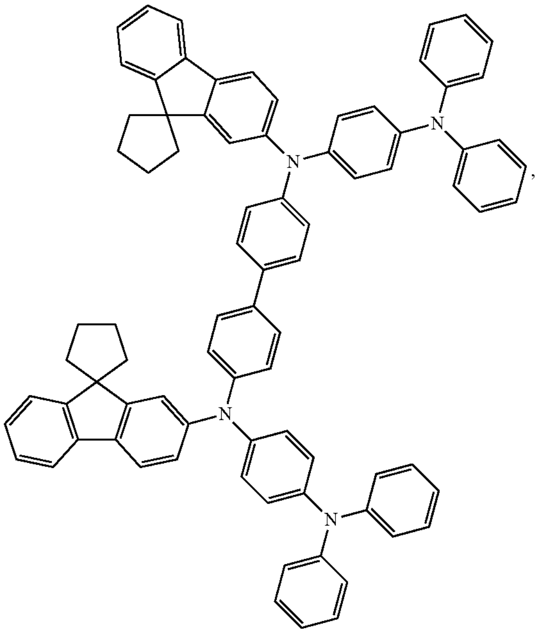
,
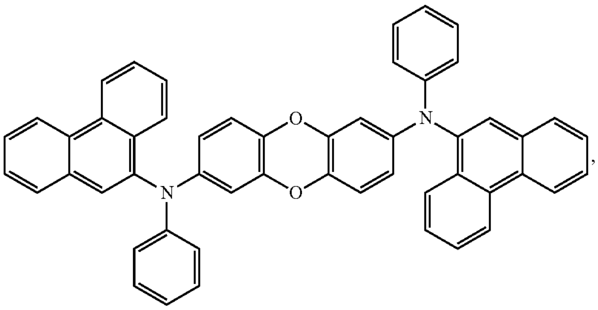
,
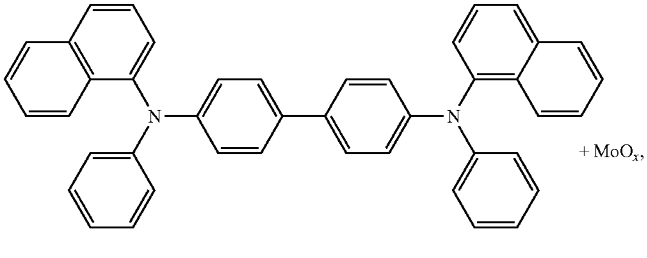
+ $MoO_x$,

-continued
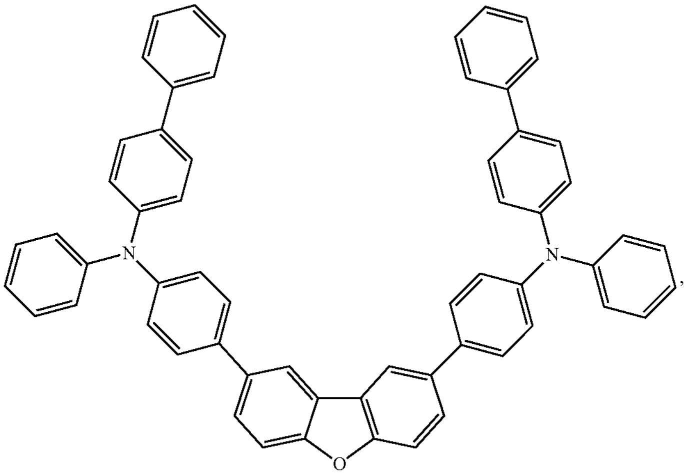
,
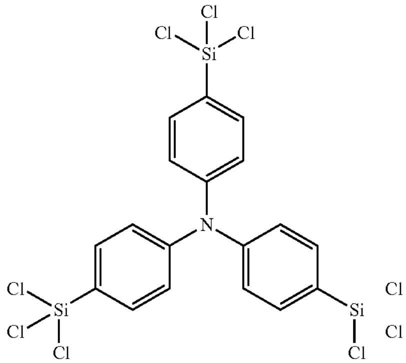
,
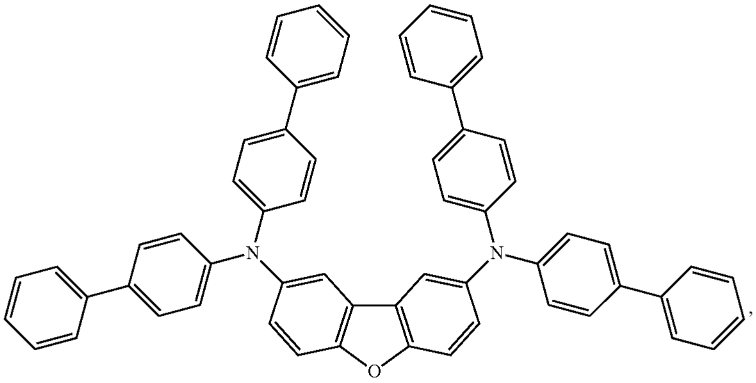
,
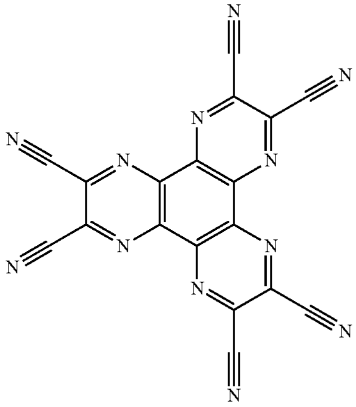
,
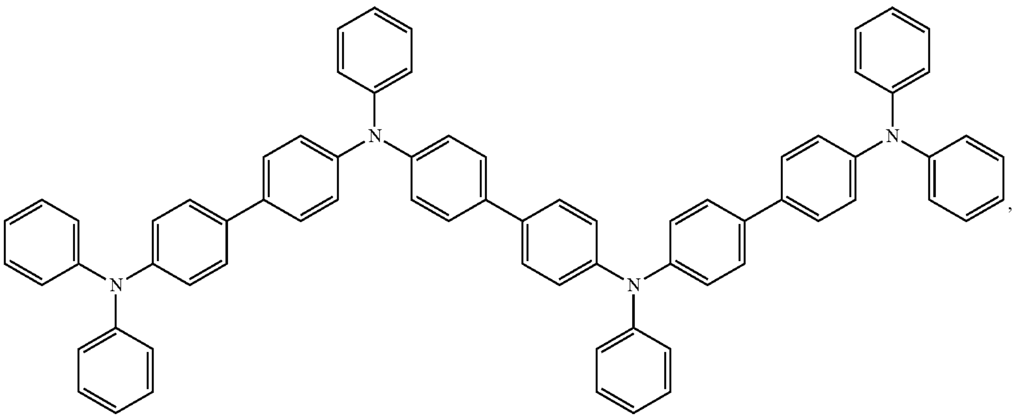
, -continued
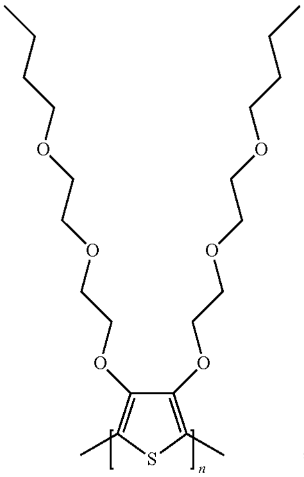
,
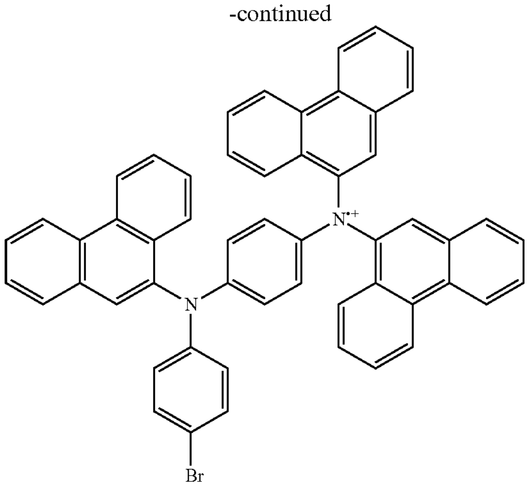
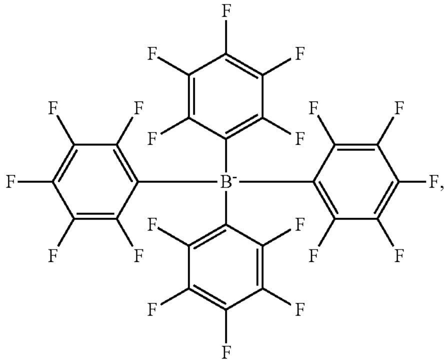
,
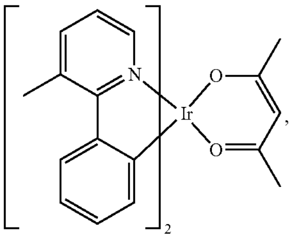
,
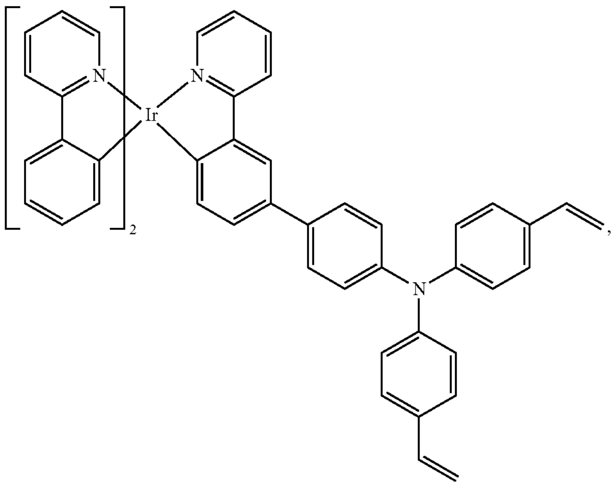
, -continued
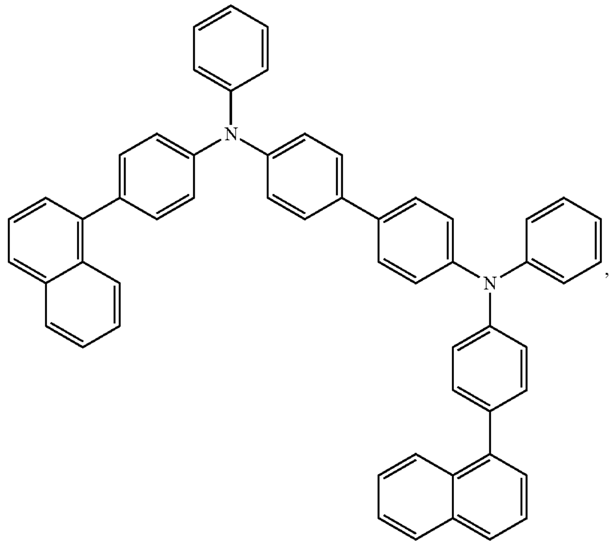
,
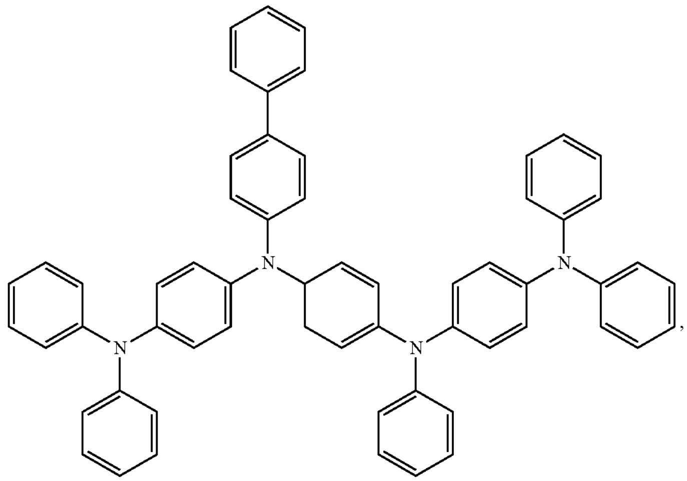
,
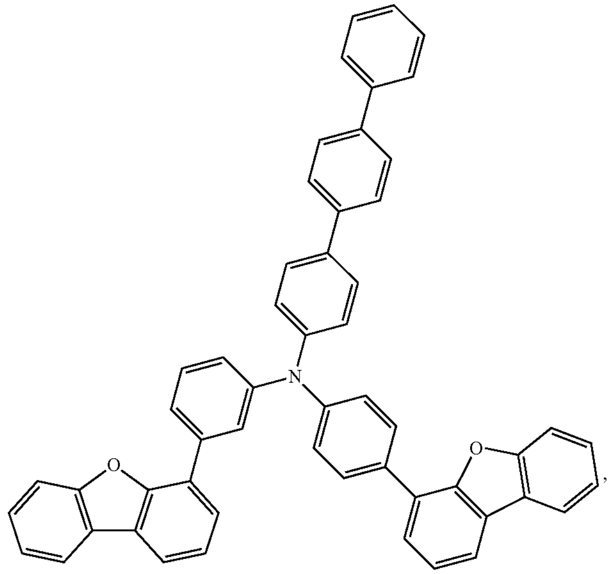
, -continued
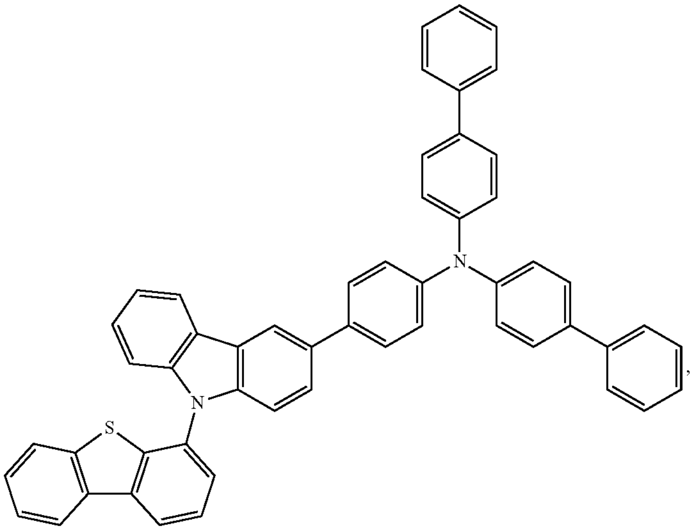
,
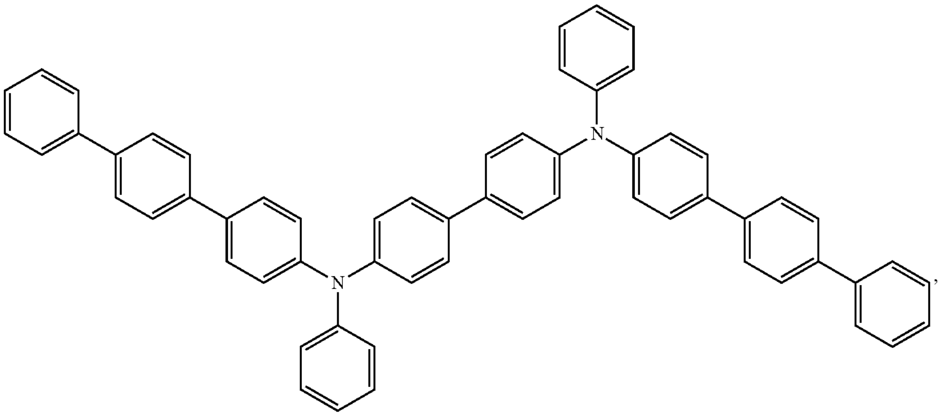
,
,
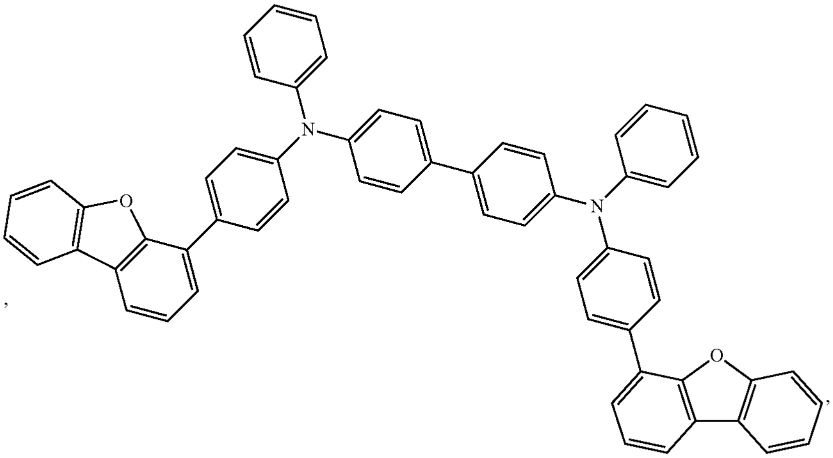
, -continued
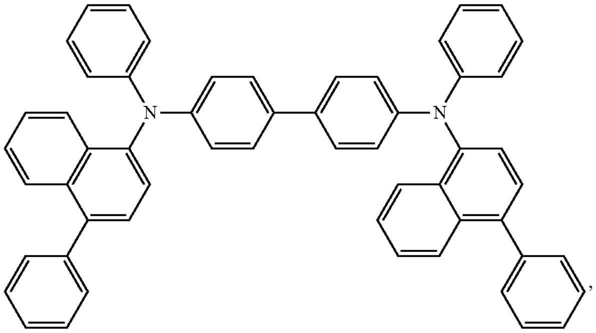
,
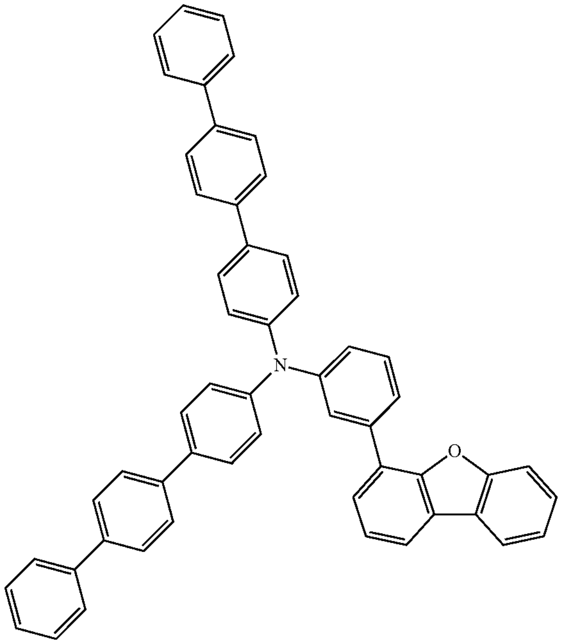
,
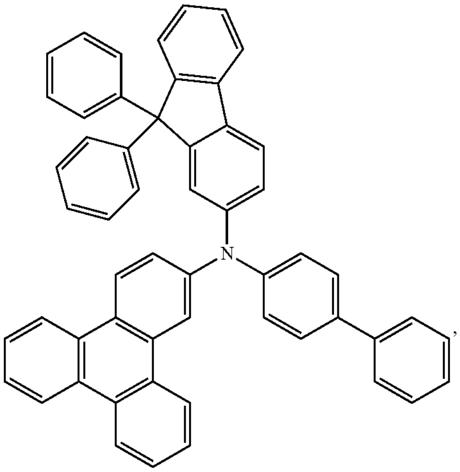
,
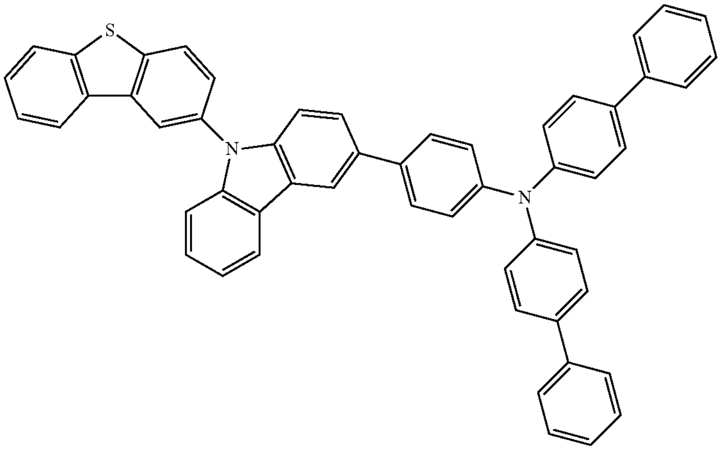
,
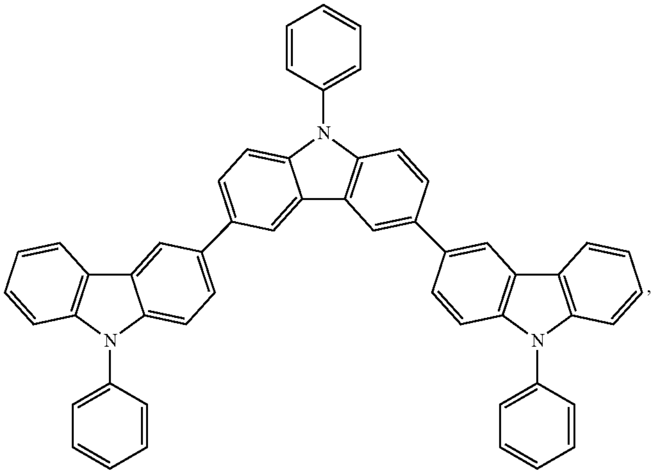
,
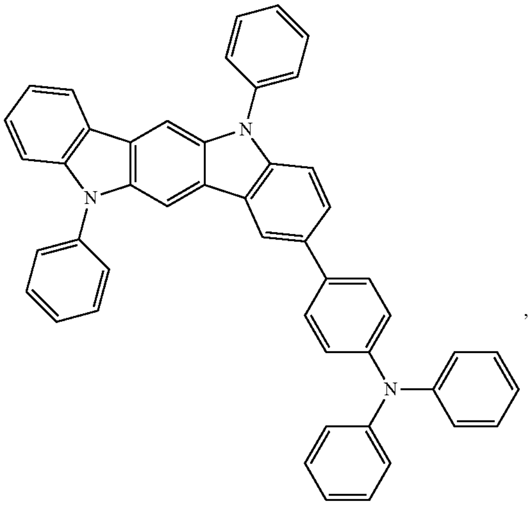
, -continued
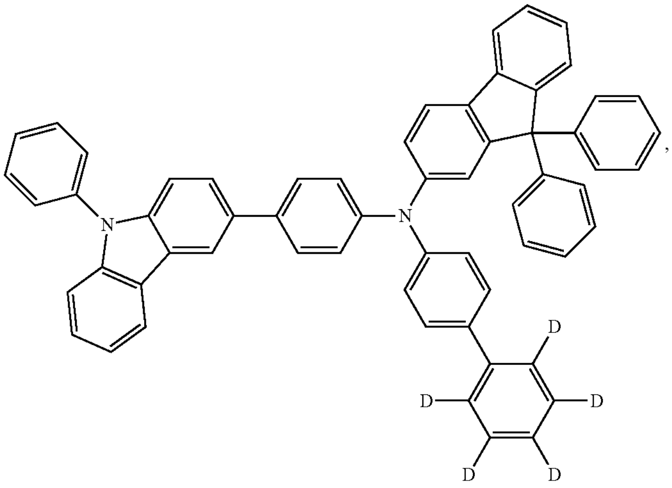
,
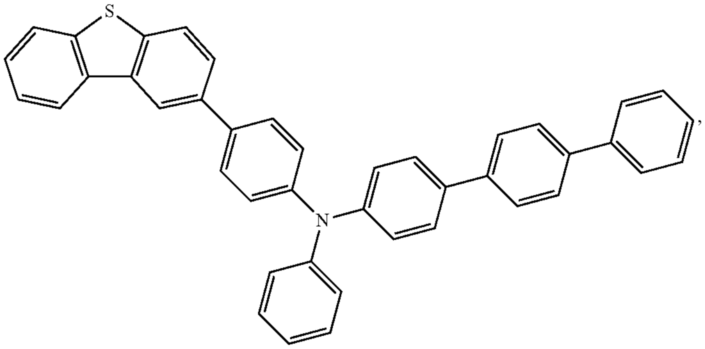
,
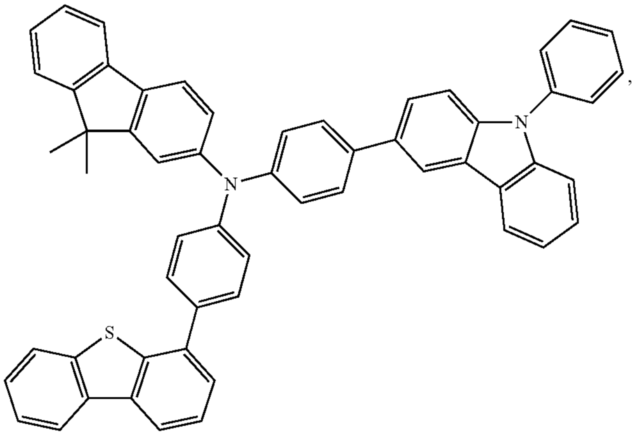
,
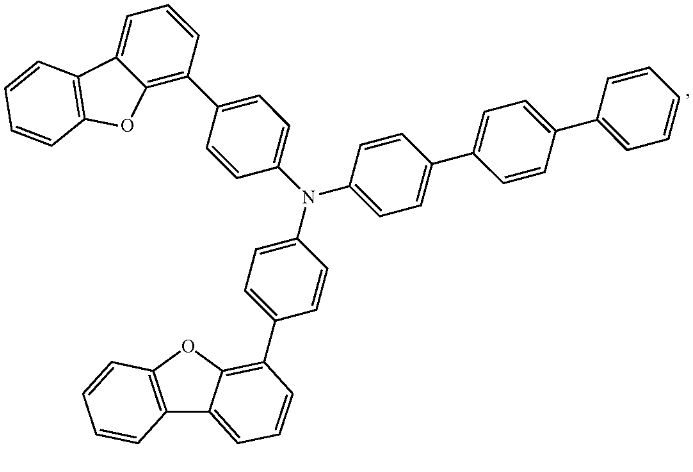
, -continued
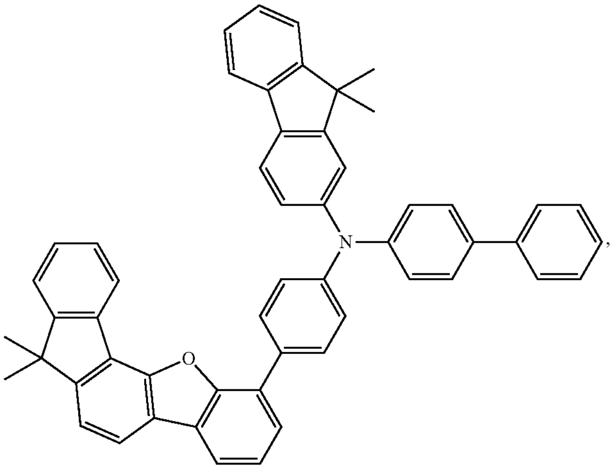
,
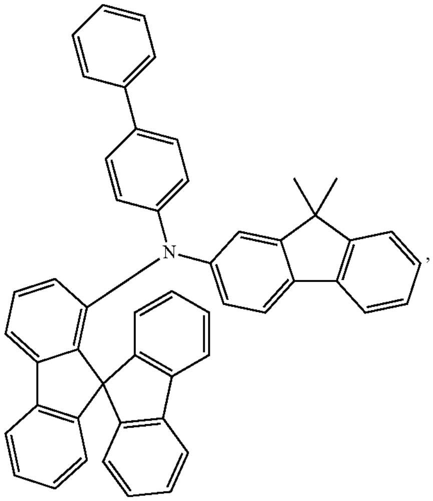
,
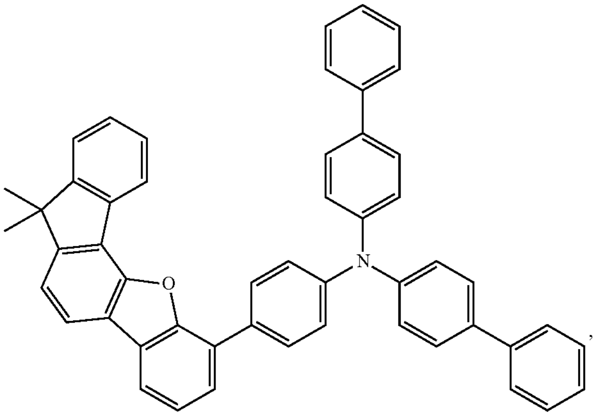
,
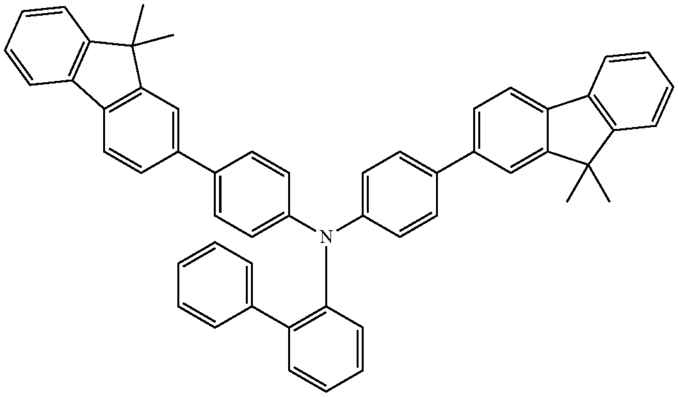
,
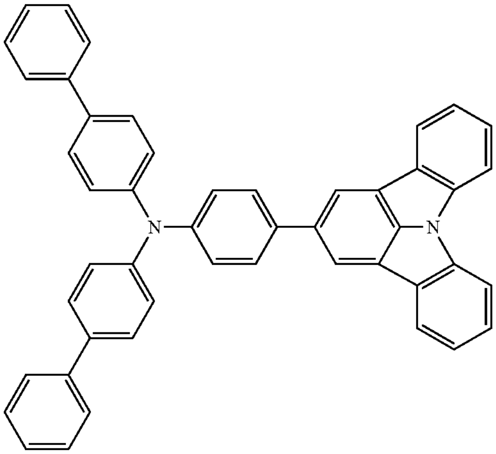
, -continued
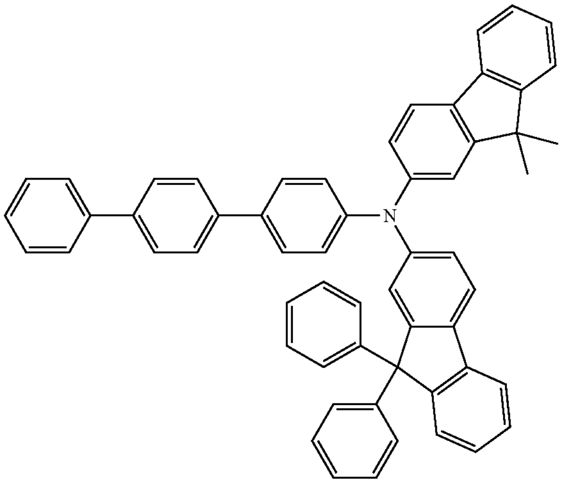
,
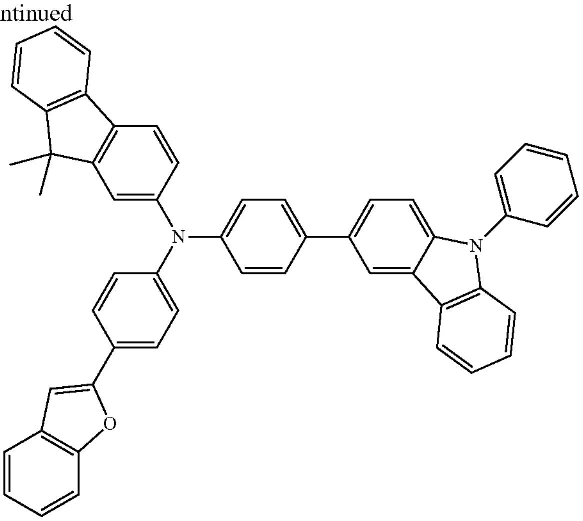
,
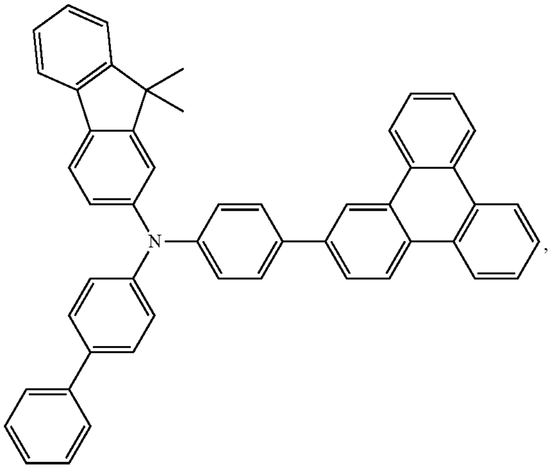
,
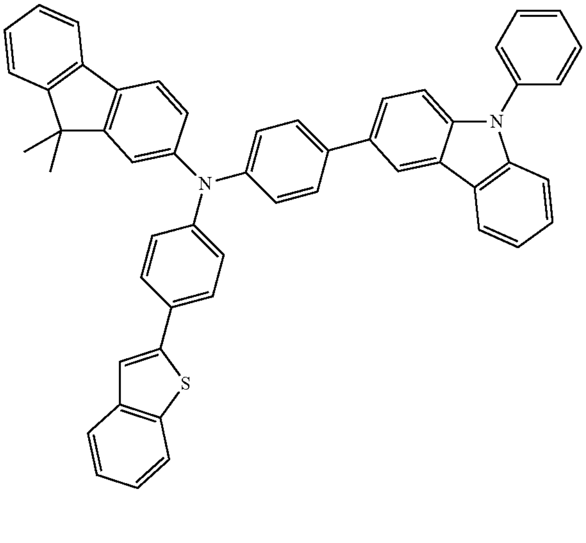
,
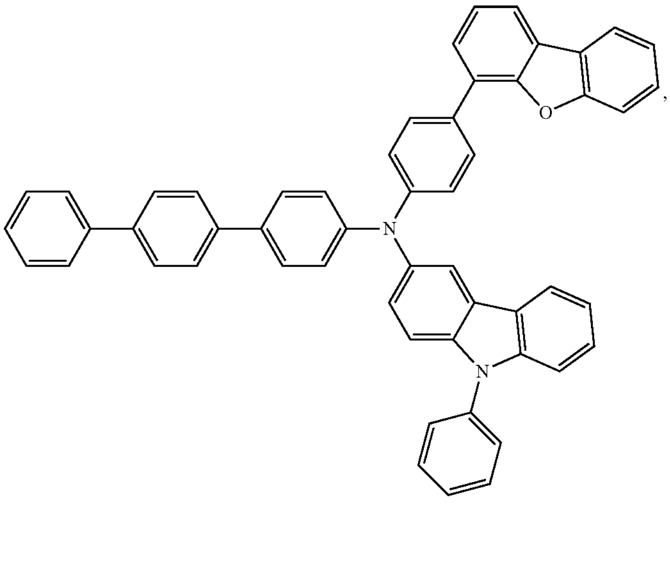
, -continued
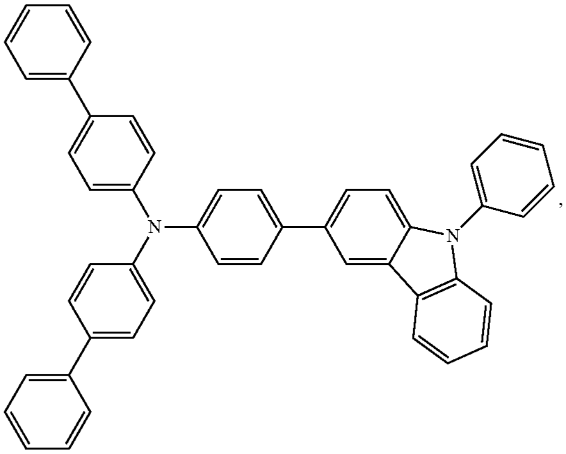
,
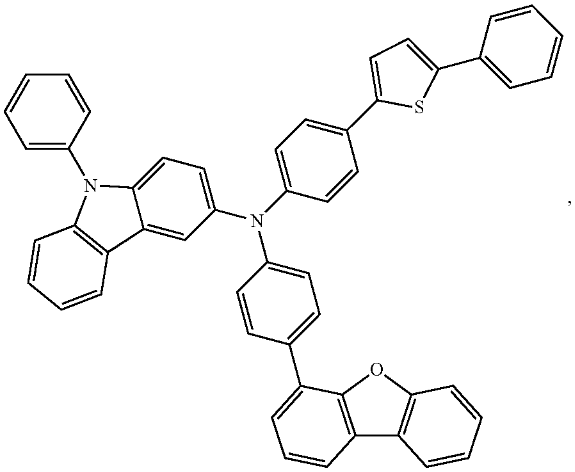
,
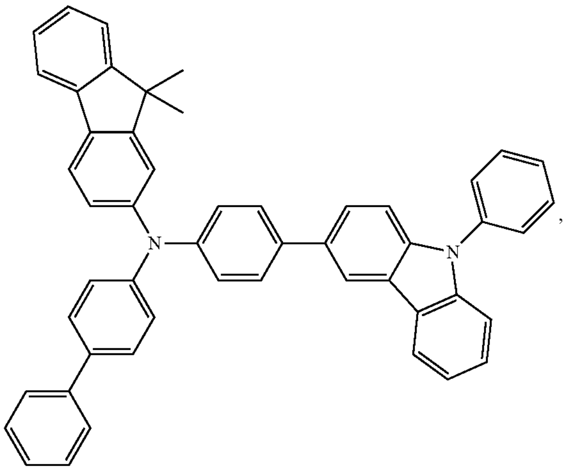
,
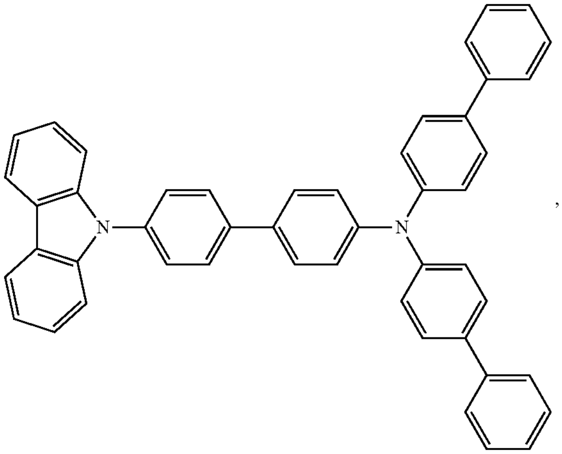
,
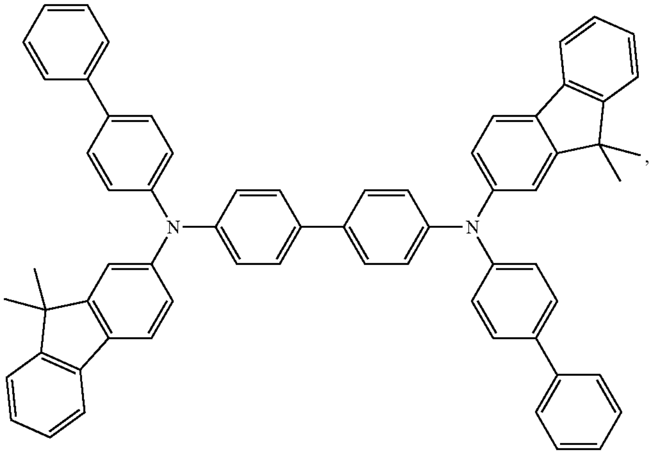
, -continued
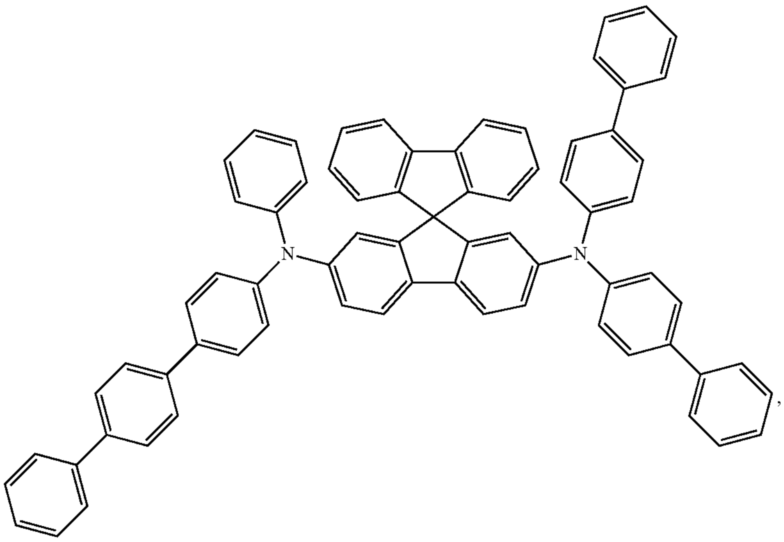
,
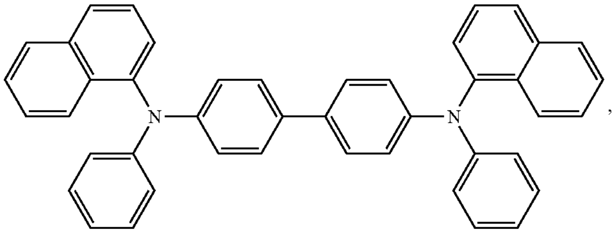
,
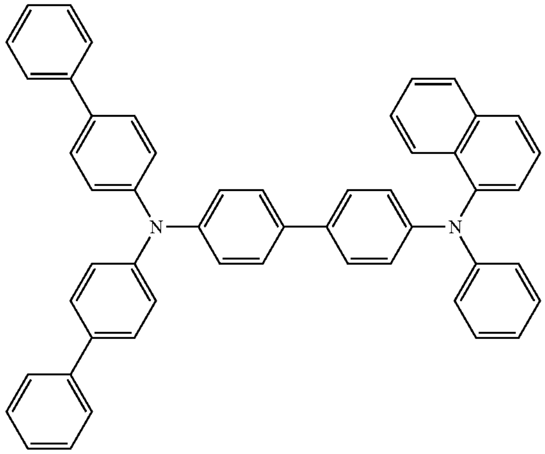
,
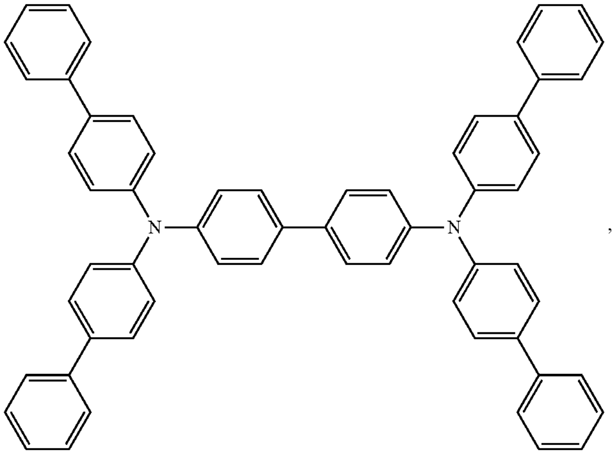
, -continued
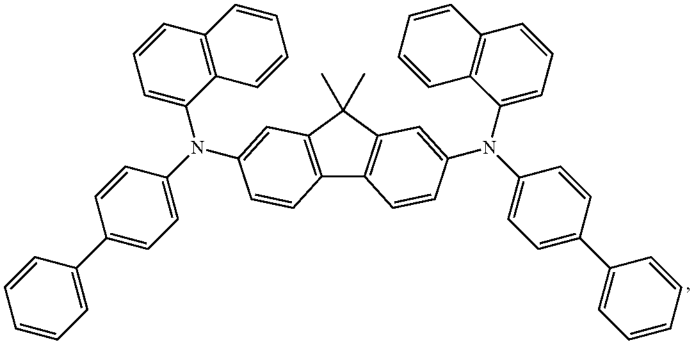
,
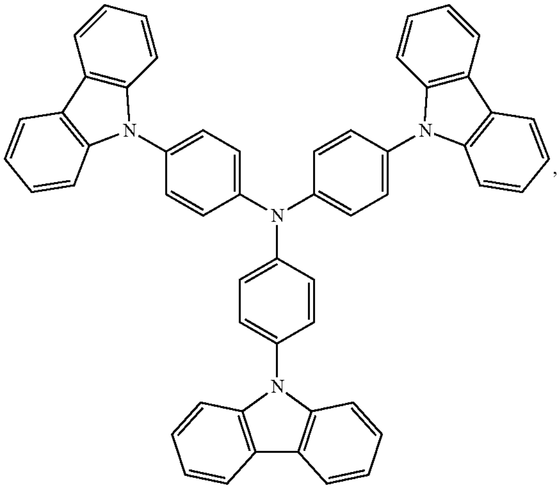
,
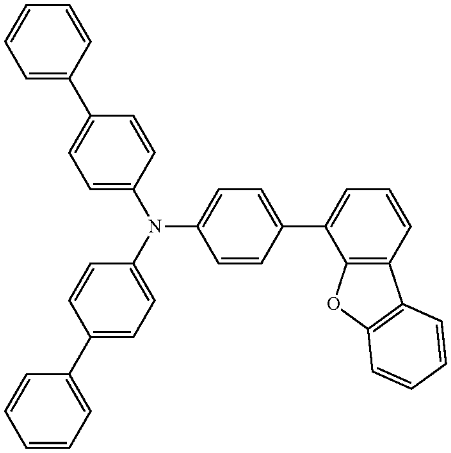
,
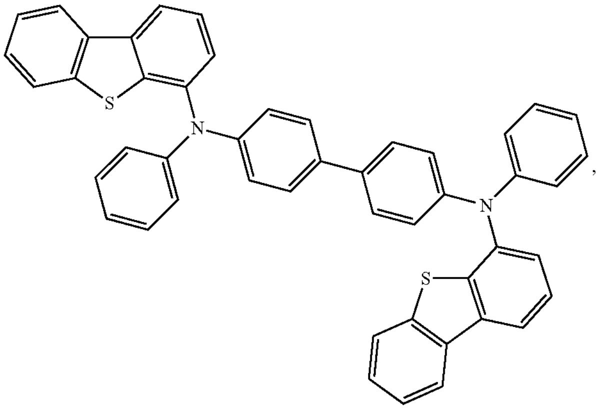
,
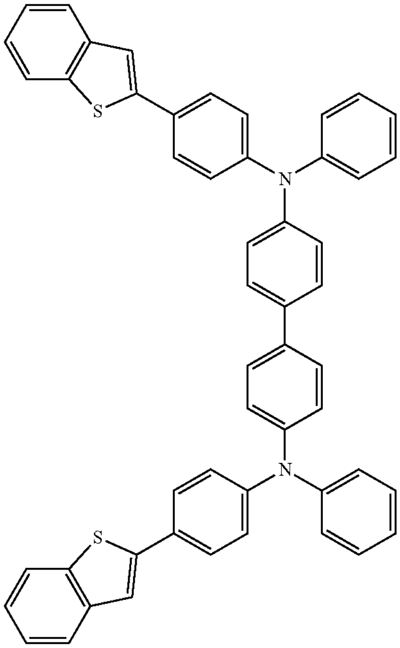
, and -continued

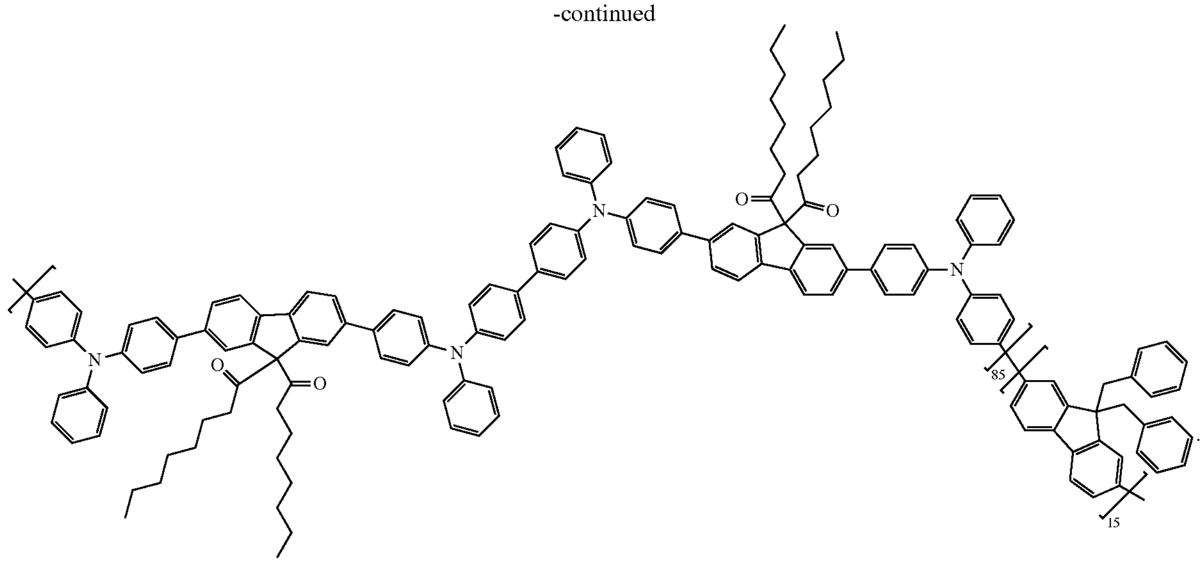

EBL:

An electron blocking layer (EBL) may be used to reduce the number of electrons and/or excitons that leave the emissive layer. The presence of such a blocking layer in a device may result in substantially higher efficiencies, and or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and or higher triplet energy than one or more of the hosts closest to the EBL interface. In one aspect, the compound used in EBL contains the same molecule or the same functional groups used as one of the hosts described below.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

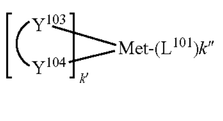

wherein Met is a metal; ($Y^{103}$-$Y^{104}$)) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

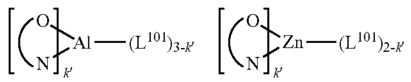

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of other organic compounds used as host are selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

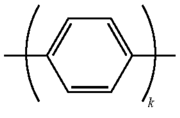
,
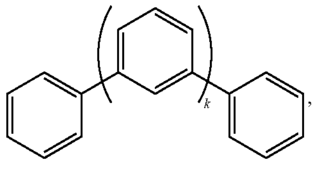
,
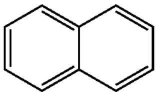
,
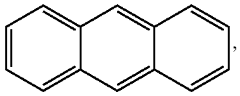
,
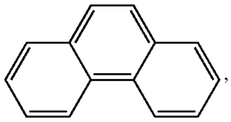
,
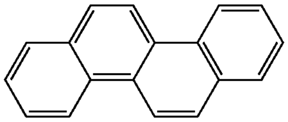
,
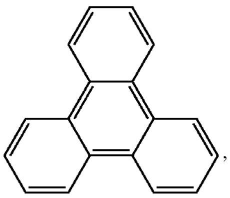
,
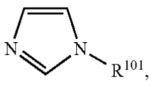
,
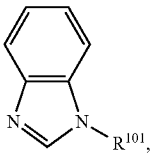
,
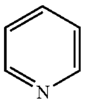
,
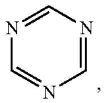
,
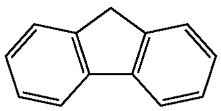
,
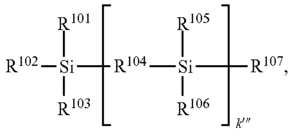
,
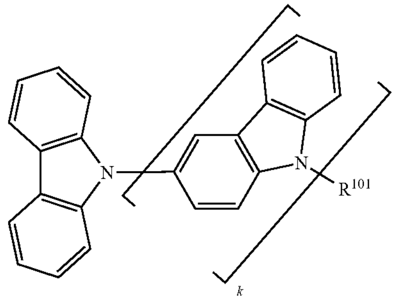
,
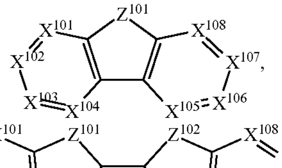
,
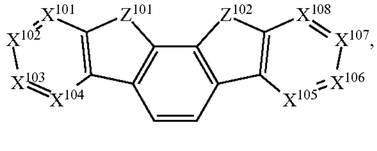

-continued

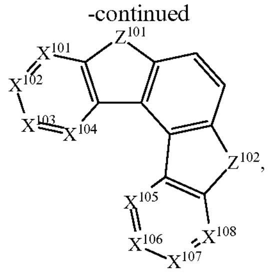
,
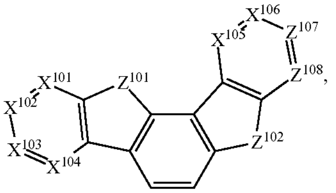
,
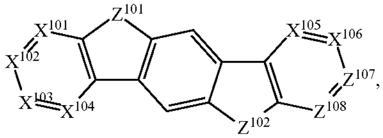
, and
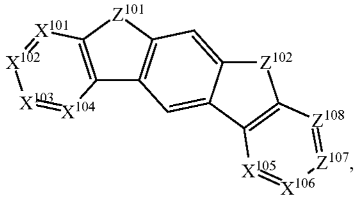
, wherein each of $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472,

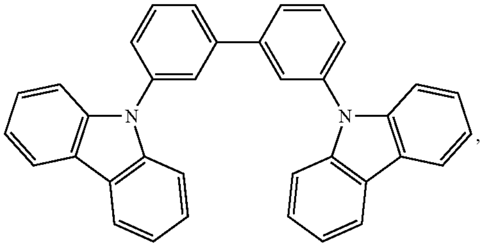,
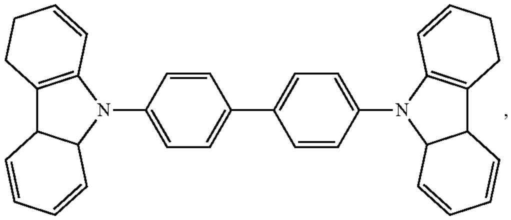,
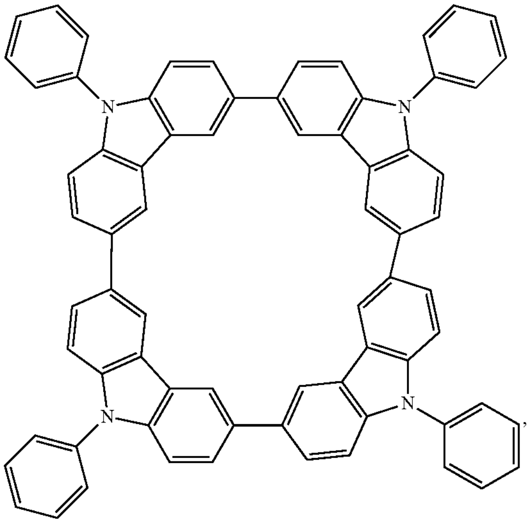,
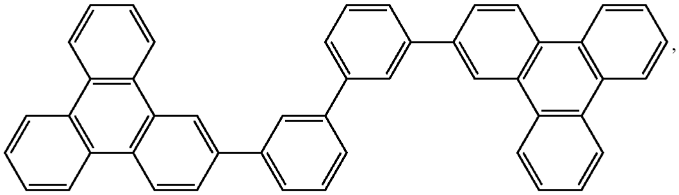,
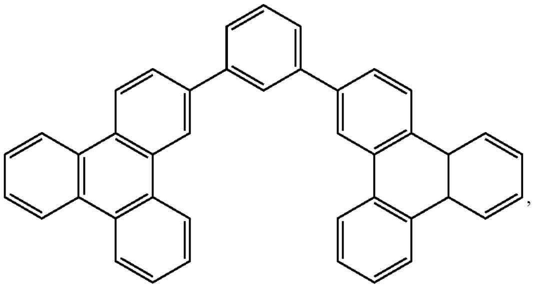,
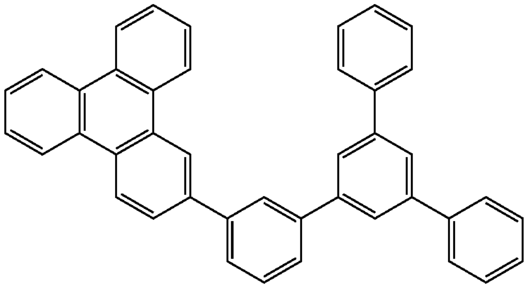,
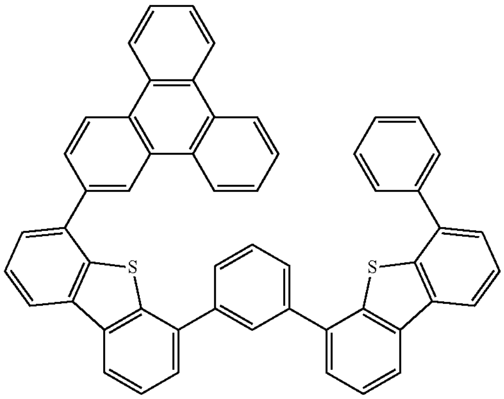,
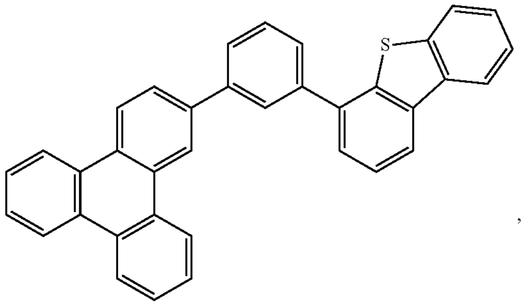, -continued
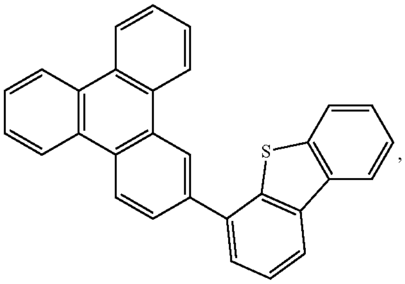,
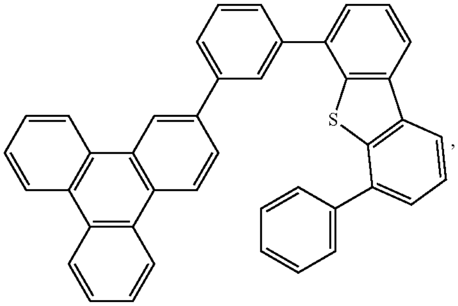,
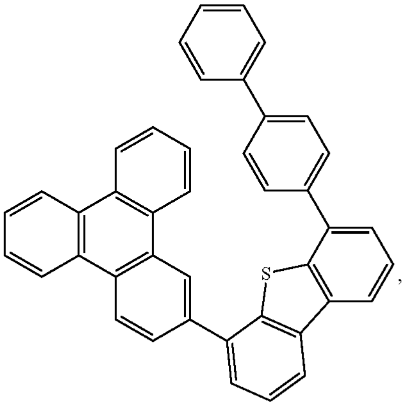,
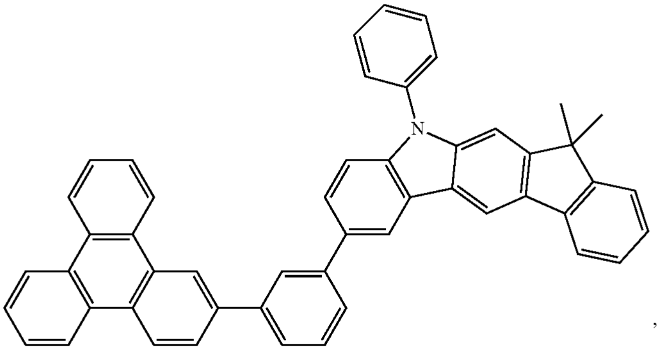,
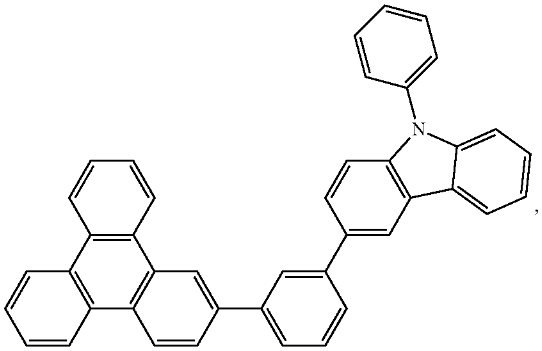,
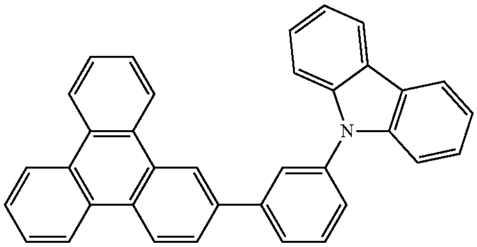,
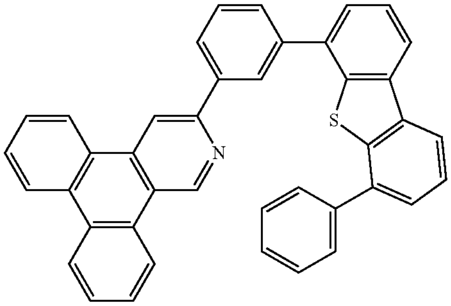,
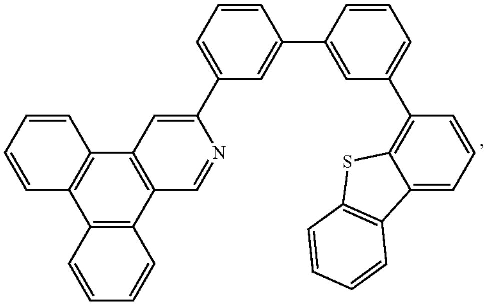, -continued
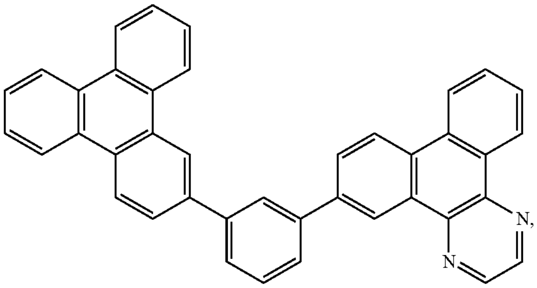
,
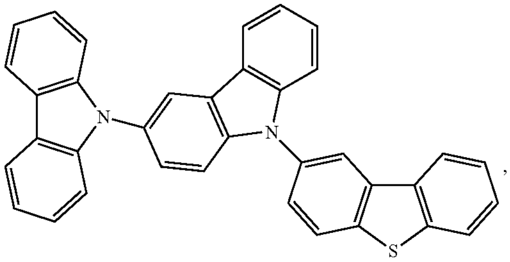
,
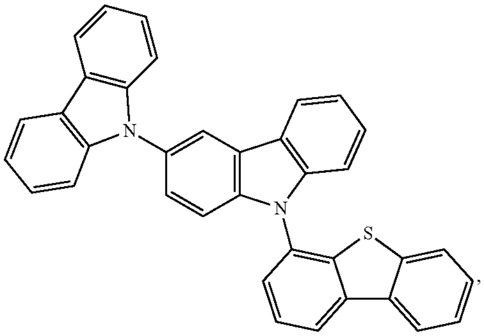
,
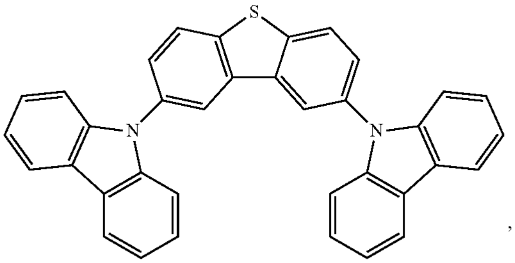
,
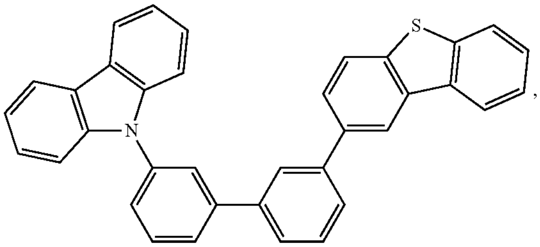
,
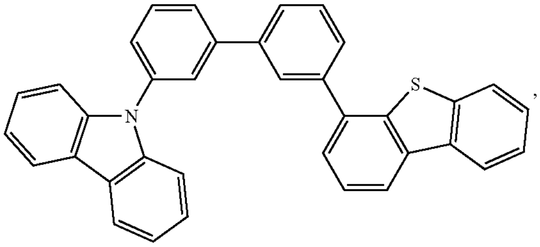
,
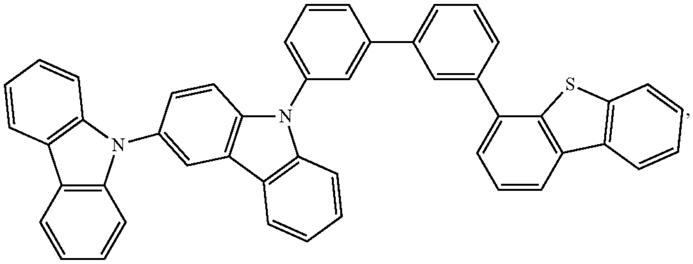
,
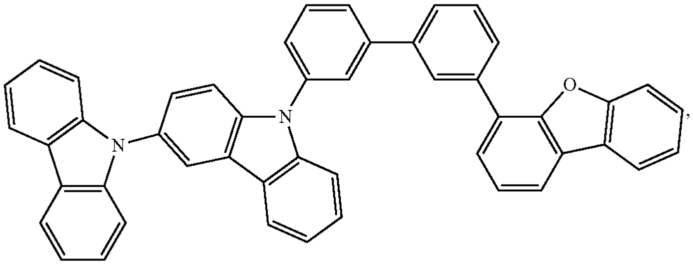
,
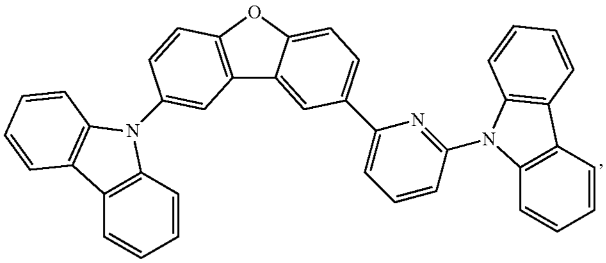
, -continued
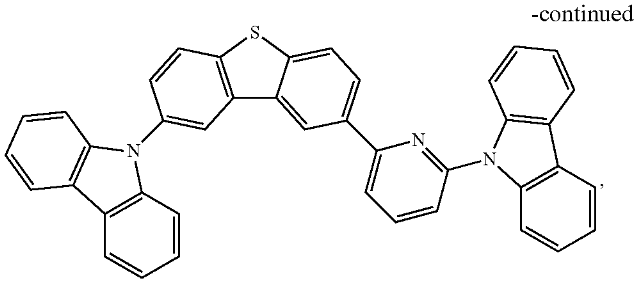
,
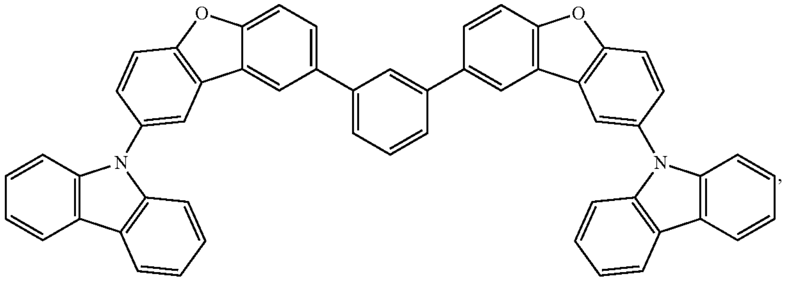
,
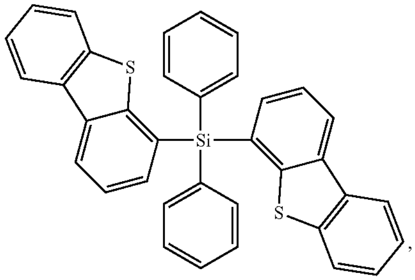
,
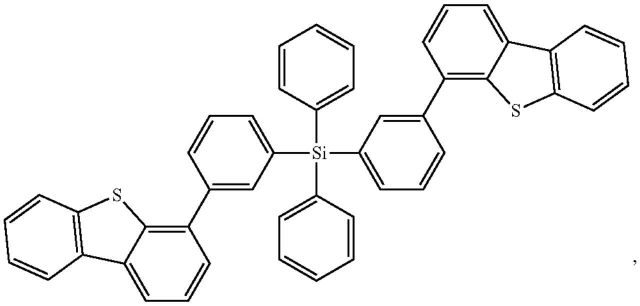
,
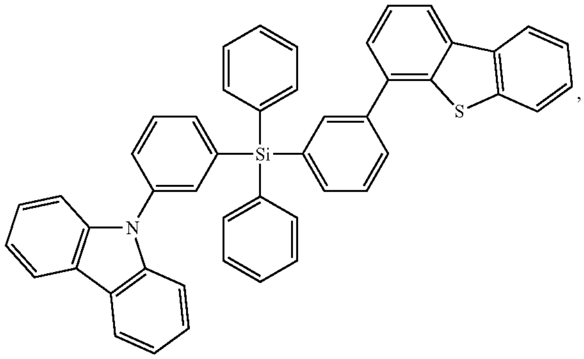
,
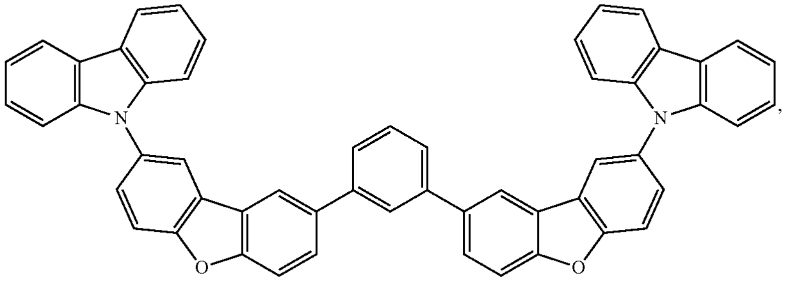
, -continued
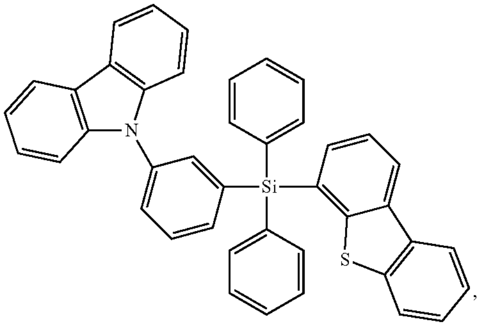,
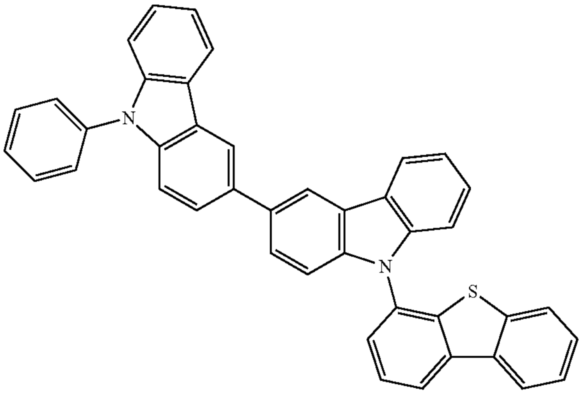,
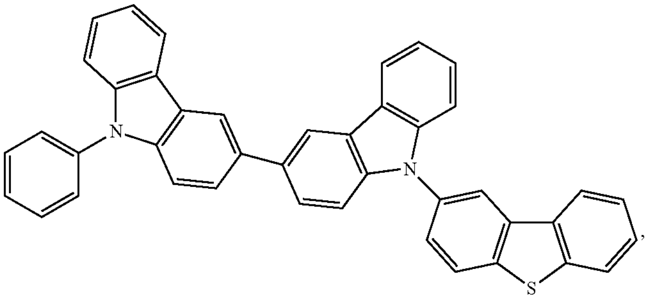,
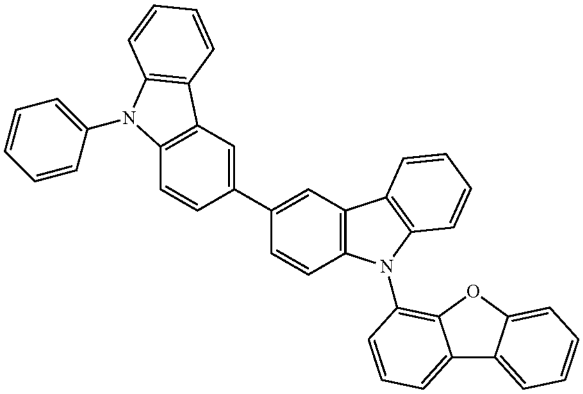,
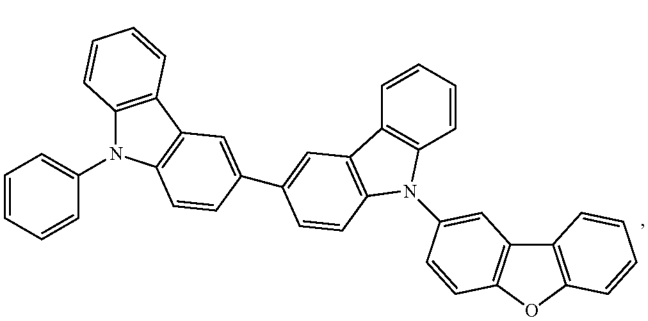,
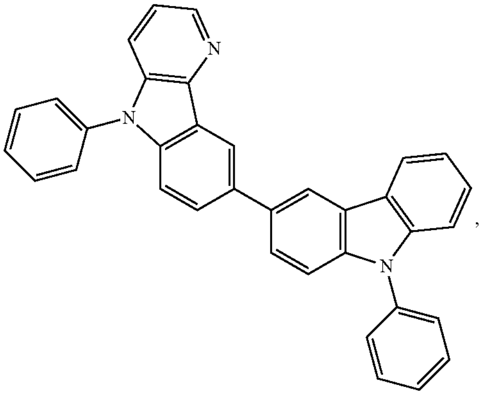, -continued
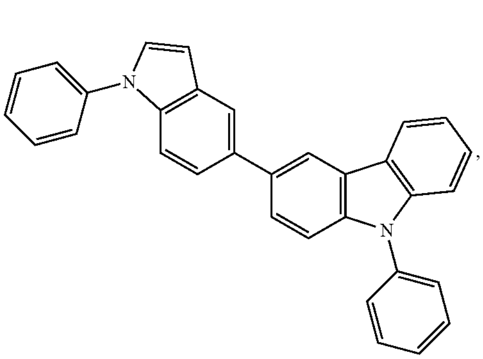
,
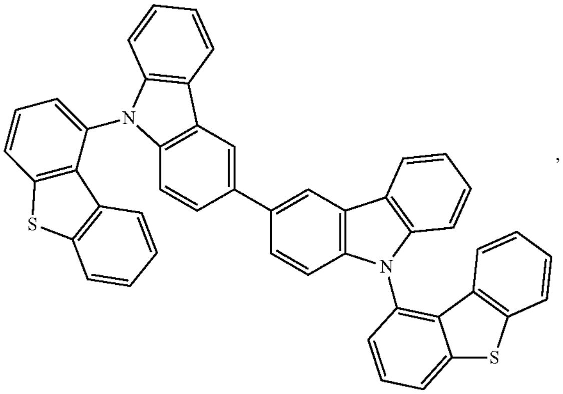
,
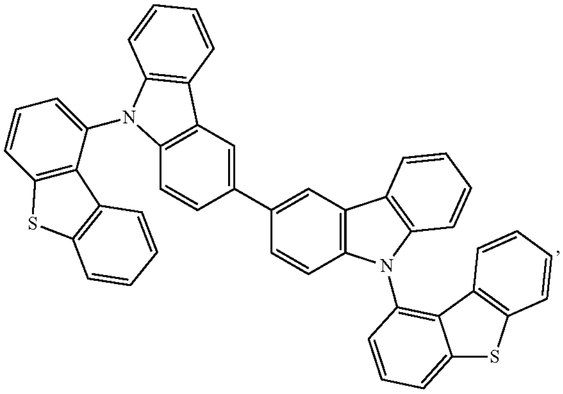
,
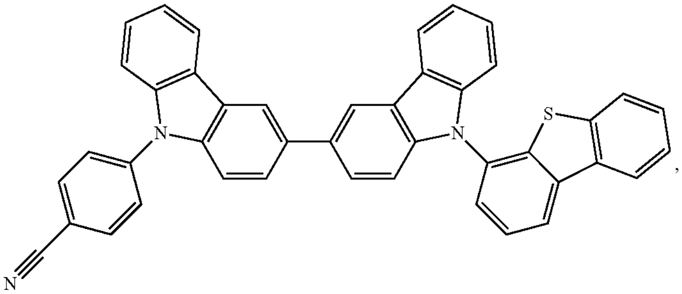
,
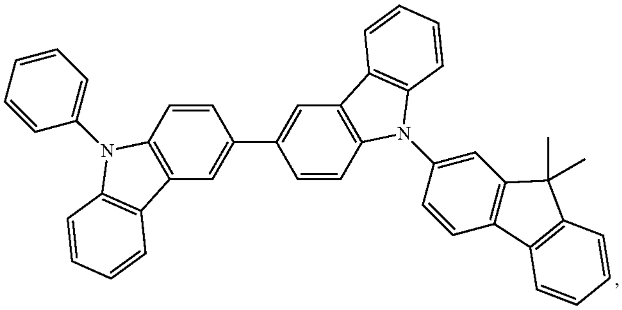
, -continued
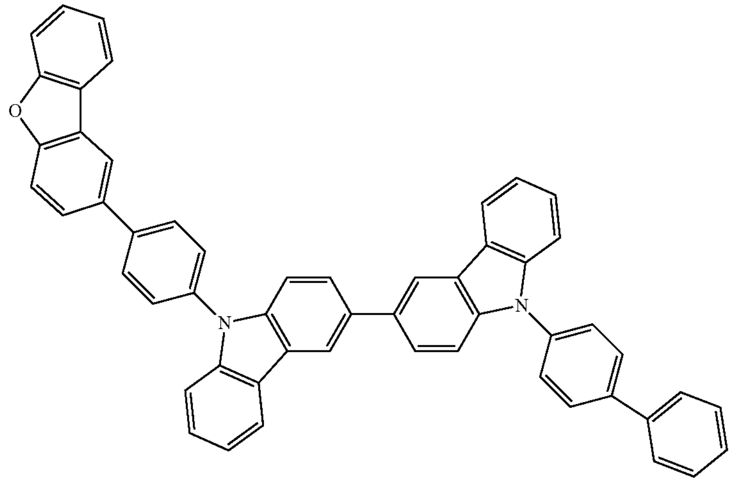
,
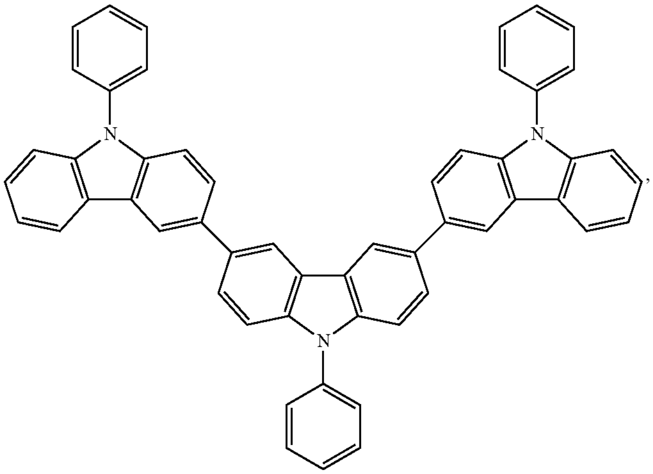
,
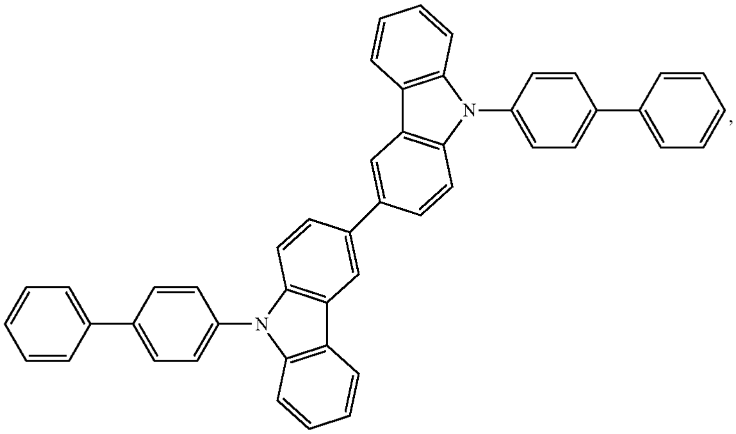
,
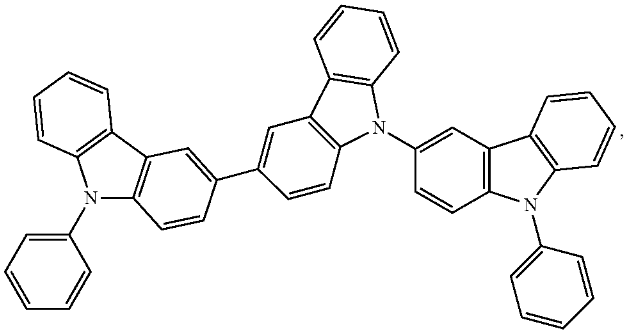
, -continued
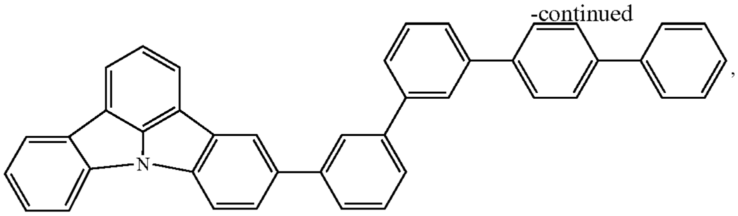,
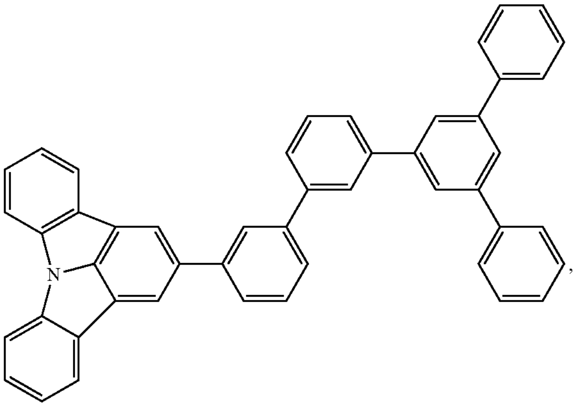,
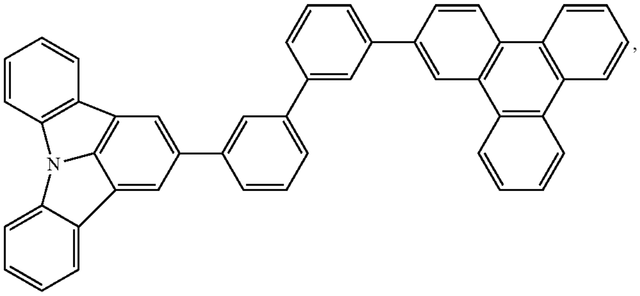,
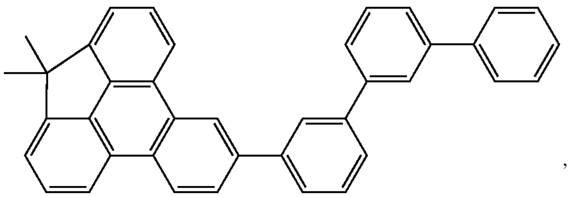, 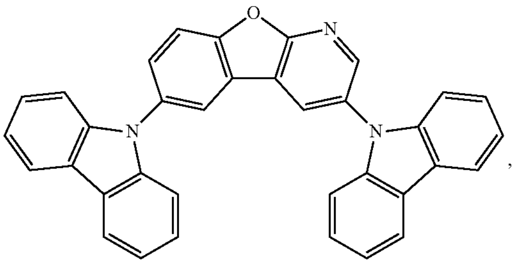,
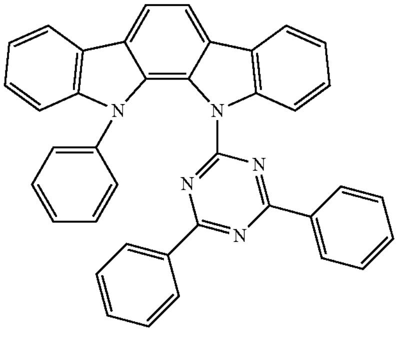, 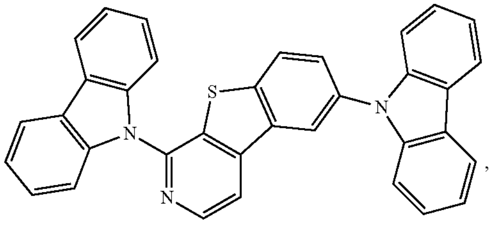, -continued
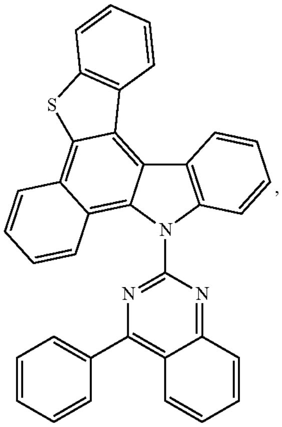
,
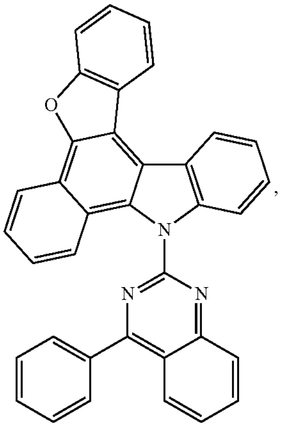
,
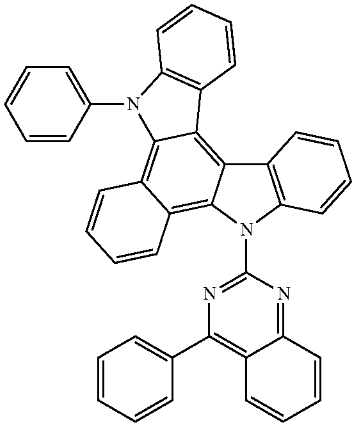
,
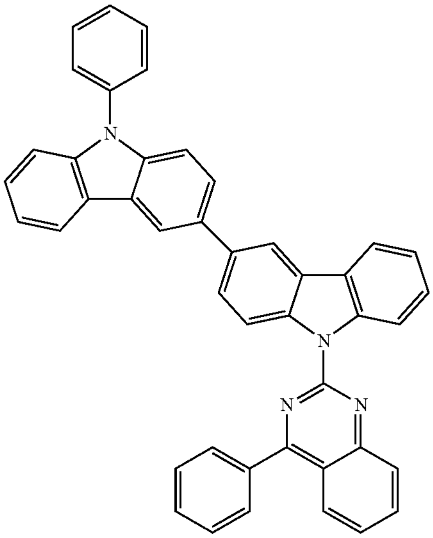
,
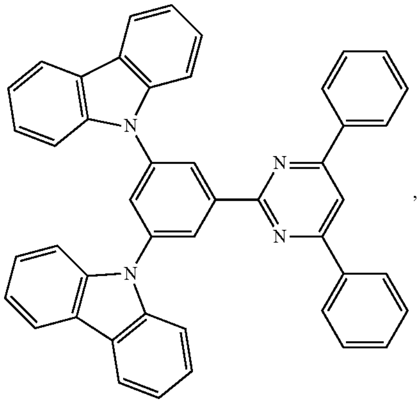
,
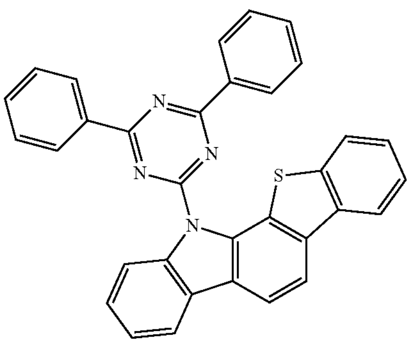
,
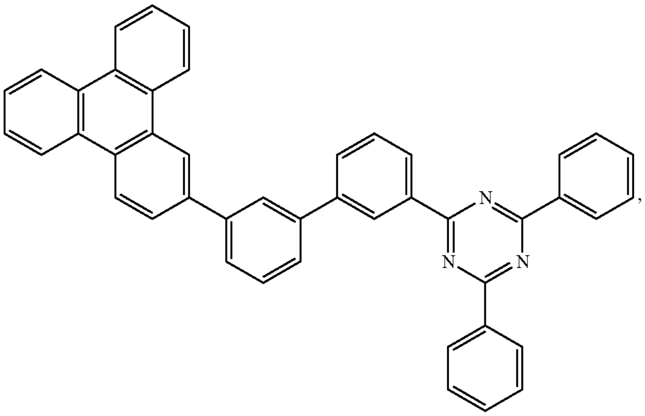
, -continued
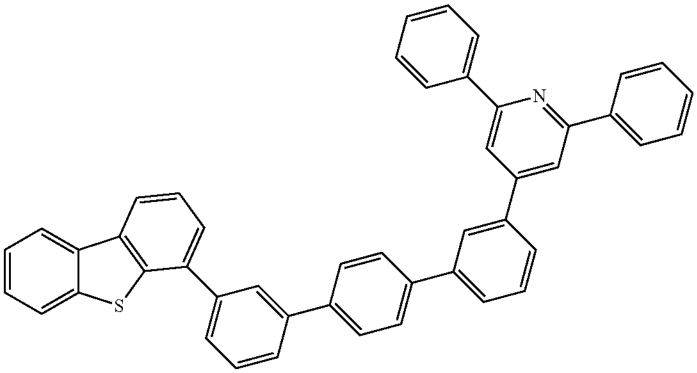
,
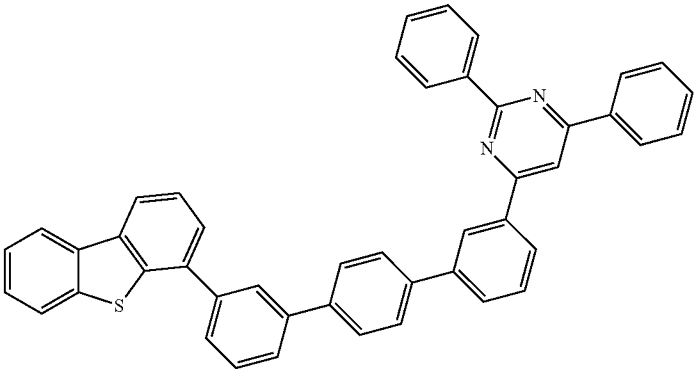
,
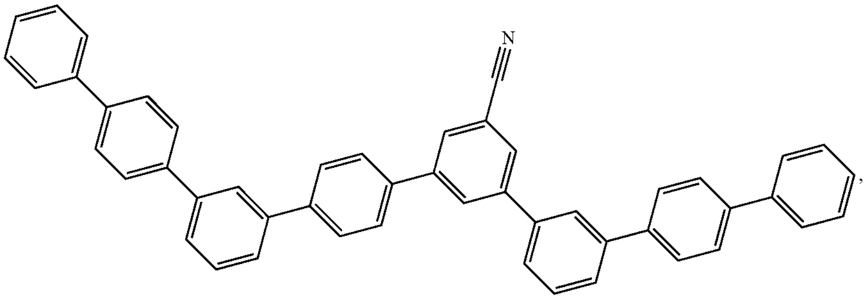
,
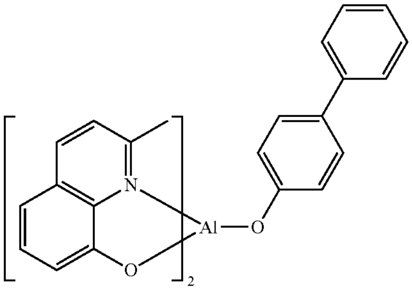
,
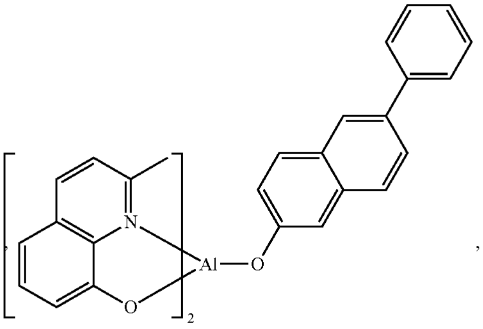
,
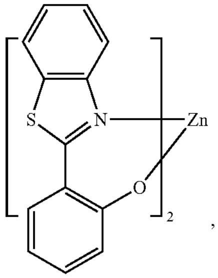
,
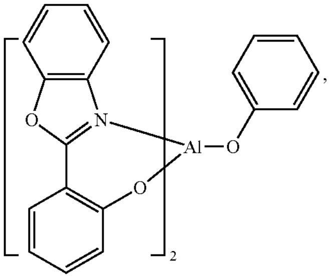
,
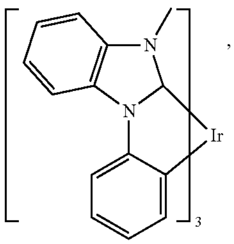
,
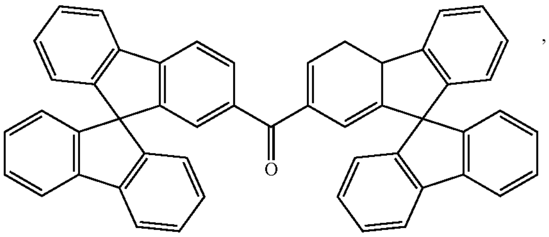
, -continued

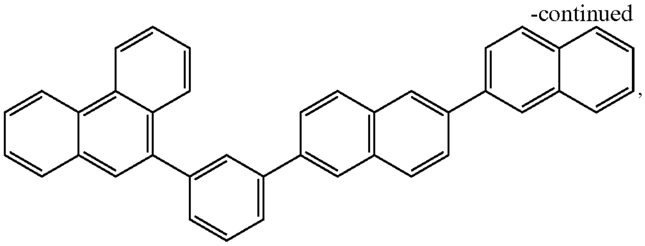

,

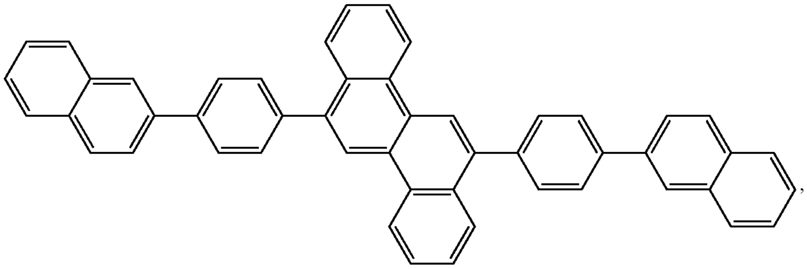

, and

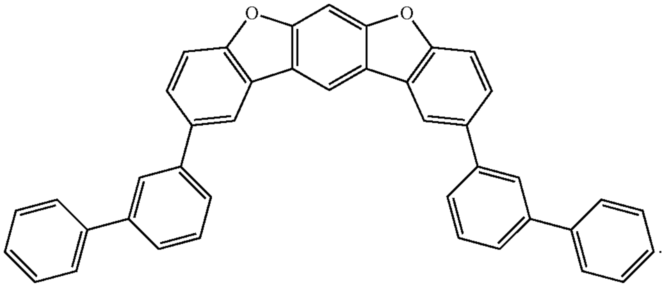 [SMILES: c1ccc(-c2cccc(-c3ccc4oc5cc6oc7ccc(-c8cccc(-c9ccccc9)c8)cc7c6cc5c4c3)c2)cc1]

.

Additioinal Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Pat. Nos. 6,699,599, 6,916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.
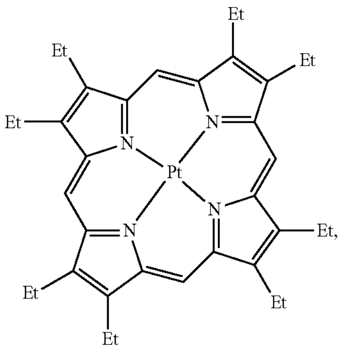
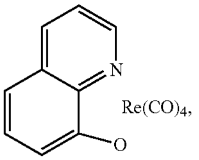
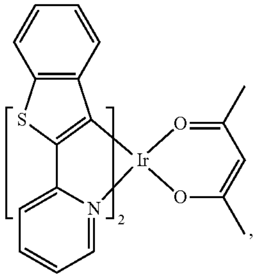
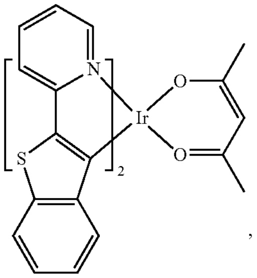
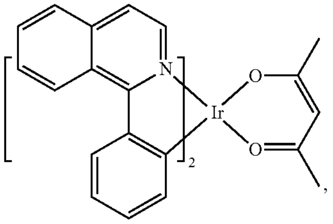
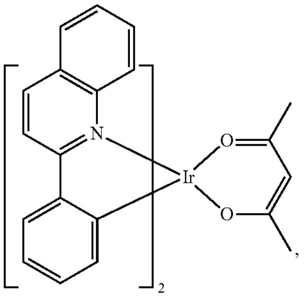
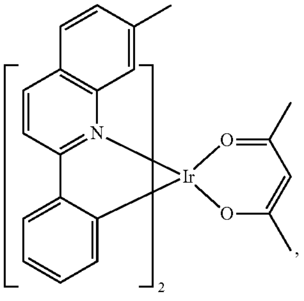
-continued
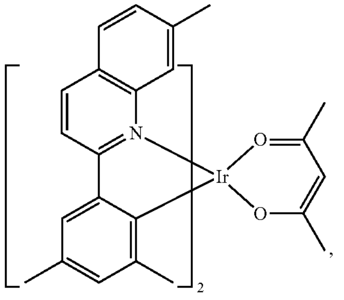
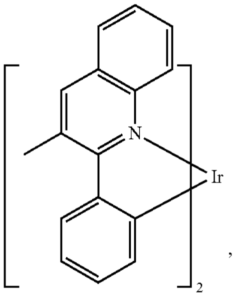
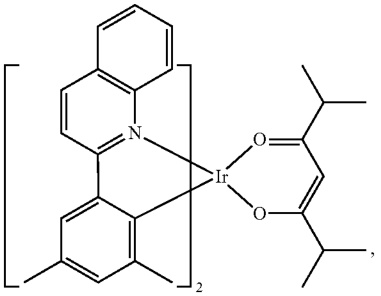
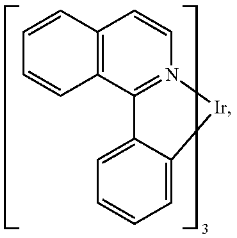
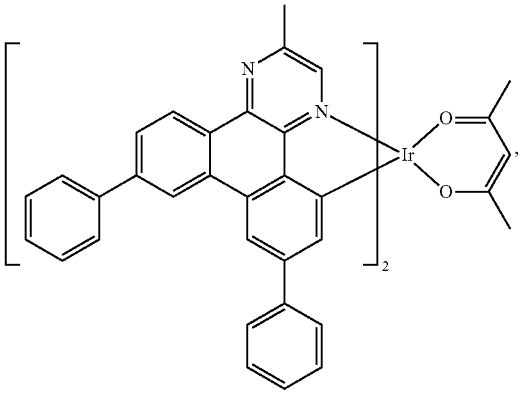
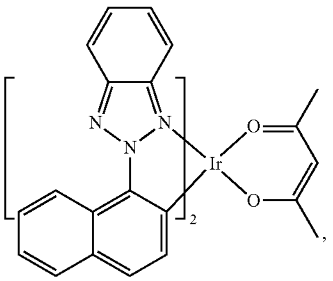

-continued
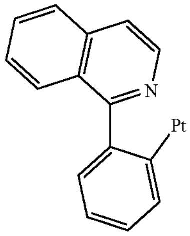
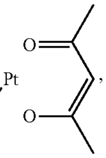
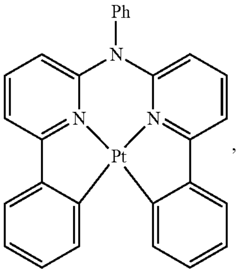
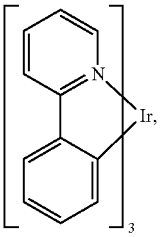
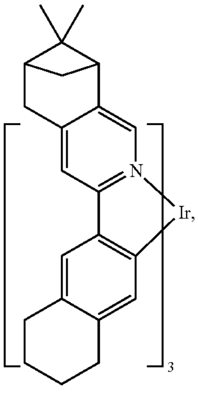
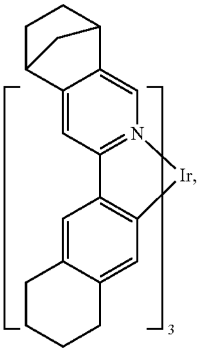
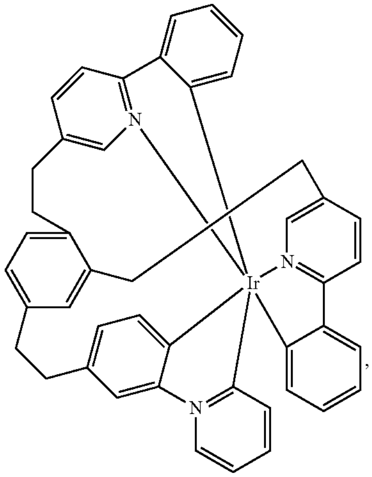
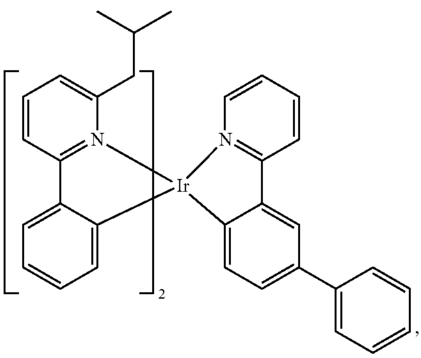
-continued
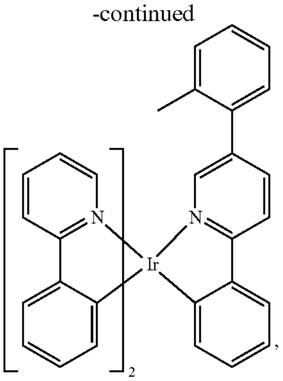
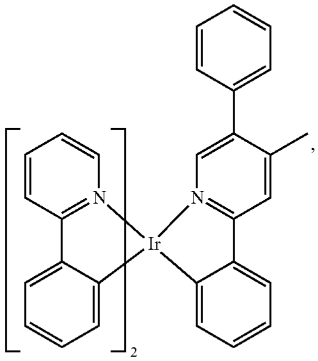
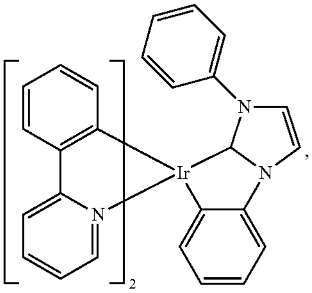
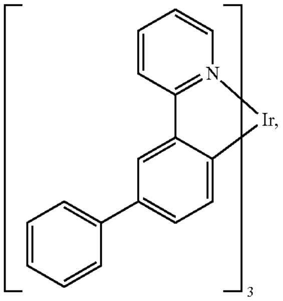
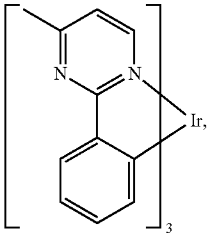
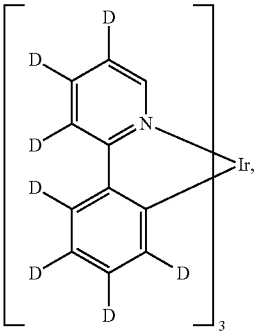
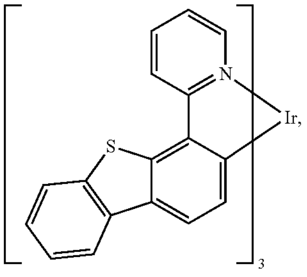

-continued
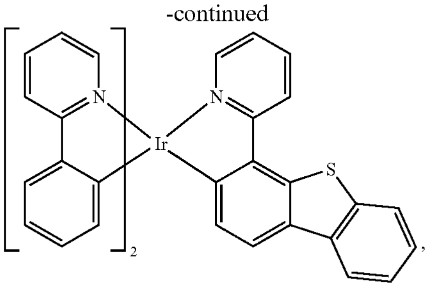
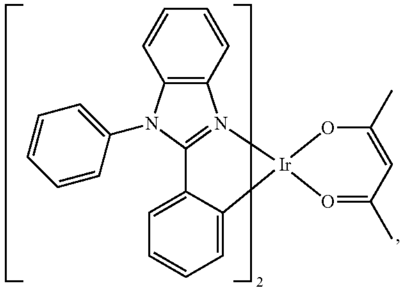
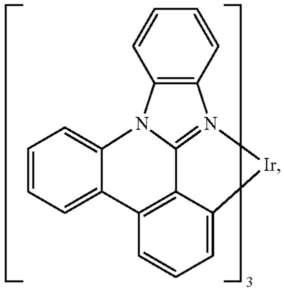
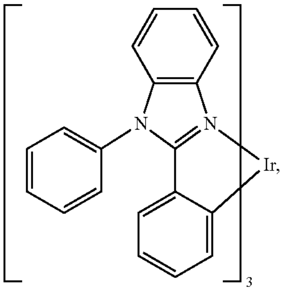
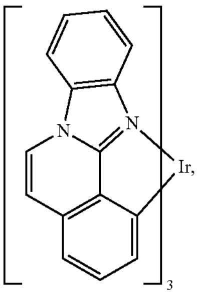
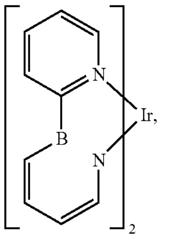
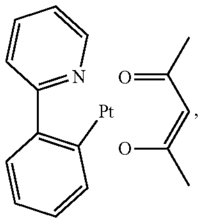
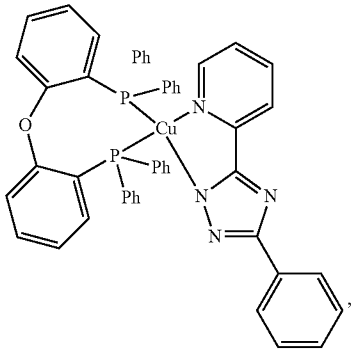
-continued
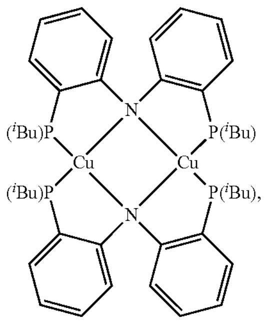
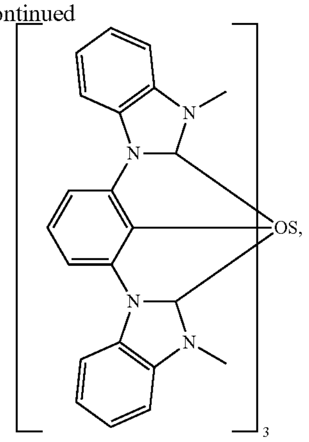
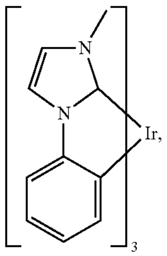
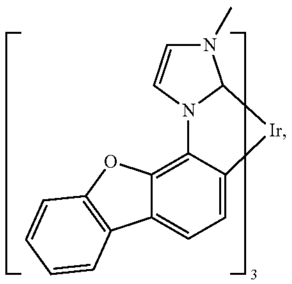
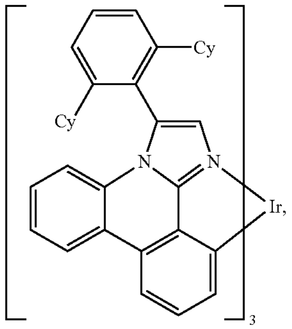
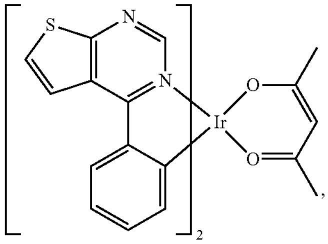
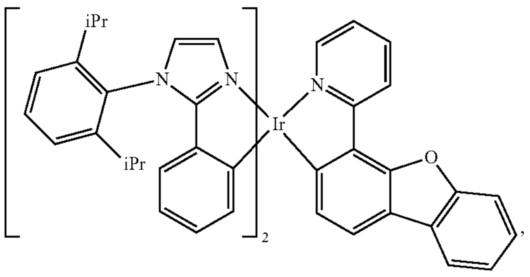

-continued
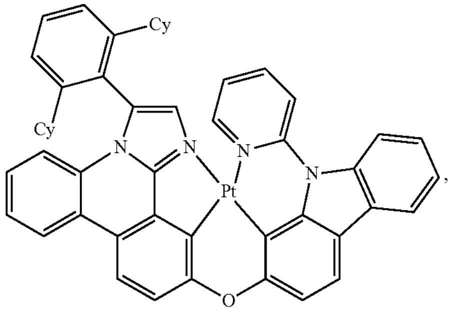
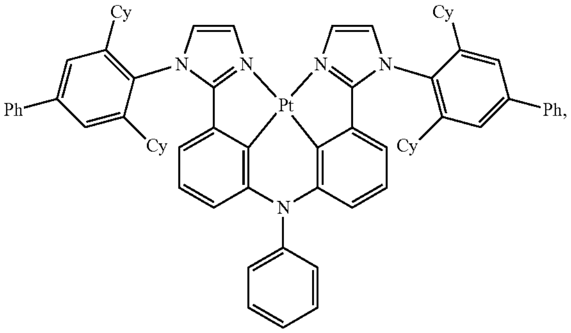
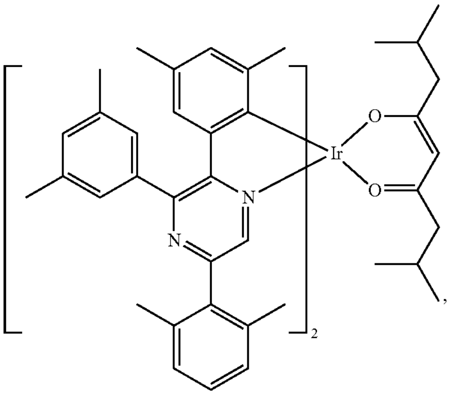
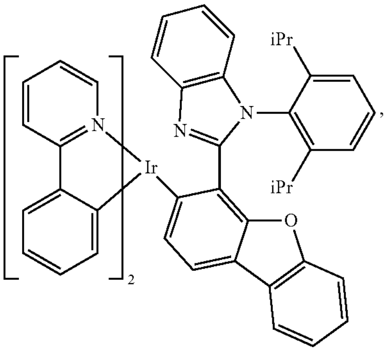
-continued
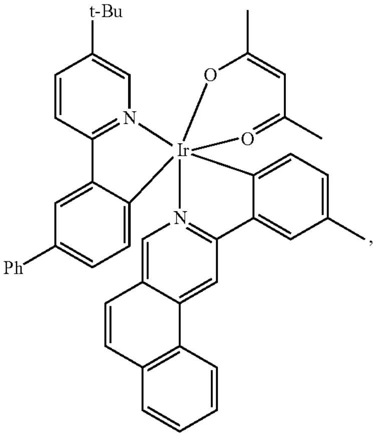
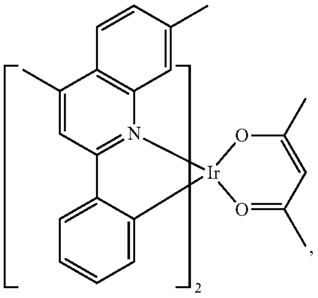
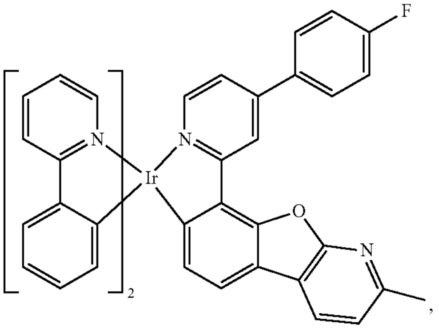
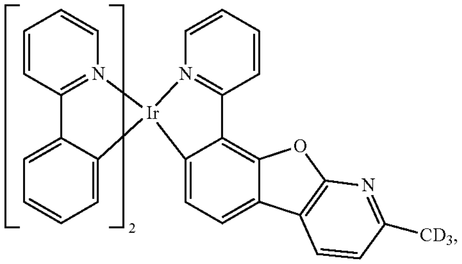
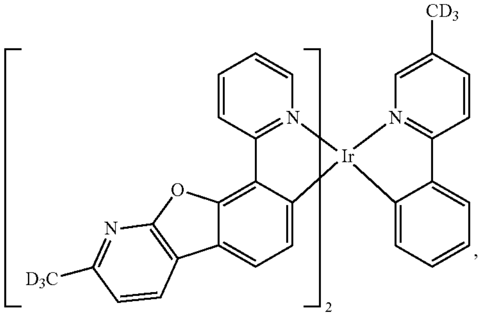

-continued
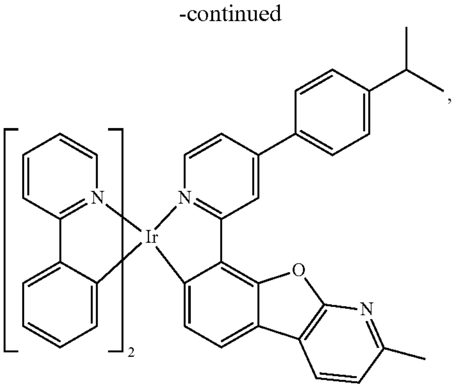
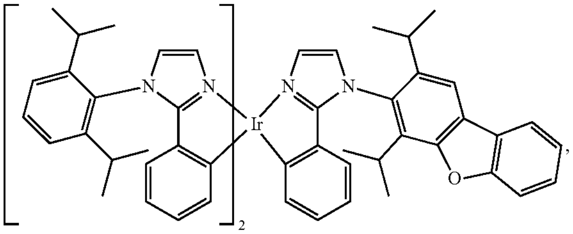
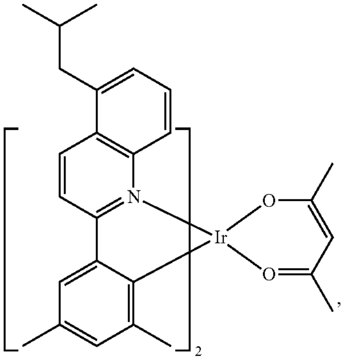
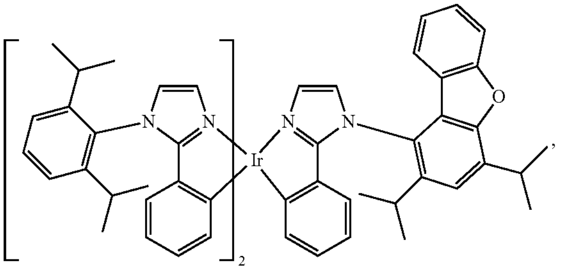
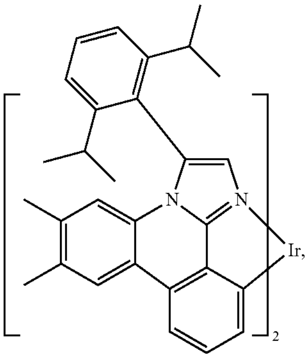
-continued
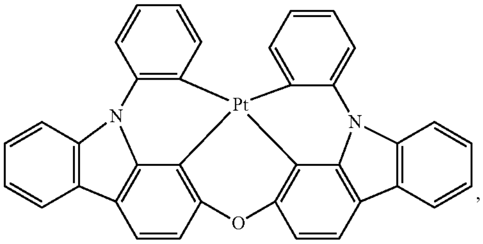
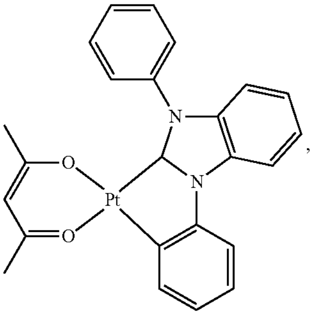
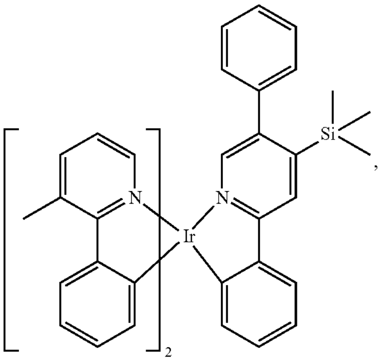
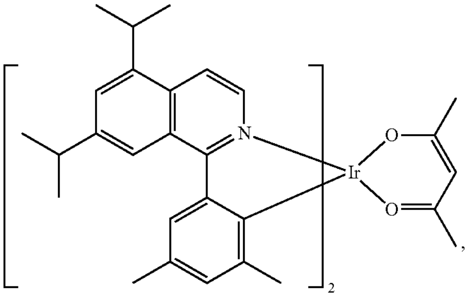
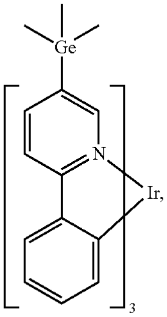
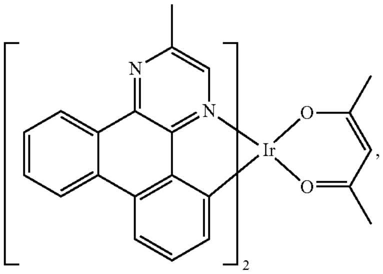

-continued
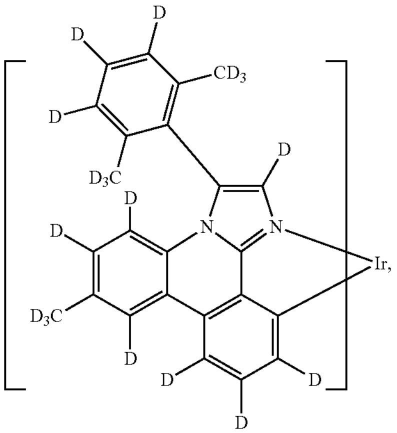
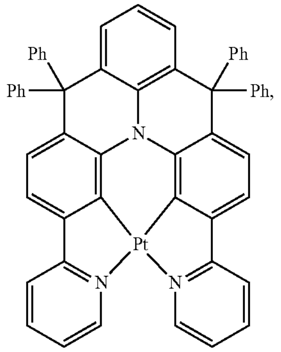
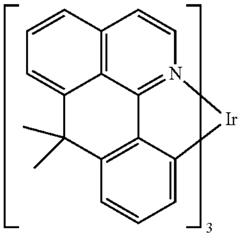
,
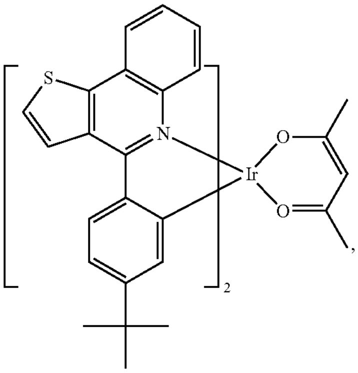
,
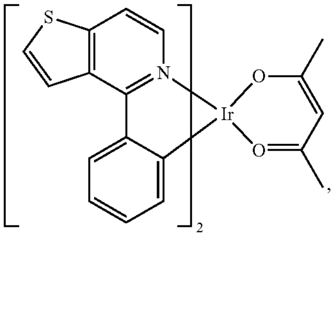
,
-continued
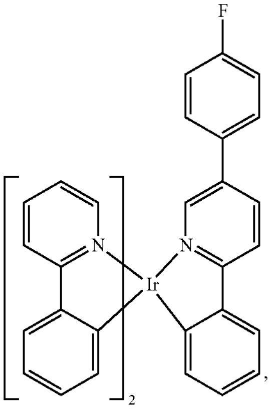
,
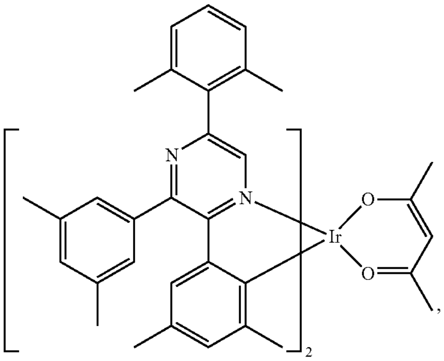
,
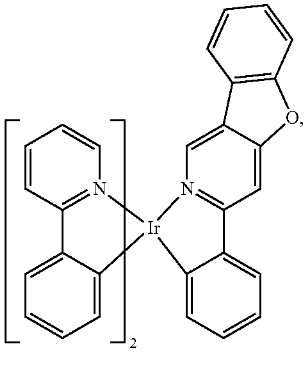
,
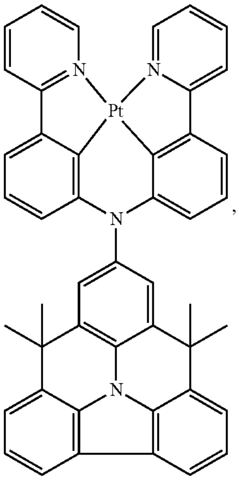
,
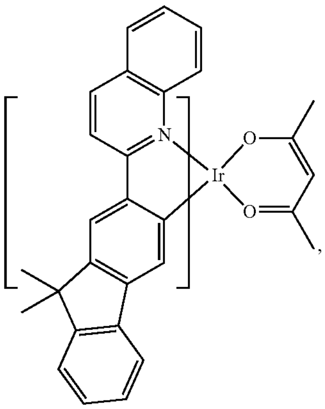
, -continued
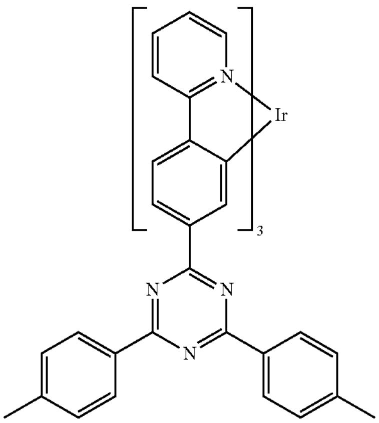
,
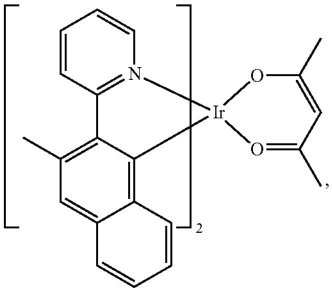
,
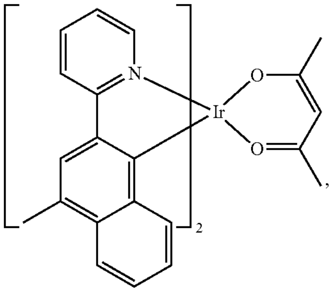
,
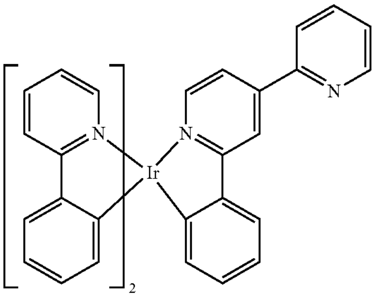
,
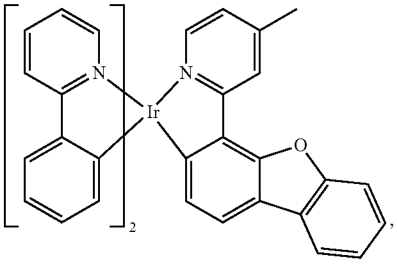
,
-continued
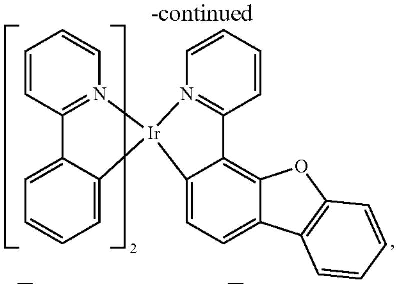
,
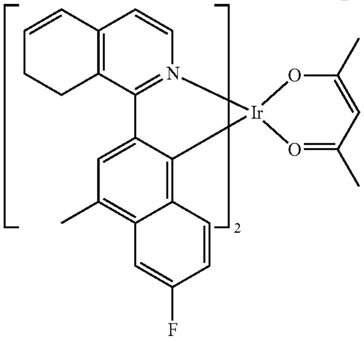
,
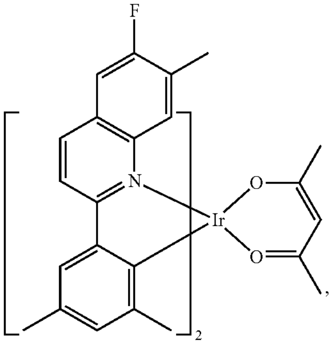
,
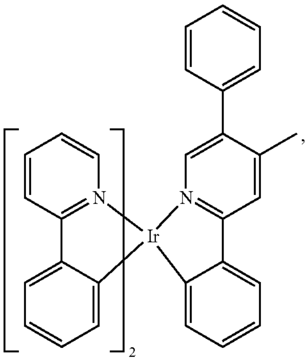
,
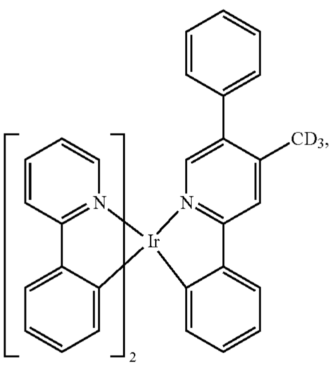
,
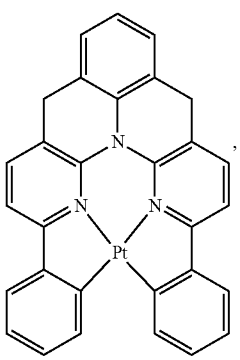
, -continued
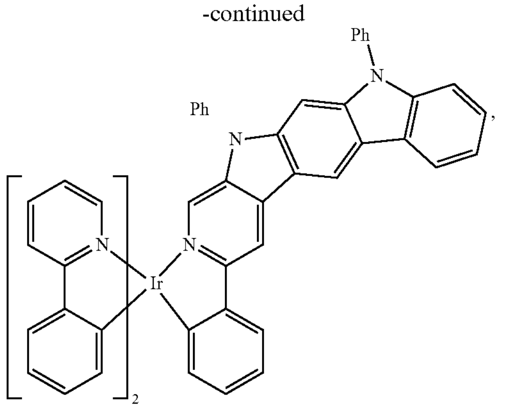
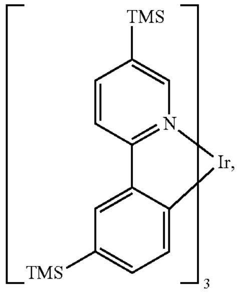
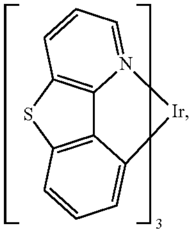
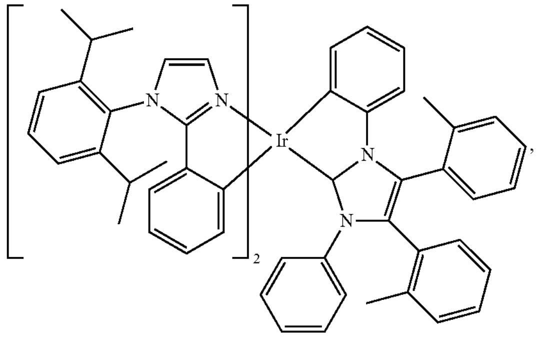
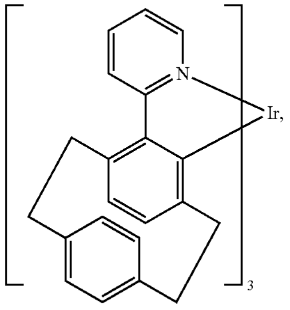
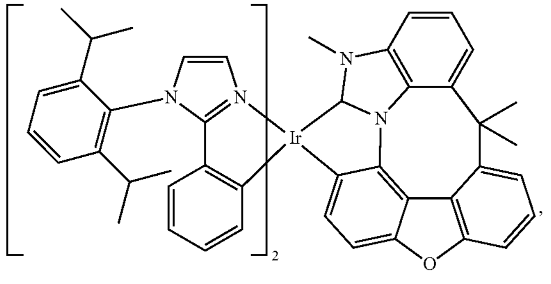
-continued
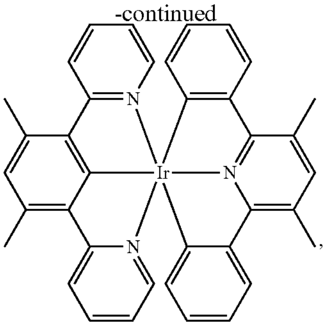
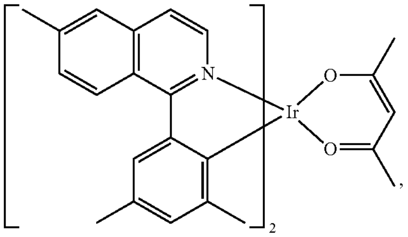
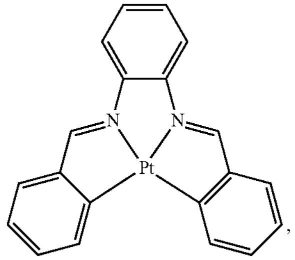
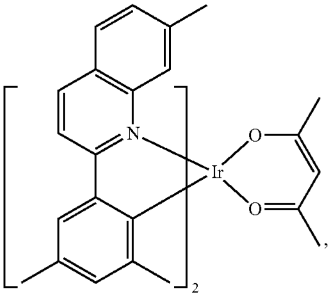
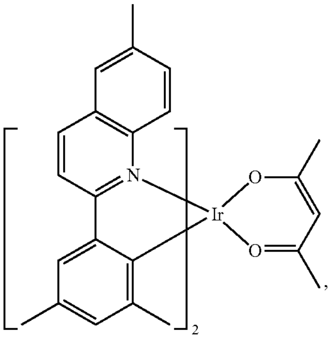
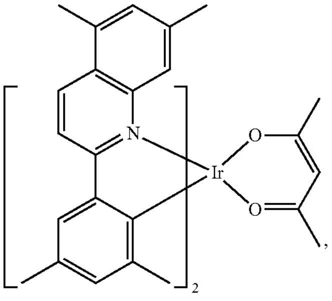

-continued
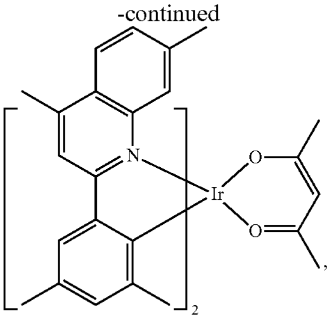
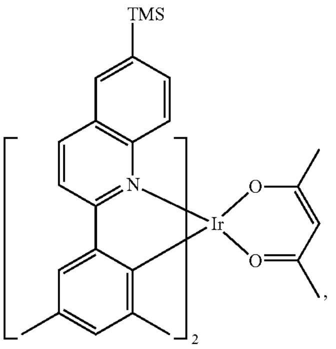
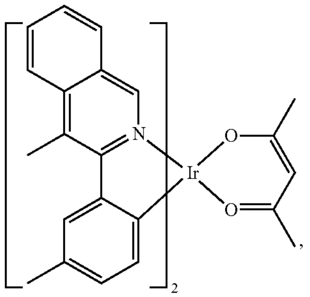
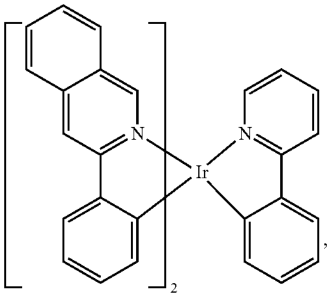
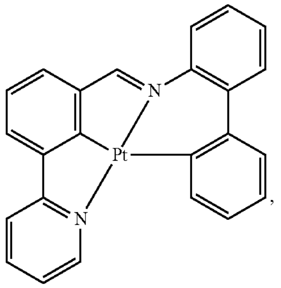
-continued
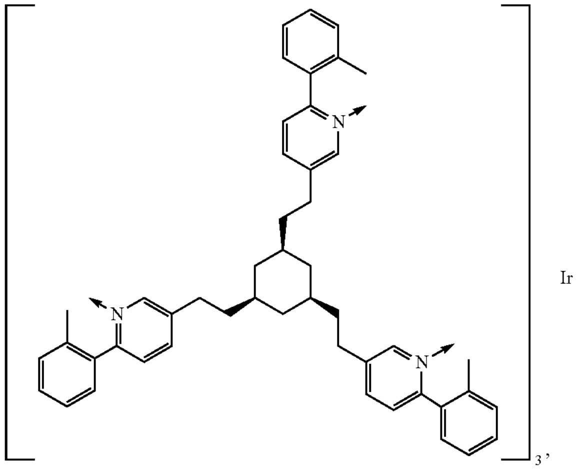
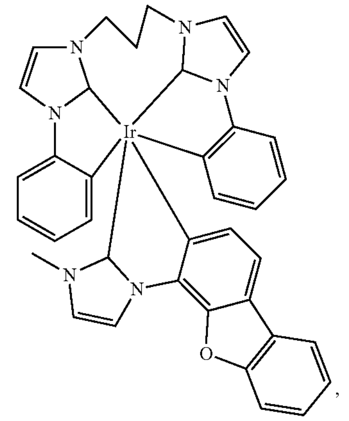
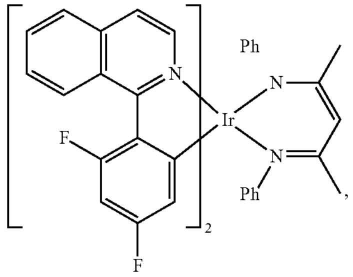
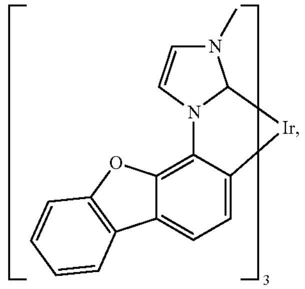

-continued
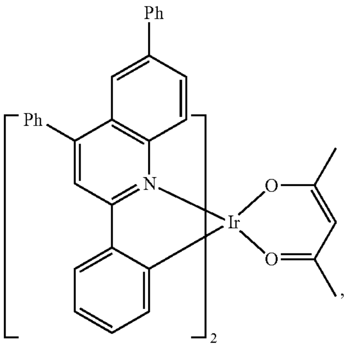
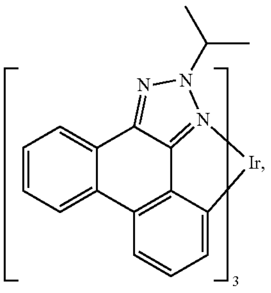
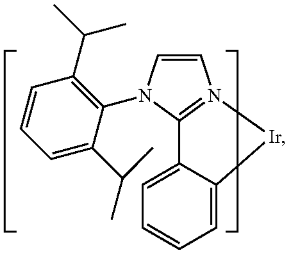
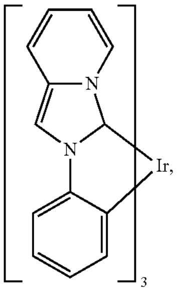
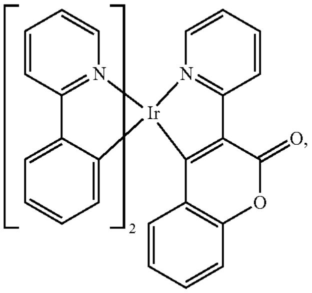
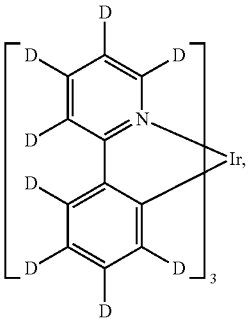
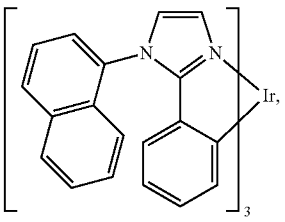
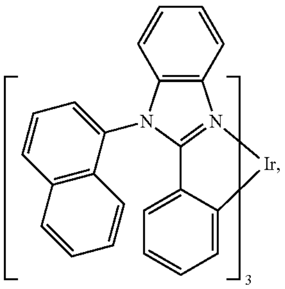
-continued
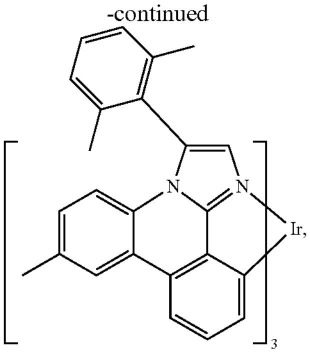
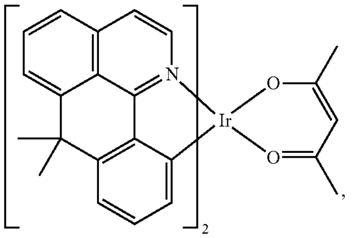
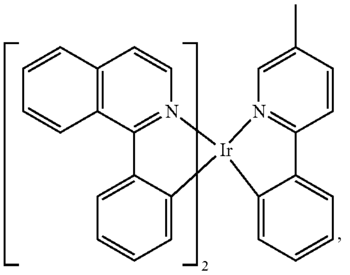
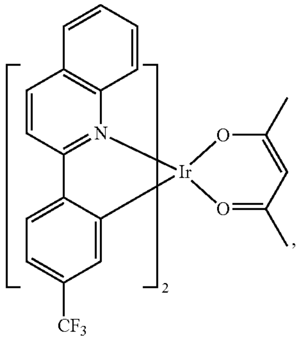
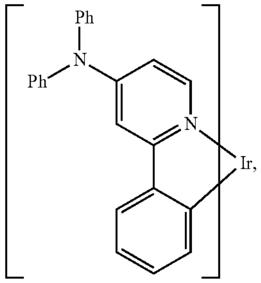
and -continued

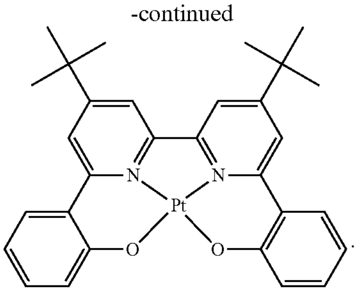

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and or higher triplet energy than the emitter closest to the HBL interface. In some embodiments, the HBL material has a lower HOMO (further from the vacuum level) and or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

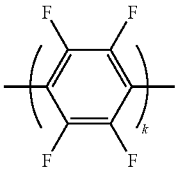
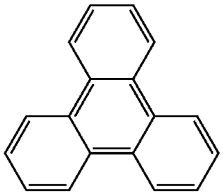
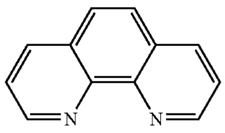
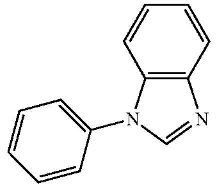
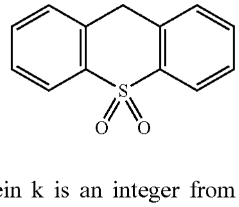
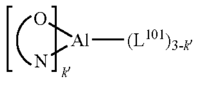

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

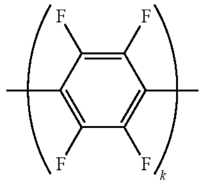
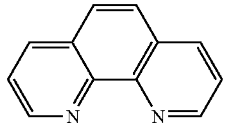
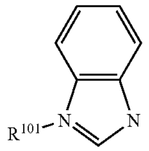
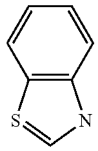
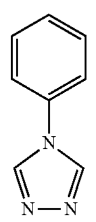
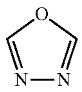
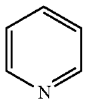
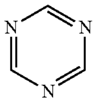
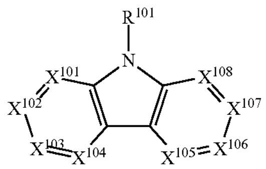
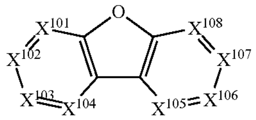
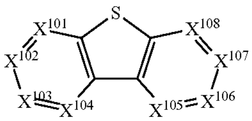
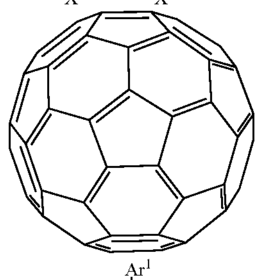
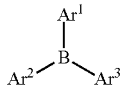

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

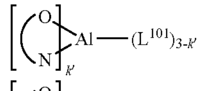
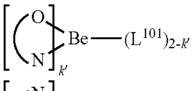
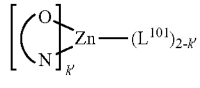
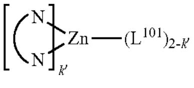

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

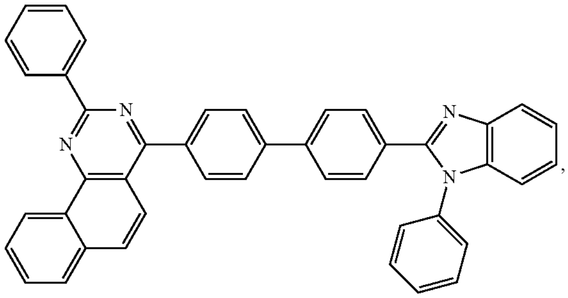,

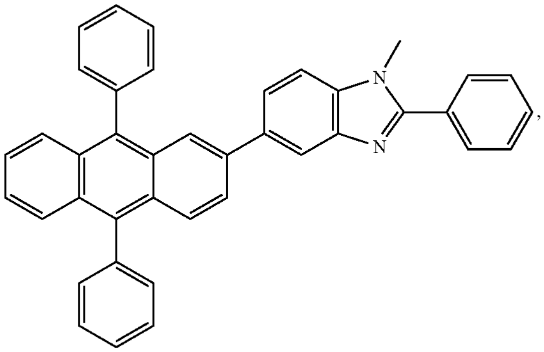,

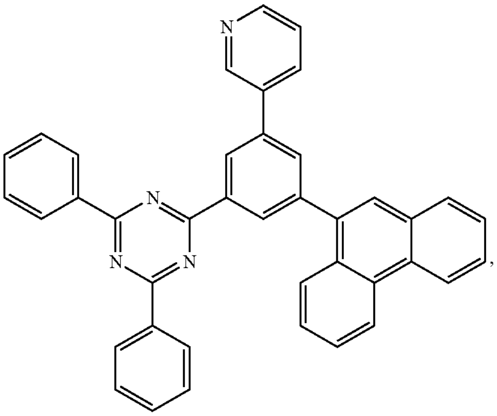,

-continued

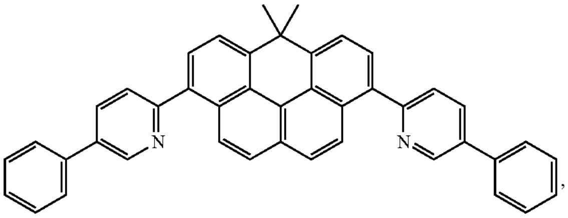,

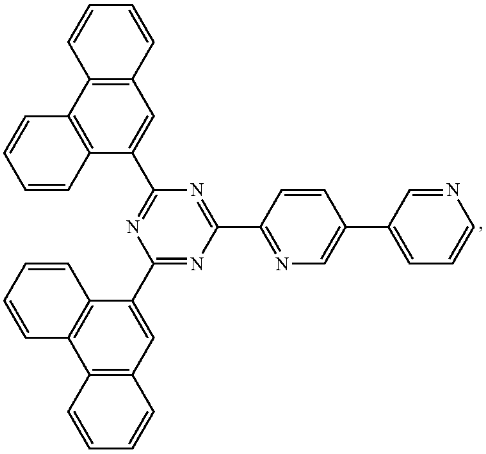,

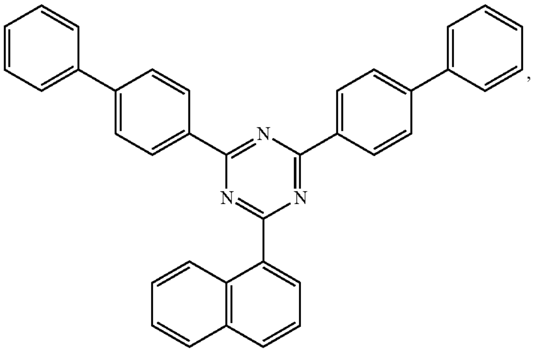,

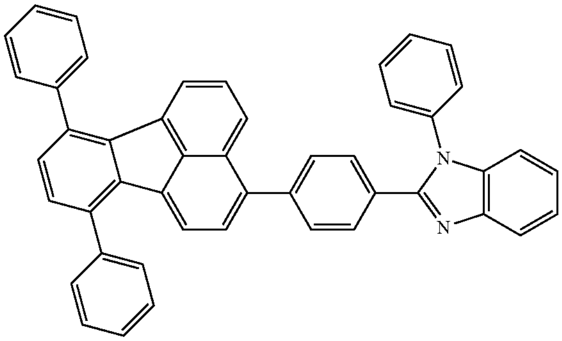,

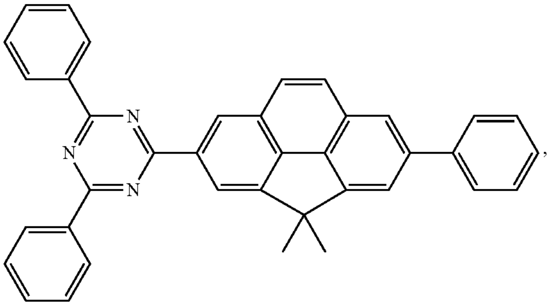,

-continued
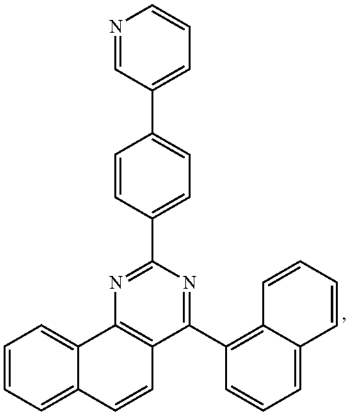
,
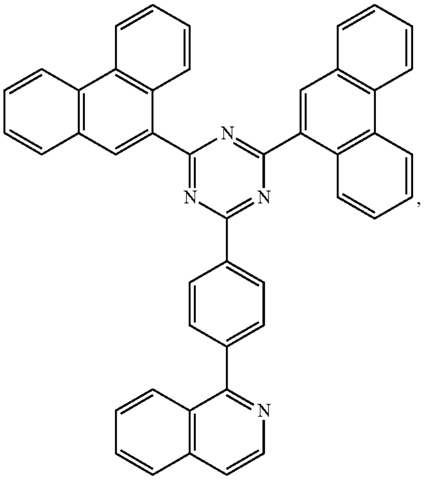
,
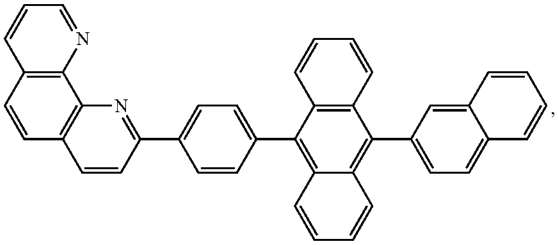
,
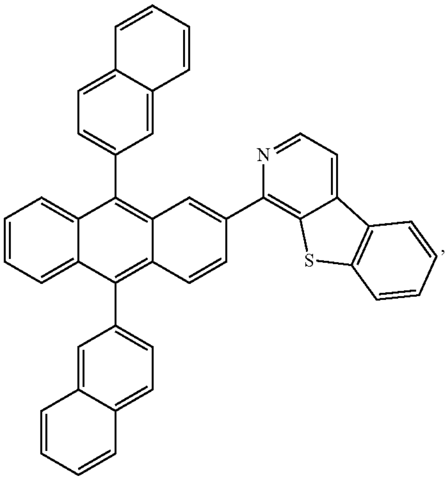
,
-continued
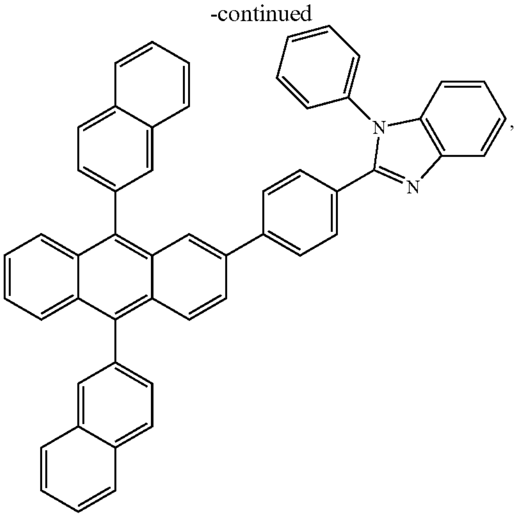
,
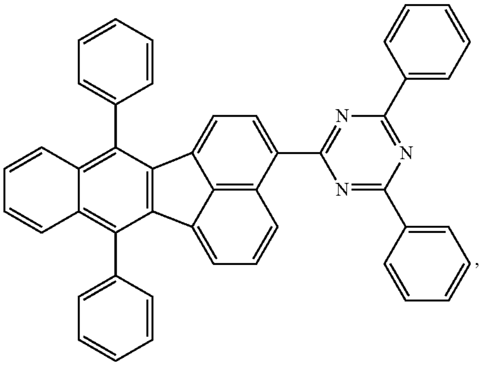
,
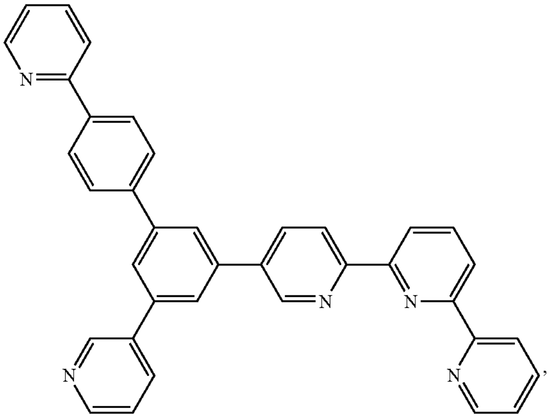
, -continued
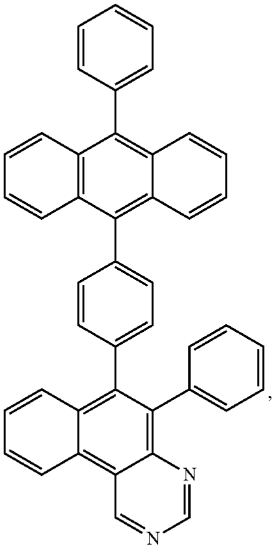
,
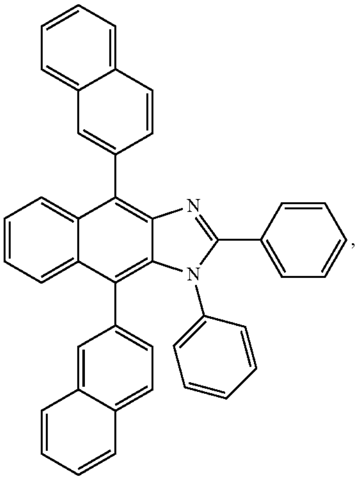
,
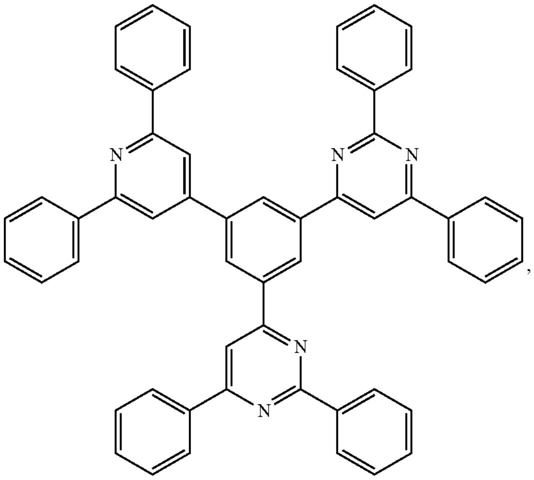
,
-continued
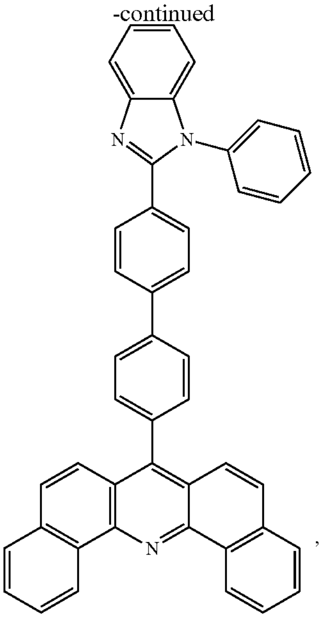
,
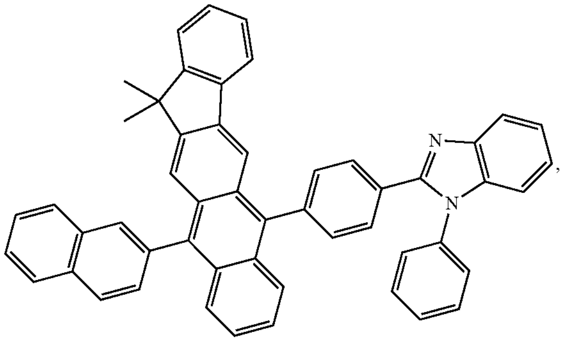
,
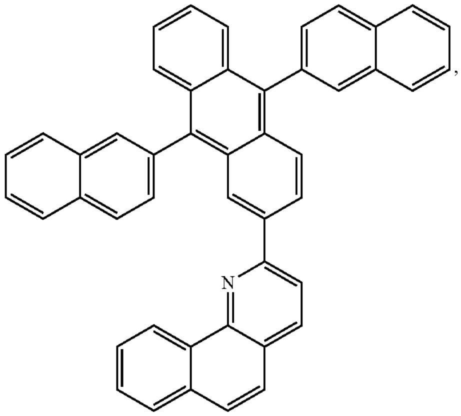
,
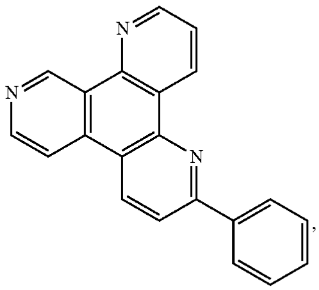
, -continued
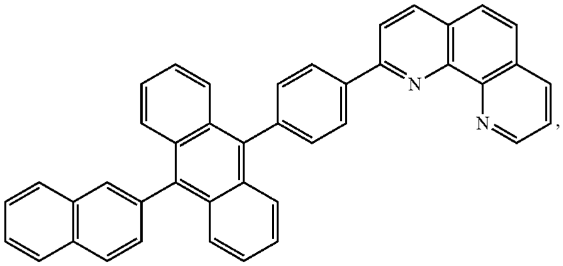
,
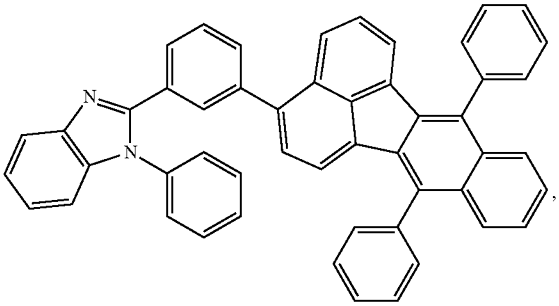
,
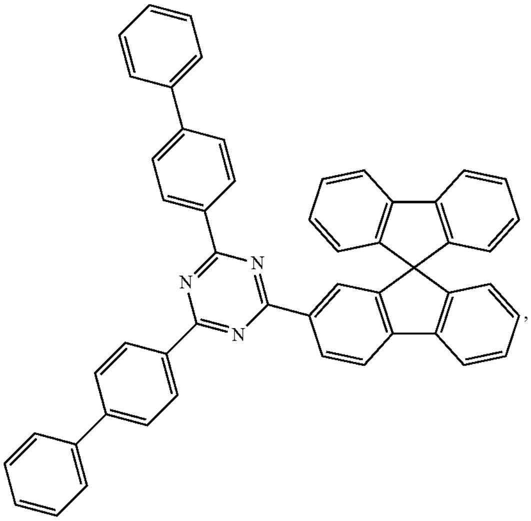
,
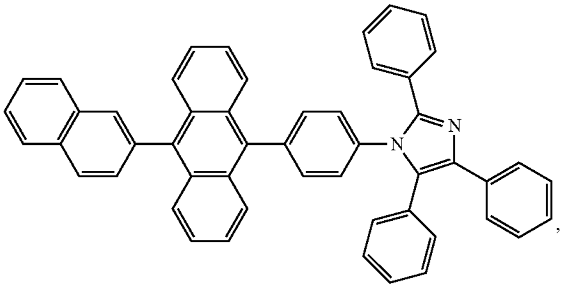
,
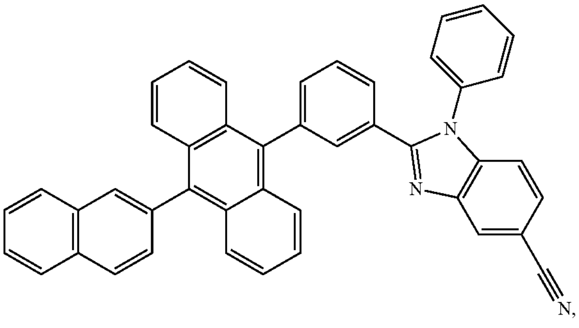
,
-continued
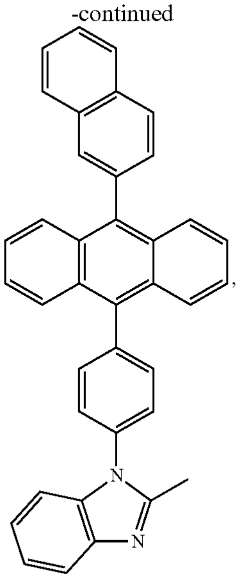
,
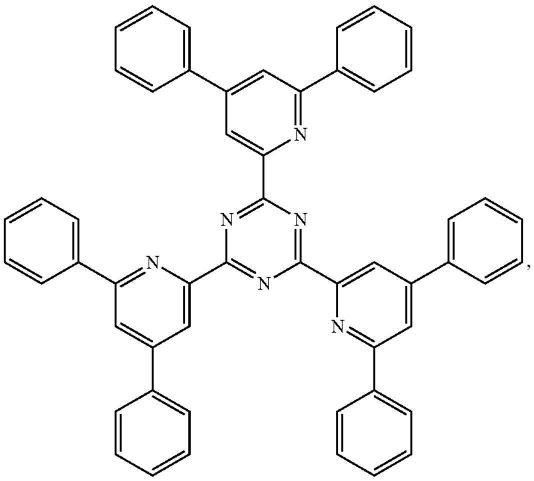
,
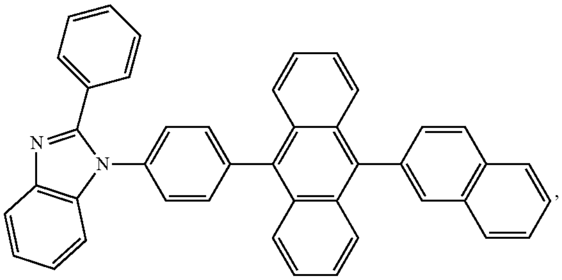
,
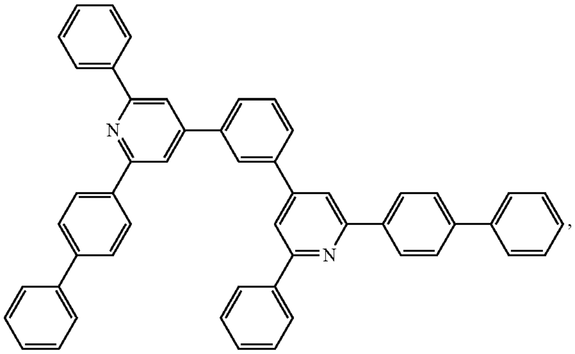
, -continued

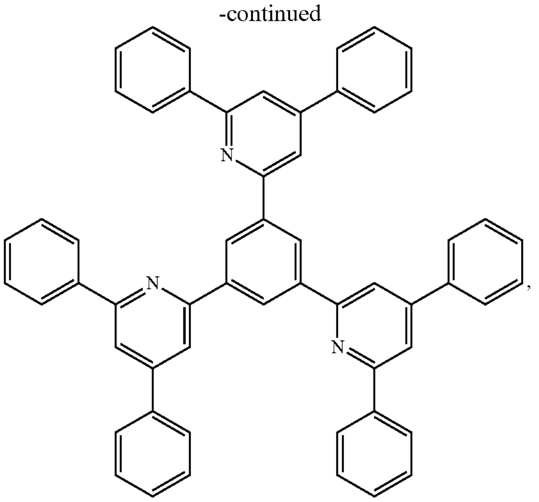

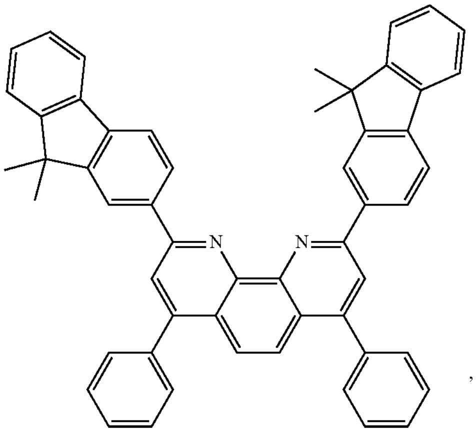

, and

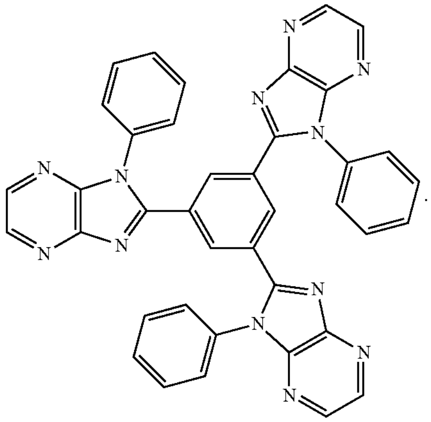 [SMILES: c1ccc(-n2c(-c3cc(-c4nc5nccnc5n4-c4ccccc4)cc(-c4nc5nccnc5n4-c4ccccc4)c3)nc3nccnc32)cc1]

.

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

EXPERIMENTAL

Synthesis of Materials

Inventive compound $Ir(L_{B183})_2L_{A21}$ can be synthesized by the procedure shown in the following scheme.

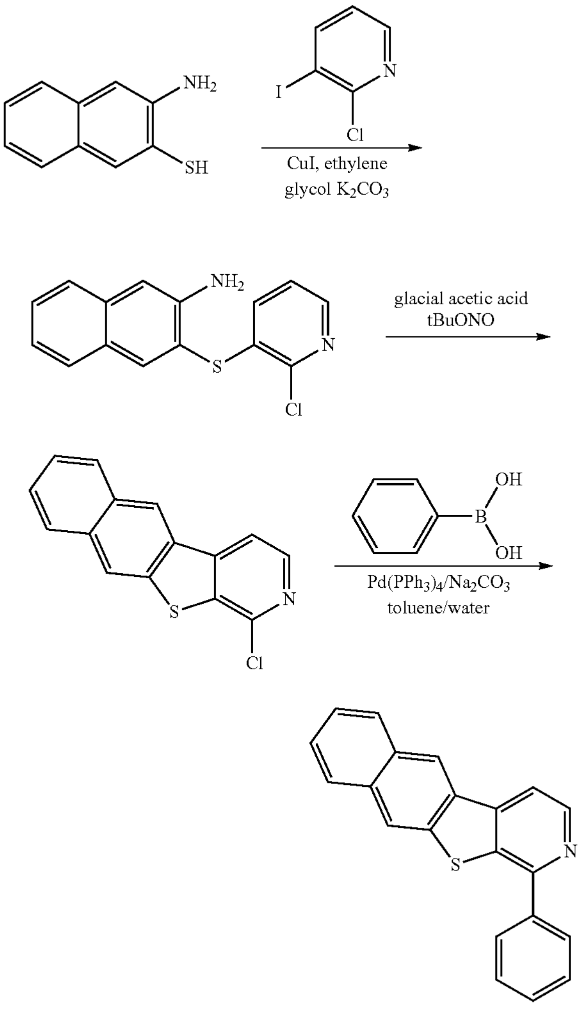

$L_{A21}$

-continued

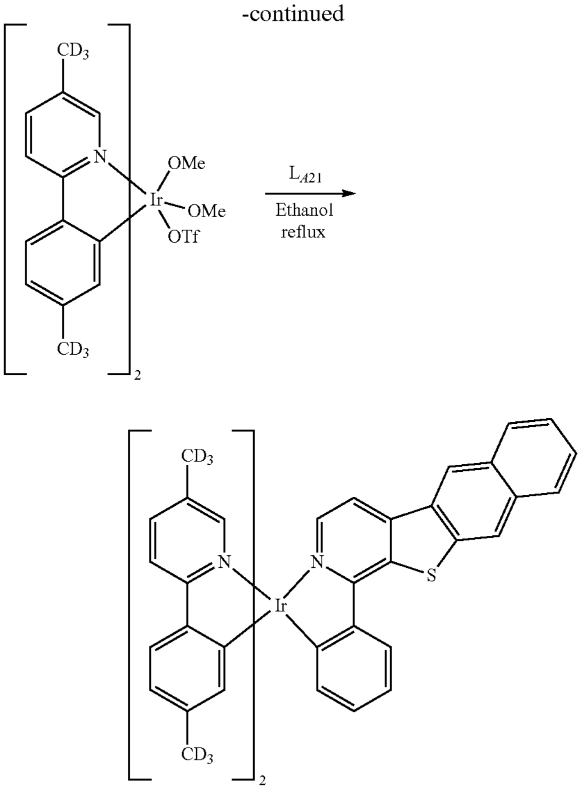

$Ir(L_{B183})_2L_{A21}$

The intermediate materials of 3-((2-chloropyridin-3-yl)thio)naphthalen-2-amine and 1-chloronaphtho[2',3':4,5]thieno[2,3-c]pyridine can be synthesized by modifying the procedure reported in WO2010118029. 3-aminonaphthalene-2-thiol reacts with 2-chloro-3-iodopyridine in the presence of of CuI and $K_2CO_3$ in ethylene glycol at reflux to give 3-((2-chloropyridin-3-yl)thio)naphthalen-2-amine. A solution of 3-((2-chloropyridin-3-yl)thio)naphthalen-2-amine in glacial acetic acid is treated with tert-butyl nitrite to give 1-chloronaphtho[2',3':4,5]thieno[2,3-c]pyridine. The latter will react with phenylboronic acid in under standard Suzuki coupling reaction conditions to give ligand $L_{A21}$. Inventive compound $Ir(L_{B183})_2L_{A21}$ is then made by mixing Ir timer with $L_{A21}$ in ethanol at reflux.

The energy of the lowest triplet excited state ($T_1$) of the inventive compounds is estimated by theoretical calculation. $T_1$ of compound $Ir(L_{B183})_2L_{A21}$ was calculated to be 604 nm. As would be understood by one of ordinary skill in the art, the compound will emit light of amber to red color, which may be useful for display and lighting applications. because of the fused rings, the invented compounds are hypothesized to have strong interactions with host materials in the OLED devices, which may enhance the electronic conductivity of the emission layer. In addition, the invented compounds exhibit a large dipole moment lying in the same direction of the molecular long axis. Although not wishing to be bound by any particular theory, it has been suggested that this feature helps the horizontal alignment of the transition dipole moment of the emitter in order to achieve better light extraction, which will improve the efficiency of the OLED devices. As demonstrated herein, the inventive compounds are useful materials as emitters in OLED devices to improve device performance.

We claim:

1. A compound comprising a ligand LA of Formula (I):

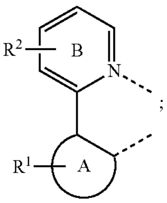

(I)

wherein ring A is a 5-membered or 6-membered carbocyclic or heterocyclic ring;

wherein $R^1$ represents from none to the maximum possible number of substitution;

wherein $R^2$ represents from two to the maximum possible number of substitution;

wherein at least two adjacent $R^2$s are joined to form ring C and have the following formula, wherein ring C is fused to ring B:

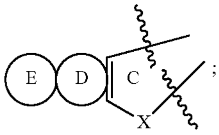

wherein the wave lines indicate bonds to ring B;

wherein ring D is benzene;

wherein ring E is a 6-membered aromatic ring;

wherein ring D fuses to ring C, and ring E fuses to ring D;

wherein ring D and ring E can be further substituted by one or more substituents;

wherein X is selected from the group consisting of O, S, Se, and NR;

wherein $R^1$, $R^2$, and R are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein any two adjacent substituents are optionally joined to form into a ring;

wherein $L_A$ is coordinated to a metal M;

wherein $L_A$ is optionally linked with other ligands to comprise a tridentate, tetradentate, pentadentate, or hexadentate ligand; and wherein M is optionally coordinated to other ligands.

2. The compound of claim 1, wherein M is selected from the group consisting of Ir, Rh, Re, Ru, Os, Pt, Au, and Cu.

3. The compound of claim 1, wherein M is Ir or Pt.

4. The compound of claim 1, wherein X is O or S.

5. The compound of claim 1, wherein X is NR.

6. The compound of claim 1, wherein ring E is benzene.

7. The compound of claim 1, wherein ring E is pyridine.

8. The compound of claim 1, wherein ring A is benzene.

9. The compound of claim 1, wherein the ligand LA is selected from the group consisting of:

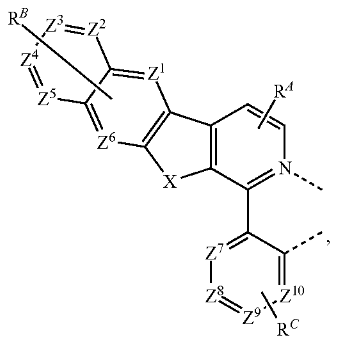
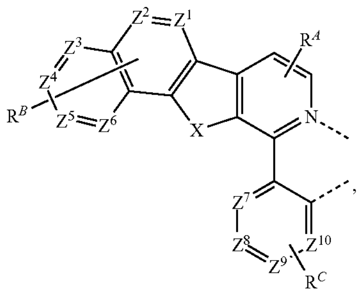
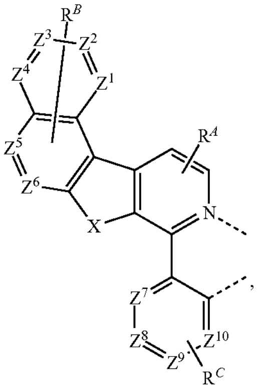
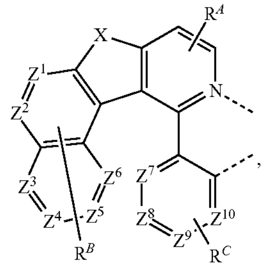
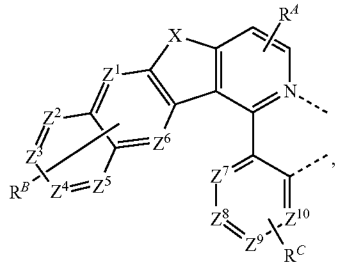
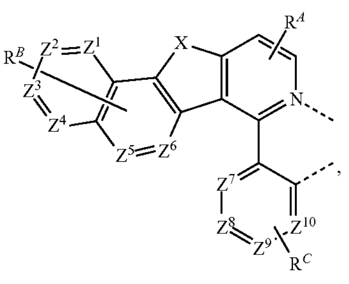
-continued
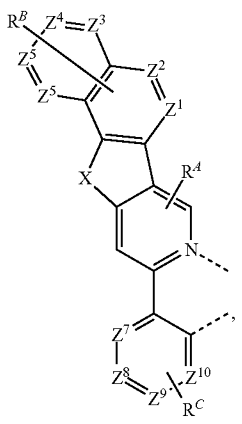
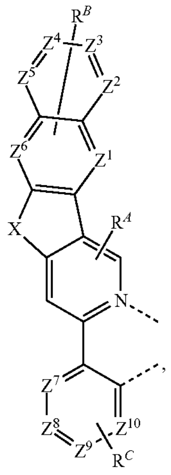
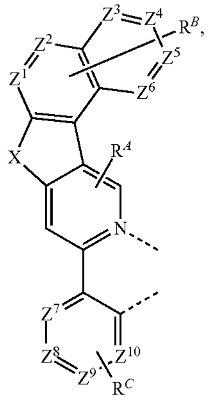
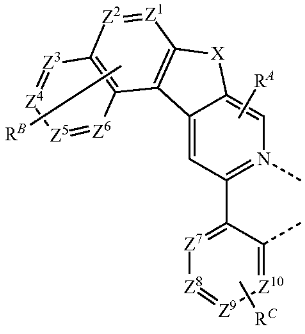
,
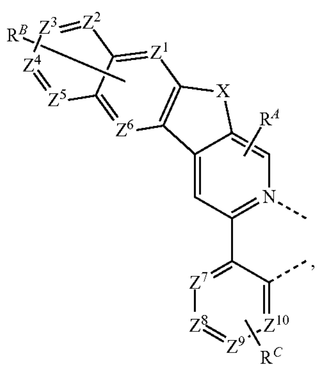
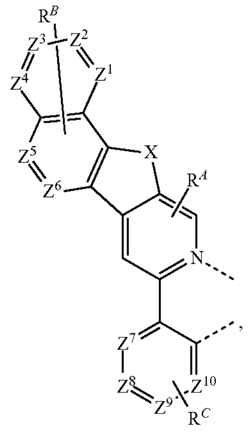
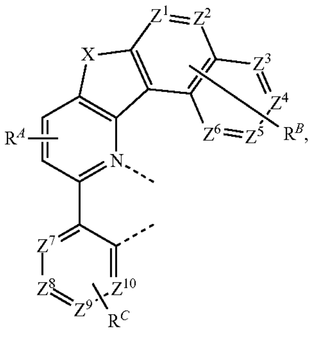

-continued
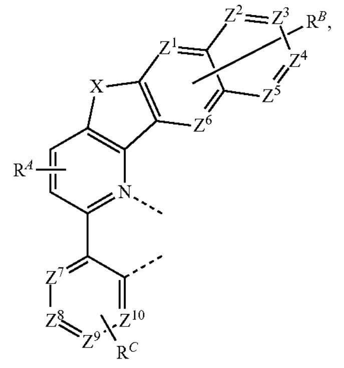
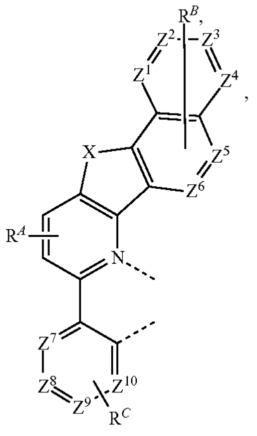
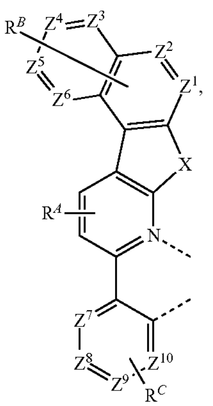
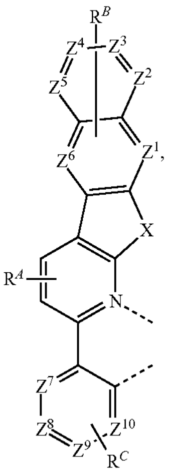
,
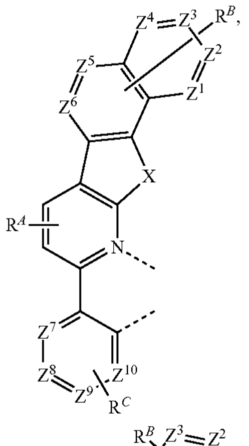
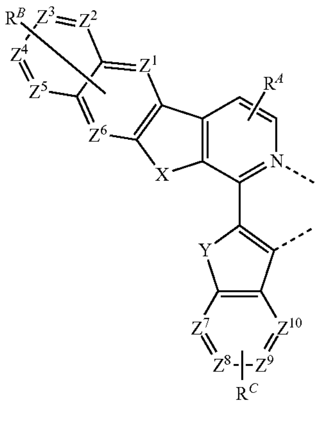
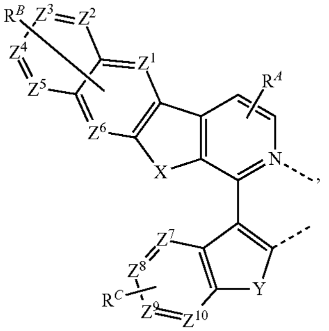
-continued
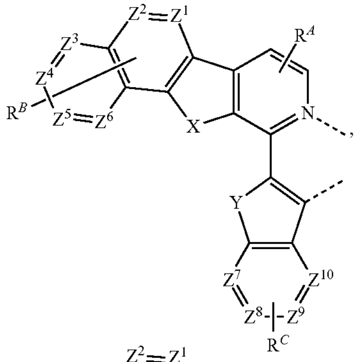
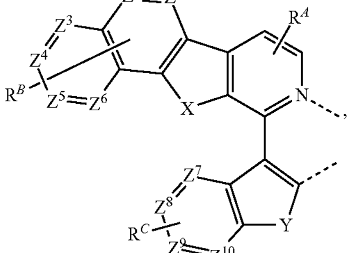
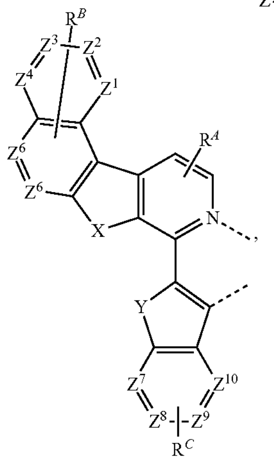
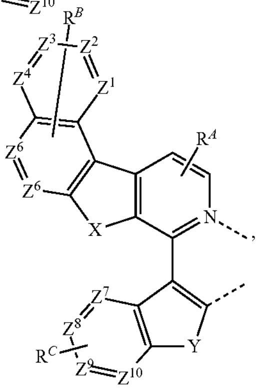
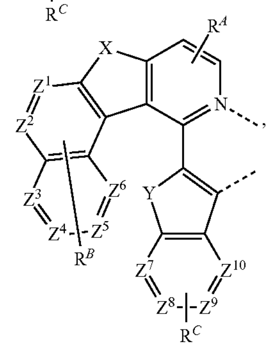
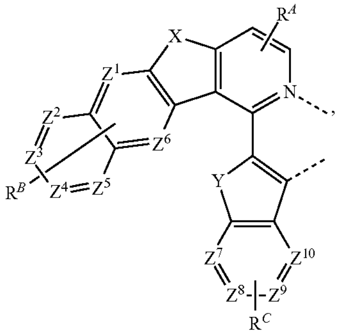

-continued
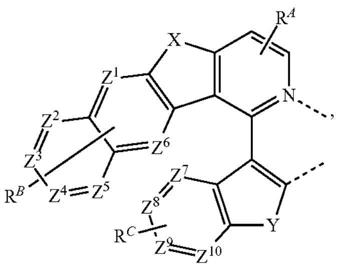
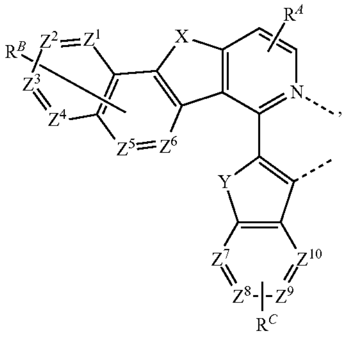
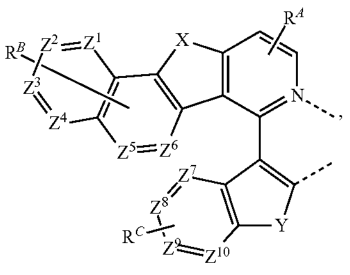
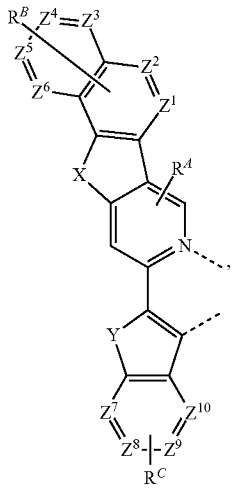
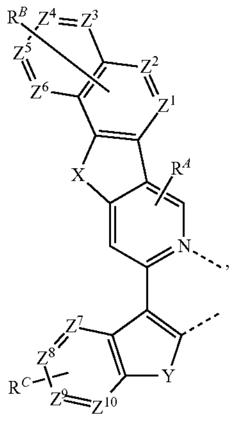
-continued
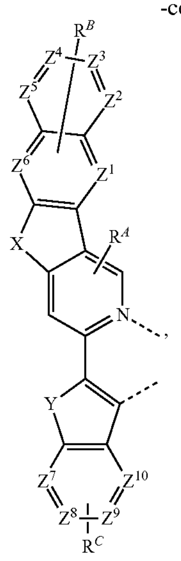
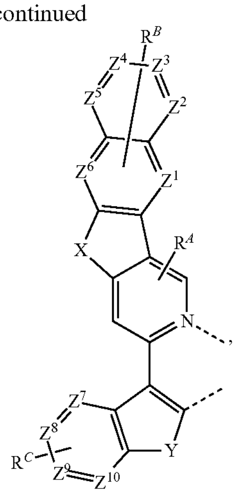
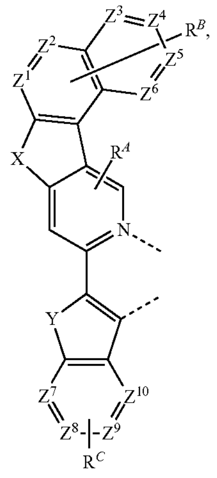
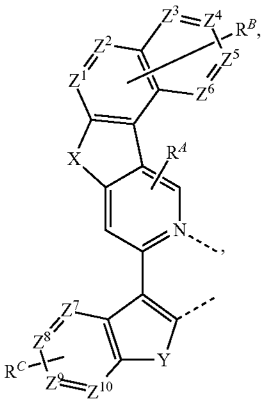
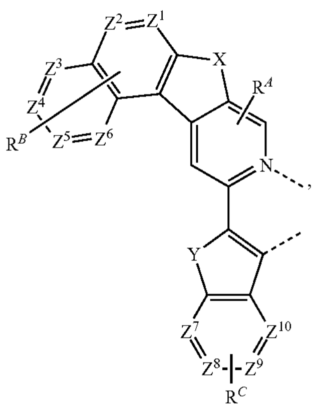

-continued
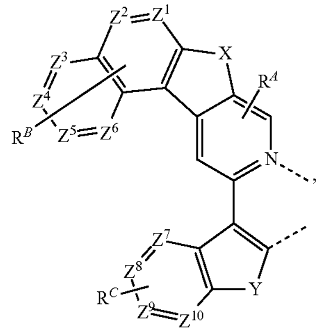
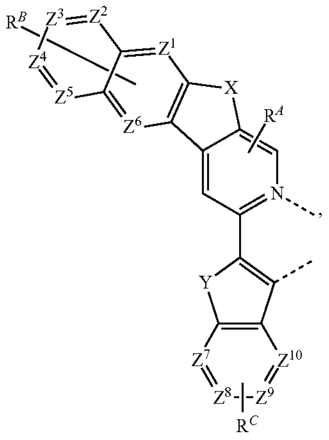
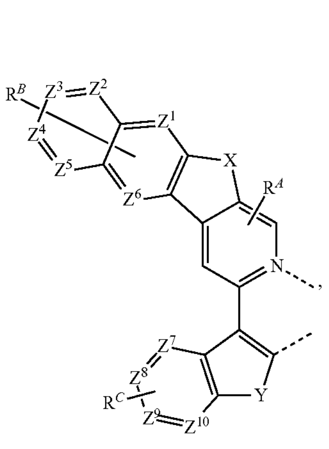
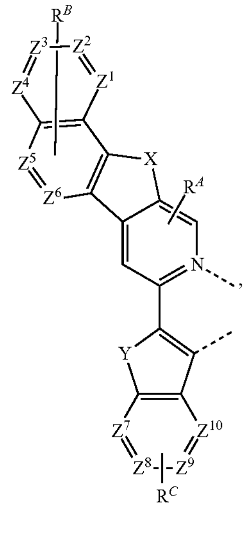
-continued
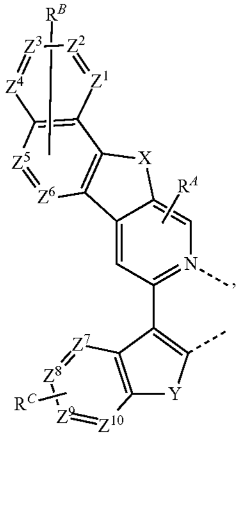
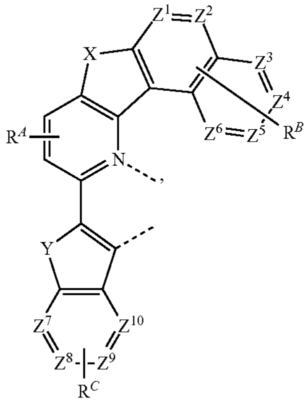
,
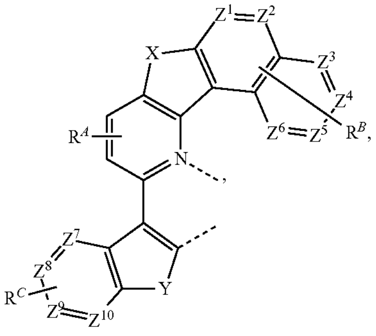
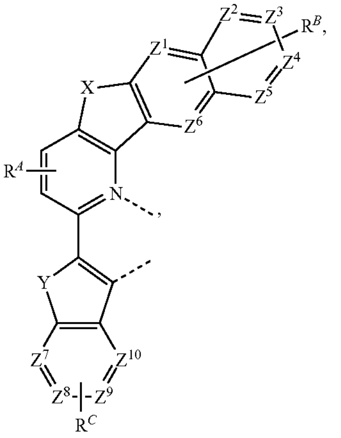
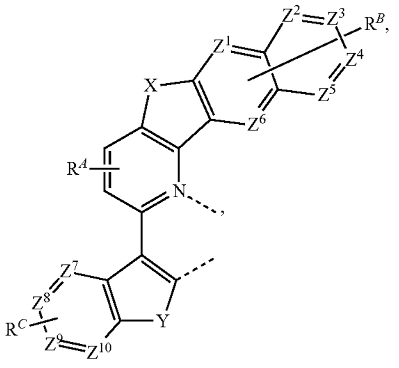

-continued

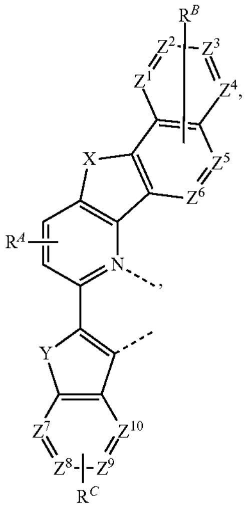

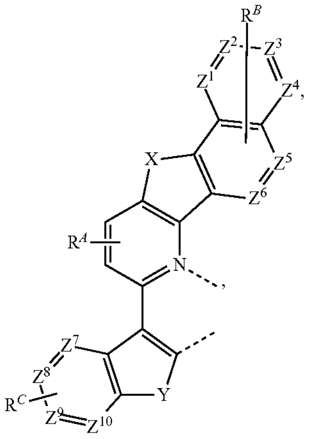

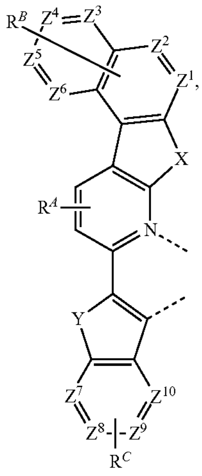

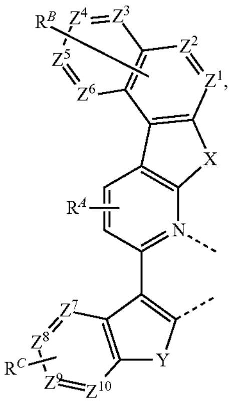

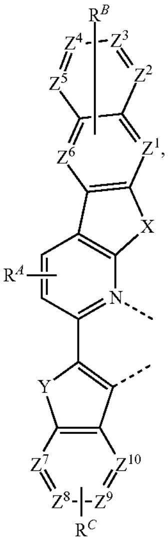

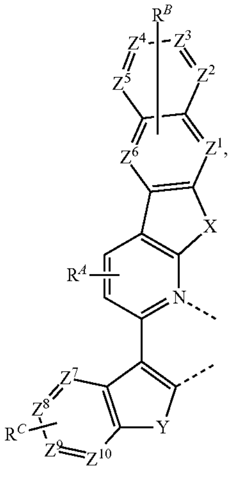

-continued

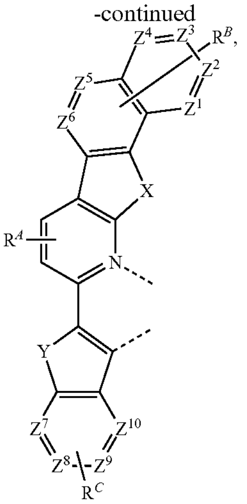

and

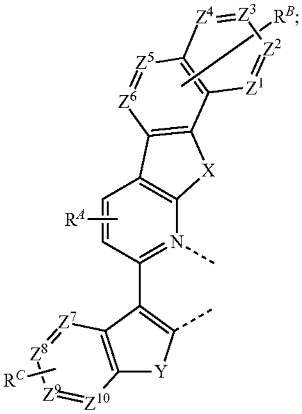

wherein Y is selected from the group consisting of O, S, Se, and $NR^D$;

wherein $R^A$, $R^B$, $R^C$, and $R^D$ each independently represents from none to the e maximum possible number of substitution;

wherein $R^A$, $R^B$, $R^C$, and $R^D$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile sulfanyl, sulfinyl, sulfonyl, phosphino, and combinations thereof; and wherein any two adjacent substituents are optionally joined to form into a ring; and wherein $Z^1$ to $Z^{10}$ is each independently selected from CH and N.

10. The compound of claim 1, wherein the ligand $L_A$ is selected from the group consisting of:

$L_{A1}$

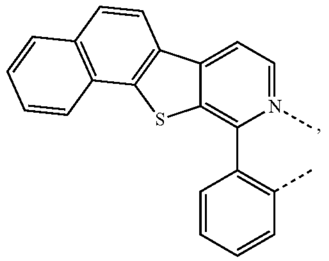

-continued
$L_{A2}$
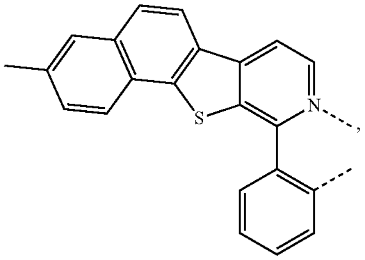
$L_{A3}$
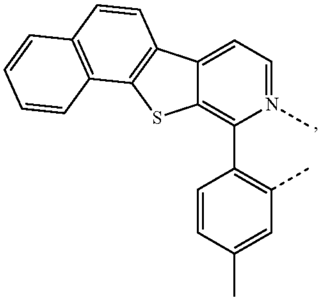
$L_{A4}$
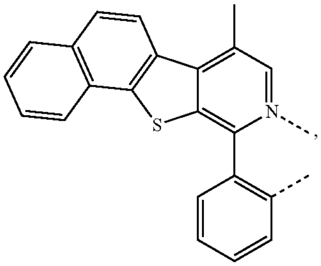
$L_{A5}$
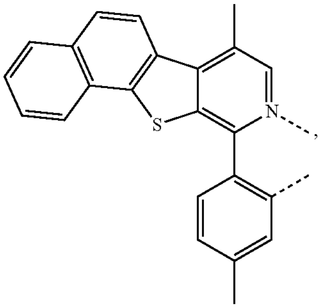
$L_{A6}$
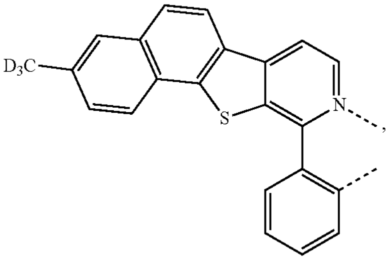
-continued
$L_{A7}$
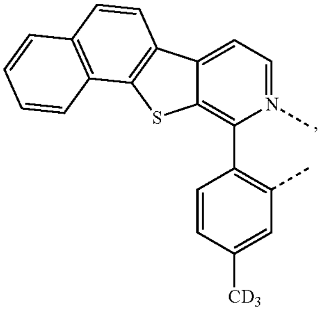
$L_{A8}$
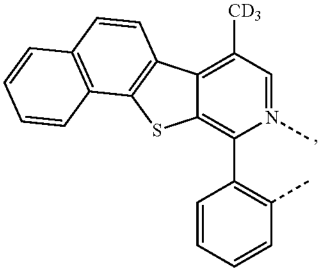
$L_{A9}$
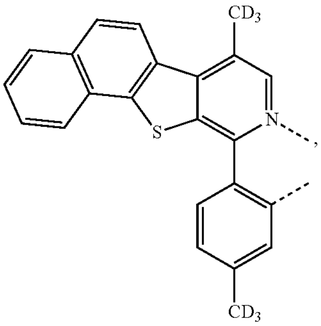
$L_{A11}$
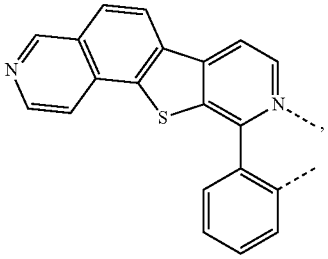
$L_{A11}$
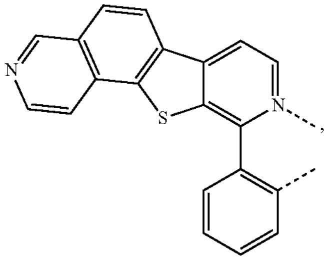

-continued
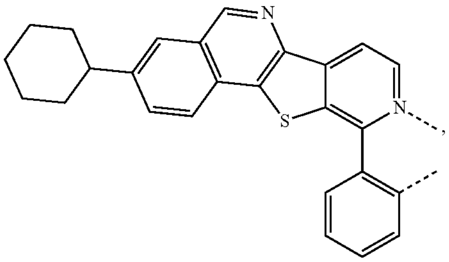
$L_{A15}$
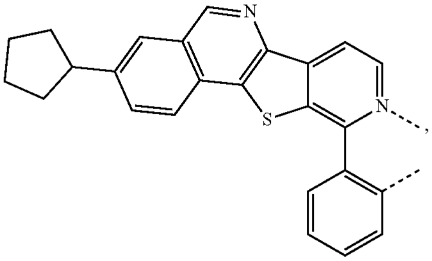
$L_{A16}$
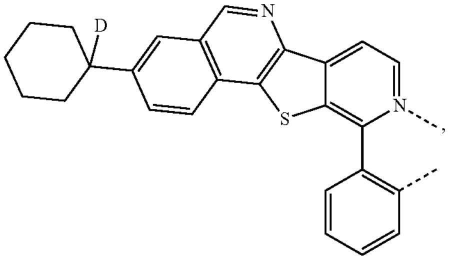
$L_{A17}$
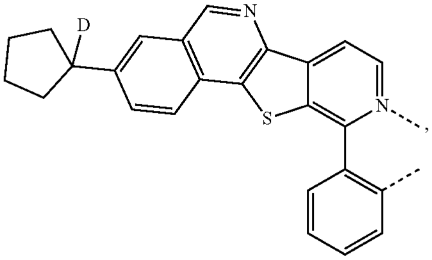
$L_{A18}$
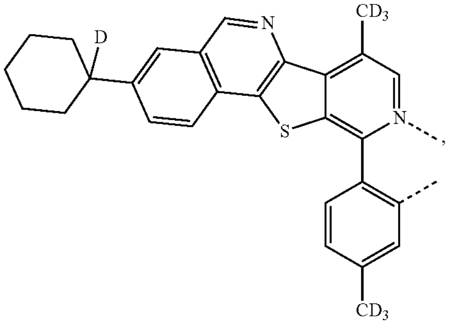
$L_{A19}$
-continued
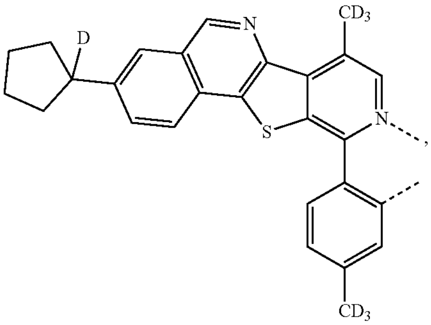
$L_{A20}$
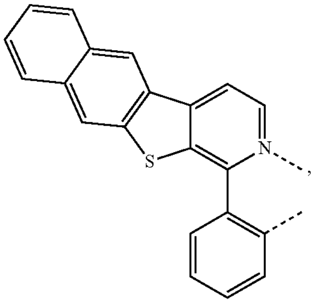
$L_{A21}$
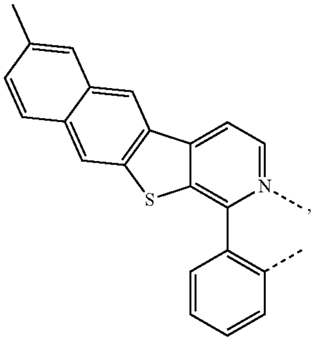
$L_{A22}$
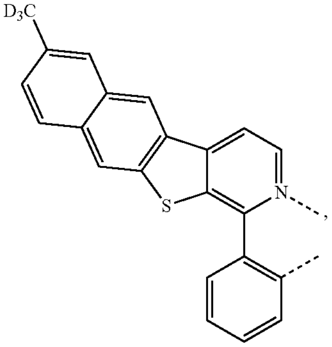
$L_{A23}$ -continued
$L_{A24}$
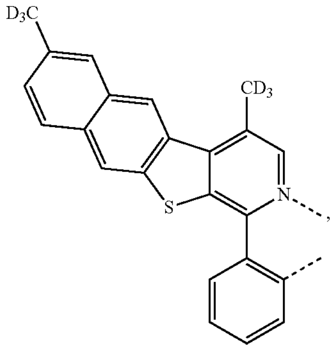
$L_{A25}$
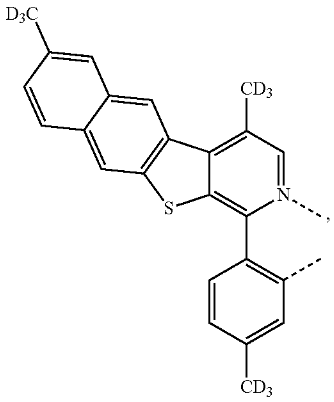
$L_{A26}$
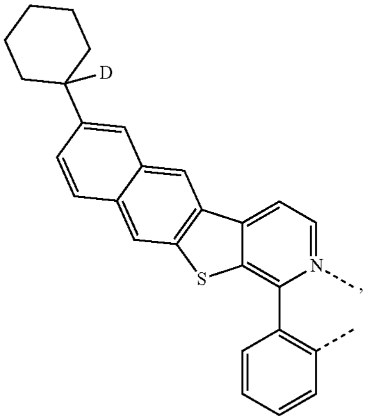
-continued
$L_{A27}$
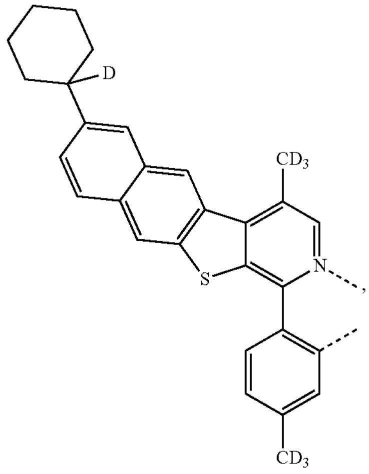
$L_{A28}$
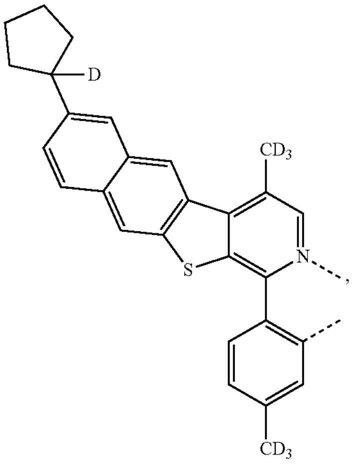
$L_{A29}$
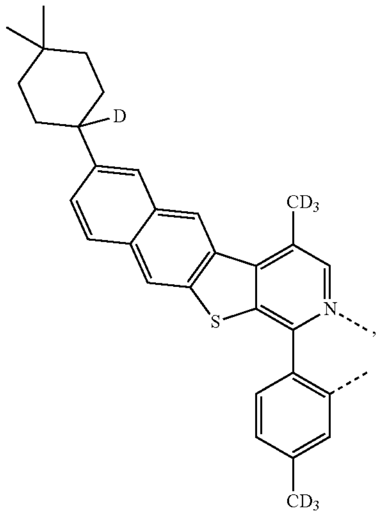

-continued
$L_{A31}$
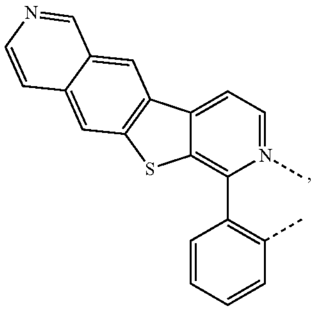
$L_{A34}$
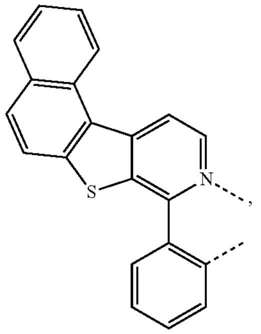
$L_{A35}$
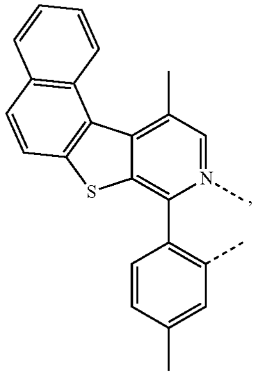
$L_{A36}$
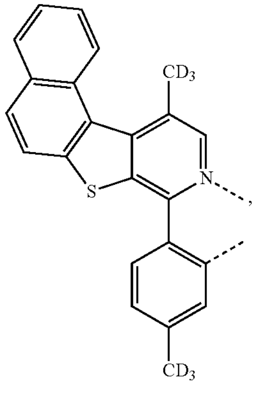
-continued
$L_{A37}$
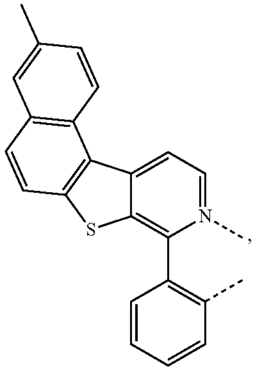
$L_{A39}$
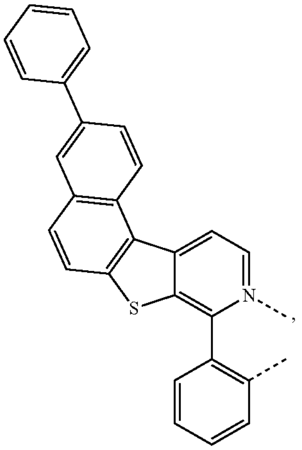
$L_{A40}$
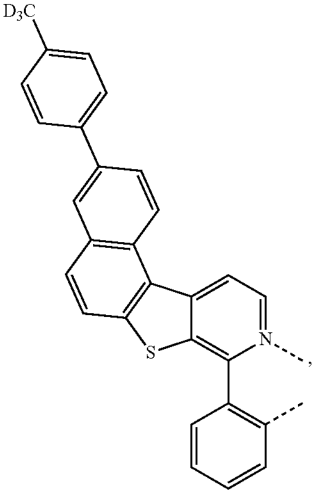

-continued
$L_{A41}$
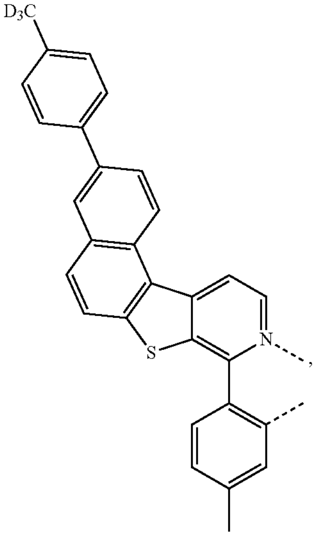
$L_{A42}$
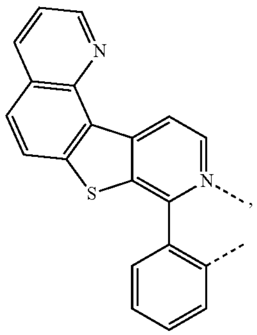
$L_{A43}$
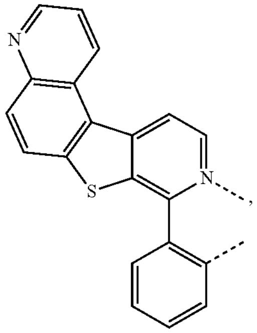
$L_{A44}$
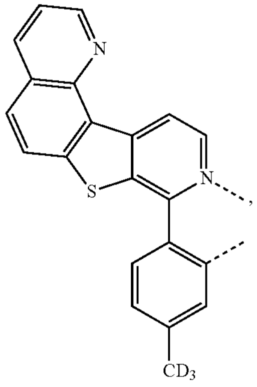
-continued
$L_{A45}$
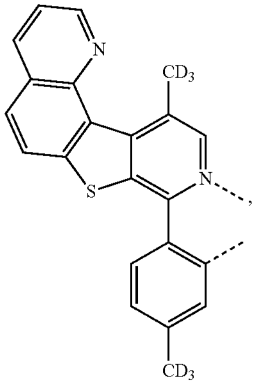
$L_{A46}$
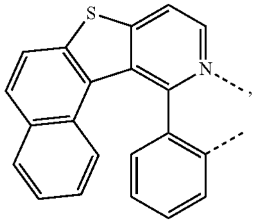
$L_{A47}$
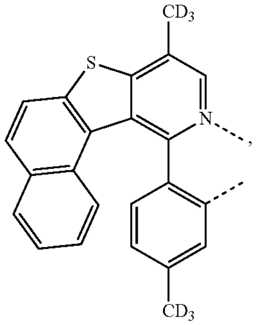
$L_{A48}$
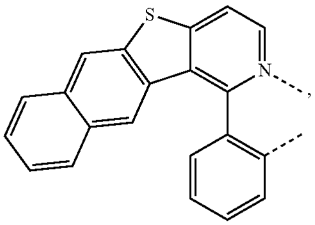
$L_{A51}$
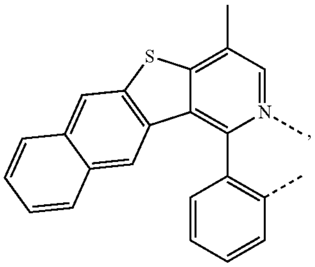

-continued
$L_{A52}$
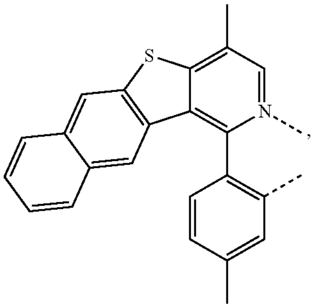
$L_{A53}$
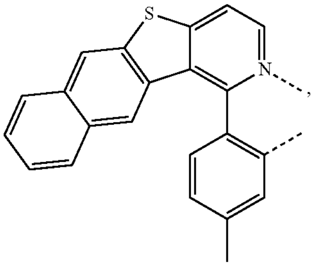
$L_{A54}$
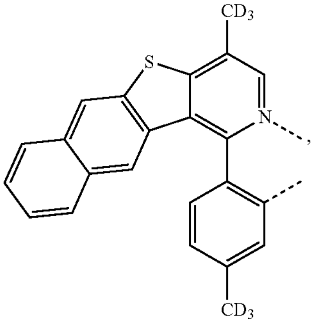
$L_{A55}$
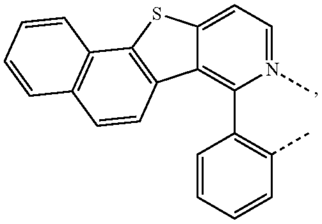
$L_{A57}$
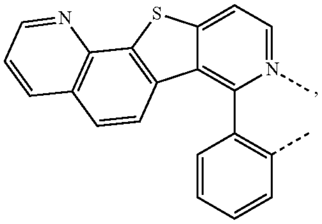
-continued
$L_{A58}$
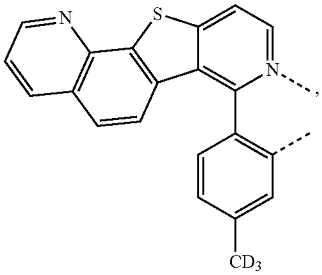
$L_{A59}$
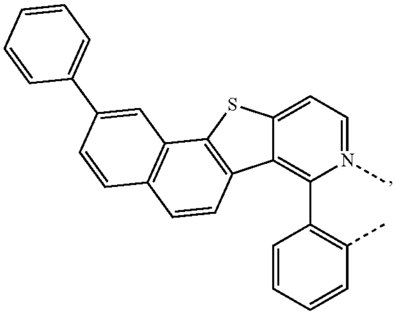
$L_{A60}$
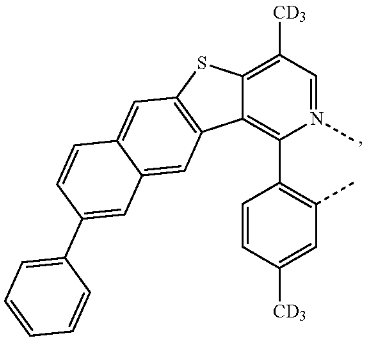
$L_{A61}$
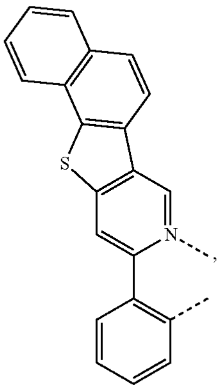

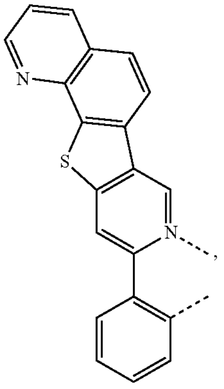
$L_{A62}$
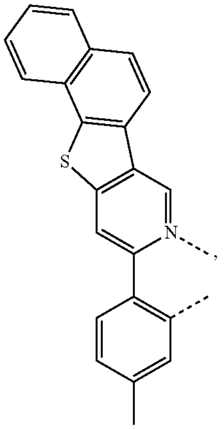
$L_{A63}$
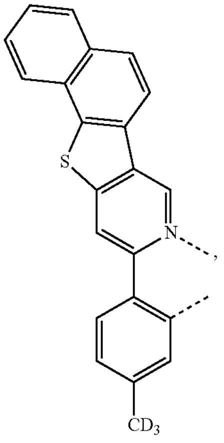
$L_{A64}$
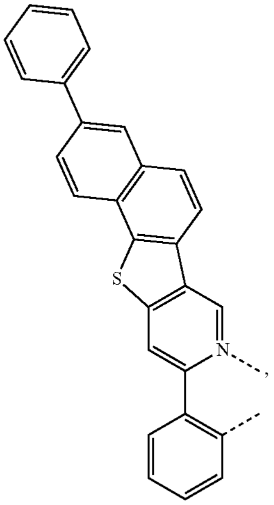
$L_{A65}$
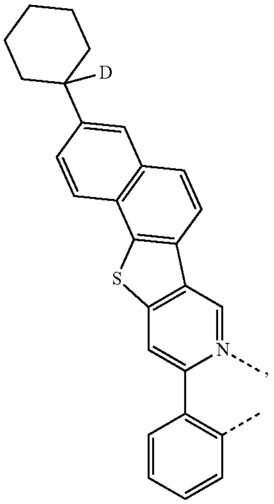
$L_{A66}$
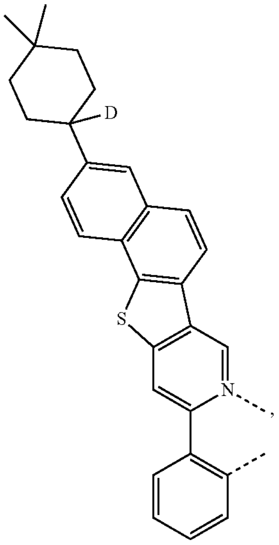
$L_{A67}$ -continued
L$_{A68}$
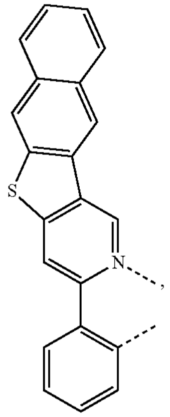
L$_{A69}$
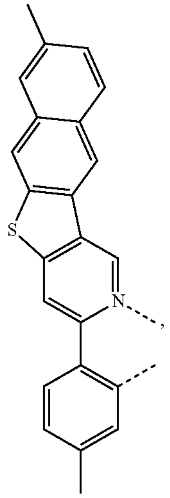
L$_{A70}$
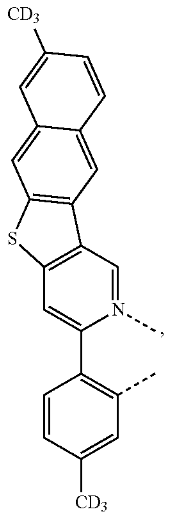
-continued
L$_{A71}$
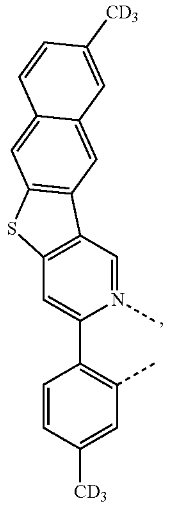
L$_{A72}$
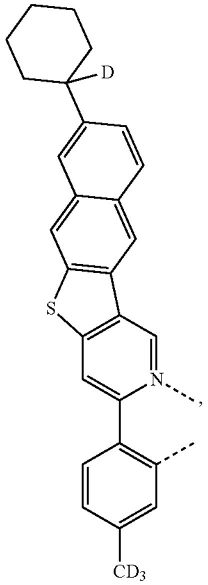
L$_{A73}$
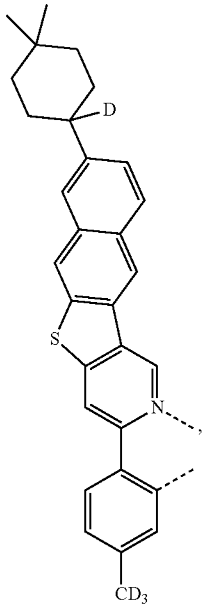

-continued
$L_{A74}$
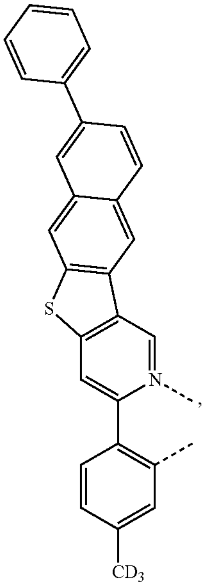
$L_{A79}$
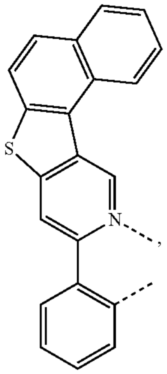
$L_{A79}$
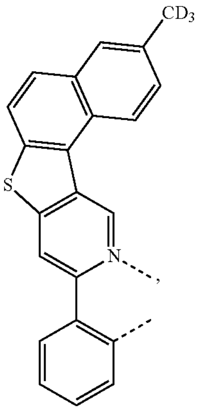
-continued
$L_{A80}$
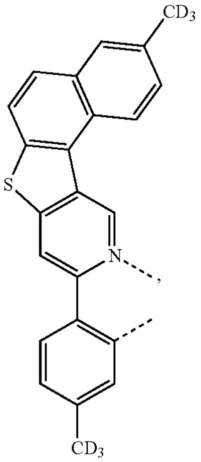
$L_{A81}$
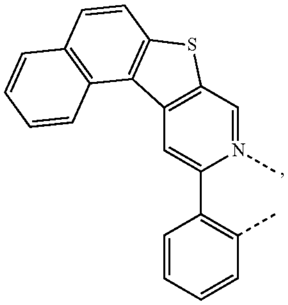
$L_{A83}$
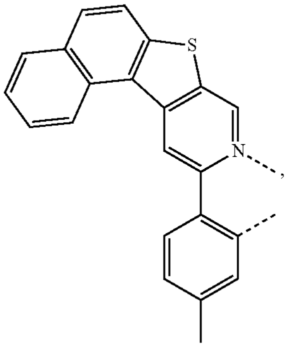
$L_{A84}$
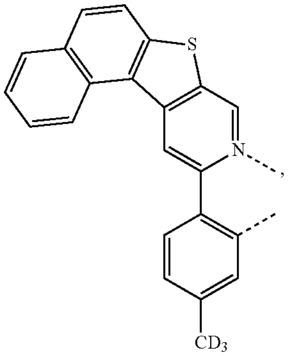

-continued
$L_{A85}$
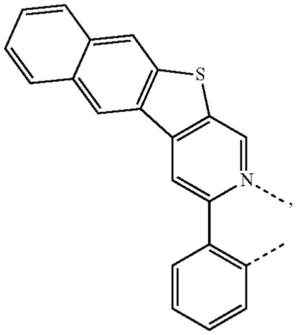
$L_{A86}$
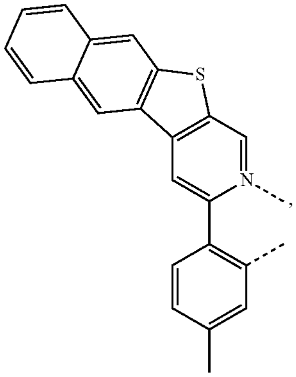
$L_{A86}$
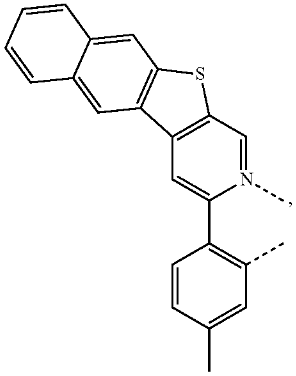
$L_{A87}$
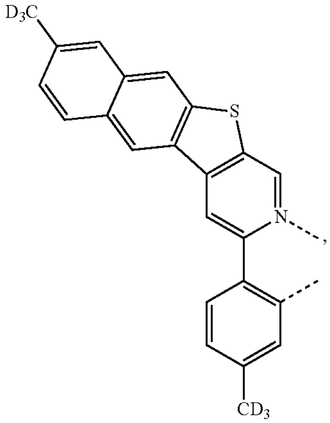
-continued
$L_{A88}$
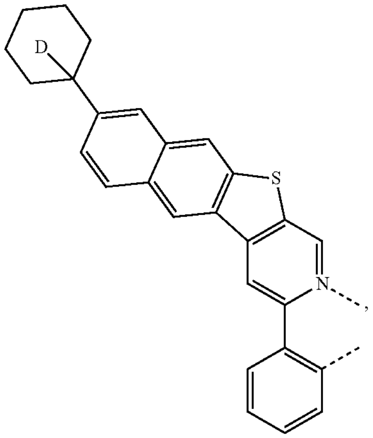
$L_{A89}$
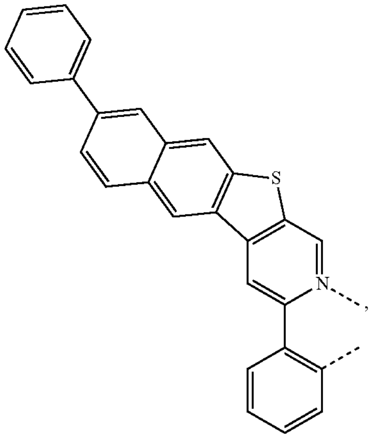
$L_{A90}$
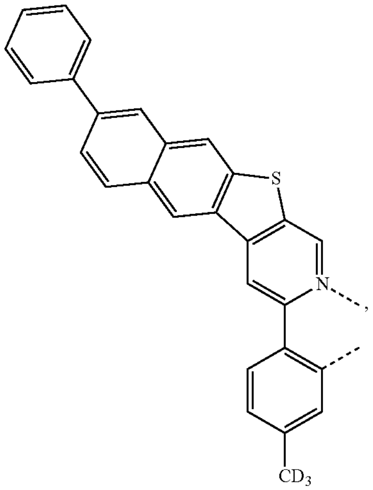

-continued
$L_{A91}$
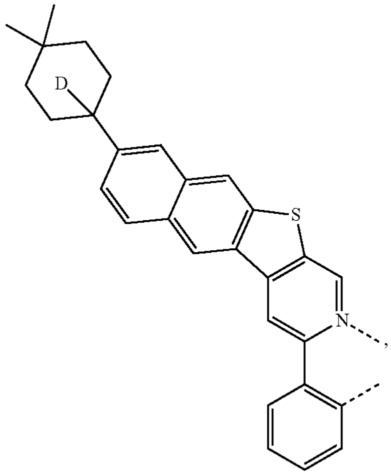
,
$L_{A92}$
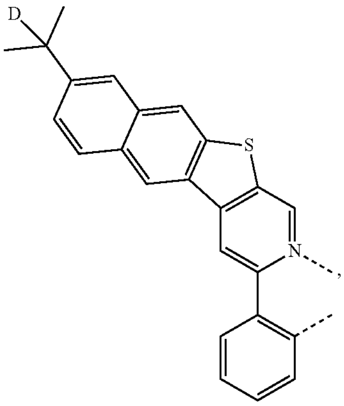
,
$L_{A93}$
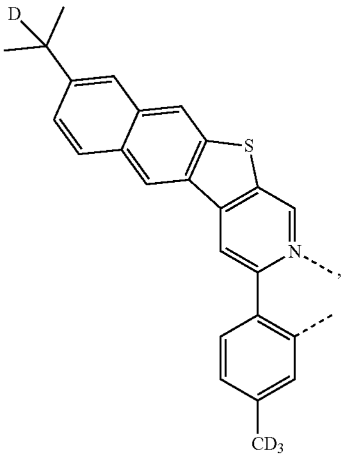
,
-continued
$L_{A99}$
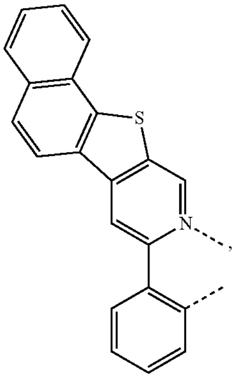
,
$L_{A100}$
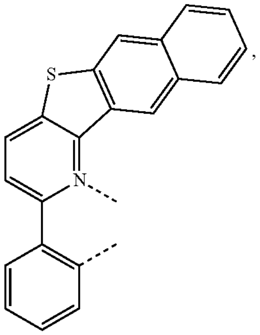
,
$L_{A101}$
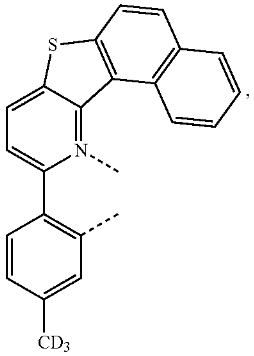
,
$L_{A104}$
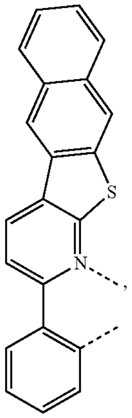
, -continued
$L_{A105}$
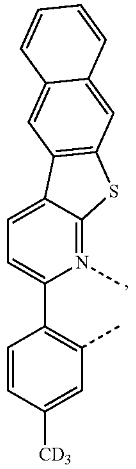
$L_{A107}$
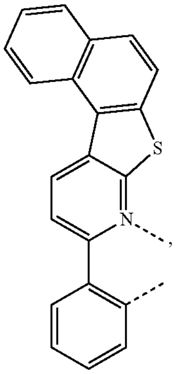
$L_{A108}$
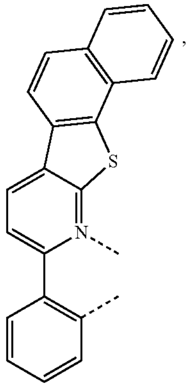
$L_{A109}$
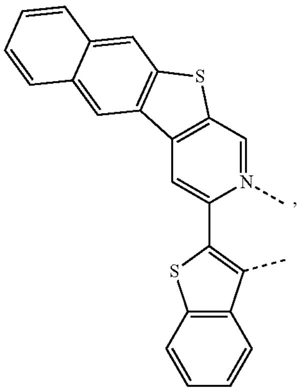
-continued
$L_{A110}$
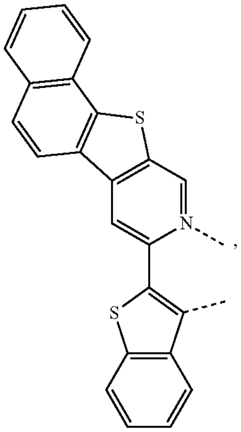
$L_{A111}$
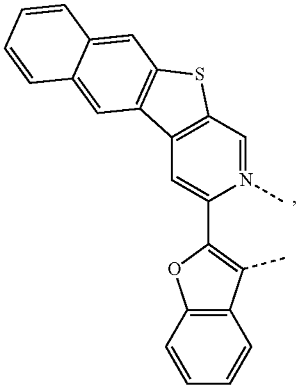
$L_{A112}$
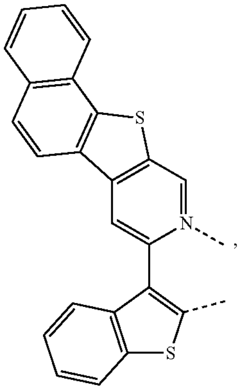
$L_{A113}$
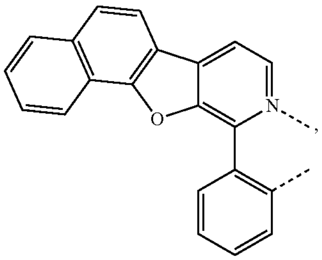

-continued
$L_{A114}$
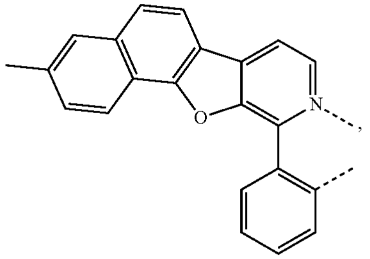
$L_{A115}$
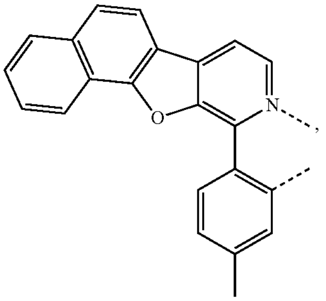
$L_{A116}$
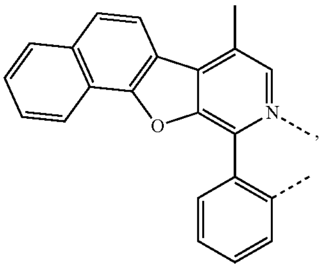
$L_{A117}$
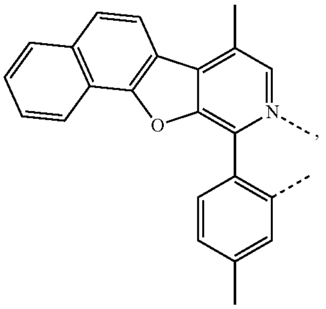
$L_{A118}$
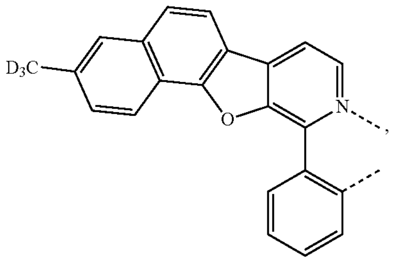
-continued
$L_{A119}$
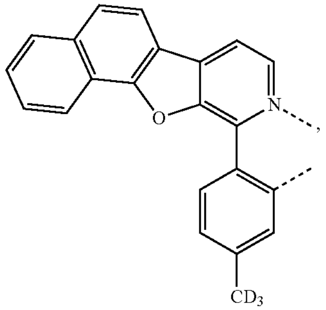
$L_{A120}$
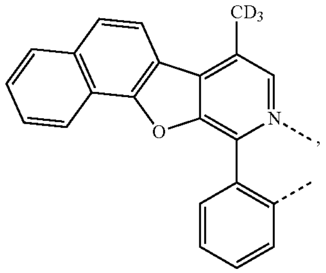
$L_{A121}$
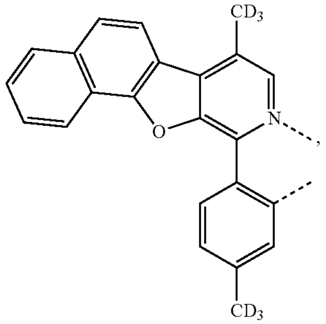
$L_{A123}$
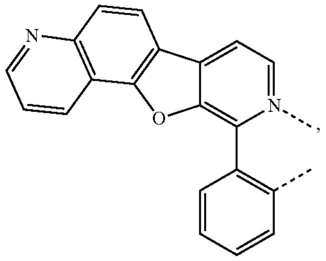
$L_{A126}$
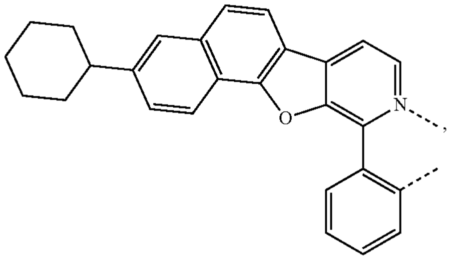

-continued
$L_{A127}$
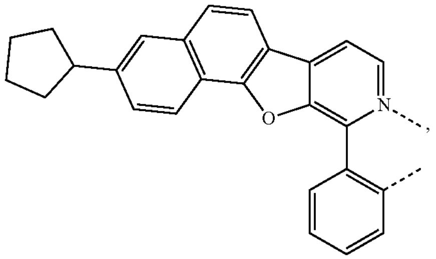
$L_{A128}$
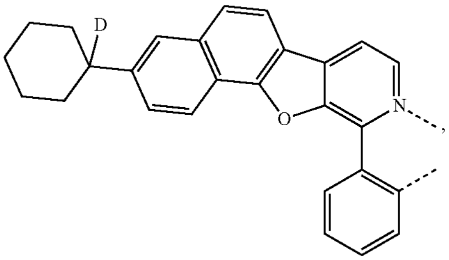
$L_{A129}$
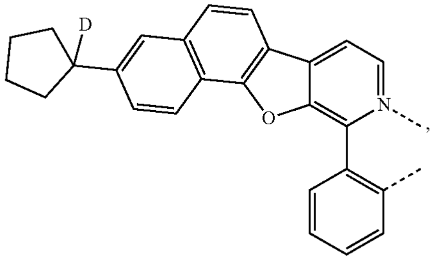
$L_{A130}$
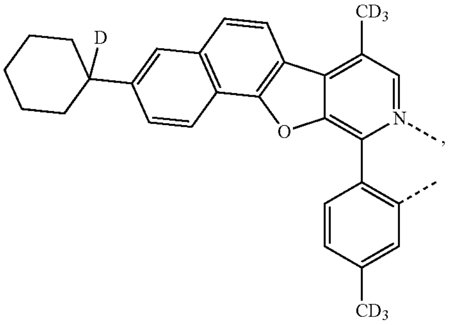
$L_{A131}$
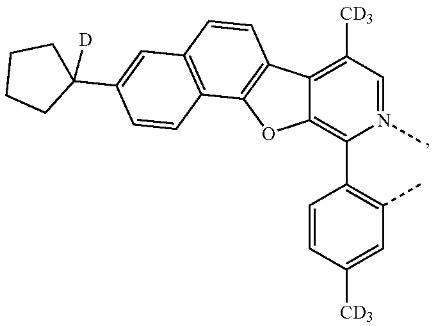
-continued
$L_{A132}$
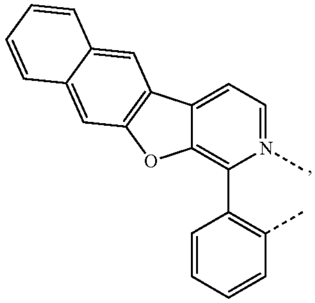
$L_{A133}$
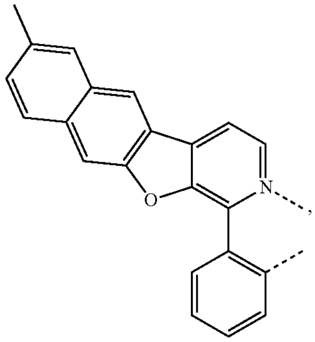
$L_{A134}$
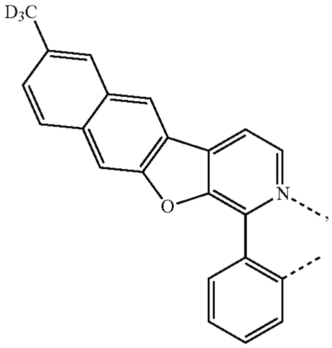
$L_{A135}$
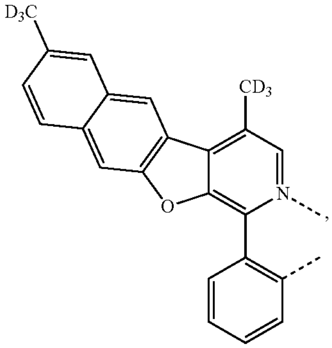

-continued
$L_{A136}$
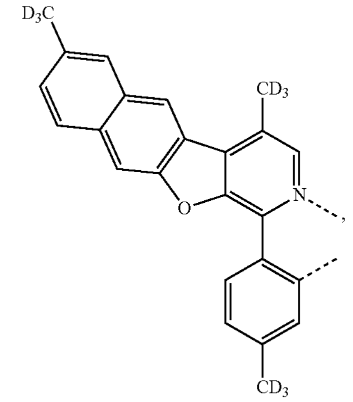
$L_{A137}$
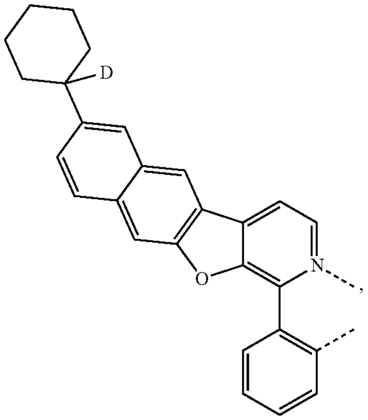
$L_{A138}$
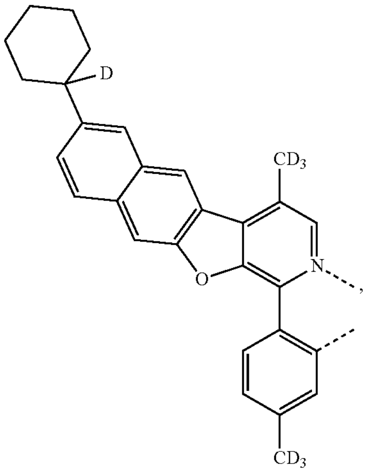
-continued
$L_{A139}$
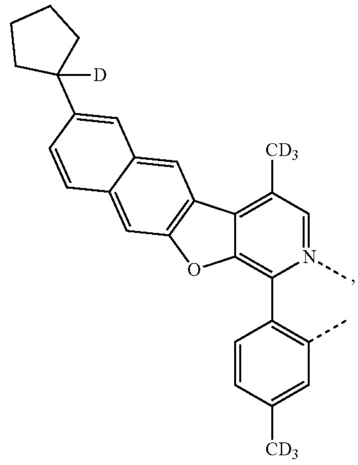
$L_{A140}$
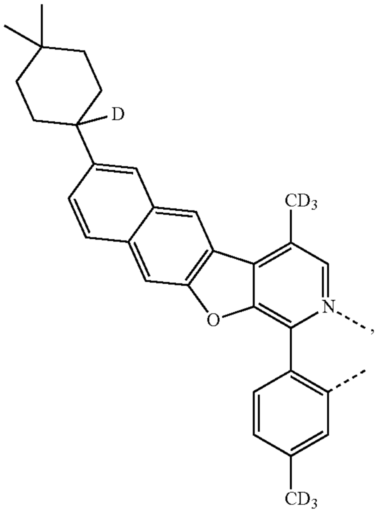
$L_{A142}$
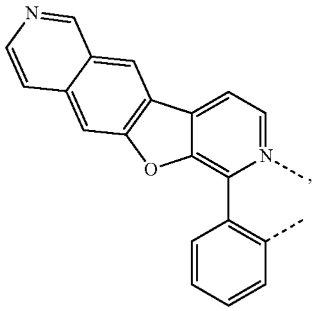
$L_{A145}$
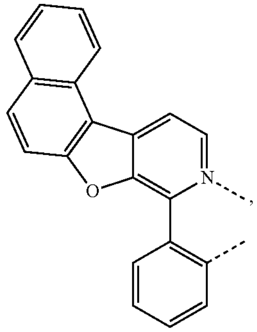

-continued
L$_{A146}$
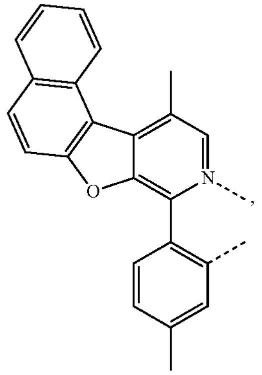
L$_{A147}$
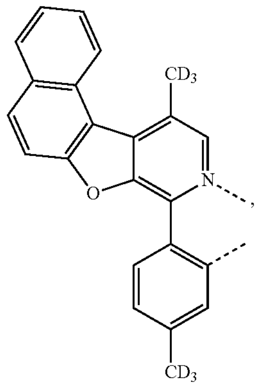
L$_{A148}$
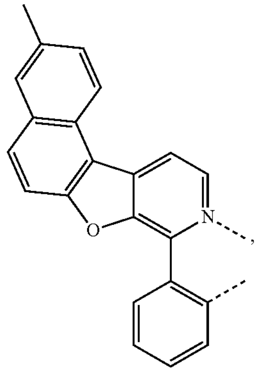
L$_{A149}$
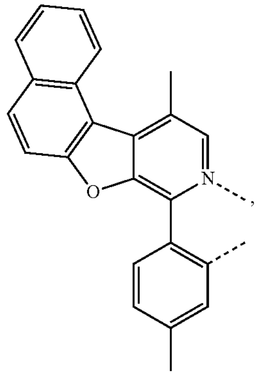
-continued
L$_{A150}$
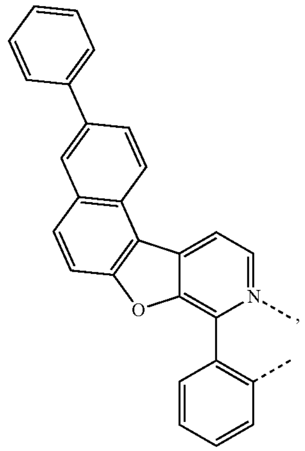
L$_{A151}$
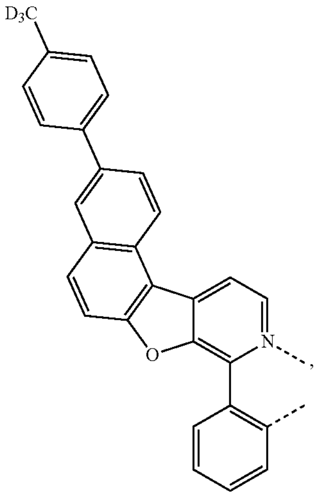
L$_{A152}$
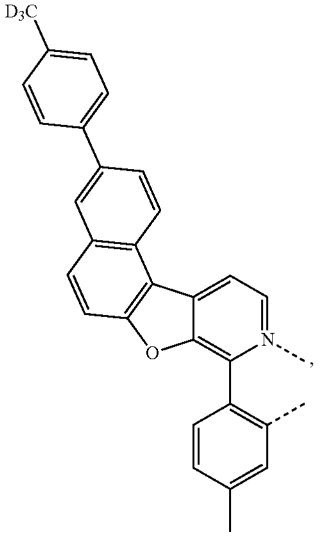

-continued
$L_{A153}$
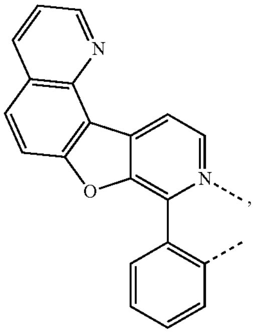
$L_{A154}$
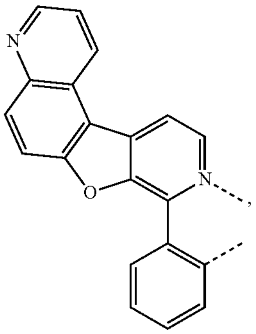
$L_{A155}$
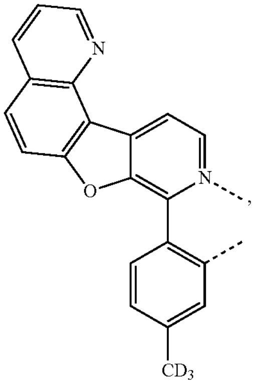
$L_{A156}$
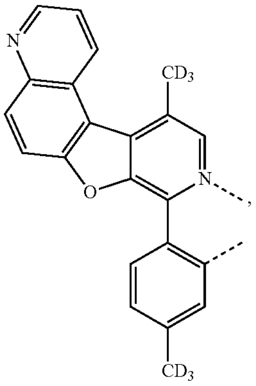
-continued
$L_{A157}$
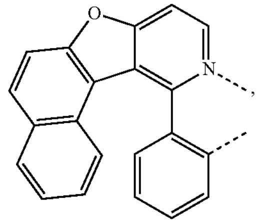
$L_{A158}$
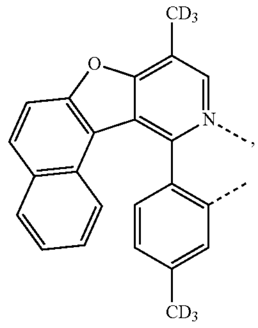
$L_{A159}$
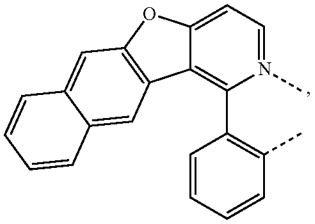
$L_{A162}$
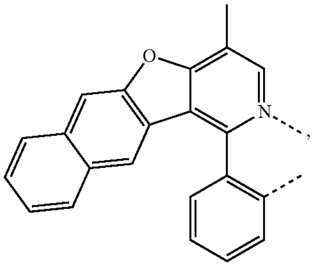
$L_{A163}$
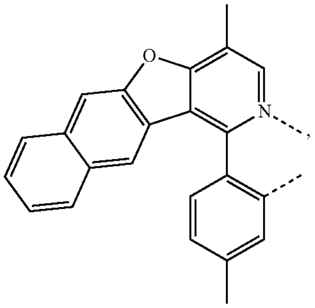

-continued
$L_{A164}$
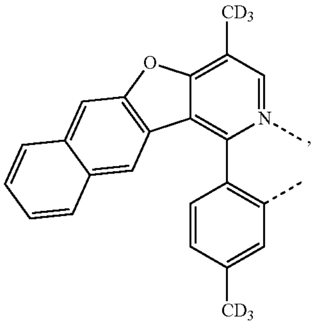
$L_{A165}$
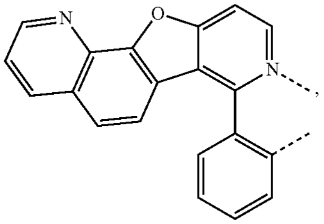
$L_{A168}$
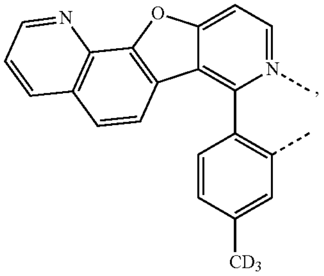
$L_{A169}$
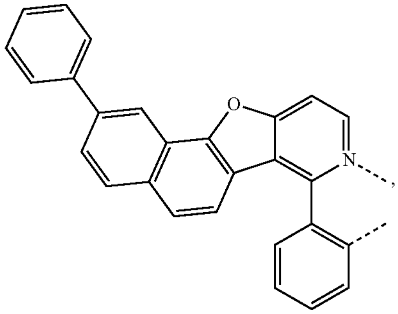
$L_{A170}$
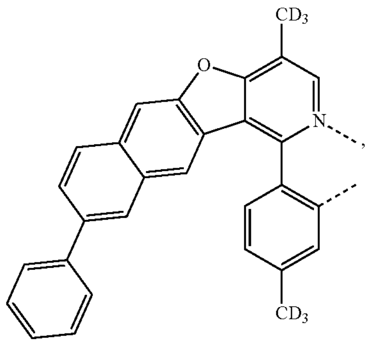
-continued
$L_{A171}$
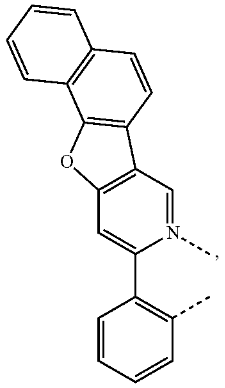
$L_{A172}$
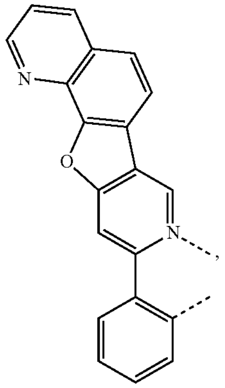
$L_{A173}$
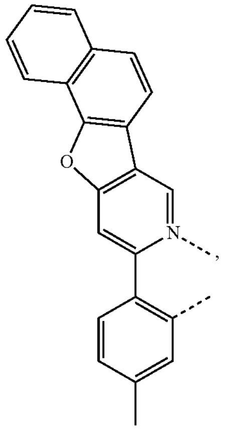
$L_{A174}$
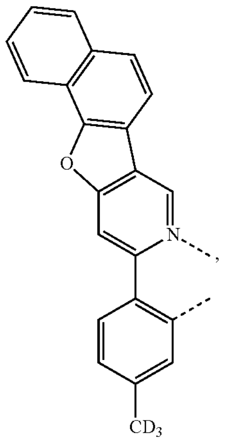

-continued
$L_{A175}$
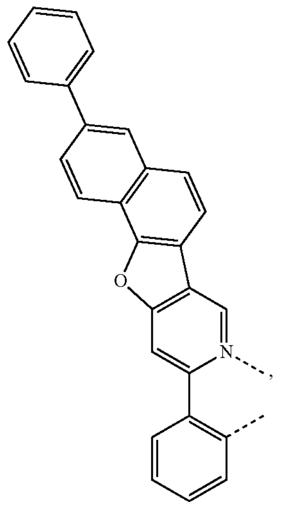
$L_{A175}$
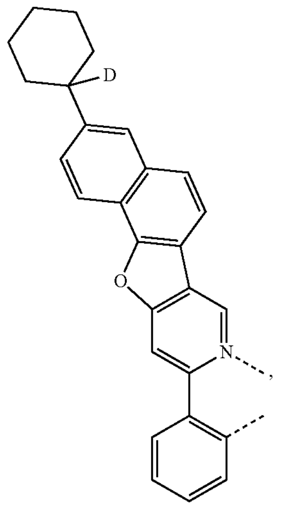
$L_{A177}$
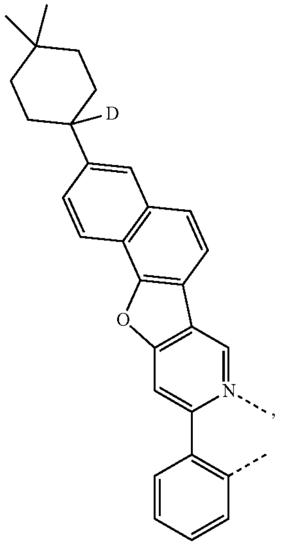
-continued
$L_{A178}$
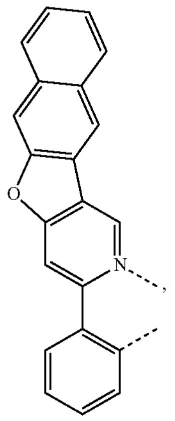
$L_{A179}$
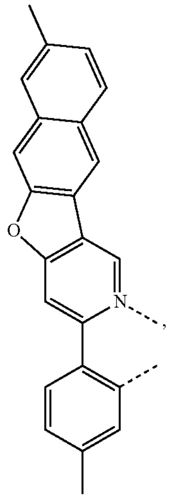
$L_{A180}$
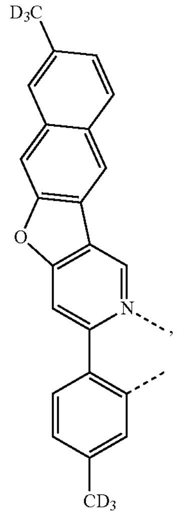

-continued
$L_{A181}$
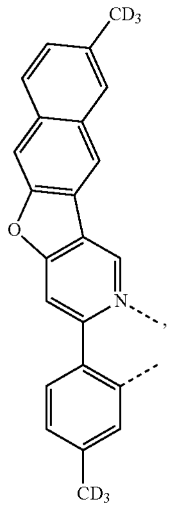
$L_{A182}$
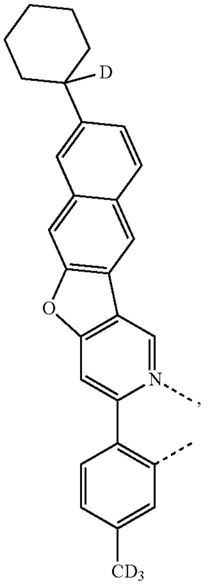
-continued
$L_{A183}$
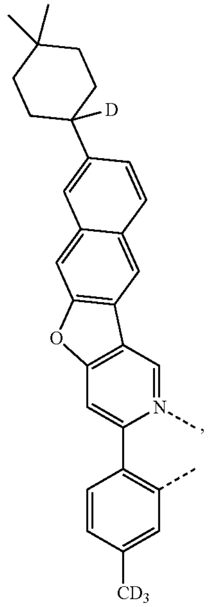
$L_{A184}$
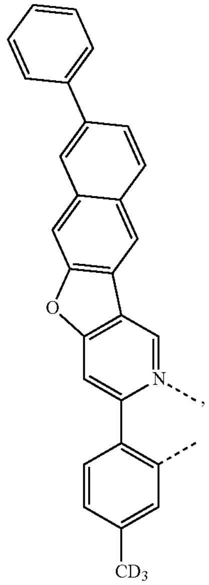
$L_{A188}$
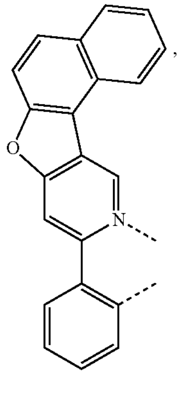

-continued
$L_{A189}$
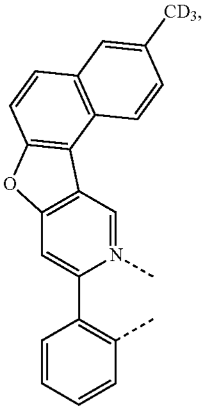
$L_{A190}$
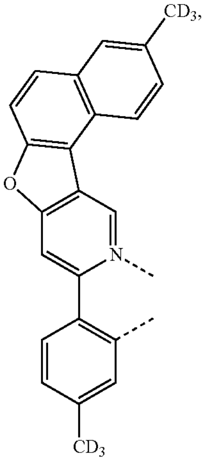
$L_{A191}$
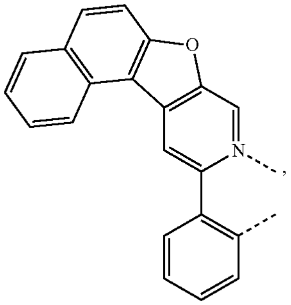
$L_{A193}$
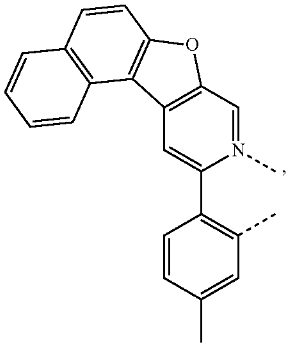
-continued
$L_{A194}$
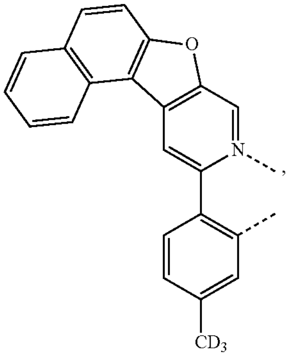
$L_{A195}$
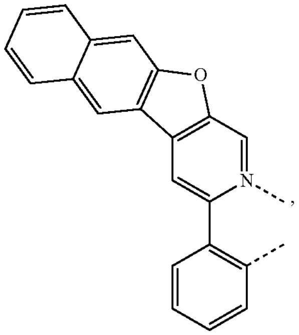
$L_{A196}$
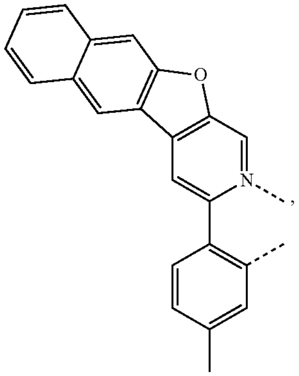
$L_{A196}$
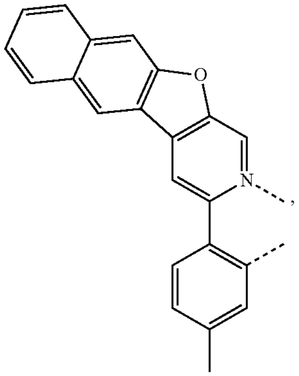

-continued
$L_{A197}$
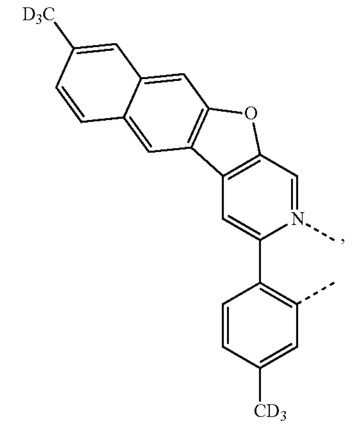
$L_{A198}$
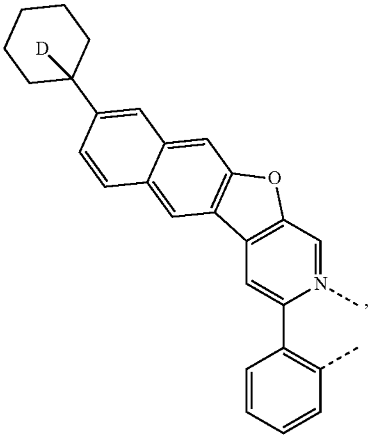
$L_{A199}$
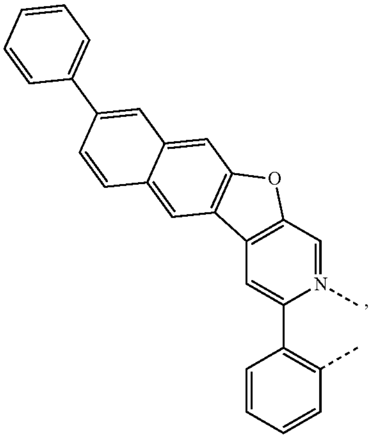
-continued
$L_{A200}$
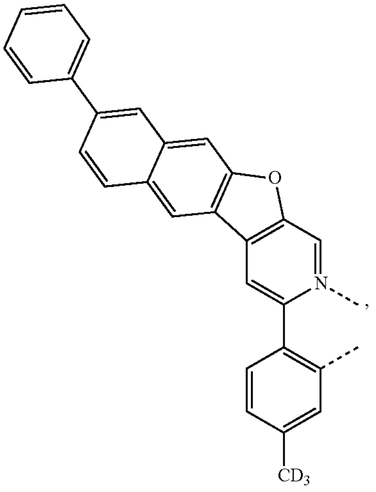
$L_{A201}$
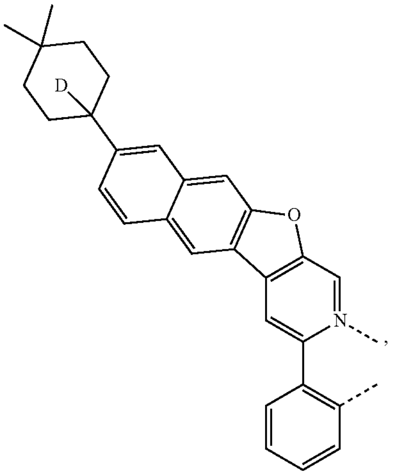
$L_{A202}$
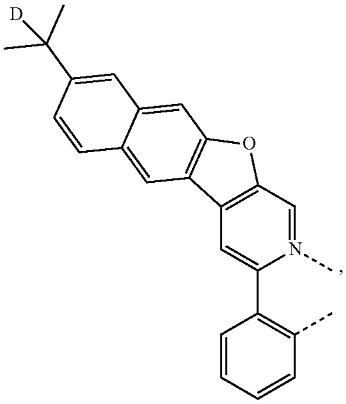

-continued
$L_{A203}$
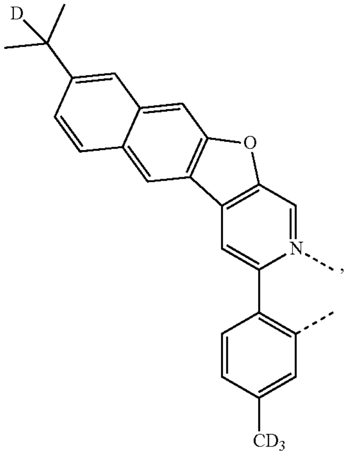
$L_{A209}$
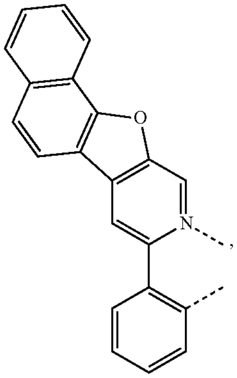
$L_{A210}$
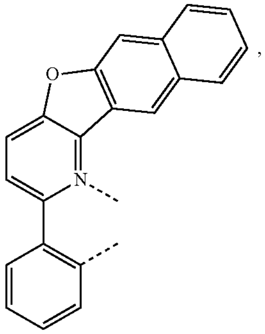
$L_{A211}$
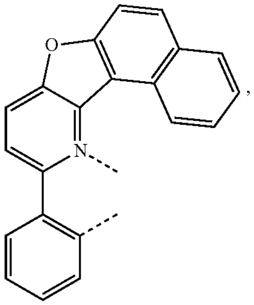
-continued
$L_{A214}$
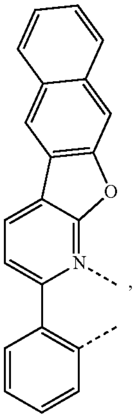
$L_{A216}$
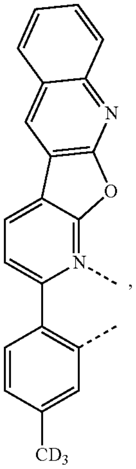
$L_{A217}$
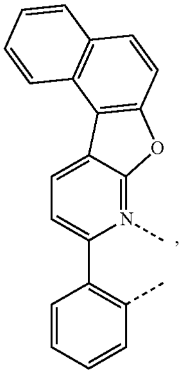
$L_{A218}$
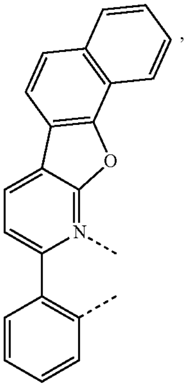

-continued
$L_{A219}$
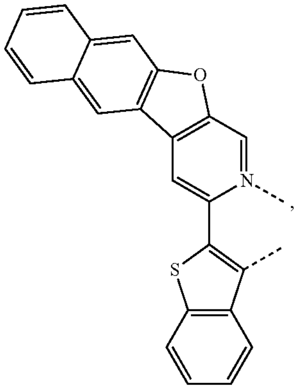
$L_{A220}$
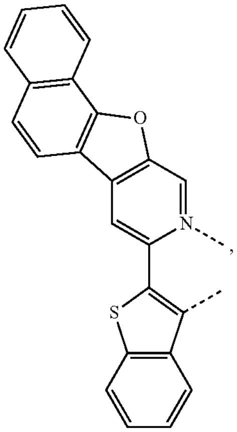
$L_{A221}$
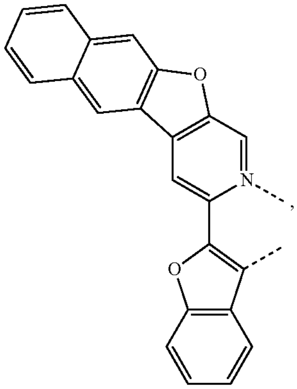
$L_{A222}$
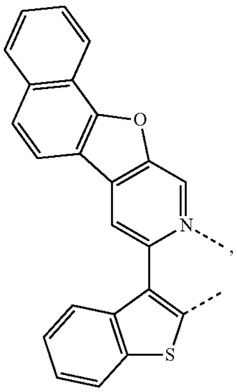
-continued
$L_{A223}$
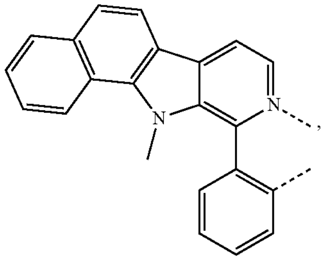
$L_{A224}$
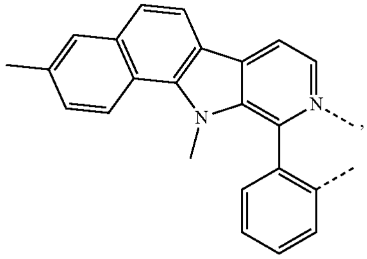
$L_{A225}$
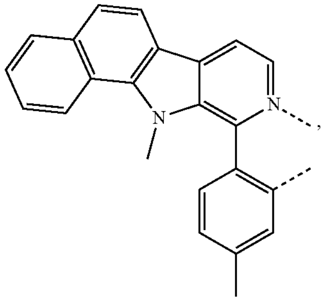
$L_{A226}$
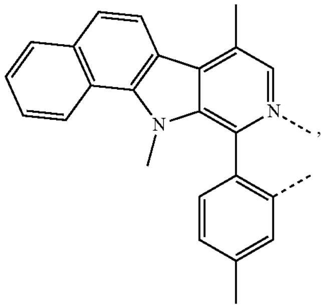
$L_{A227}$
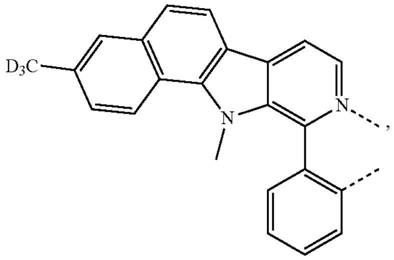

-continued
L$_{A228}$
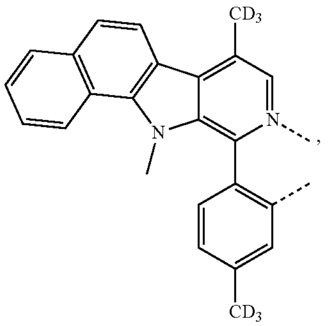
L$_{A230}$
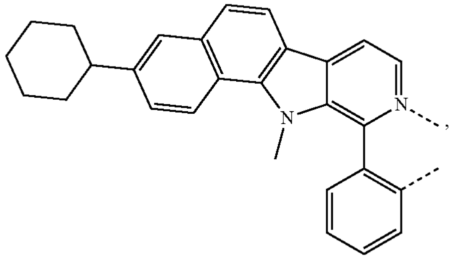
L$_{A231}$
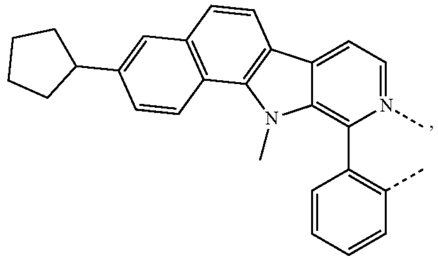
L$_{A232}$
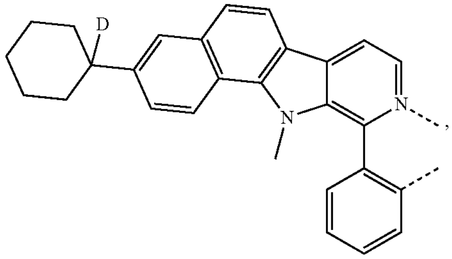
L$_{A233}$
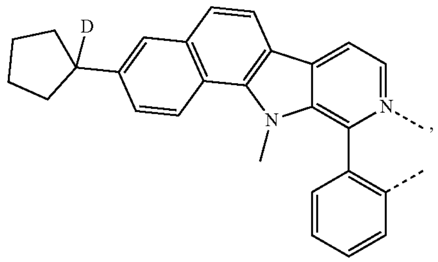
-continued
L$_{A234}$
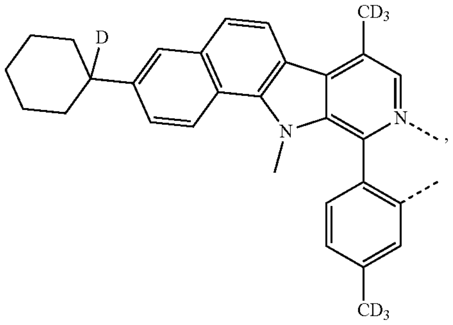
L$_{A235}$
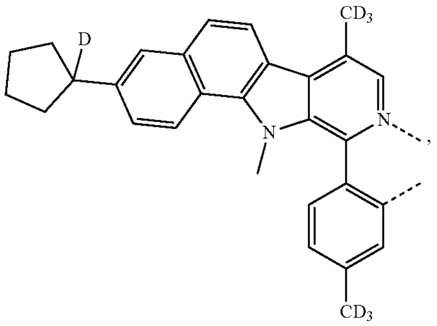
L$_{A236}$
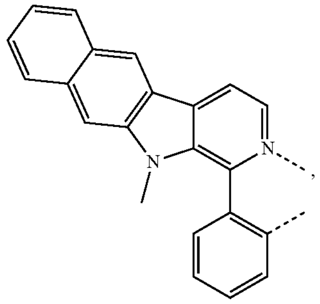
L$_{A237}$
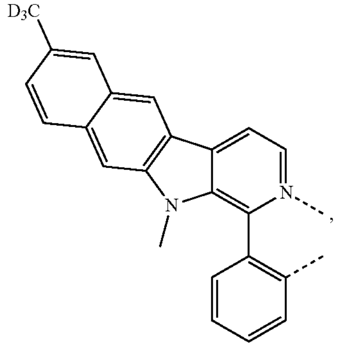

-continued
$L_{A238}$
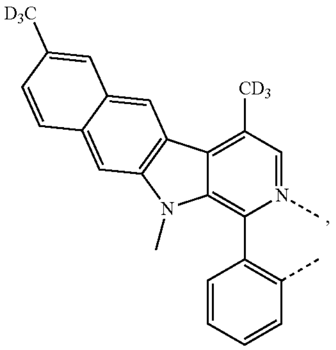
$L_{A239}$
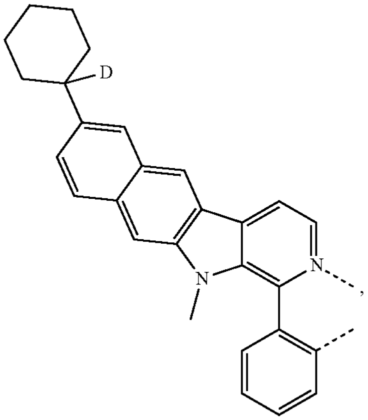
$L_{A240}$
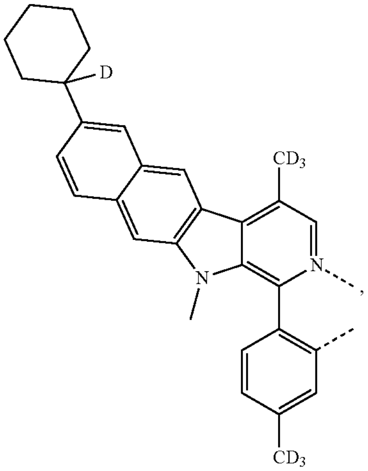
-continued
$L_{A241}$
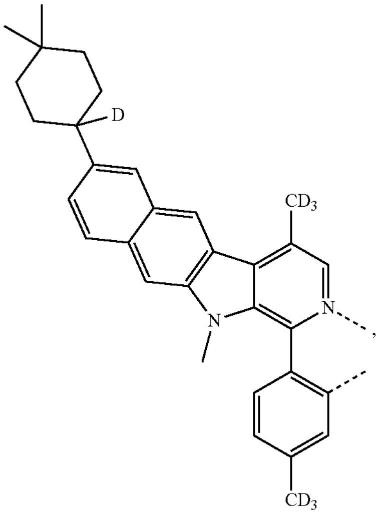
$L_{A242}$
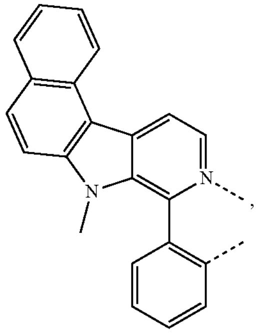
$L_{A243}$
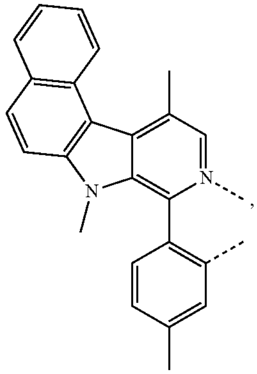
$L_{A244}$
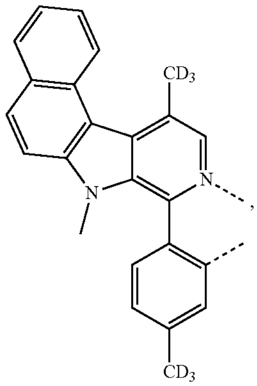

-continued
$L_{A245}$
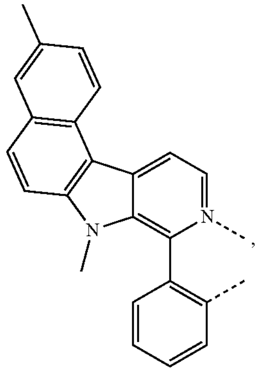
$L_{A246}$
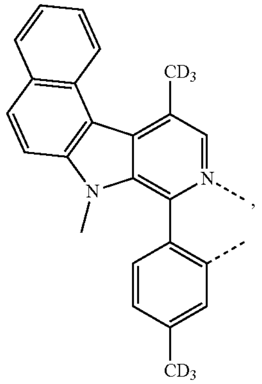
$L_{A247}$
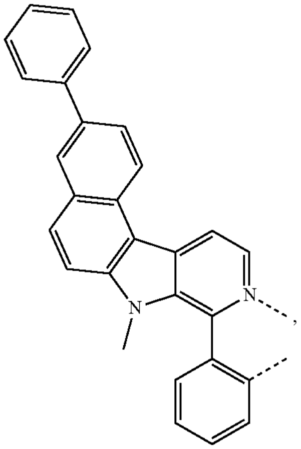
-continued
$L_{A248}$
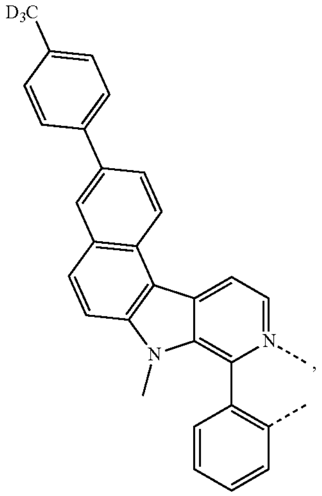
$L_{A249}$
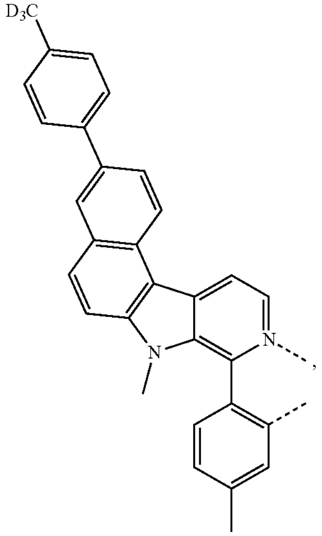
$L_{A250}$
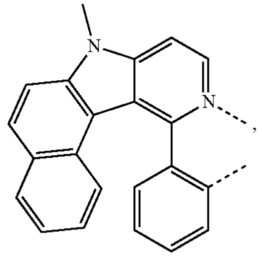
$L_{A251}$
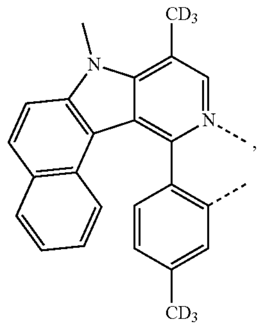

-continued
$L_{A252}$
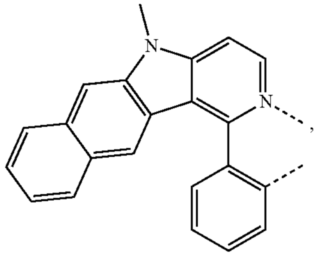
$L_{A253}$
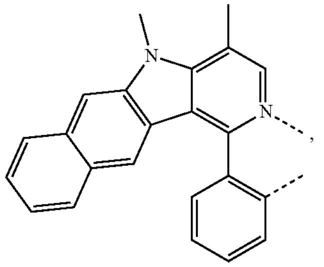
$L_{A254}$
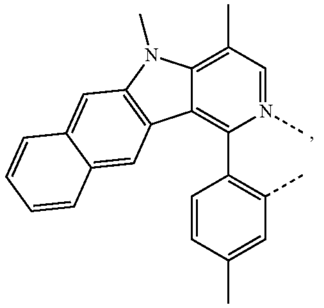
$L_{A255}$
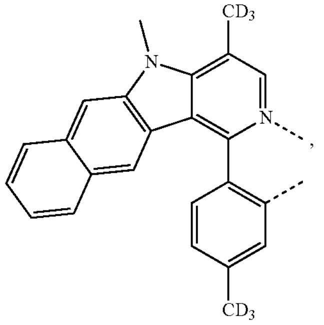
$L_{A256}$
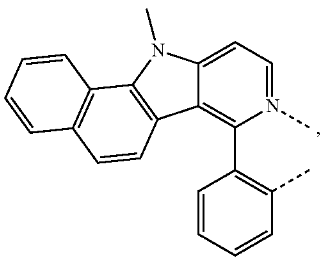
-continued
$L_{A257}$
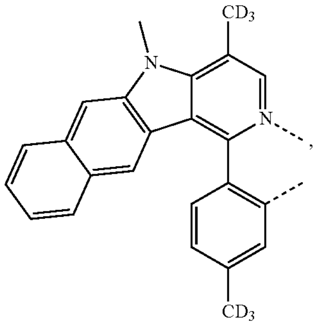
$L_{A258}$
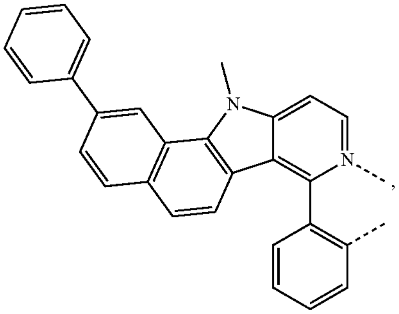
$L_{A259}$
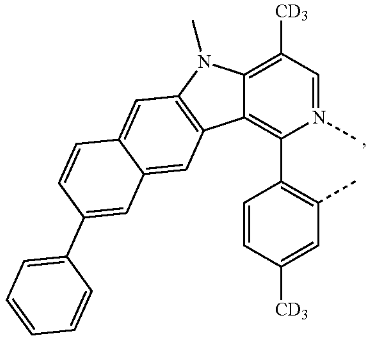
$L_{A260}$
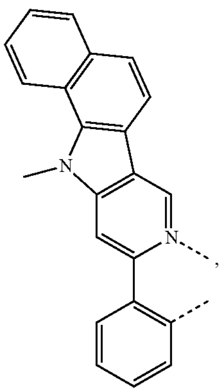

-continued
$L_{A261}$
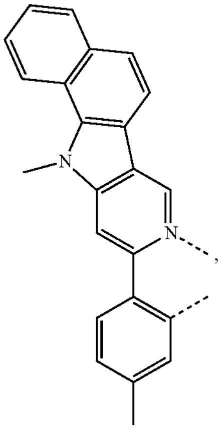
$L_{A262}$
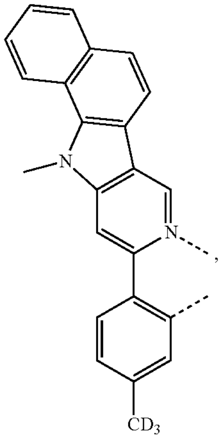
$L_{A263}$
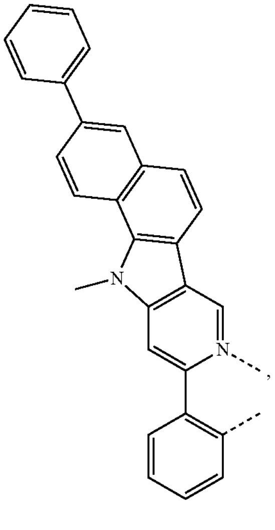
-continued
$L_{A264}$
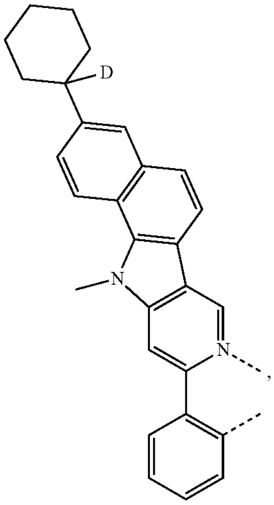
$L_{A265}$
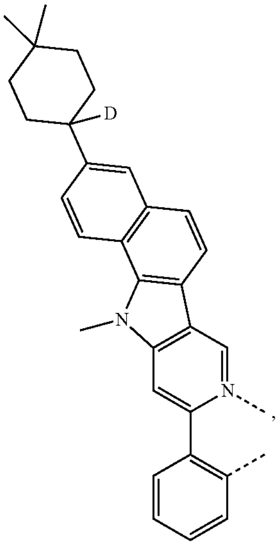
$L_{A266}$
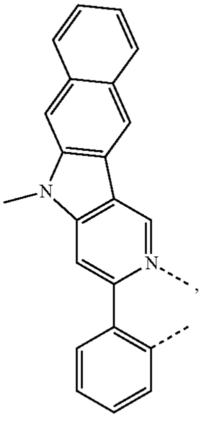

-continued
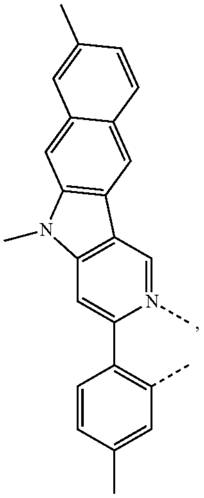
$L_{A267}$
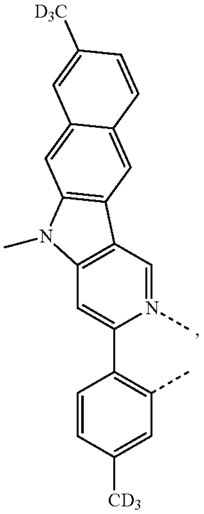
$L_{A268}$
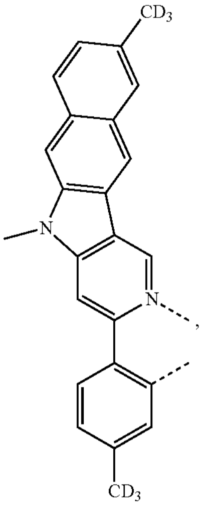
$L_{A269}$
-continued
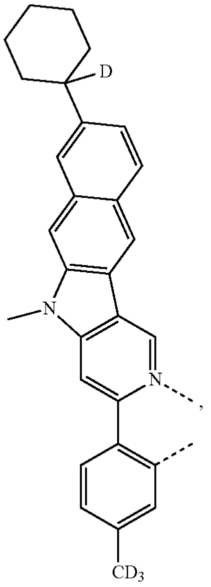
$L_{A270}$
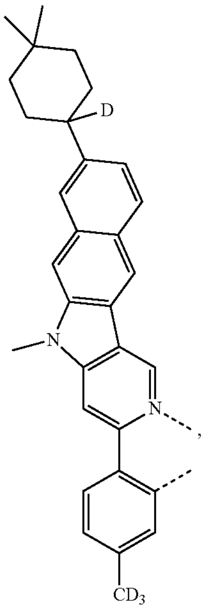
$L_{A271}$ -continued
$L_{A272}$
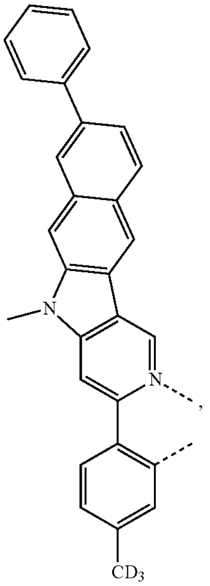
$L_{A273}$
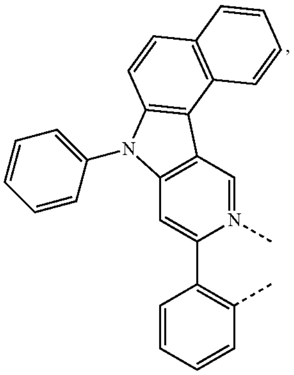
$L_{A274}$
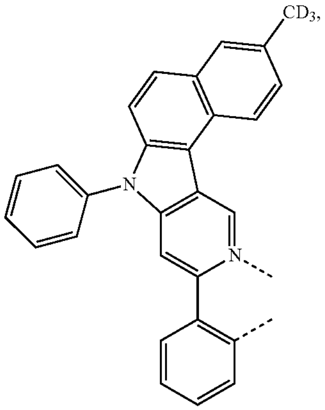
-continued
$L_{A275}$
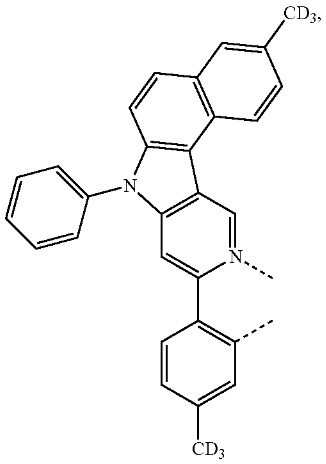
$L_{A276}$
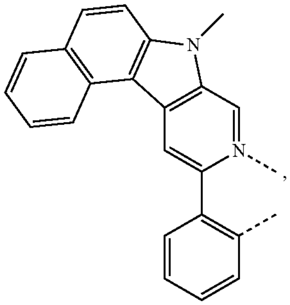
$L_{A277}$
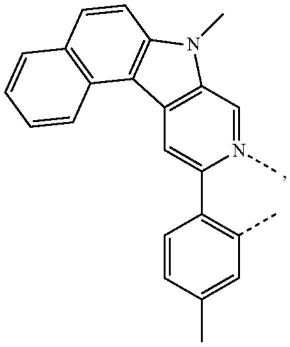
$L_{A278}$
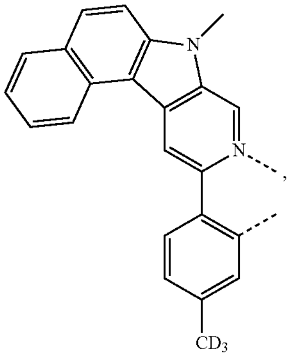

-continued
L$_{A279}$
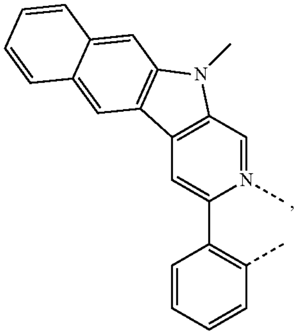
L$_{A280}$
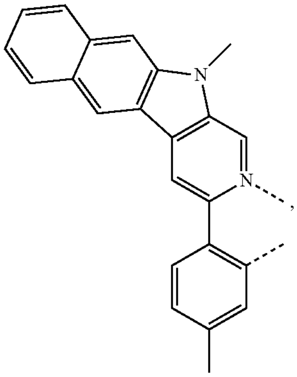
L$_{A281}$
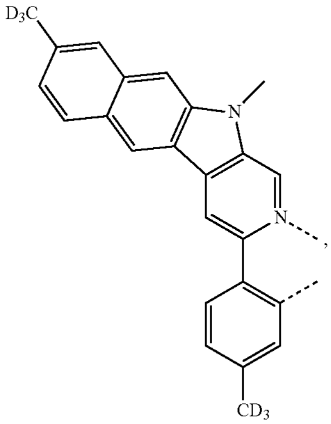
L$_{A282}$
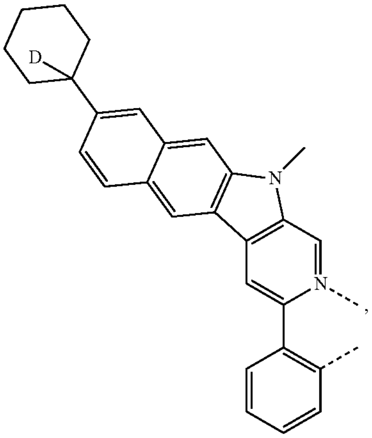
L$_{A283}$
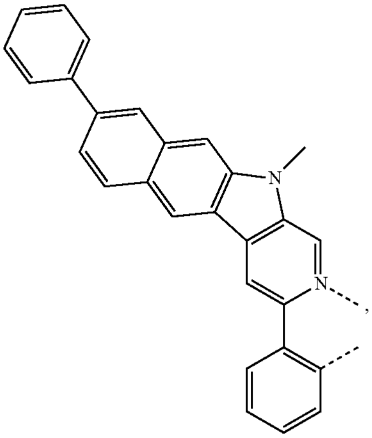
L$_{A284}$
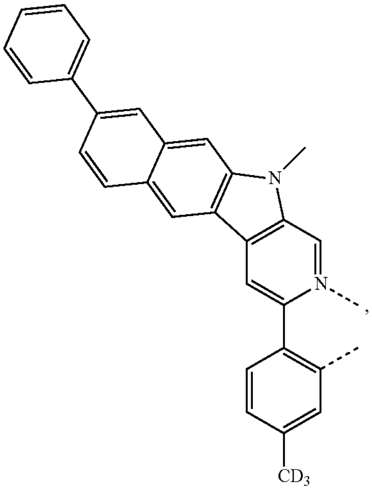
L$_{A285}$
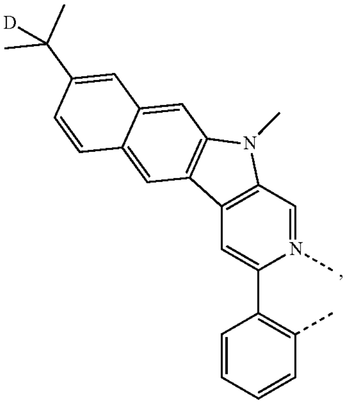

-continued
L$_{A286}$
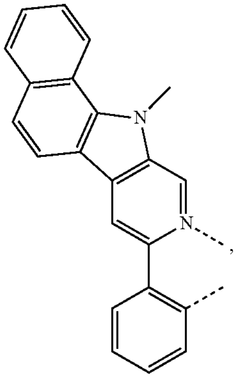
L$_{A287}$
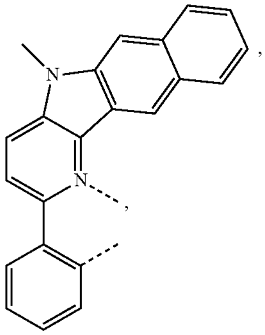
L$_{A288}$
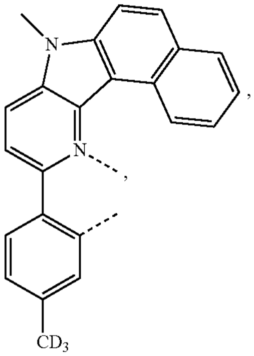
L$_{A290}$
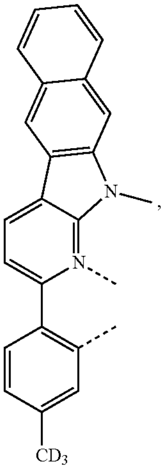
-continued
L$_{A291}$
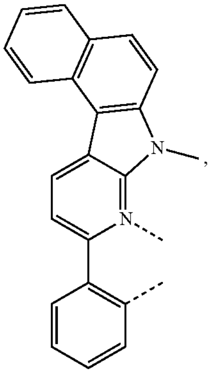
L$_{A292}$
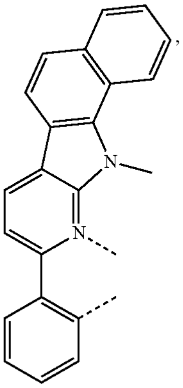
L$_{A283}$
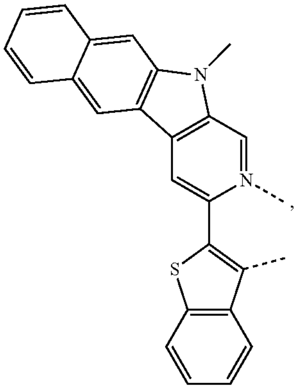
L$_{A294}$
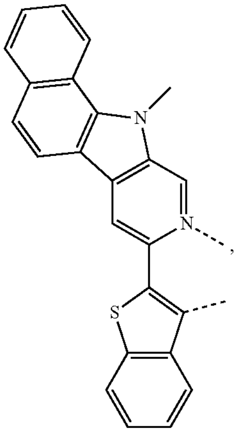

-continued
$L_{A295}$
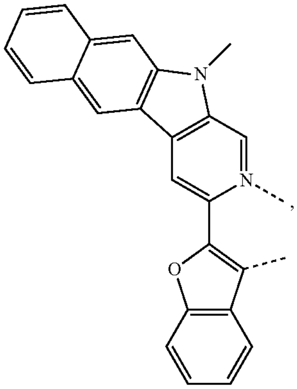
$L_{A296}$
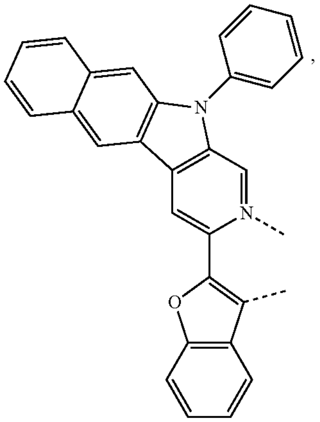
$L_{A297}$
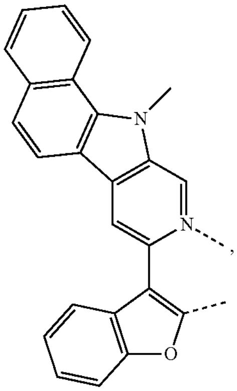
$L_{A298}$
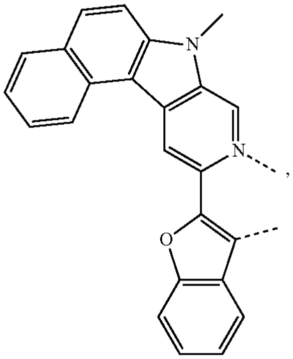
-continued
$L_{A299}$
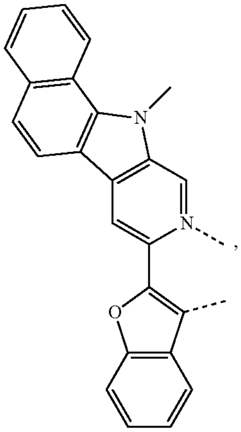
and
$L_{A300}$
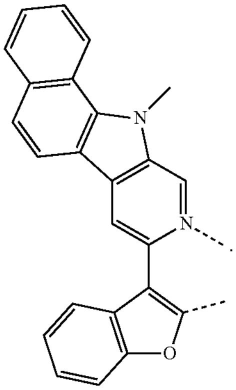
11. The compound of claim 10, wherein the compound is selected from the group consisting of Compound 1 through Compound 75650 where each Compound x has the formula $Ir(L_{Ak})(L_{Bj})_2$;
wherein x=275j+k−275, k is an integer from 1 to 300, and j is an integer from 1 to 275; and
$L_B$ is selected from the group consisting of:
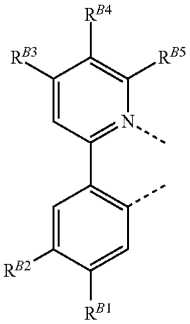

| $L_{Bj}$, j | $R^{B1}$ | $R^{B2}$ | $R^{B3}$ | $R^{B4}$ | $R^{B5}$ |
|---|---|---|---|---|---|
| 1. | H | H | H | H | H |
| 2. | $CH_3$ | H | H | H | H |
| 3. | H | $CH_3$ | H | H | H |
| 4. | H | H | $CH_3$ | H | H |
| 5. | H | H | H | $CH_3$ | H |
| 6. | $CH_3$ | H | $CH_3$ | H | H |
| 7. | $CH_3$ | H | H | $CH_3$ | H |
| 8. | H | $CH_3$ | $CH_3$ | H | H |
| 9. | H | $CH_3$ | H | $CH_3$ | H |
| 10. | H | H | $CH_3$ | $CH_3$ | H |
| 11. | $CH_3$ | $CH_3$ | $CH_3$ | H | H |
| 12. | $CH_3$ | $CH_3$ | H | $CH_3$ | H |
| 13. | $CH_3$ | H | $CH_3$ | $CH_3$ | H |
| 14. | H | $CH_3$ | $CH_3$ | $CH_3$ | H |
| 15. | $CH_3$ | $CH_3$ | $CH_3$ | $CH_3$ | H |
| 16. | 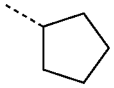 | H | H | H | H |
| 17. | 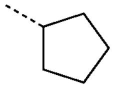 | $CH_3$ | H | H | H |
| 18. | 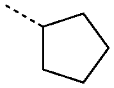 | H | $CH_3$ | H | H |
| 19. | 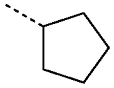 | H | H | $CH_3$ | H |
| 20. | 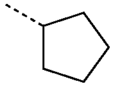 | $CH_3$ | $CH_3$ | H | H |
| 21. | 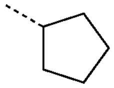 | $CH_3$ | H | $CH_3$ | H |
| 22. | 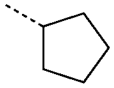 | H | $CH_3$ | $CH_3$ | H |
| 23. | 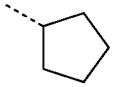 | $CH_3$ | $CH_3$ | $CH_3$ | H |
| 24. | H | 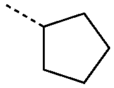 | H | H | H |
| 25. | $CH_3$ | 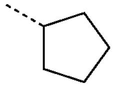 | H | H | H |
| 26. | H | 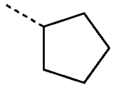 | $CH_3$ | H | H |
| 27. | H | 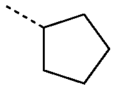 | H | $CH_3$ | H |

-continued
| $L_{Bj}$, j | $R^{B1}$ | $R^{B2}$ | $R^{B3}$ | $R^{B4}$ | $R^{B5}$ |
|---|---|---|---|---|---|
| 28. | $CH_3$ | 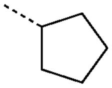 | $CH_3$ | H | H |
| 29. | $CH_3$ | 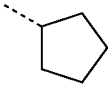 | H | $CH_3$ | H |
| 30. | H | 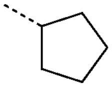 | $CH_3$ | $CH_3$ | H |
| 31. | $CH_3$ | 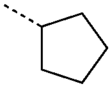 | $CH_3$ | $CH_3$ | H |
| 32. | H | H | 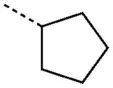 | H | H |
| 33. | $CH_3$ | H | 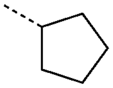 | H | H |
| 34. | H | $CH_3$ | 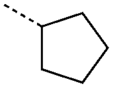 | H | H |
| 35. | H | H | 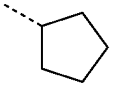 | $CH_3$ | H |
| 36. | $CH_3$ | $CH_3$ | 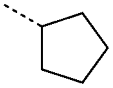 | H | H |
| 37. | $CH_3$ | H | 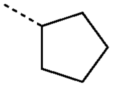 | $CH_3$ | H |
| 38. | H | $CH_3$ | 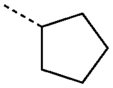 | $CH_3$ | H |
| 39. | $CH_3$ | $CH_3$ | 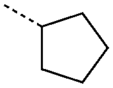 | $CH_3$ | H |
| 40. | 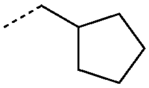 | H | H | H | H |
| 41. | 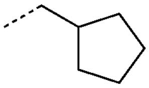 | $CH_3$ | H | H | H |
| 42. | 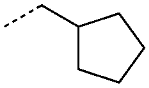 | H | $CH_3$ | H | H |

-continued
| $L_{Bj}$, j | $R^{B1}$ | $R^{B2}$ | $R^{B3}$ | $R^{B4}$ | $R^{B5}$ |
|---|---|---|---|---|---|
| 43. | 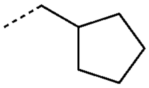 | H | H | $CH_3$ | H |
| 44. | 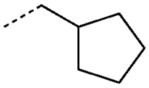 | $CH_3$ | $CH_3$ | H | H |
| 45. | 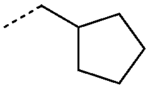 | $CH_3$ | H | $CH_3$ | H |
| 46. | 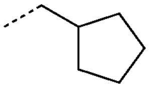 | H | $CH_3$ | $CH_3$ | H |
| 47. | 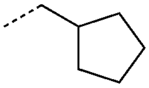 | $CH_3$ | $CH_3$ | $CH_3$ | H |
| 48. | H | 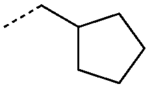 | H | H | H |
| 49. | $CH_3$ | 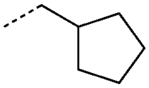 | H | H | H |
| 50. | H | 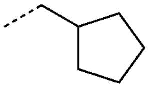 | $CH_3$ | H | H |
| 51. | H | 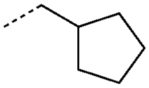 | H | $CH_3$ | H |
| 52. | $CH_3$ | 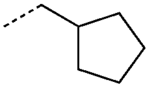 | $CH_3$ | H | H |
| 53. | $CH_3$ | 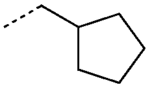 | H | $CH_3$ | H |
| 54. | H | 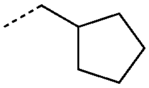 | $CH_3$ | $CH_3$ | H |
| 55. | $CH_3$ | 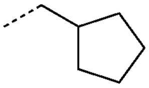 | $CH_3$ | $CH_3$ | H |
| 56. | H | H | 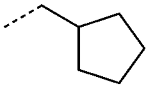 | H | H |
| 57. | $CH_3$ | H | 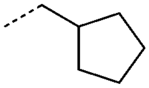 | H | H |

-continued
| $L_{Bj}$, j | $R^{B1}$ | $R^{B2}$ | $R^{B3}$ | $R^{B4}$ | $R^{B5}$ |
|---|---|---|---|---|---|
| 58. | H | $CH_3$ | 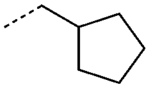 | H | H |
| 59. | H | H | 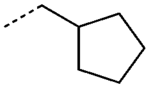 | $CH_3$ | H |
| 60. | $CH_3$ | $CH_3$ | 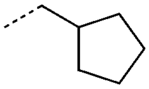 | H | H |
| 61. | $CH_3$ | H | 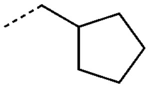 | $CH_3$ | H |
| 62. | H | $CH_3$ | 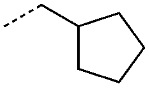 | $CH_3$ | H |
| 63. | $CH_3$ | $CH_3$ | 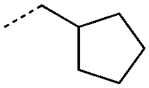 | $CH_3$ | H |
| 64. | 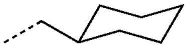 | H | H | H | H |
| 65. | 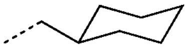 | $CH_3$ | H | H | H |
| 66. | 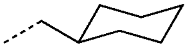 | H | $CH_3$ | H | H |
| 67. | 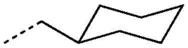 | H | H | $CH_3$ | H |
| 68. | 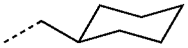 | $CH_3$ | $CH_3$ | H | H |
| 69. | 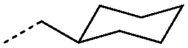 | $CH_3$ | H | $CH_3$ | H |
| 70. | 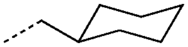 | H | $CH_3$ | $CH_3$ | H |
| 71. | 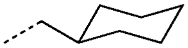 | $CH_3$ | $CH_3$ | $CH_3$ | H |
| 72. | H | 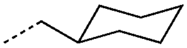 | H | H | H |
| 73. | $CH_3$ | 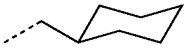 | H | H | H |
| 74. | H | 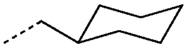 | $CH_3$ | H | H |
| 75. | H | 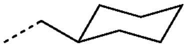 | H | $CH_3$ | H |
| 76. | $CH_3$ | 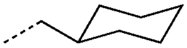 | $CH_3$ | H | H |
| 77. | $CH_3$ | 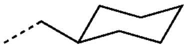 | H | $CH_3$ | H |

-continued
| $L_{Bj}$, j | $R^{B1}$ | $R^{B2}$ | $R^{B3}$ | $R^{B4}$ | $R^{B5}$ |
| --- | --- | --- | --- | --- | --- |
| 78. | H | 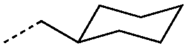 | $CH_3$ | $CH_3$ | H |
| 79. | $CH_3$ | 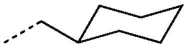 | $CH_3$ | $CH_3$ | H |
| 80. | H | H | 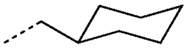 | H | H |
| 81. | $CH_3$ | H | 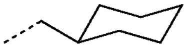 | H | H |
| 82. | H | $CH_3$ | 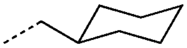 | H | H |
| 83. | H | H | 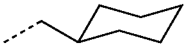 | $CH_3$ | H |
| 84. | $CH_3$ | $CH_3$ | 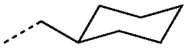 | H | H |
| 85. | $CH_3$ | H | 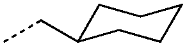 | $CH_3$ | H |
| 86. | H | $CH_3$ | 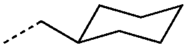 | $CH_3$ | H |
| 87. | $CH_3$ | $CH_3$ | 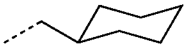 | $CH_3$ | H |
| 88. | 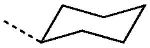 | H | H | H | H |
| 89. | 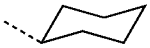 | $CH_3$ | H | H | H |
| 90. | 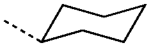 | H | $CH_3$ | H | H |
| 91. | 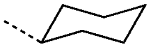 | H | H | $CH_3$ | H |
| 92. | 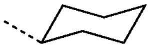 | $CH_3$ | $CH_3$ | H | H |
| 93. | 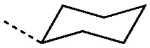 | $CH_3$ | H | $CH_3$ | H |
| 94. | 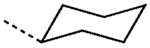 | H | $CH_3$ | $CH_3$ | H |
| 95. | 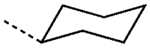 | $CH_3$ | $CH_3$ | $CH_3$ | H |
| 96. | H | 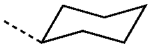 | H | H | H |
| 97. | $CH_3$ | 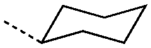 | H | H | H |
| 98. | H | 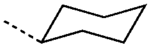 | $CH_3$ | H | H |
| 99. | H | 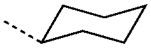 | H | $CH_3$ | H |
| 100. | $CH_3$ | 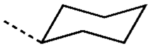 | $CH_3$ | H | H |
| 101. | $CH_3$ | 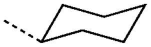 | H | $CH_3$ | H |

-continued
| $L_{Bj}$, j | $R^{B1}$ | $R^{B2}$ | $R^{B3}$ | $R^{B4}$ | $R^{B5}$ |
|---|---|---|---|---|---|
| 102. | H | 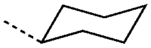 | $CH_3$ | $CH_3$ | H |
| 103. | $CH_3$ | 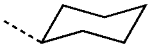 | $CH_3$ | $CH_3$ | H |
| 104. | H | H | 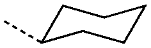 | H | H |
| 105. | $CH_3$ | H | 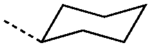 | H | H |
| 106. | H | $CH_3$ | 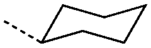 | H | H |
| 107. | H | H | 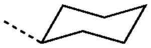 | $CH_3$ | H |
| 108. | $CH_3$ | $CH_3$ | 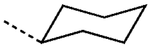 | H | H |
| 109. | $CH_3$ | H | 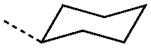 | $CH_3$ | H |
| 110. | H | $CH_3$ | 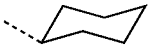 | $CH_3$ | H |
| 111. | $CH_3$ | $CH_3$ | 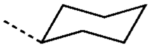 | $CH_3$ | H |
| 112. | 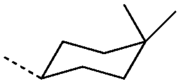 | H | H | H | H |
| 113. | 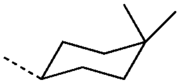 | $CH_3$ | H | H | H |
| 114. | 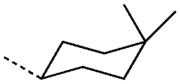 | H | $CH_3$ | H | H |
| 115. | 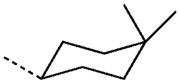 | H | H | $CH_3$ | H |
| 116. | 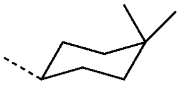 | $CH_3$ | $CH_3$ | H | H |
| 117. | 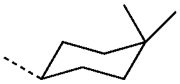 | $CH_3$ | H | $CH_3$ | H |
| 118. | 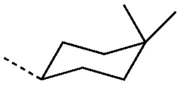 | H | $CH_3$ | $CH_3$ | H |
| 119. | 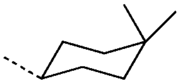 | $CH_3$ | $CH_3$ | $CH_3$ | H |
| 120. | H | 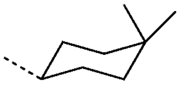 | H | H | H |

-continued
| $L_{Bj}$, j | $R^{B1}$ | $R^{B2}$ | $R^{B3}$ | $R^{B4}$ | $R^{B5}$ |
| --- | --- | --- | --- | --- | --- |
| 121. | $CH_3$ | 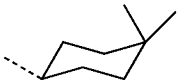 | H | H | H |
| 122. | H | 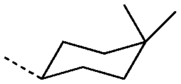 | $CH_3$ | H | H |
| 123. | H | 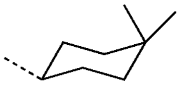 | H | $CH_3$ | H |
| 124. | $CH_3$ | 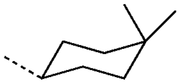 | $CH_3$ | H | H |
| 125. | $CH_3$ | 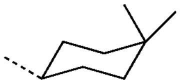 | H | $CH_3$ | H |
| 126. | H | 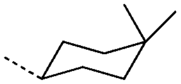 | $CH_3$ | $CH_3$ | H |
| 127. | $CH_3$ | 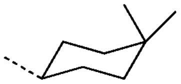 | $CH_3$ | $CH_3$ | H |
| 128. | H | H | 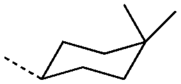 | H | H |
| 129. | $CH_3$ | H | 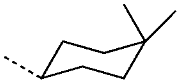 | H | H |
| 130. | H | $CH_3$ | 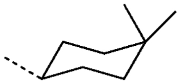 | H | H |
| 131. | H | H | 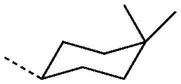 | $CH_3$ | H |
| 132. | $CH_3$ | $CH_3$ | 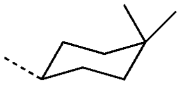 | H | H |
| 133. | $CH_3$ | H | 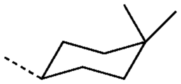 | $CH_3$ | H |
| 134. | H | $CH_3$ | 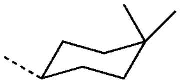 | $CH_3$ | H |
| 135. | $CH_3$ | $CH_3$ | 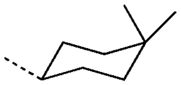 | $CH_3$ | H |
| 136. | 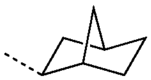 | H | H | H | H |

-continued
| $L_{Bj}$, j | $R^{B1}$ | $R^{B2}$ | $R^{B3}$ | $R^{B4}$ | $R^{B5}$ |
|---|---|---|---|---|---|
| 137. | 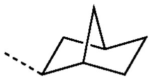 | $CH_3$ | H | H | H |
| 138. | 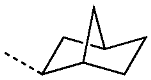 | H | $CH_3$ | H | H |
| 139. | 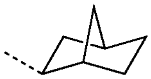 | H | H | $CH_3$ | H |
| 140. | 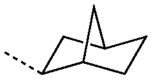 | $CH_3$ | $CH_3$ | H | H |
| 141. | 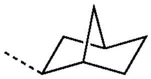 | $CH_3$ | H | $CH_3$ | H |
| 142. | 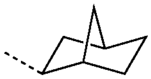 | H | $CH_3$ | $CH_3$ | H |
| 143. | 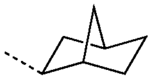 | $CH_3$ | $CH_3$ | $CH_3$ | H |
| 144. | H | 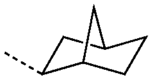 | H | H | H |
| 145. | $CH_3$ | 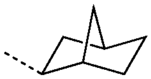 | H | H | H |
| 146. | H | 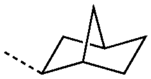 | $CH_3$ | H | H |
| 147. | H | 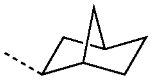 | H | $CH_3$ | H |
| 148. | $CH_3$ | 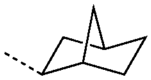 | $CH_3$ | H | H |
| 149. | $CH_3$ | 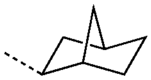 | H | $CH_3$ | H |
| 150. | H | 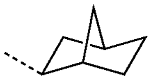 | $CH_3$ | $CH_3$ | H |
| 151. | $CH_3$ | 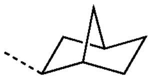 | $CH_3$ | $CH_3$ | H |
| 152. | H | H | 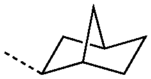 | H | H |
| 153. | $CH_3$ | H | 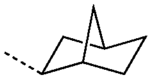 | H | H |

-continued
| $L_{Bj}$, j | $R^{B1}$ | $R^{B2}$ | $R^{B3}$ | $R^{B4}$ | $R^{B5}$ |
|---|---|---|---|---|---|
| 154. | H | $CH_3$ | 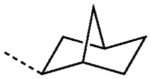 | H | H |
| 155. | H | H | 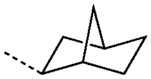 | $CH_3$ | H |
| 156. | $CH_3$ | $CH_3$ | 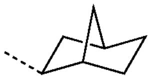 | H | H |
| 157. | $CH_3$ | H | 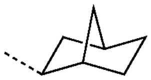 | $CH_3$ | H |
| 158. | H | $CH_3$ | 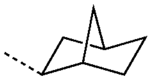 | $CH_3$ | H |
| 159. | $CH_3$ | $CH_3$ | 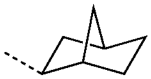 | $CH_3$ | H |
| 160. | 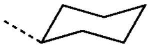 | H | 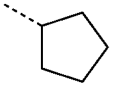 | H | H |
| 161. | 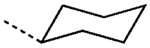 | H | 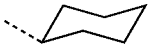 | H | H |
| 162. | 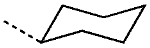 | H | 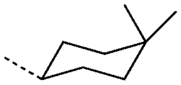 | H | H |
| 163. | 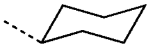 | H | 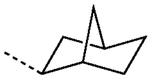 | H | H |
| 164. | 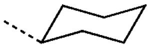 | H | 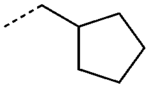 | H | H |
| 165. | 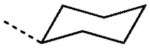 | H | 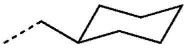 | H | H |
| 166. | 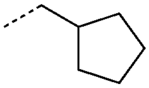 | H | 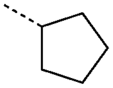 | H | H |
| 167. | 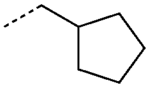 | H | 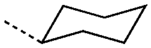 | H | H |
| 168. | 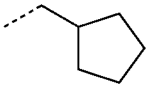 | H | 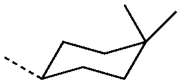 | H | H |
| 169. | 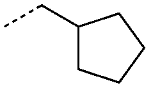 | H | 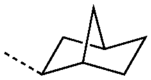 | H | H |

-continued

| $L_{Bj}$, j | $R^{B1}$ | $R^{B2}$ | $R^{B3}$ | $R^{B4}$ | $R^{B5}$ |
|---|---|---|---|---|---|
| 170. | 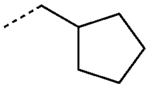 | H | 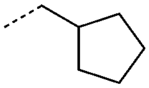 | H | H |
| 171. | 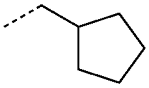 | H | 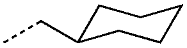 | H | H |
| 172. | 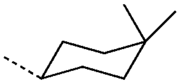 | H | 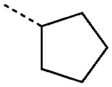 | H | H |
| 173. | 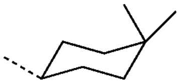 | H | 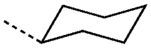 | H | H |
| 174. | 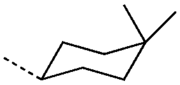 | H | 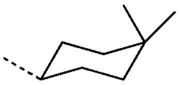 | H | H |
| 175. | 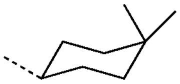 | H | 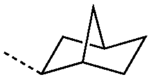 | H | H |
| 176. | 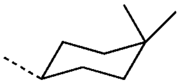 | H | 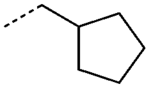 | H | H |
| 177. | 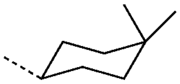 | H | 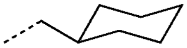 | H | H |
| 178. | $CD_3$ | H | H | H | H |
| 179. | H | $CD_3$ | H | H | H |
| 180. | H | H | $CD_3$ | H | H |
| 181. | H | H | H | $CD_3$ | H |
| 182. | $CD_3$ | H | $CD_3$ | H | H |
| 183. | $CD_3$ | H | H | $CD_3$ | H |
| 184. | H | $CD_3$ | $CD_3$ | H | H |
| 185. | H | $CD_3$ | H | $CD_3$ | H |
| 186. | H | H | $CD_3$ | $CD_3$ | H |
| 187. | $CD_3$ | $CD_3$ | $CD_3$ | H | H |
| 188. | $CD_3$ | $CD_3$ | H | $CD_3$ | H |
| 189. | $CD_3$ | H | $CD_3$ | $CD_3$ | H |
| 190. | H | $CD_3$ | $CD_3$ | $CD_3$ | H |
| 191. | $CD_3$ | $CD_3$ | $CD_3$ | $CD_3$ | H |
| 192. | H | H | H | H | $CD_3$ |
| 193. | $CH_3$ | H | H | H | $CD_3$ |
| 194. | H | $CH_3$ | H | H | $CD_3$ |
| 195. | H | H | $CH_3$ | H | $CD_3$ |
| 196. | H | H | H | $CH_3$ | $CD_3$ |
| 197. | $CH_3$ | H | $CH_3$ | H | $CD_3$ |
| 198. | $CH_3$ | H | H | $CH_3$ | $CD_3$ |
| 199. | H | $CH_3$ | $CH_3$ | H | $CD_3$ |
| 200. | H | $CH_3$ | H | $CH_3$ | $CD_3$ |
| 201. | H | H | $CH_3$ | $CH_3$ | $CD_3$ |
| 202. | $CH_3$ | $CH_3$ | $CH_3$ | H | $CD_3$ |
| 203. | $CH_3$ | $CH_3$ | H | $CH_3$ | $CD_3$ |
| 204. | $CH_3$ | H | $CH_3$ | $CH_3$ | $CD_3$ |
| 205. | H | $CH_3$ | $CH_3$ | $CH_3$ | $CD_3$ |
| 206. | $CH_3$ | $CH_3$ | $CH_3$ | $CH_3$ | $CD_3$ |
| 207. | 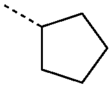 | H | H | H | $CD_3$ |

-continued
| $L_{Bj}$, j | $R^{B1}$ | $R^{B2}$ | $R^{B3}$ | $R^{B4}$ | $R^{B5}$ |
|---|---|---|---|---|---|
| 208. | 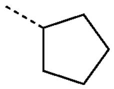 | $CH_3$ | H | H | $CD_3$ |
| 209. | 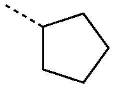 | H | $CH_3$ | H | $CD_3$ |
| 210. | 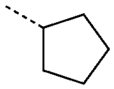 | H | H | $CH_3$ | $CD_3$ |
| 211. | 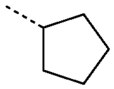 | $CH_3$ | $CH_3$ | H | $CD_3$ |
| 212. | 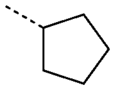 | $CH_3$ | H | $CH_3$ | $CD_3$ |
| 213. | 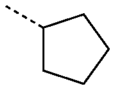 | H | $CH_3$ | $CH_3$ | $CD_3$ |
| 214. | 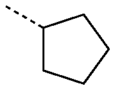 | $CH_3$ | $CH_3$ | $CH_3$ | $CD_3$ |
| 215. | H | 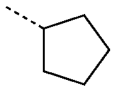 | H | H | $CD_3$ |
| 216. | $CH_3$ | 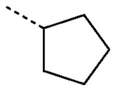 | H | H | $CD_3$ |
| 217. | H | 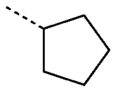 | $CH_3$ | H | $CD_3$ |
| 218. | H | 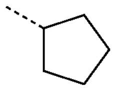 | H | $CH_3$ | $CD_3$ |
| 219. | $CH_3$ | 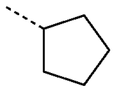 | $CH_3$ | H | $CD_3$ |
| 220. | $CH_3$ | 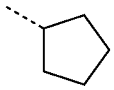 | H | $CH_3$ | $CD_3$ |
| 221. | H | 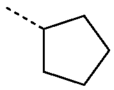 | $CH_3$ | $CH_3$ | $CD_3$ |
| 222. | $CH_3$ | 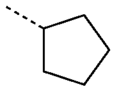 | $CH_3$ | $CH_3$ | $CD_3$ |

-continued
| $L_{Bj}$, j | $R^{B1}$ | $R^{B2}$ | $R^{B3}$ | $R^{B4}$ | $R^{B5}$ |
|---|---|---|---|---|---|
| 223. | H | H | 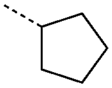 | H | $CD_3$ |
| 224. | $CH_3$ | H | 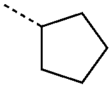 | H | $CD_3$ |
| 225. | H | $CH_3$ | 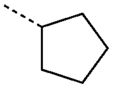 | H | $CD_3$ |
| 226. | H | H | 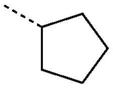 | $CH_3$ | $CD_3$ |
| 227. | $CH_3$ | $CH_3$ | 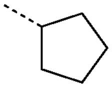 | H | $CD_3$ |
| 228. | $CH_3$ | H | 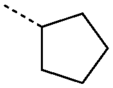 | $CH_3$ | $CD_3$ |
| 229. | H | $CH_3$ | 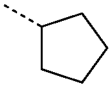 | $CH_3$ | $CD_3$ |
| 230. | $CH_3$ | $CH_3$ | 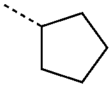 | $CH_3$ | $CD_3$ |
| 231. | 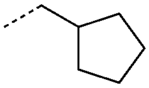 | H | H | H | $CD_3$ |
| 232. | 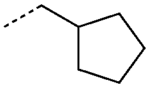 | $CH_3$ | H | H | $CD_3$ |
| 233. | 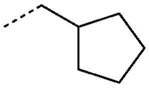 | H | $CH_3$ | H | $CD_3$ |
| 234. | 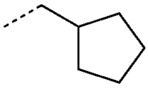 | H | H | $CH_3$ | $CD_3$ |
| 235. | 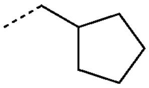 | $CH_3$ | $CH_3$ | H | $CD_3$ |
| 236. | 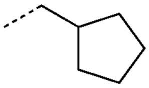 | $CH_3$ | H | $CH_3$ | $CD_3$ |
| 237. | 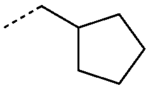 | H | $CH_3$ | $CH_3$ | $CD_3$ |

-continued
| $L_{Bj}$, j | $R^{B1}$ | $R^{B2}$ | $R^{B3}$ | $R^{B4}$ | $R^{B5}$ |
|---|---|---|---|---|---|
| 238. | 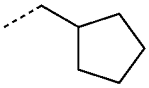 | $CH_3$ | $CH_3$ | $CH_3$ | $CD_3$ |
| 239. | H | 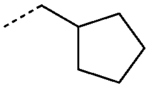 | H | H | $CD_3$ |
| 240. | $CH_3$ | 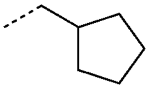 | H | H | $CD_3$ |
| 241. | H | 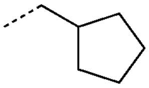 | $CH_3$ | H | $CD_3$ |
| 242. | H | 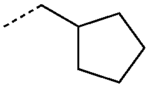 | H | $CH_3$ | $CD_3$ |
| 243. | $CH_3$ | 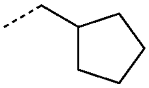 | $CH_3$ | H | $CD_3$ |
| 244. | $CH_3$ | 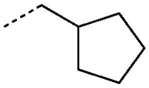 | H | $CH_3$ | $CD_3$ |
| 245. | H | 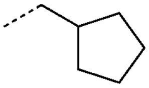 | $CH_3$ | $CH_3$ | $CD_3$ |
| 246. | $CH_3$ | 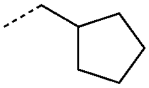 | $CH_3$ | $CH_3$ | $CD_3$ |
| 247. | H | H | 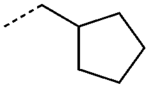 | H | $CD_3$ |
| 248. | $CH_3$ | H | 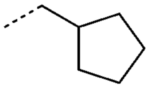 | H | $CD_3$ |
| 249. | H | $CH_3$ | 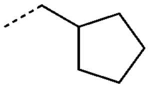 | H | $CD_3$ |
| 250. | H | H | 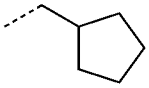 | $CH_3$ | $CD_3$ |
| 251. | $CH_3$ | $CH_3$ | 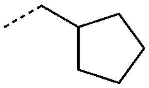 | H | $CD_3$ |
| 252. | $CH_3$ | H | 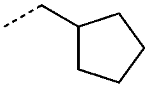 | $CH_3$ | $CD_3$ |

-continued

| $L_{Bj}$, j | $R^{B1}$ | $R^{B2}$ | $R^{B3}$ | $R^{B4}$ | $R^{B5}$ |
|---|---|---|---|---|---|
| 253. | H | $CH_3$ | 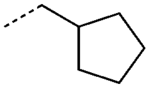 | $CH_3$ | $CD_3$ |
| 254. | $CH_3$ | $CH_3$ | 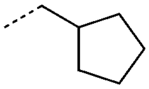 | $CH_3$ | $CD_3$ |
| 255. | 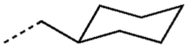 | H | H | H | $CD_3$ |
| 256. | 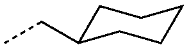 | $CH_3$ | H | H | $CD_3$ |
| 257. | 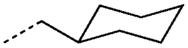 | H | $CH_3$ | H | $CD_3$ |
| 258. | 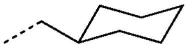 | H | H | $CH_3$ | $CD_3$ |
| 259. | 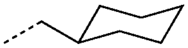 | $CH_3$ | $CH_3$ | H | $CD_3$ |
| 260. | 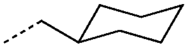 | $CH_3$ | H | $CH_3$ | $CD_3$ |
| 261. | 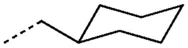 | H | $CH_3$ | $CH_3$ | $CD_3$ |
| 262. | 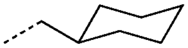 | $CH_3$ | $CH_3$ | $CH_3$ | $CD_3$ |
| 263. | H | 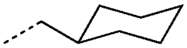 | H | H | $CD_3$ |
| 264. | $CH_3$ | 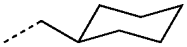 | H | H | $CD_3$ |
| 265. | H | 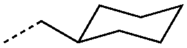 | $CH_3$ | H | $CD_3$ |
| 266. | H | 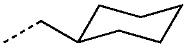 | H | $CH_3$ | $CD_3$ |
| 267. | $CH_3$ | 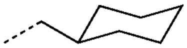 | $CH_3$ | H | $CD_3$ |
| 268. | $CH_3$ | 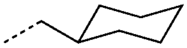 | H | $CH_3$ | $CD_3$ |
| 269. | H | 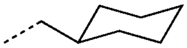 | $CH_3$ | $CH_3$ | $CD_3$ |
| 270. | $CH_3$ | 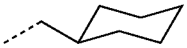 | $CH_3$ | $CH_3$ | $CD_3$ |
| 271. | H | H | 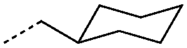 | H | $CD_3$ |
| 272. | $CH_3$ | H | 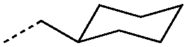 | H | $CD_3$ |
| 273. | H | $CH_3$ | 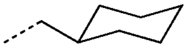 | H | $CD_3$ |
| 274. | H | H | 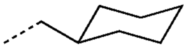 | $CH_3$ | $CD_3$ |
| 275. | $CD_3$ | $CD_3$ | $CD_3$ | $CD_3$ | $CD_3$ |

12. The compound of claim 1, wherein the compound has formula $(L_A)_n Ir(L_B)_{3-n}$;

wherein $L_B$ is a bidentate ligand; and n is 1, 2, or 3.

13. The compound of claim 12, wherein L is selected from the group consisting of:

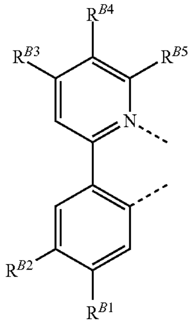

| $L_{Bj}$, j | $R^{B1}$ | $R^{B2}$ | $R^{B3}$ | $R^{B4}$ | $R^{B5}$ |
|---|---|---|---|---|---|
| 1. | H | H | H | H | H |
| 2. | $CH_3$ | H | H | H | H |
| 3. | H | $CH_3$ | H | H | H |
| 4. | H | H | $CH_3$ | H | H |
| 5. | H | H | H | $CH_3$ | H |
| 6. | $CH_3$ | H | $CH_3$ | H | H |
| 7. | $CH_3$ | H | H | $CH_3$ | H |
| 8. | H | $CH_3$ | $CH_3$ | H | H |
| 9. | H | $CH_3$ | H | $CH_3$ | H |
| 10. | H | H | $CH_3$ | $CH_3$ | H |
| 11. | $CH_3$ | $CH_3$ | $CH_3$ | H | H |
| 12. | $CH_3$ | $CH_3$ | H | $CH_3$ | H |
| 13. | $CH_3$ | H | $CH_3$ | $CH_3$ | H |
| 14. | H | $CH_3$ | $CH_3$ | $CH_3$ | H |
| 15. | $CH_3$ | $CH_3$ | $CH_3$ | $CH_3$ | H |
| 16. | 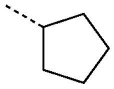 | H | H | H | H |
| 17. | 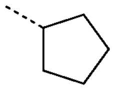 | $CH_3$ | H | H | H |
| 18. | 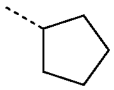 | H | $CH_3$ | H | H |
| 19. | 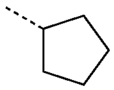 | H | H | $CH_3$ | H |
| 20. | 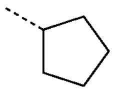 | $CH_3$ | $CH_3$ | H | H |
| 21. | 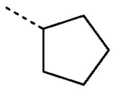 | $CH_3$ | H | $CH_3$ | H |
| 22. | 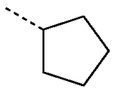 | H | $CH_3$ | $CH_3$ | H |

-continued
| $L_{Bj}$, j | $R^{B1}$ | $R^{B2}$ | $R^{B3}$ | $R^{B4}$ | $R^{B5}$ |
|---|---|---|---|---|---|
| 23. | 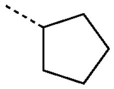 | $CH_3$ | $CH_3$ | $CH_3$ | H |
| 24. | H | 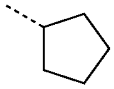 | H | H | H |
| 25. | $CH_3$ | 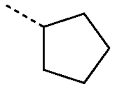 | H | H | H |
| 26. | H | 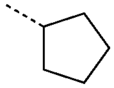 | $CH_3$ | H | H |
| 27. | H | 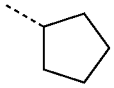 | H | $CH_3$ | H |
| 28. | $CH_3$ | 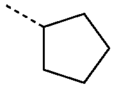 | $CH_3$ | H | H |
| 29. | $CH_3$ | 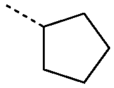 | H | $CH_3$ | H |
| 30. | H | 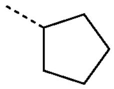 | $CH_3$ | $CH_3$ | H |
| 31. | $CH_3$ | 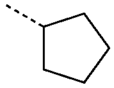 | $CH_3$ | $CH_3$ | H |
| 32. | H | H | 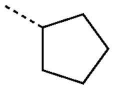 | H | H |
| 33. | $CH_3$ | H | 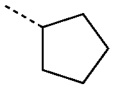 | H | H |
| 34. | H | $CH_3$ | 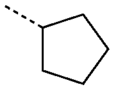 | H | H |
| 35. | H | H | 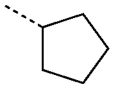 | $CH_3$ | H |
| 36. | $CH_3$ | $CH_3$ | 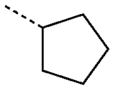 | H | H |
| 37. | $CH_3$ | H | 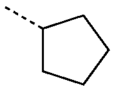 | $CH_3$ | H |

-continued
| $L_{Bj}$, j | $R^{B1}$ | $R^{B2}$ | $R^{B3}$ | $R^{B4}$ | $R^{B5}$ |
|---|---|---|---|---|---|
| 38. | H | $CH_3$ | 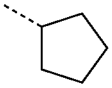 | $CH_3$ | H |
| 39. | $CH_3$ | $CH_3$ | 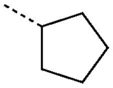 | $CH_3$ | H |
| 40. | 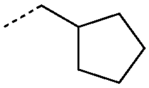 | H | H | H | H |
| 41. | 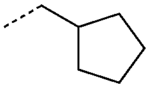 | $CH_3$ | H | H | H |
| 42. | 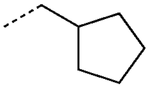 | H | $CH_3$ | H | H |
| 43. | 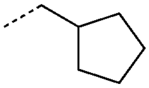 | H | H | $CH_3$ | H |
| 44. | 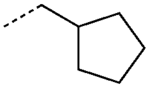 | $CH_3$ | $CH_3$ | H | H |
| 45. | 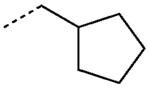 | $CH_3$ | H | $CH_3$ | H |
| 46. | 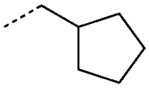 | H | $CH_3$ | $CH_3$ | H |
| 47. | 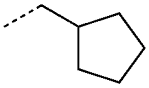 | $CH_3$ | $CH_3$ | $CH_3$ | H |
| 48. | H | 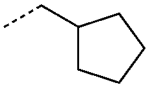 | H | H | H |
| 49. | $CH_3$ | 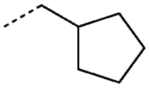 | H | H | H |
| 50. | H | 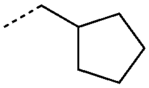 | $CH_3$ | H | H |
| 51. | H | 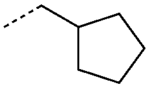 | H | $CH_3$ | H |
| 52. | $CH_3$ | 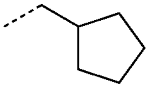 | $CH_3$ | H | H |

-continued
| $L_{Bj}$, j | $R^{B1}$ | $R^{B2}$ | $R^{B3}$ | $R^{B4}$ | $R^{B5}$ |
|---|---|---|---|---|---|
| 53. | $CH_3$ | 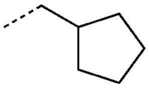 | H | $CH_3$ | H |
| 54. | H | 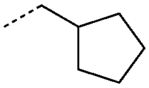 | $CH_3$ | $CH_3$ | H |
| 55. | $CH_3$ | 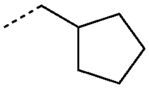 | $CH_3$ | $CH_3$ | H |
| 56. | H | H | 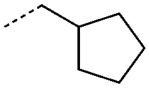 | H | H |
| 57. | $CH_3$ | H | 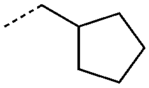 | H | H |
| 58. | H | $CH_3$ | 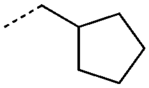 | H | H |
| 59. | H | H | 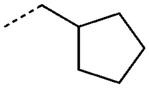 | $CH_3$ | H |
| 60. | $CH_3$ | $CH_3$ | 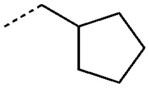 | H | H |
| 61. | $CH_3$ | H | 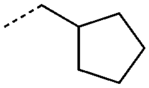 | $CH_3$ | H |
| 62. | H | $CH_3$ | 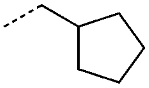 | $CH_3$ | H |
| 63. | $CH_3$ | $CH_3$ | 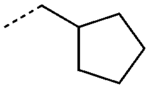 | $CH_3$ | H |
| 64. | 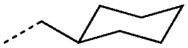 | H | H | H | H |
| 65. | 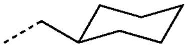 | $CH_3$ | H | H | H |
| 66. | 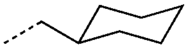 | H | $CH_3$ | H | H |
| 67. | 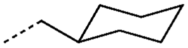 | H | H | $CH_3$ | H |
| 68. | 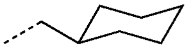 | $CH_3$ | $CH_3$ | H | H |
| 69. | 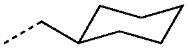 | $CH_3$ | H | $CH_3$ | H |

-continued
| $L_{Bj}$, j | $R^{B1}$ | $R^{B2}$ | $R^{B3}$ | $R^{B4}$ | $R^{B5}$ |
|---|---|---|---|---|---|
| 70. | 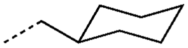 | H | $CH_3$ | $CH_3$ | H |
| 71. | 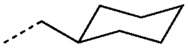 | $CH_3$ | $CH_3$ | $CH_3$ | H |
| 72. | H | 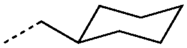 | H | H | H |
| 73. | $CH_3$ | 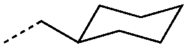 | H | H | H |
| 74. | H | 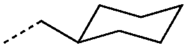 | $CH_3$ | H | H |
| 75. | H | 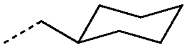 | H | $CH_3$ | H |
| 76. | $CH_3$ | 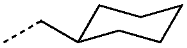 | $CH_3$ | H | H |
| 77. | $CH_3$ | 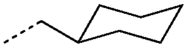 | H | $CH_3$ | H |
| 78. | H | 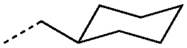 | $CH_3$ | $CH_3$ | H |
| 79. | $CH_3$ | 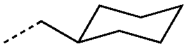 | $CH_3$ | $CH_3$ | H |
| 80. | H | H | 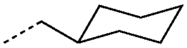 | H | H |
| 81. | $CH_3$ | H | 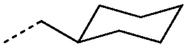 | H | H |
| 82. | H | $CH_3$ | 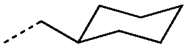 | H | H |
| 83. | H | H | 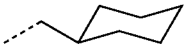 | $CH_3$ | H |
| 84. | $CH_3$ | $CH_3$ | 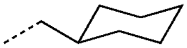 | H | H |
| 85. | $CH_3$ | H | 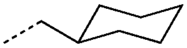 | $CH_3$ | H |
| 86. | H | $CH_3$ | 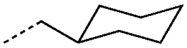 | $CH_3$ | H |
| 87. | $CH_3$ | $CH_3$ | 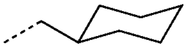 | $CH_3$ | H |
| 88. | 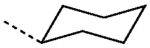 | H | H | H | H |
| 89. | 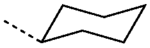 | $CH_3$ | H | H | H |
| 90. | 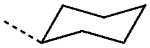 | H | $CH_3$ | H | H |
| 91. | 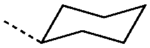 | H | H | $CH_3$ | H |
| 92. | 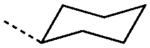 | $CH_3$ | $CH_3$ | H | H |
| 93. | 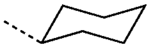 | $CH_3$ | H | $CH_3$ | H |

-continued
| $L_{Bj}$, j | $R^{B1}$ | $R^{B2}$ | $R^{B3}$ | $R^{B4}$ | $R^{B5}$ |
|---|---|---|---|---|---|
| 94. | 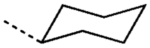 | H | $CH_3$ | $CH_3$ | H |
| 95. | 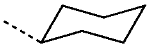 | $CH_3$ | $CH_3$ | $CH_3$ | H |
| 96. | H | 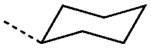 | H | H | H |
| 97. | $CH_3$ | 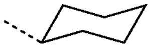 | H | H | H |
| 98. | H | 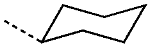 | $CH_3$ | H | H |
| 99. | H | 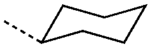 | H | $CH_3$ | H |
| 100. | $CH_3$ | 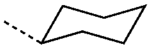 | $CH_3$ | H | H |
| 101. | $CH_3$ | 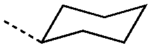 | H | $CH_3$ | H |
| 102. | H | 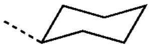 | $CH_3$ | $CH_3$ | H |
| 103. | $CH_3$ | 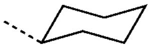 | $CH_3$ | $CH_3$ | H |
| 104. | H | H | 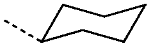 | H | H |
| 105. | $CH_3$ | H | 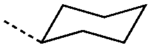 | H | H |
| 106. | H | $CH_3$ | 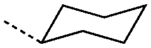 | H | H |
| 107. | H | H | 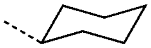 | $CH_3$ | H |
| 108. | $CH_3$ | $CH_3$ | 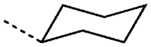 | H | H |
| 109. | $CH_3$ | H | 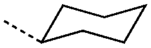 | $CH_3$ | H |
| 110. | H | $CH_3$ | 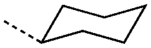 | $CH_3$ | H |
| 111. | $CH_3$ | $CH_3$ | 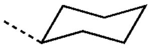 | $CH_3$ | H |
| 112. | 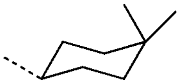 | H | H | H | H |
| 113. | 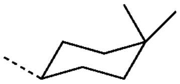 | $CH_3$ | H | H | H |
| 114. | 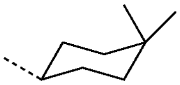 | H | $CH_3$ | H | H |
| 115. | 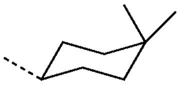 | H | H | $CH_3$ | H |

-continued
| $L_{Bj}$, j | $R^{B1}$ | $R^{B2}$ | $R^{B3}$ | $R^{B4}$ | $R^{B5}$ |
|---|---|---|---|---|---|
| 116. | 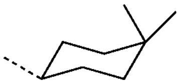 | $CH_3$ | $CH_3$ | H | H |
| 117. | 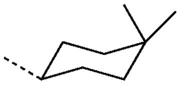 | $CH_3$ | H | $CH_3$ | H |
| 118. | 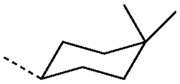 | H | $CH_3$ | $CH_3$ | H |
| 119. | 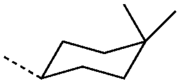 | $CH_3$ | $CH_3$ | $CH_3$ | H |
| 120. | H | 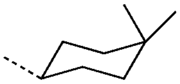 | H | H | H |
| 121. | $CH_3$ | 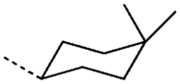 | H | H | H |
| 122. | H | 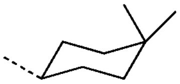 | $CH_3$ | H | H |
| 123. | H | 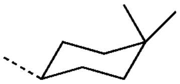 | H | $CH_3$ | H |
| 124. | $CH_3$ | 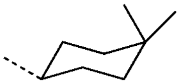 | $CH_3$ | H | H |
| 125. | $CH_3$ | 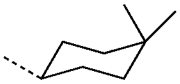 | H | $CH_3$ | H |
| 126. | H | 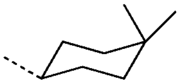 | $CH_3$ | $CH_3$ | H |
| 127. | $CH_3$ | 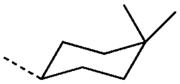 | $CH_3$ | $CH_3$ | H |
| 128. | H | H | 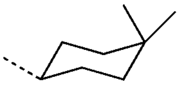 | H | H |
| 129. | $CH_3$ | H | 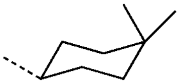 | H | H |
| 130. | H | $CH_3$ | 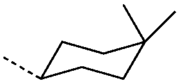 | H | H |
| 131. | H | H | 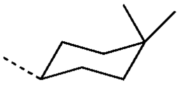 | $CH_3$ | H |

-continued
| $L_{Bj}$, j | $R^{B1}$ | $R^{B2}$ | $R^{B3}$ | $R^{B4}$ | $R^{B5}$ |
|---|---|---|---|---|---|
| 132. | $CH_3$ | $CH_3$ | 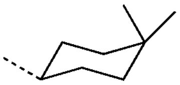 | H | H |
| 133. | $CH_3$ | H | 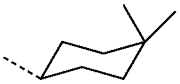 | $CH_3$ | H |
| 134. | H | $CH_3$ | 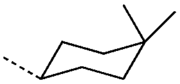 | $CH_3$ | H |
| 135. | $CH_3$ | $CH_3$ | 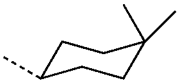 | $CH_3$ | H |
| 136. | 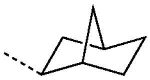 | H | H | H | H |
| 137. | 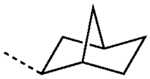 | $CH_3$ | H | H | H |
| 138. | 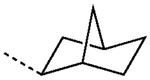 | H | $CH_3$ | H | H |
| 139. | 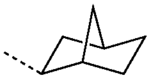 | H | H | $CH_3$ | H |
| 140. | 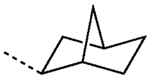 | $CH_3$ | $CH_3$ | H | H |
| 141. | 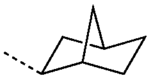 | $CH_3$ | H | $CH_3$ | H |
| 142. | 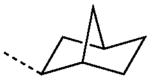 | H | $CH_3$ | $CH_3$ | H |
| 143. | 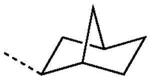 | $CH_3$ | $CH_3$ | $CH_3$ | H |
| 144. | H | 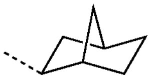 | H | H | H |
| 145. | $CH_3$ | 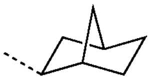 | H | H | H |
| 146. | H | 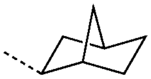 | $CH_3$ | H | H |
| 147. | H | 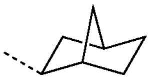 | H | $CH_3$ | H |

-continued
| $L_{Bj}$, j | $R^{B1}$ | $R^{B2}$ | $R^{B3}$ | $R^{B4}$ | $R^{B5}$ |
|---|---|---|---|---|---|
| 148. | $CH_3$ | 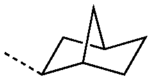 | $CH_3$ | H | H |
| 149. | $CH_3$ | 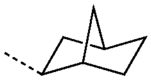 | H | $CH_3$ | H |
| 150. | H | 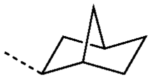 | $CH_3$ | $CH_3$ | H |
| 151. | $CH_3$ | 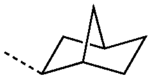 | $CH_3$ | $CH_3$ | H |
| 152. | H | H | 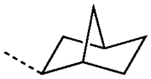 | H | H |
| 153. | $CH_3$ | H | 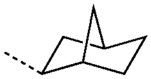 | H | H |
| 154. | H | $CH_3$ | 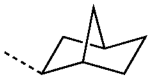 | H | H |
| 155. | H | H | 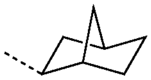 | $CH_3$ | H |
| 156. | $CH_3$ | $CH_3$ | 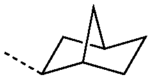 | H | H |
| 157. | $CH_3$ | H | 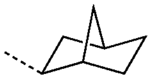 | $CH_3$ | H |
| 158. | H | $CH_3$ | 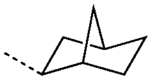 | $CH_3$ | H |
| 159. | $CH_3$ | $CH_3$ | 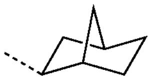 | $CH_3$ | H |
| 160. | 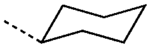 | H | 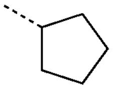 | H | H |
| 161. | 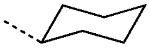 | H | 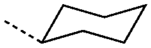 | H | H |
| 162. | 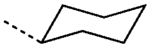 | H | 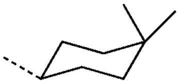 | H | H |
| 163. | 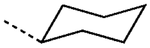 | H | 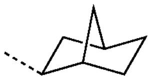 | H | H |
| 164. | 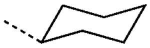 | H | 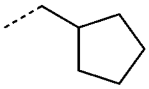 | H | H |

-continued
| $L_{Bj}$, j | $R^{B1}$ | $R^{B2}$ | $R^{B3}$ | $R^{B4}$ | $R^{B5}$ |
|---|---|---|---|---|---|
| 165. | 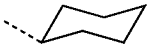 | H | 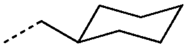 | H | H |
| 166. | 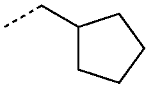 | H | 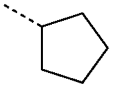 | H | H |
| 167. | 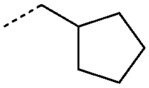 | H | 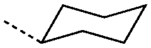 | H | H |
| 168. | 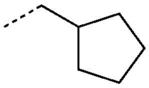 | H | 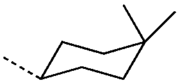 | H | H |
| 169. | 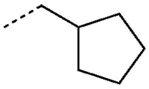 | H | 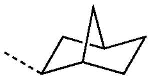 | H | H |
| 170. | 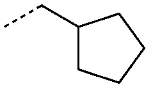 | H | 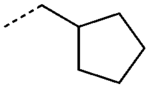 | H | H |
| 171. | 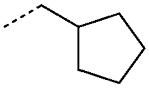 | H | 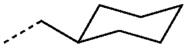 | H | H |
| 172. | 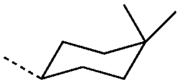 | H | 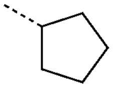 | H | H |
| 173. | 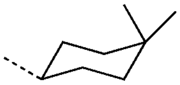 | H | 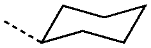 | H | H |
| 174. | 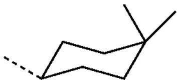 | H | 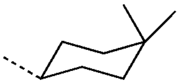 | H | H |
| 175. | 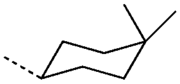 | H | 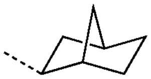 | H | H |
| 176. | 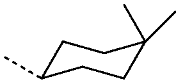 | H | 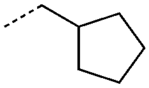 | H | H |
| 177. | 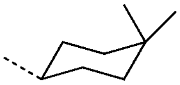 | H | 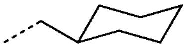 | H | H |
| 178. | $CD_3$ | H | H | H | H |
| 179. | H | $CD_3$ | H | H | H |
| 180. | H | H | $CD_3$ | H | H |
| 181. | H | H | H | $CD_3$ | H |
| 182. | $CD_3$ | H | $CD_3$ | H | H |
| 183. | $CD_3$ | H | H | $CD_3$ | H |
| 184. | H | $CD_3$ | $CD_3$ | H | H |
| 185. | H | $CD_3$ | H | $CD_3$ | H |
| 186. | H | H | $CD_3$ | $CD_3$ | H |
| 187. | $CD_3$ | $CD_3$ | $CD_3$ | H | H |
| 188. | $CD_3$ | $CD_3$ | H | $CD_3$ | H |
| 189. | $CD_3$ | H | $CD_3$ | $CD_3$ | H |
| 190. | H | $CD_3$ | $CD_3$ | $CD_3$ | H |
| 191. | $CD_3$ | $CD_3$ | $CD_3$ | $CD_3$ | H |

-continued

| $L_{Bj}$, j | $R^{B1}$ | $R^{B2}$ | $R^{B3}$ | $R^{B4}$ | $R^{B5}$ |
|---|---|---|---|---|---|
| 192. | H | H | H | H | $CD_3$ |
| 193. | $CH_3$ | H | H | H | $CD_3$ |
| 194. | H | $CH_3$ | H | H | $CD_3$ |
| 195. | H | H | $CH_3$ | H | $CD_3$ |
| 196. | H | H | H | $CH_3$ | $CD_3$ |
| 197. | $CH_3$ | H | $CH_3$ | H | $CD_3$ |
| 198. | $CH_3$ | H | H | $CH_3$ | $CD_3$ |
| 199. | H | $CH_3$ | $CH_3$ | H | $CD_3$ |
| 200. | H | $CH_3$ | H | $CH_3$ | $CD_3$ |
| 201. | H | H | $CH_3$ | $CH_3$ | $CD_3$ |
| 202. | $CH_3$ | $CH_3$ | $CH_3$ | H | $CD_3$ |
| 203. | $CH_3$ | $CH_3$ | H | $CH_3$ | $CD_3$ |
| 204. | $CH_3$ | H | $CH_3$ | $CH_3$ | $CD_3$ |
| 205. | H | $CH_3$ | $CH_3$ | $CH_3$ | $CD_3$ |
| 206. | $CH_3$ | $CH_3$ | $CH_3$ | $CH_3$ | $CD_3$ |
| 207. | 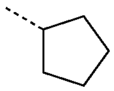 | H | H | H | $CD_3$ |
| 208. | 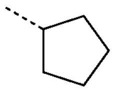 | $CH_3$ | H | H | $CD_3$ |
| 209. | 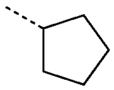 | H | $CH_3$ | H | $CD_3$ |
| 210. | 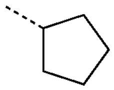 | H | H | $CH_3$ | $CD_3$ |
| 211. | 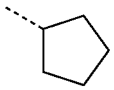 | $CH_3$ | $CH_3$ | H | $CD_3$ |
| 212. | 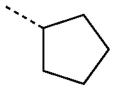 | $CH_3$ | H | $CH_3$ | $CD_3$ |
| 213. | 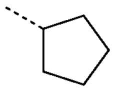 | H | $CH_3$ | $CH_3$ | $CD_3$ |
| 214. | 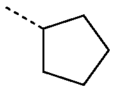 | $CH_3$ | $CH_3$ | $CH_3$ | $CD_3$ |
| 215. | H | 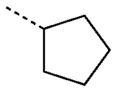 | H | H | $CD_3$ |
| 216. | $CH_3$ | 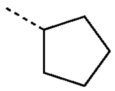 | H | H | $CD_3$ |
| 217. | H | 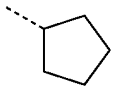 | $CH_3$ | H | $CD_3$ |
| 218. | H | 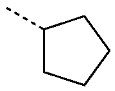 | H | $CH_3$ | $CD_3$ |

-continued
| $L_{Bj}$, j | $R^{B1}$ | $R^{B2}$ | $R^{B3}$ | $R^{B4}$ | $R^{B5}$ |
|---|---|---|---|---|---|
| 219. | $CH_3$ | 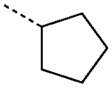 | $CH_3$ | H | $CD_3$ |
| 220. | $CH_3$ | 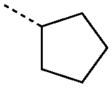 | H | $CH_3$ | $CD_3$ |
| 221. | H | 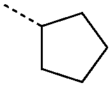 | $CH_3$ | $CH_3$ | $CD_3$ |
| 222. | $CH_3$ | 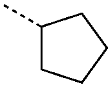 | $CH_3$ | $CH_3$ | $CD_3$ |
| 223. | H | H | 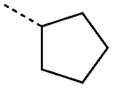 | H | $CD_3$ |
| 224. | $CH_3$ | H | 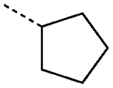 | H | $CD_3$ |
| 225. | H | $CH_3$ | 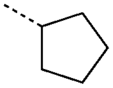 | H | $CD_3$ |
| 226. | H | H | 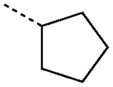 | $CH_3$ | $CD_3$ |
| 227. | $CH_3$ | $CH_3$ | 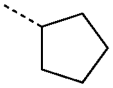 | H | $CD_3$ |
| 228. | $CH_3$ | H | 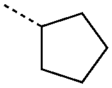 | $CH_3$ | $CD_3$ |
| 229. | H | $CH_3$ | 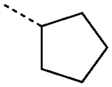 | $CH_3$ | $CD_3$ |
| 230. | $CH_3$ | $CH_3$ | 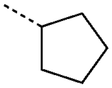 | $CH_3$ | $CD_3$ |
| 231. | 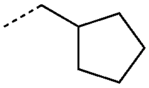 | H | H | H | $CD_3$ |
| 232. | 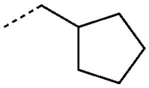 | $CH_3$ | H | H | $CD_3$ |
| 233. | 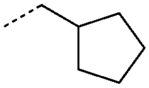 | H | $CH_3$ | H | $CD_3$ |

-continued
| $L_{Bj}$, j | $R^{B1}$ | $R^{B2}$ | $R^{B3}$ | $R^{B4}$ | $R^{B5}$ |
|---|---|---|---|---|---|
| 234. | 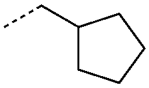 | H | H | $CH_3$ | $CD_3$ |
| 235. | 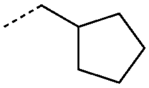 | $CH_3$ | $CH_3$ | H | $CD_3$ |
| 236. | 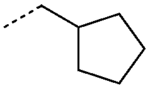 | $CH_3$ | H | $CH_3$ | $CD_3$ |
| 237. | 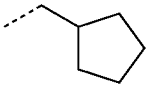 | H | $CH_3$ | $CH_3$ | $CD_3$ |
| 238. | 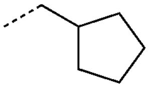 | $CH_3$ | $CH_3$ | $CH_3$ | $CD_3$ |
| 239. | H | 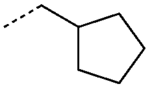 | H | H | $CD_3$ |
| 240. | $CH_3$ | 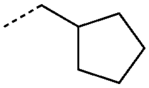 | H | H | $CD_3$ |
| 241. | H | 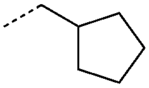 | $CH_3$ | H | $CD_3$ |
| 242. | H | 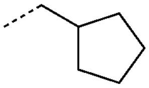 | H | $CH_3$ | $CD_3$ |
| 243. | $CH_3$ | 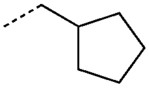 | $CH_3$ | H | $CD_3$ |
| 244. | $CH_3$ | 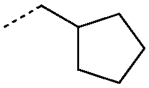 | H | $CH_3$ | $CD_3$ |
| 245. | H | 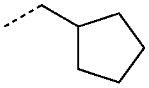 | $CH_3$ | $CH_3$ | $CD_3$ |
| 246. | $CH_3$ | 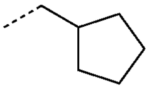 | $CH_3$ | $CH_3$ | $CD_3$ |
| 247. | H | H | 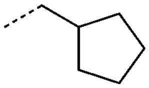 | H | $CD_3$ |
| 248. | $CH_3$ | H | 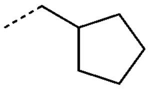 | H | $CD_3$ |

-continued
| $L_{Bj}$, j | $R^{B1}$ | $R^{B2}$ | $R^{B3}$ | $R^{B4}$ | $R^{B5}$ |
|---|---|---|---|---|---|
| 249. | H | $CH_3$ | 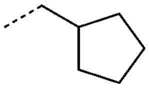 | H | $CD_3$ |
| 250. | H | H | 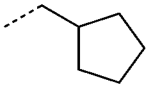 | $CH_3$ | $CD_3$ |
| 251. | $CH_3$ | $CH_3$ | 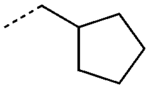 | H | $CD_3$ |
| 252. | $CH_3$ | H | 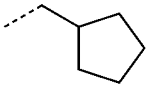 | $CH_3$ | $CD_3$ |
| 253. | H | $CH_3$ | 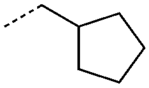 | $CH_3$ | $CD_3$ |
| 254. | $CH_3$ | $CH_3$ | 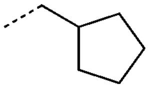 | $CH_3$ | $CD_3$ |
| 255. | 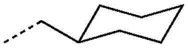 | H | H | H | $CD_3$ |
| 256. | 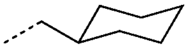 | $CH_3$ | H | H | $CD_3$ |
| 257. | 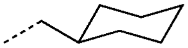 | H | $CH_3$ | H | $CD_3$ |
| 258. | 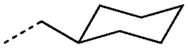 | H | H | $CH_3$ | $CD_3$ |
| 259. | 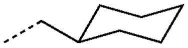 | $CH_3$ | $CH_3$ | H | $CD_3$ |
| 260. | 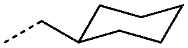 | $CH_3$ | H | $CH_3$ | $CD_3$ |
| 261. | 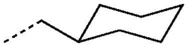 | H | $CH_3$ | $CH_3$ | $CD_3$ |
| 262. | 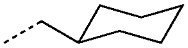 | $CH_3$ | $CH_3$ | $CH_3$ | $CD_3$ |
| 263. | H | 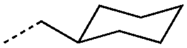 | H | H | $CD_3$ |
| 264. | $CH_3$ | 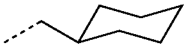 | H | H | $CD_3$ |
| 265. | H | 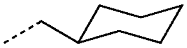 | $CH_3$ | H | $CD_3$ |
| 266. | H | 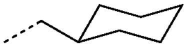 | H | $CH_3$ | $CD_3$ |
| 267. | $CH_3$ | 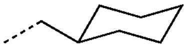 | $CH_3$ | H | $CD_3$ |
| 268. | $CH_3$ | 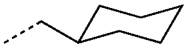 | H | $CH_3$ | $CD_3$ |

-continued

| $L_{Bj}$, j | $R^{B1}$ | $R^{B2}$ | $R^{B3}$ | $R^{B4}$ | $R^{B5}$ |
|---|---|---|---|---|---|
| 269. | H | 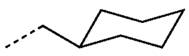 | $CH_3$ | $CH_3$ | $CD_3$ |
| 270. | $CH_3$ | 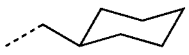 | $CH_3$ | $CH_3$ | $CD_3$ |
| 271. | H | H | 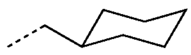 | H | $CD_3$ |
| 272. | $CH_3$ | H | 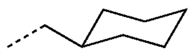 | H | $CD_3$ |
| 273. | H | $CH_3$ | 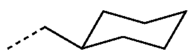 | H | $CD_3$ |
| 274. | H | H | 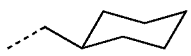 | $CH_3$ | $CD_3$ |
| 275. | $CD_3$ | $CD_3$ | $CD_3$ | $CD_3$ | $CD_3$ |

14. The compound of claim 1, wherein the compound has formula $(L_A)_mPt(L_C)_{2-m}$;

wherein $L_C$ is a bidentate ligand; and m is 1, or 2.

15. An organic light-emitting device (OLED) comprising:

an anode;

a cathode; and an organic layer, disposed between the anode and the cathode, comprising a compound comprising a ligand $L_A$ of Formula I:

(I)

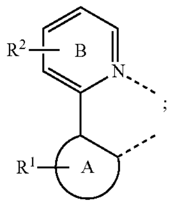

wherein ring A is a 5-membered or 6-membered carbocyclic or heterocyclic ring;

wherein $R^1$ represents from none to the maximum possible number of substitution;

wherein $R^2$ represents from two to the maximum possible number of substitution;

wherein at least two adjacent $R^2$s are joined to form ring C and have the following formula, wherein ring C is fused to ring B:

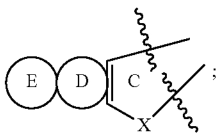

wherein the wave lines indicate bonds to ring B;

wherein ring D is benzene;

wherein ring E is a 6-membered aromatic ring;

wherein ring D fuses to ring C, and ring E fuses to ring D;

wherein ring D and ring E can be further substituted by one or more substituents;

wherein X is selected from the group consisting of O, S, Se, and NR;

wherein $R^1$, $R^2$, and R are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein any two adjacent substituents are optionally joined to form into a ring;

wherein $L_A$ is coordinated to a metal M;

wherein $L_A$ is optionally linked with other ligands to comprise a tridentate, tetradentate, pentadentate, or hexadentate ligand; and wherein M is optionally coordinated to other ligands.

16. The OLED of claim 15, wherein the organic layer is an emissive layer and the compound is an emissive dopant or a non-emissive dopant.

17. The OLED of claim 15, wherein the organic layer further comprises a host, wherein host comprises at least one chemical group selected from the group consisting of triphenylene, carbazole, dibenzothiophene, dibenzofuran, dibenzoselenophene, aza-triphenylene, azacarbazole, aza-dibenzothiophene, aza-dibenzofuran, and aza-dibenzoselenophene.

18. The OLED of claim 15, wherein the organic layer further comprises a host, wherein the host is selected from the group consisting of:

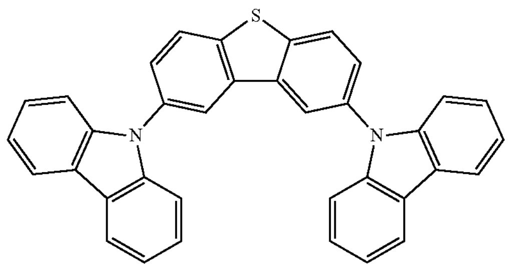
,

-continued
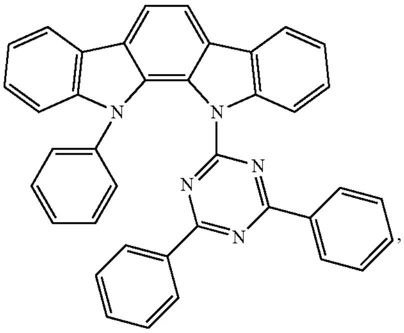,
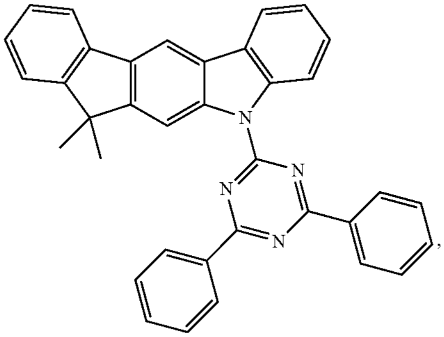,
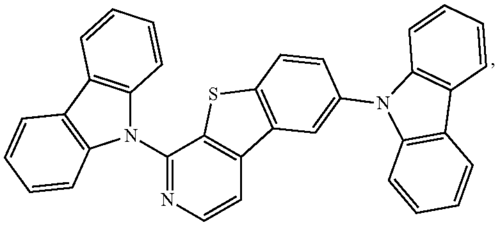,
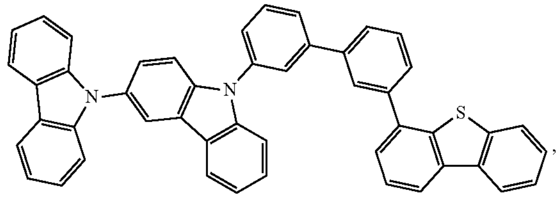,
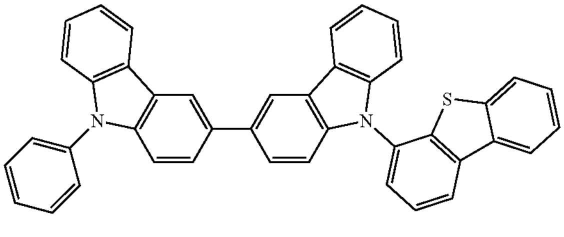,
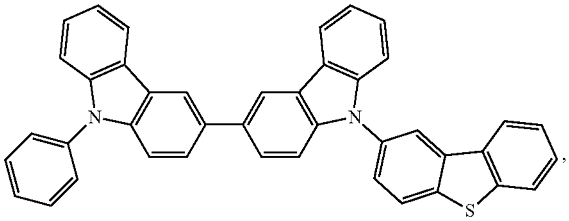,
-continued
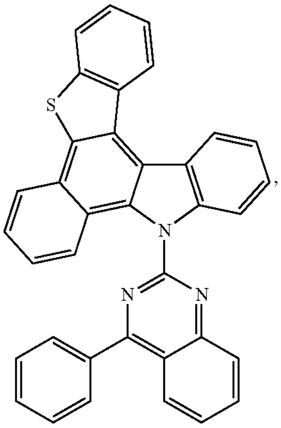,
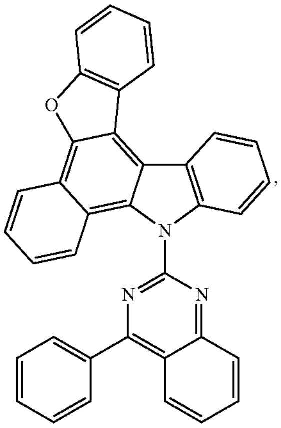,
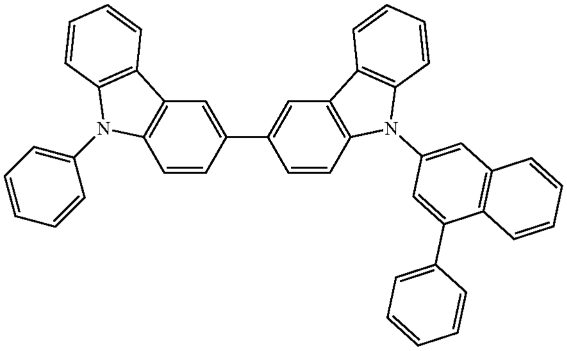,
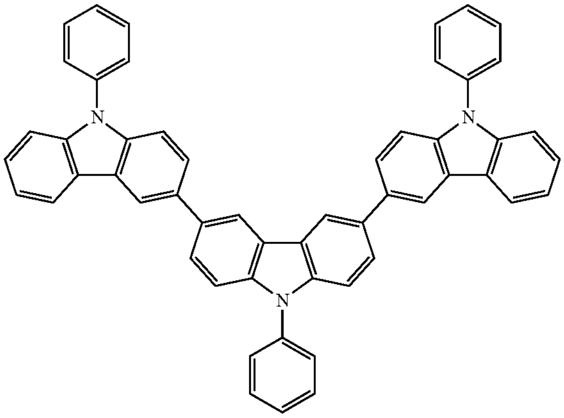,
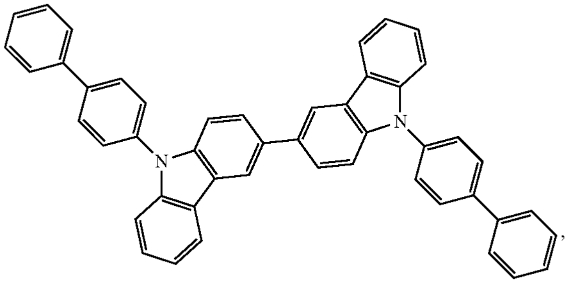,
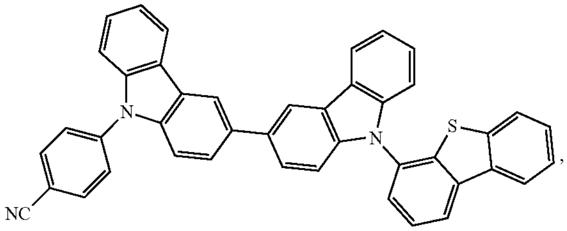, -continued
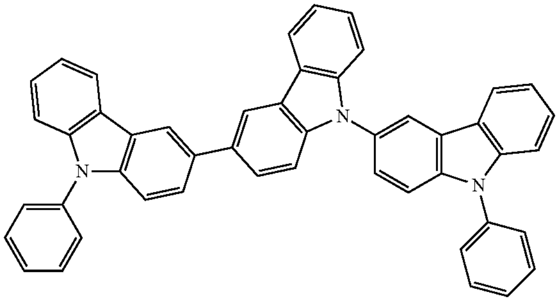
,
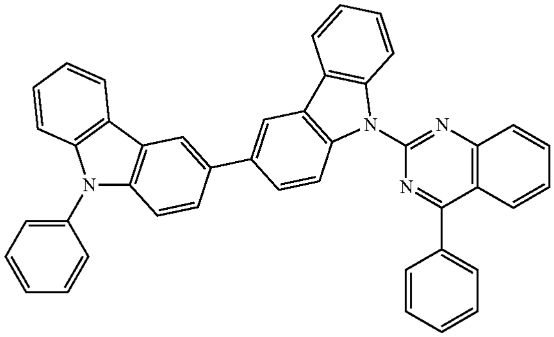
,
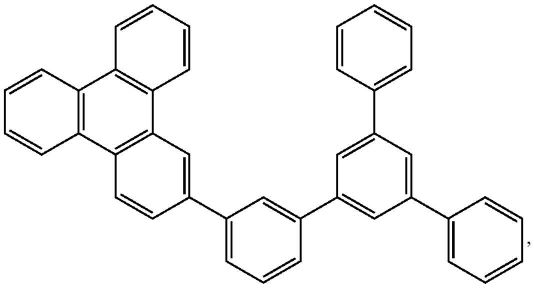
,
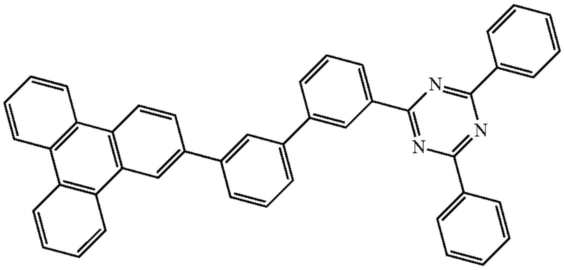
,
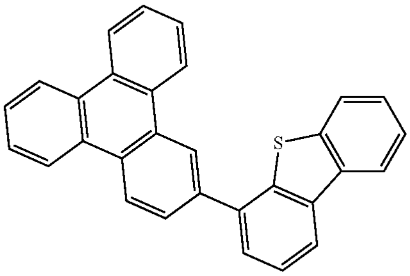
,
-continued
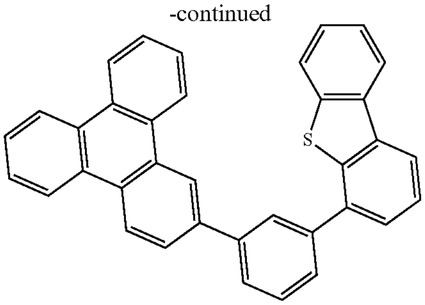
,
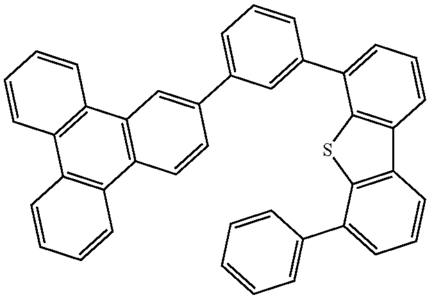
,
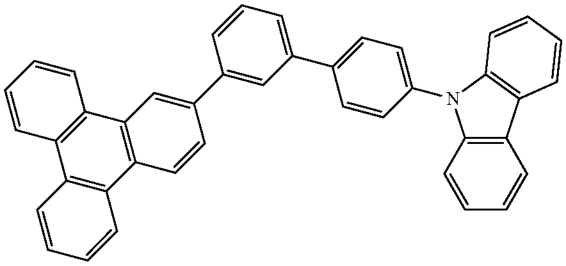
,
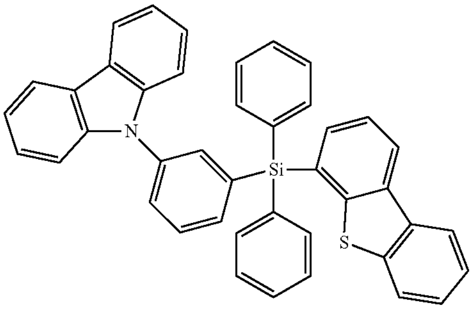
,
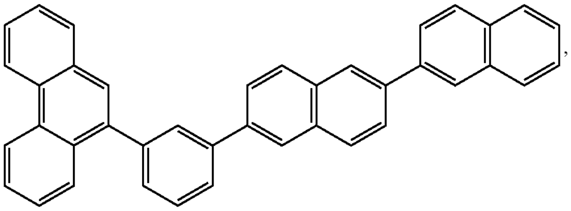
,
and combinations thereof.
19. A consumer product comprising an organic light-emitting device (OLED) comprising:
an anode;
a cathode; and
an organic layer, disposed between the anode and the cathode, comprising a compound of Formula (I):

(I)

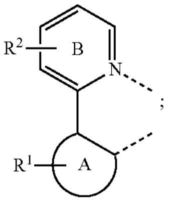

wherein ring A is a 5-membered or 6-membered carbocyclic or heterocyclic ring;

wherein $R^1$ represents from none to the maximum possible number of substitution;

wherein $R^2$ represents from two to the maximum possible number of substitution;

wherein at least two adjacent $R^2$s are joined to form ring C and have the following formula, wherein ring C is fused to ring B:

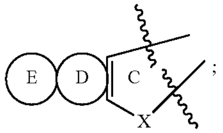

wherein the wave lines indicate bonds to ring B;

wherein ring D is benzene;

wherein ring E is a 6-membered aromatic ring;

wherein ring D fuses to ring C, and ring E fuses to ring D;

wherein ring D and ring E can be further substituted by one or more substituents;

wherein X is selected from the group consisting of O, S, Se, and NR;

wherein $R^1$, $R^2$, and R are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein any two adjacent substituents are optionally joined to form into a ring;

wherein $L_A$ is coordinated to a metal M;

wherein $L_A$ is optionally linked with other ligands to comprise a tridentate, tetradentate, pentadentate, or hexadentate ligand; and wherein M is optionally coordinated to other ligands.

20. The consumer product of claim 19, wherein the consumer product is selected from the group consisting of a flat panel display, a computer monitor, a medical monitors television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video walls comprising multiple displays tiled together, a theater or stadium screen, and a sign.

* * * * *